United States Patent
Sun et al.

(10) Patent No.: US 9,732,119 B2
(45) Date of Patent: Aug. 15, 2017

(54) IMMUNOMODULATORS

(71) Applicant: BRISTOL-MYERS SQUIBB COMPANY, Princeton, NJ (US)

(72) Inventors: Li-Qiang Sun, Glastonbury, CT (US); Qian Zhao, Wallingford, CT (US); Eric Mull, Guilford, CT (US); Eric P. Gillis, Cheshire, CT (US); Paul Michael Scola, Glastonbury, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/874,886

(22) Filed: Oct. 5, 2015

(65) Prior Publication Data

US 2016/0102122 A1 Apr. 14, 2016

Related U.S. Application Data

(60) Provisional application No. 62/062,240, filed on Oct. 10, 2014.

(51) Int. Cl.

| | | |
|---|---|---|
| *C07K 7/50* | (2006.01) | |
| *C07K 7/54* | (2006.01) | |
| *A61K 38/12* | (2006.01) | |
| *A01N 43/00* | (2006.01) | |
| *C07K 7/64* | (2006.01) | |
| *A61K 45/06* | (2006.01) | |
| *C07K 7/56* | (2006.01) | |
| *C07K 7/08* | (2006.01) | |
| *A61K 38/10* | (2006.01) | |
| *G01N 33/574* | (2006.01) | |
| *A61K 38/00* | (2006.01) | |

(52) U.S. Cl.
CPC .............. *C07K 7/64* (2013.01); *A61K 38/12* (2013.01); *A61K 45/06* (2013.01); *C07K 7/08* (2013.01); *C07K 7/56* (2013.01); *A61K 38/00* (2013.01); *A61K 38/10* (2013.01); *G01N 33/574* (2013.01); *G01N 2333/70532* (2013.01); *G01N 2500/02* (2013.01); *G01N 2800/26* (2013.01)

(58) Field of Classification Search
None
See application file for complete search history.

(56) References Cited

U.S. PATENT DOCUMENTS

| 5,869,451 A | 2/1999 | Dower et al. |
| 9,090,668 B2 | 7/2015 | Suga et al. |
| 9,308,236 B2 * | 4/2016 | Miller .................... A61K 38/10 |
| 9,410,148 B2 | 8/2016 | Suga et al. |

| 2014/0018257 A1 | 1/2014 | Suga et al. |
| 2016/0158349 A1 | 6/2016 | Miller et al. |
| 2016/0272680 A1 | 9/2016 | Boy et al. |
| 2016/0340391 A1 | 11/2016 | Miller et al. |

FOREIGN PATENT DOCUMENTS

| WO | WO 00/26353 | 5/2000 |
| WO | WO 2010/027828 A2 | 3/2010 |
| WO | WO 2011/161699 A2 | 12/2011 |
| WO | WO 2012/168944 A1 | 12/2012 |
| WO | WO 2013/144704 A1 | 10/2013 |
| WO | WO 2013/182240 A1 | 12/2013 |
| WO | WO 2013/183707 A1 | 12/2013 |
| WO | WO 2014/151006 A2 | 9/2014 |
| WO | WO2014/151634 | 9/2014 |
| WO | WO 2015/033303 A1 | 3/2015 |
| WO | WO 2015/044900 A1 | 4/2015 |
| WO | WO2016/039749 A1 | 3/2016 |
| WO | WO2016/077518 A1 | 5/2016 |
| WO | WO2016/100285 A1 | 6/2016 |
| WO | WO2016/100608 A1 | 6/2016 |
| WO | WO2016/126646 A1 | 8/2016 |

OTHER PUBLICATIONS

Hayashi, Y. et al., "In Vitro Selection of Anti-Akt2 Thioether-Macrocyclic Peptides Leading to Isoform-Selective Inhibitors", ACS Chemical Biology, vol. 7, pp. 607-613 (2012).
Morimoto, J. et al., "Discovery of Macrocyclic Peptides Armed with a Mechanism-Based Warhead: Isoform-Selective Inhibition of Human Deacetylase SIRT2", Angewandte Chemie, International Edition, vol. 51, pp. 3423-3427 (2012).
Yamagishi, Y. et al., "Natural Product-Like Macrocyclic N-Methyl-Peptide Inhibitors against a Ubiquitin Ligase Uncovered from a Ribosome-Expressed De Novo Library", Chemistry & Biology, vol. 18, pp. 1562-1570 (2011).
Cook, W. J. et al., Crystal Structure and Confirmation of the Cyclic Trimer of a Repeat Pentapeptide of Elastin, *cyclo*-(L-Valyl-L-prolylglycyl-L-valylglycyl)$_3$, J. Am. Chem. Soc., vol. 102, No. 17, p. 5502-5505 (1980).
Hoyer, K. M. et al., "The Iterative Gramicidin S Thioesterase Catalyzes Peptide Ligation and Cyclization," Chemistry & Biology, vol. 14, No. 1, p. 13-22 (2007).
Tamaki, M. et al., "Cyclization of Penta- and Hexapeptide Active Esters Related to Gramicidin S and Gratisin," Bulletin of the Chemical Society of Japan, vol. 62, No. 2, p. 594-596 (1989).
Karle, I. L., "Conformation of Cyclic Pentapeptides in the Crystalline State. Cyclic (D-Phe-L-Pro-Gly-D-Ala-L-Pro) with 3.fwdarw. 1 and 4.fwdarw. 1 Intramolecular Hydrogen Bonds", Database Accession No. 1981: 498291; Compound 78221-87-1.
Rothe, M. et al., Interchain Reactions (Cyclo-Oligomerizations) During the Cyclization of Resin-Bound Peptides, Database Accesion No. 1978: 424771; Compound RN: 66517-17-7.

\* cited by examiner

*Primary Examiner* — Satyanarayana R Gudibande
*Assistant Examiner* — Jia-Hai Lee
(74) *Attorney, Agent, or Firm* — Pamela A. Mingo

(57) ABSTRACT

The present disclosure provides novel macrocyclic peptides which inhibit the PD-1/PD-L1 and PD-L1/CD80 protein/protein interaction, and thus are useful for the amelioration of various diseases, including cancer and infectious diseases.

8 Claims, No Drawings

SEQUENCE LISTING

<160> NUMBER OF SEQ ID NOS: 2

<210> SEQ ID NO 1
<211> LENGTH: 384
<212> TYPE: PRT
<213> ORGANISM: Homo sapiens

<400> SEQUENCE: 1

```
Leu Asp Ser Pro Asp Arg Pro Trp Asn Pro Thr Phe Ser Pro Ala
1               5                   10                  15

Leu Leu Val Val Thr Glu Gly Asp Asn Ala Thr Phe Thr Cys Ser Phe
            20                  25                  30

Ser Asn Thr Ser Glu Ser Phe Val Leu Asn Trp Tyr Arg Met Ser Pro
            35                  40                  45

Ser Asn Gln Thr Asp Lys Leu Ala Ala Phe Pro Glu Asp Arg Ser Gln
        50                  55                  60

Pro Gly Gln Asp Cys Arg Phe Arg Val Thr Gln Leu Pro Asn Gly Arg
65                  70                  75                  80

Asp Phe His Met Ser Val Val Arg Ala Arg Arg Asn Asp Ser Gly Thr
                85                  90                  95

Tyr Leu Cys Gly Ala Ile Ser Leu Ala Pro Lys Ala Gln Ile Lys Glu
            100                 105                 110

Ser Leu Arg Ala Glu Leu Arg Val Thr Glu Arg Arg Ala Glu Val Pro
            115                 120                 125

Thr Ala His Pro Ser Pro Ser Pro Arg Pro Ala Gly Gln Phe Gln Gly
        130                 135                 140

Ser Pro Gly Gly Gly Gly Arg Glu Pro Lys Ser Ser Asp Lys Thr
145                 150                 155                 160

His Thr Ser Pro Pro Ser Pro Ala Pro Glu Leu Leu Gly Gly Ser Ser
                165                 170                 175

Val Phe Leu Phe Pro Pro Lys Pro Lys Asp Thr Leu Met Ile Ser Arg
            180                 185                 190

Thr Pro Glu Val Thr Cys Val Val Val Asp Val Ser His Glu Asp Pro
            195                 200                 205

Glu Val Lys Phe Asn Trp Tyr Val Asp Gly Val Glu Val His Asn Ala
        210                 215                 220

Lys Thr Lys Pro Arg Glu Glu Gln Tyr Asn Ser Thr Tyr Arg Val Val
225                 230                 235                 240

Ser Val Leu Thr Val Leu His Gln Asp Trp Leu Asn Gly Lys Glu Tyr
                245                 250                 255

Lys Cys Lys Val Ser Asn Lys Ala Leu Pro Ala Pro Ile Glu Lys Thr
            260                 265                 270

Ile Ser Lys Ala Lys Gly Gln Pro Arg Glu Pro Gln Val Tyr Thr Leu
            275                 280                 285

Pro Pro Ser Arg Asp Glu Leu Thr Lys Asn Gln Val Ser Leu Thr Cys
        290                 295                 300

Leu Val Lys Gly Phe Tyr Pro Ser Asp Ile Ala Val Glu Trp Glu Ser
305                 310                 315                 320
```

```
Asn Gly Gln Pro Glu Asn Asn Tyr Lys Thr Thr Pro Pro Val Leu Asp
                325                 330                 335

Ser Asp Gly Ser Phe Phe Leu Tyr Ser Lys Leu Thr Val Asp Lys Ser
            340                 345                 350

Arg Trp Gln Gln Gly Asn Val Phe Ser Cys Ser Val Met His Glu Ala
        355                 360                 365

Leu His Asn His Tyr Thr Gln Lys Ser Leu Ser Leu Ser Pro Gly Lys
    370                 375                 380

<210> SEQ ID NO 2
<211> LENGTH: 237
<212> TYPE: PRT
<213> ORGANISM: Homo sapiens

<400> SEQUENCE: 2

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu Pro Leu Ala His Pro Pro Asn Glu Arg Thr Gly Ser Ser
    210                 215                 220

Glu Thr Val Arg Phe Gln Gly His His His His His
225                 230                 235
```

IMMUNOMODULATORS

CROSS-REFERENCE TO RELATED APPLICATIONS

This application claims priority to U.S. Provisional Patent Application 62/062,240 filed Oct. 10, 2014, hereby incorporated by reference in its entirety.

The present disclosure provides novel macrocyclic peptides which inhibit the PD-1/PD-L1 and CD80/PD-L1 protein/protein interaction, and are thus useful for the amelioration of various diseases, including cancer and infectious diseases.

The protein Programmed Death 1 (PD-1) is an inhibitory member of the CD28 family of receptors, that also includes CD28, CTLA-4, ICOS and BTLA. PD-1 is expressed on activated B cells, T cells, and myeloid cells (Agata et al., supra; Okazaki et al., Curr. Opin. Immunol., 14:779-782 (2002); Bennett et al., J. Immunol., 170:711-718 (2003)).

The PD-1 protein is a 55 kDa type I transmembrane protein that is part of the Ig gene superfamily (Agata et al., Int. Immunol., 8:765-772 (1996)). PD-1 contains a membrane proximal immunoreceptor tyrosine inhibitory motif (ITIM) and a membrane distal tyrosine-based switch motif (ITSM) (Thomas, M. L., J. Exp. Med., 181:1953-1956 (1995); Vivier, E. et al., Immunol. Today, 18:286-291 (1997)). Although structurally similar to CTLA-4, PD-1 lacks the MYPPY motif that is critical for CD80 CD86 (B7-2) binding. Two ligands for PD-1 have been identified, PD-L1 (B7-H1) and PD-L2 (b7-DC). The activation of T cells expressing PD-1 has been shown to be downregulated upon interaction with cells expressing PD-L1 or PD-L2 (Freeman et al., J. Exp. Med., 192:1027-1034 (2000); Latchman et al., Nat. Immunol., 2:261-268 (2001); Carter et al., Eur. J. Immunol., 32:634-643 (2002)). Both PD-L1 and PD-L2 are B7 protein family members that bind to PD-1, but do not bind to other CD28 family members. The PD-L1 ligand is abundant in a variety of human cancers (Dong et al., Nat. Med., 8:787-789 (2002)). The interaction between PD-1 and PD-L1 results in a decrease in tumor infiltrating lymphocytes, a decrease in T-cell receptor mediated proliferation, and immune evasion by the cancerous cells (Dong et al., J. Mol. Med., 81:281-287 (2003); Blank et al., Cancer Immunol. Immunother., 54:307-314 (2005); Konishi et al., Clin. Cancer Res., 10:5094-5100 (2004)). Immune suppression can be reversed by inhibiting the local interaction of PD-1 with PD-L1, and the effect is additive when the interaction of PD-1 with PD-L2 is blocked as well (Iwai et al., Proc. Natl. Acad. Sci. USA, 99:12293-12297 (2002); Brown et al., J. Immunol., 170:1257-1266 (2003)).

PD-L1 has also been shown to interact with CD80 (Butte M J et al, Immunity; 27:111-122 (2007)). The interaction PD-L1/CD80 on expressing immune cells has been shown to be an inhibitory one. Blockade of this interaction has been shown to abrogate this inhibitory interaction (Paterson A M, et al., J Immunol., 187:1097-1105 (2011); Yang J, et al. J Immunol. August 1; 187(3):1113-9 (2011)).

When PD-1 expressing T cells contact cells expressing its ligands, functional activities in response to antigenic stimuli, including proliferation, cytokine secretion, and cytotoxicity, are reduced. PD-1/PD-L1 or PD-L2 interactions down regulate immune responses during resolution of an infection or tumor, or during the development of self tolerance (Keir, M. E. et al., Annu. Rev. Immunol., 26:Epub (2008)). Chronic antigen stimulation, such as that which occurs during tumor disease or chronic infections, results in T cells that express elevated levels of PD-1 and are dysfunctional with respect to activity towards the chronic antigen (reviewed in Kim et al., Curr. Opin. Imm. (2010)). This is termed "T cell exhaustion". B cells also display PD-1/PD-ligand suppression and "exhaustion".

Blockade of PD-1/PD-L1 ligation using antibodies to PD-L1 has been shown to restore and augment T cell activation in many systems. Patients with advanced cancer benefit from therapy with a monoclonal antibody to PD-L1 (Brahmer et al., New Engl. J. Med. (2012)). Preclinical animal models of tumors and chronic infections have shown that blockade of the PD-1/PD-L1 pathway by monoclonal antibodies can enhance the immune response and result in tumor rejection or control of infection. Antitumor immunotherapy via PD-1/PD-L1 blockade may augment therapeutic immune response to a number of histologically distinct tumors (Dong, H. et al., "B7-H1 pathway and its role in the evasion of tumor immunity", J. Mol. Med., 81(5):281-287 (2003); Dong, H. et al., "Tumor-associated B7-H1 promotes T-cell apoptosis: a potential mechanism of immune evasion", Nat. Med., 8(8):793-800 (2002)).

Interference with the PD-1/PD-L1 interaction causes enhanced T cell activity in systems with chronic infection. Blockade of PD-L1 caused improved viral clearance and restored immunity in mice with chromoic lymphocytic chorio meningitis virus infection (Barber, D. L. et al., "Restoring function in exhausted CD8 T cells during chronic viral infection", Nature, 439(7077):682-687 (2006)). Humanized mice infected with HIV-1 show enhanced protection against viremia and viral depletion of CD4+ T cells (Palmer et al., J. Immunol. (2013)). Blockade of PD-1/PD-L1 through monoclonal antibodies to PD-L1 can restore in vitro antigen-specific functionality to T cells from HIV patients (Day, Nature (2006); Petrovas, J. Exp. Med. (2006); Trautman, Nature Med. (2006); D'Souza, J. Immunol. (2007); Zhang, Blood (2007); Kaufmann, Nature Imm. (2007); Kasu, J. Immunol. (2010); Porichis, Blood (2011)), HCV patients (Golden-Mason, J. Virol. (2007); Jeung, J. Leuk. Biol. (2007); Urbani, J. Hepatol. (2008); Nakamoto, PLoS Path. (2009); Nakamoto, Gastroenterology (2008)) and HBV patients (Boni, J. Virol. (2007); Fisicaro, Gastro. (2010); Fisicaro et al., Gastroenterology (2012); Boni et al., Gastro. (2012); Penna et al., J. Hep. (2012); Raziorrough, Hepatology (2009); Liang, World J. Gastro. (2010); Zhang, Gastro. (2008)).

Blockade of the PD-L1/CD80 interaction has also been shown to stimulate immunity (Yang J., et al., J Immunol. August 1; 187(3):1113-9 (2011)). Immune stimulation resulting from blockade of the PD-L1/CD80 interaction has been shown to be enhanced through combination with blockade of further PD-1/PD-L1 or PD-1/PD-L2 interactions.

Alterations in immune cell phenotypes are hypothesized to be an important factor in septic shock (Hotchkiss, et al., Nat Rev Immunol (2013)). These include increased levels of PD-1 and PD-L1 (Guignant, et al, Crit. Care (2011)), Cells from septic shock patients with increased levels of PD-1 and PD-L1 exhibit an increased level of T cell apoptosis. Antibodies directed to PD-L1, can reduce the level of Immune cell apoptosis (Zhang et al, Crit. Care (2011)). Furthermore, mice lacking PD-1 expression are more resistant to septic shock symptoms than wildtype mice. Yang J., et al. J Immunol. August 1; 187(3):1113-9 (2011)). Studies have revealed that blockade of the interactions of PD-L1 using antibodies can suppress inappropriate immune responses and ameliorate disease signs.

In addition to enhancing immunologic responses to chronic antigens, blockade of the PD-1/PD-L1 pathway has also been shown to enhance responses to vaccination, including therapeutic vaccination in the context of chronic infection (Ha, S. J. et al., "Enhancing therapeutic vaccination by blocking PD-1-mediated inhibitory signals during chronic infection", *J. Exp. Med.*, 205(3):543-555 (2008); Finnefrock, A. C. et al., "PD-1 blockade in rhesus macaques: impact on chronic infection and prophylactic vaccination", *J. Immunol.*, 182(2):980-987 (2009); Song, M.-Y. et al., "Enhancement of vaccine-induced primary and memory CD8+t-cell responses by soluble PD-1", *J. Immunother.*, 34(3):297-306 (2011)).

The molecules described herein demonstrate the ability to block the interaction of PD-L1 with PD-1, in both biochemical and cell-based experimental systems. These results are consistent with a potential for therapeutic administration to enhance immunity in cancer or chronic infection, including therapeutic vaccine.

The macrocyclic peptides described herein are capable of inhibiting the interaction of PD-L1 with PD-1 and with CD80. These compounds have demonstrated highly efficacious binding to PD-L1, blockade of the interaction of PD-L1 with either PD-1 or CD80, and are capable of promoting enhanced T cell functional activity, thus making them candidates for parenteral, oral, pulmonary, nasal, buccal and sustained release formulations.

In one aspect the present disclosure provides a compound of formula (I)

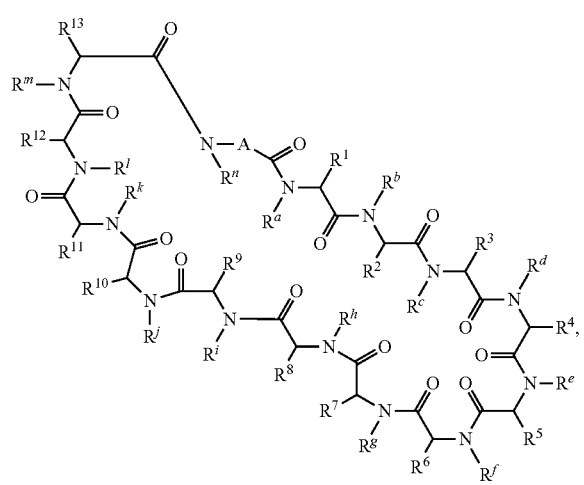

or a pharmaceutically acceptable salt thereof, wherein:
A is selected from —CH$_2$CH$_2$—;

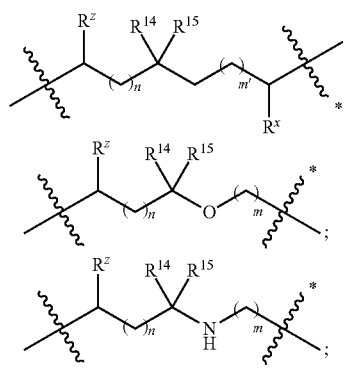

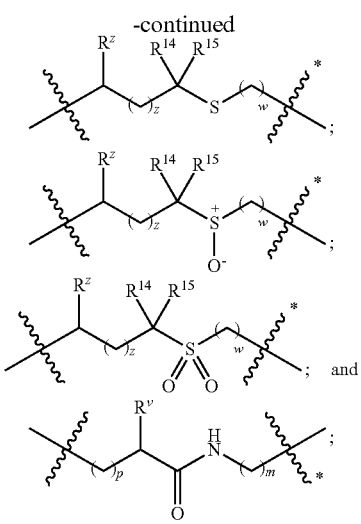

wherein:

$\sim\!\!*$ denotes the point of attachment to the carbonyl group and $\sim\!\!$ denotes the point of attachment to the nitrogen atom;

n is 0, 1, or 2;
m is 1 or 2;
m' is 0 or 1;
z is 1 or 2;
when z is 1, w is 2;
when z is 2, w is 1 or 2;
p is 0, 1, or 2;
$R^{14}$ and $R^{15}$ are independently selected from hydrogen and methyl;
$R^x$ is selected from hydrogen, amino, hydroxy, and methyl; and
$R^z$ is selected from hydrogen and —C(O)NHR$^{16}$; wherein $R^{16}$ is selected from hydrogen, —CHR$^{17}$C(O)NH$_2$, —CHR$^{17}$C(O)NHCHR$^{18}$C(O)NH$_2$, and —CHR$^{17}$C(O)NHCHR$^{18}$C(O)NHCH$_2$C(O)NH$_2$; wherein $R^{17}$ is selected from hydrogen and —CH$_2$OH and wherein $R^{18}$ is selected from hydrogen and methyl;
$R^v$ is hydrogen, methyl, or a natural amino acid side chain;
$R^c$, $R^f$, $R^h$, $R^i$, and $R^m$ are hydrogen;
$R^n$ is hydrogen or methyl or $R^v$ and $R^n$ form a pyrrolidine ring;
$R^a$, $R^e$, $R^j$, and $R^k$, are each independently selected from hydrogen and methyl;
$R^1$, $R^2$, $R^3$, $R^4$, $R^5$, $R^6$, $R^7$, $R^8$, $R^9$, $R^{10}$, $R^{11}$, $R^{12}$, and $R^{13}$ are independently selected from a natural amino acid side chain and an unnatural amino acid side chain or form a ring with the corresponding vicinal R group as described below;
$R^e$ and $R^k$ can each form a ring with the corresponding vicinal R group and the atoms to which they are attached selected from azetidine, pyrollidine, morpholine, piperidine, piperazine, and tetrahydrothiazole; wherein each ring is optionally substituted with one to four groups independently selected from amino, cyano, methyl, halo, and hydroxy;
$R^b$ is methyl or, $R^b$ and $R^2$, together with the atoms to which they are attached, form a ring selected from azetidine, pyrollidine, morpholine, piperidine, piperazine, and tetrahydrothiazole; wherein each ring is optionally substituted with one to four groups independently selected from amino, cyano, methyl, halo, and hydroxy;

$R^d$ is hydrogen or methyl, or, $R^d$ and $R^4$, together with the atoms to which they are attached, can form a ring selected from azetidine, pyrollidine, morpholine, piperidine, piperazine, and tetrahydrothiazole; wherein each ring is optionally substituted with one to four groups independently selected from amino, cyano, methyl, halo, hydroxy, and phenyl;

$R^g$ is hydrogen or methyl or $R^g$ and $R^7$, together with the atoms to which they are attached, can form a ring selected from azetidine, pyrollidine, morpholine, piperidine, piperazine, and tetrahydrothiazole; wherein each ring is optionally substituted with one to four groups independently selected from amino, benzyl optionally substituted with a halo group, benzyloxy, cyano, cyclohexyl, methyl, halo, hydroxy, isoquinolinyloxy optionally substituted with a methoxy group, quinolinyloxy optionally substituted with a halo group, and tetrazolyl; and wherein the pyrrolidine and the piperidine ring are optionally fused to a cyclohexyl, phenyl, or indole group; and $R^L$ is methyl or, $R^L$ and $R^{12}$, together with the atoms to which they are attached, form a ring selected from azetidine and pyrollidine, wherein each ring is optionally substituted with one to four groups independently selected from amino, cyano, methyl, halo, and hydroxy.

In a first embodiment of the first aspect the present disclosure provides a compound of formula (I), or a pharmaceutically acceptable salt thereof, wherein:

$R^d$ and $R^4$, together with the atoms to which they are attached, form a pyrollidine ring;

$R^g$ and $R^7$, together with the atoms to which they are attached, form a pyrollidine ring, wherein said ring is optionally substituted with one hydroxy group; and $R^k$ is methyl.

In a second embodiment of the first aspect the present disclosure provides a compound of formula (I) or a therapeutically acceptable salt thereof, wherein:

$R^d$ and $R^4$, together with the atoms to which they are attached, form a pyrollidine ring;

$R^g$ and $R^7$, together with the atoms to which they are attached, form a pyrollidine ring, wherein said ring is optionally substituted with one hydroxy group;

$R^k$ is methyl $R^a$, $R^e$, and $R^j$ hydrogen;

$R^b$ and $R^2$ are each methyl or, $R^b$ and $R^2$, together with the atoms to which they are attached, form a piperidine ring;

$R^L$ is methyl;

$R^n$ is hydrogen, methyl, or $R^n$ and $R^v$ form a pyrrolidine ring;

$R^1$ is phenylmethyl wherein the phenyl is substituted with one group selected from halo, hydroxy, methoxy, or methyl;

$R^3$ is selected from —$CH_2C(O)NH_2$ and —$CH_2CO_2H$;

$R^5$ is selected from hydrogen, —$CH_2NH_2$, —$CH_2$(imidazolyl), and —$CH_2C(O)NH_2$;

$R^6$ is selected from —$CH_2CH(CH_3)_2$, —$(CH_2)_4NH_2$, —$(CH_2)_2CO_2H$, and $(CH_2)_2C(O)NH_2$;

$R^8$ and $R^{10}$ are —$CH_2$(indolyl), wherein the indolyl is optionally substituted with —$CH_2CO_2H$;

$R^9$ is selected from hydrogen, —$(CH_2)_2NH_2$, —$(CH_2)_4NH_2$, —$CH_2OH$, and —$CH_2C(O)NH_2$;

$R^{11}$ and $R^{12}$ are —$(CH_2)_3CH_3$; and $R^{13}$ is selected from methyl, —$CH_2OH$, —$CH_2CH(CH_3)_2$, and —$(CH_2)_2CO_2H$.

In a third embodiment of the first aspect the present disclosure provides a compound of formula (I) or a therapeutically acceptable salt thereof, wherein:

$R^d$ and $R^4$, together with the atoms to which they are attached, form a pyrollidine ring;

$R^g$ and $R^7$, together with the atoms to which they are attached, form a pyrollidine ring, wherein said ring is optionally substituted with one hydroxy group;

$R^k$ is methyl $R^a$, $R^e$, and $R^j$ hydrogen;

$R^b$ and $R^2$ are each methyl or, $R^b$ and $R^2$, together with the atoms to which they are attached, form a piperidine ring;

$R^L$ is methyl;

$R^n$ is hydrogen, methyl, or $R^n$ and $R^v$ form a pyrrolidine ring;

$R^1$ is phenylmethyl wherein the phenyl is substituted with one group selected from halo, hydroxy, methoxy, or methyl;

$R^3$ is selected from —$CH_2C(O)NH_2$ and —$CH_2CO_2H$;

$R^5$ is selected from hydrogen, —$CH_2NH_2$, —$CH_2$(imidazolyl), and —$CH_2C(O)NH_2$;

$R^6$ is selected from —$CH_2CH(CH_3)_2$, —$(CH_2)_4NH_2$, —$(CH_2)_2CO_2H$, and $(CH_2)_2C(O)NH_2$;

$R^8$ and $R^{10}$ are —$CH_2$(indolyl), wherein the indolyl is optionally substituted with —$CH_2CO_2H$;

$R^9$ is selected from hydrogen, —$(CH_2)_2NH_2$, —$(CH_2)_4NH_2$, —$CH_2OH$, and —$CH_2C(O)NH_2$;

$R^{11}$ and $R^{12}$ are —$(CH_2)_3CH_3$; and $R^{13}$ is selected from methyl, —$CH_2OH$, —$CH_2CH(CH_3)_2$, and —$(CH_2)_2CO_2H$; and A is —$CH_2CH_2$.

In a fourth embodiment of the first aspect the present disclosure provides a compound of formula (I) or a therapeutically acceptable salt thereof, wherein:

$R^d$ and $R^4$, together with the atoms to which they are attached, form a pyrollidine ring;

$R^g$ and $R^7$, together with the atoms to which they are attached, form a pyrollidine ring, wherein said ring is optionally substituted with one hydroxy group;

$R^k$ is methyl $R^a$, $R^e$, and $R^j$ hydrogen;

$R^b$ and $R^2$ are each methyl or, $R^b$ and $R^2$, together with the atoms to which they are attached, form a piperidine ring;

$R^L$ is methyl;

$R^n$ is hydrogen, methyl, or $R^n$ and $R^v$ form a pyrrolidine ring;

$R^1$ is phenylmethyl wherein the phenyl is substituted with one group selected from halo, hydroxy, methoxy, or methyl;

$R^3$ is selected from —$CH_2C(O)NH_2$ and —$CH_2CO_2H$;

$R^5$ is selected from hydrogen, —$CH_2NH_2$, —$CH_2$(imidazolyl), and —$CH_2C(O)NH_2$;

$R^6$ is selected from —$CH_2CH(CH_3)_2$, —$(CH_2)_4NH_2$, —$(CH_2)_2CO_2H$, and $(CH_2)_2C(O)NH_2$;

$R^8$ and $R^{10}$ are —$CH_2$(indolyl), wherein the indolyl is optionally substituted with —$CH_2CO_2H$;

$R^9$ is selected from hydrogen, —$(CH_2)_2NH_2$, —$(CH_2)_4NH_2$, —$CH_2OH$, and —$CH_2C(O)NH_2$;

$R^{11}$ and $R^{12}$ are —$(CH_2)_3CH_3$; and $R^{13}$ is selected from methyl, —$CH_2OH$, —$CH_2CH(CH_3)_2$, and —$(CH_2)_2CO_2H$; and A is In a fifth embodiment of the first aspect the present disclosure provides a compound of formula (I), or a pharmaceutically acceptable salt thereof, wherein:

$R^d$ and $R^4$, together with the atoms to which they are attached, form a pyrollidine ring;

$R^g$ and $R^7$, together with the atoms to which they are attached, form a pyrollidine ring, wherein said ring is optionally substituted with one hydroxy group;

$R^k$ is methyl;

$R^a$, $R^e$, and $R^j$ hydrogen;

$R^b$ and $R^2$ are each methyl or, $R^b$ and $R^2$, together with the atoms to which they are attached, form a piperidine ring;

$R^L$ is methyl;

$R^n$ is hydrogen, methyl, or $R^n$ and $R^v$ form a pyrrolidine ring;

$R^1$ is phenylmethyl wherein the phenyl is substituted with one group selected from halo, hydroxy, methoxy, or methyl;

$R^3$ is selected from —$CH_2C(O)NH_2$ and —$CH_2CO_2H$;

$R^5$ is selected from hydrogen, —$CH_2NH_2$, —$CH_2$(imidazolyl), and —$CH_2C(O)NH_2$;

$R^6$ is selected from —$CH_2CH(CH_3)_2$, —$(CH_2)_4NH_2$, —$(CH_2)_2CO_2H$, and $(CH_2)_2C(O)NH_2$;

$R^8$ and $R^{10}$ are —$CH_2$(indolyl), wherein the indolyl is optionally substituted with —$CH_2CO_2H$;

$R^9$ is selected from hydrogen, —$(CH_2)_2NH_2$, —$(CH_2)_4NH_2$, —$CH_2OH$, and —$CH_2C(O)NH_2$;

$R^{11}$ and $R^{12}$ are —$(CH_2)_3CH_3$; and $R^{13}$ is selected from methyl, —$CH_2OH$, —$CH_2CH(CH_3)_2$, and —$(CH_2)_2CO_2H$; and A is In a sixth embodiment of the first aspect the present disclosure provides a compound of formula (I), or a pharmaceutically acceptable salt thereof, wherein:

$R^d$ and $R^4$, together with the atoms to which they are attached, form a pyrollidine ring;

$R^g$ and $R^7$, together with the atoms to which they are attached, form a pyrollidine ring, wherein said ring is optionally substituted with one hydroxy group;

$R^k$ is methyl $R^a$, $R^e$, and $R^j$ hydrogen;

$R^b$ and $R^2$ are each methyl or, $R^b$ and $R^2$, together with the atoms to which they are attached, form a piperidine ring;

$R^L$ is methyl;

$R^n$ is hydrogen, methyl, or $R^n$ and $R^v$ form a pyrrolidine ring;

$R^1$ is phenylmethyl wherein the phenyl is substituted with one group selected from halo, hydroxy, methoxy, or methyl;

$R^3$ is selected from —$CH_2C(O)NH_2$ and —$CH_2CO_2H$;

$R^5$ is selected from hydrogen, —$CH_2NH_2$, —$CH_2$(imidazolyl), and —$CH_2C(O)NH_2$;

$R^6$ is selected from —$CH_2CH(CH_3)_2$, —$(CH_2)_4NH_2$, —$(CH_2)_2CO_2H$, and $(CH_2)_2C(O)NH_2$;

$R^8$ and $R^{10}$ are —$CH_2$(indolyl), wherein the indolyl is optionally substituted with —$CH_2CO_2H$;

$R^9$ is selected from hydrogen, —$(CH_2)_2NH_2$, —$(CH_2)_4NH_2$, —$CH_2OH$, and —$CH_2C(O)NH_2$;

$R^{11}$ and $R^{12}$ are —$(CH_2)_3CH_3$; and $R^{13}$ is selected from methyl, —$CH_2OH$, —$CH_2CH(CH_3)_2$, and —$(CH_2)_2CO_2H$; and A is In a seventh embodiment of the first aspect the present disclosure provides a compound of formula (I), or a pharmaceutically acceptable salt thereof, wherein:

$R^d$ and $R^4$, together with the atoms to which they are attached, form a pyrollidine ring;

$R^g$ and $R^7$, together with the atoms to which they are attached, form a pyrollidine ring, wherein said ring is optionally substituted with one hydroxy group;

$R^k$ is methyl $R^a$, $R^e$, and $R^j$ hydrogen;

$R^b$ and $R^2$ are each methyl or, $R^b$ and $R^2$, together with the atoms to which they are attached, form a piperidine ring;

$R^L$ is methyl;

$R^n$ is hydrogen, methyl, or $R^n$ and $R^v$ form a pyrrolidine ring;

$R^1$ is phenylmethyl wherein the phenyl is substituted with one group selected from halo, hydroxy, methoxy, or methyl;

$R^3$ is selected from —$CH_2C(O)NH_2$ and —$CH_2CO_2H$;

$R^5$ is selected from hydrogen, —$CH_2NH_2$, —$CH_2$(imidazolyl), and —$CH_2C(O)NH_2$;

$R^6$ is selected from —$CH_2CH(CH_3)_2$, —$(CH_2)_4NH_2$, —$(CH_2)_2CO_2H$, and $(CH_2)_2C(O)NH_2$;

$R^8$ and $R^{10}$ are —$CH_2$(indolyl), wherein the indolyl is optionally substituted with —$CH_2CO_2H$;

$R^9$ is selected from hydrogen, —$(CH_2)_2NH_2$, —$(CH_2)_4NH_2$, —$CH_2OH$, and —$CH_2C(O)NH_2$;

$R^{11}$ and $R^{12}$ are —$(CH_2)_3CH_3$; and $R^{13}$ is selected from methyl, —$CH_2OH$, —$CH_2CH(CH_3)_2$, and —$(CH_2)_2CO_2H$; and A is In a second aspect the present disclosure provides a compound of formula (II), (II)

or a pharmaceutically acceptable salt thereof, wherein:

A is selected from —CH$_2$CH$_2$—;

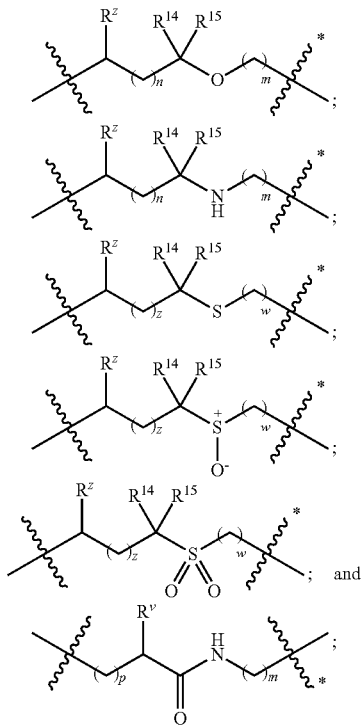

wherein:

 denotes the point of attachment to the carbonyl group and  denotes the point of attachment to the nitrogen atom;

n is 0 or 1;
m is 1 or 2;
z is 1 or 2;
when z is 1, w is 2;
when z is 2, w is 1 or 2;
p is 0, 1, or 2;
R$^{14}$ and R$^{15}$ are independently selected from hydrogen and methyl; and R$^z$ is selected from hydrogen and —C(O)NHR$^{16}$; wherein R$^{16}$ is selected from hydrogen, —CHR$^{17}$C(O)NH$_2$, —CHR$^{17}$C(O)NHCHR$^{18}$C(O)NH$_2$, and —CHR$^{17}$C(O)NHCHR$^{18}$C(O)NHCH$_2$C(O)NH$_2$; wherein R$^{17}$ is selected from hydrogen and CH$_2$OH and wherein R$^{18}$ is selected from hydrogen and methyl;

R$^v$ is hydrogen or a natural amino acid side chain;

R$^c$, R$^f$, R$^h$, R$^i$, and R$^m$ are hydrogen;

R$^n$ is hydrogen or methyl or R$^v$ and R$^n$ form a pyrrolidine ring;

R$^a$, R$^e$, R$^j$, and R$^k$, are each independently selected from hydrogen and methyl;

R$^1$, R$^2$, R$^3$, R$^4$, R$^5$, R$^6$, R$^7$, R$^8$, R$^9$, R$^{10}$, R$^{11}$, R$^{12}$, and R$^{13}$ are independently selected from a natural amino acid side chain and an unnatural amino acid side chain or form a ring with the corresponding vicinal R group as described below;

R$^e$ and R$^k$ can each form a ring with the corresponding vicinal R group and the atoms to which they are attached selected from azetidine, pyrollidine, morpholine, piperidine, piperazine, and tetrahydrothiazole; wherein each ring is optionally substituted with one to four groups independently selected from amino, cyano, methyl, halo, and hydroxy;

R$^b$ is methyl or, R$^b$ and R$^2$, together with the atoms to which they are attached, form a ring selected from azetidine, pyrollidine, morpholine, piperidine, piperazine, and tetrahydrothiazole; wherein each ring is optionally substituted with one to four groups independently selected from amino, cyano, methyl, halo, and hydroxy;

R$^d$ is hydrogen or methyl, or, R$^d$ and R$^4$, together with the atoms to which they are attached, can form a ring selected from azetidine, pyrollidine, morpholine, piperidine, piperazine, and tetrahydrothiazole; wherein each ring is optionally substituted with one to four groups independently selected from amino, cyano, methyl, halo, hydroxy, and phenyl;

R$^g$ is hydrogen or methyl or R$^g$ and R$^7$, together with the atoms to which they are attached, can form a ring selected from azetidine, pyrollidine, morpholine, piperidine, piperazine, and tetrahydrothiazole; wherein each ring is optionally substituted with one to four groups independently selected from amino, benzyl optionally substituted with a halo group, benzyloxy, cyano, cyclohexyl, methyl, halo, hydroxy, isoquinolinyloxy optionally substituted with a methoxy group, quinolinyloxy optionally substituted with a halo group, and tetrazolyl; and wherein the pyrrolidine and the piperidine ring are optionally fused to a cyclohexyl, phenyl, or indole group; and R$^L$ is methyl or, R$^L$ and R$^{12}$, together with the atoms to which they are attached, form a ring selected from azetidine and pyrollidine, wherein each ring is optionally substituted with one to four groups independently selected from amino, cyano, methyl, halo, and hydroxy.

In a third aspect the present disclosure provides a method of enhancing, stimulating, and/or increasing the immune response in a subject in need thereof, said method comprising administering to the subject a therapeutically effective amount of a compound of formula (I) or a therapeutically acceptable salt thereof. In a first embodiment the method further comprises administering an additional agent prior to, after, or simultaneously with the compound of formula (I) or a therapeutically acceptable salt thereof. In a second embodiment the additional agent is an antimicrobial agent, an antiviral agent, a cytotoxic agent, and/or an immune response modifier. In a third embodiment the additional agent is an HDAC inhibitor. In a fourth embodiment the additional agent is a TLR7 and/or TLR8 agonist.

In a fourth aspect the present disclosure provides a method of inhibiting growth, proliferation, or metastasis of cancer cells in a subject in need thereof, said method comprising administering to the subject a therapeutically effective amount of a compound of formula (I) or a therapeutically acceptable salt thereof. It should be understood that said inhibition can be direct or indirect. In a first embodiment the cancer is selected from melanoma, renal cell carcinoma, squamous non-small cell lung cancer (NSCLC), non-squamous NSCLC, colorectal cancer, castration-resistant prostate cancer, ovarian cancer, gastric cancer, hepatocellular carcinoma, pancreatic carcinoma, squamous cell carcinoma of the head and neck, carcinomas of the esophagus, gastrointestinal tract and breast, and a hematological malignancy.

In a fifth aspect the present disclosure provides a method of treating an infectious disease in a subject in need thereof, the method comprising administering to the subject a therapeutically effective amount of a compound of formula (I) or a therapeutically acceptable salt thereof. In a first embodiment the infectious disease is caused by a virus. In a second embodiment embodiment the virus is selected from HIV, Hepatitis A, Hepatitis B, Hepatitis C, herpes virus, and influenza.

In a sixth aspect the present disclosure provides a method of treating septic shock in a subject in need thereof, the method comprising administering to the subject a therapeutically effective amount of one or more macrocyclic peptides described herein.

In a seventh aspect the present disclosure provides a method blocking the interaction of PD-L1 with PD-1 and/or CD80 in a subject, said method comprising administering to the subject a therapeutically effective amount of at least one macrocyclic peptide described herein.

In compounds of formula (I) and (II) where the R side chains are part of a ring that is substituted with methyl, it is understood that the methyl group may be on any substitutable carbon atom in the ring, including the carbon that is part of the macrocyclic parent structure.

In compounds of formula (I), preferred $R^1$ side chains are: phenylalanine, tyrosine, 3-thien-2-yl, 4-methylphenylalanine, 4-chlorophenylalanine, 3-methoxyphenylalananine, isotryptophan, 3-methylphenylalanine, 1-naphthylalanine, 3,4-difluorophenylalanine, 4-fluorophenylalanine, 3,4-dimethoxyphenylalanine, 3,4-dichlorophenylalanine, 4-difluoromethylphenylalanine, 2-methylphenylalanine, 2-naphthylalanine, tryptophan, 4-pyridinyl, 4-bromophenylalanine, 3-pyridinyl, 4-trifluoromethylphenylalanine, 4-carboxyphenylalanine, 4-methoxyphenylalanine, biphenylalanine, and 3-chlorophenylalanine; and 2,4-diaminobutane.

In compounds of formula (I) where $R^2$ is not part of a ring, preferred $R^2$ side chains are: alanine, serine, and glycine.

In compounds of formula (I), preferred $R^3$ side chains are: asparagine, aspartic acid, glutamic acid, glutamine, serine, ornithine, lysine, histidine, threonine, leucine, alanine, 2,3-diaminopropane, and 2,4-diaminobutane.

In compounds of formula (I) where $R^4$ is not part of a ring, preferred $R^4$ side chains are: valine, alanine, isoleucine, and glycine.

In compounds of formula (I), preferred $R^5$ side chains are: histidine, asparagine, 2,3-diaminopropane, serine, glycine, 2,4-diaminobutane, threonine, alanine, lysine, aspartic acid, alanine, and 3-thiazolylalanine.

In compounds of formula (I), preferred $R^6$ side chains are: leucine, aspartic acid, asparagine, glutamic acid, glutamine, serine, lysine, 3-cyclohexane, threonine, ornithine, 2,4-diaminobutane, alanine, arginine, and ornithine ($COCH_3$).

In compounds of formula (I) where $R^7$ is not part of a ring, preferred $R^7$ side chains are: glycine, 2,4-diaminobutane, serine, lysine, arginine, ornithine, histidine, asparagine, glutamine, alanine, and 2,4-diaminobutane (C(O)cyclobutane).

In compounds of formula (I) preferred $R^8$ side chains are tryptophan and 1,2-benzisothiazolinylalanine.

In compounds of formula (I) preferred $R^9$ side chains are: serine, histidine, lysine, ornithine, 2,4-dibutylamine, threonine, lysine, glycine, glutamic acid, valine, 2,3-diaminopropane, arginine, aspartic acid, and tyrosine.

In compounds of formula (I) preferred $R^{10}$ side chains are: optionally substituted tryptophan, benzisothiazolylalanine, 1-napththylalanine, and methionine.

In compounds of formula (I) preferred $R^{11}$ side chains are: norleucine, leucine, asparagine, phenylalanine, methionine, ethoxymethane, alanine, tryptophan, isoleucine, phenylpropane, glutamic acid, hexane, and heptane.

In compounds of formula (I) where $R^{12}$ is not part of a ring, preferred $R^{12}$ side chains are: norleucine, alanine, ethoxymethane, methionine, serine, phenylalanine, methoxyethane, leucine, tryptophan, isoleucine, glutamic acid, hexane, heptane, and glycine.

In compounds of formula (I) preferred $R^{13}$ side chains: arginine, ornithine, alanine, 2,4-diaminobutane, 2,3-diaminopropane, leucine, aspartic acid, glutamic acid, serine, lysine, threonine, cyclopropylmethane, glycine, valine, isoleucine, histidine, and 2-aminobutane.

In accordance with the present disclosure, we have discovered peptides that specifically bind to PD-L1 and are capable of inhibiting the interaction of PD-L1 with PD-1 and CD80. These macrocyclic peptides exhibit in vitro immunomodulatory efficacy thus making them therapeutic candidates for the treatment of various diseases including cancer and infectious diseases.

The terms "specific binding" or "specifically bind" refer to the interaction between a protein and a binding molecule, such as a compound or ligand. The interaction is dependent upon the presence of a particular structure (i.e., an enzyme binding site, an antigenic determinant or epitope) of the protein that is recognized by the binding molecule. For example, if a compound has specific binding for protein binding site "A", the presence of the compound in a reaction containing a protein including binding site A, and a labeled peptide that specifically binds to protein binding site A will reduce the amount of labeled peptide bound to the protein. In contrast, nonspecific binding of a compound to the protein does not result in a concentration-dependent displacement of the labeled peptide from the protein.

The present disclosure is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

An additional aspect of the subject matter described herein is the use of the disclosed peptides as radiolabeled ligands for development of ligand binding assays or for monitoring of in vivo adsorption, metabolism, distribution, receptor binding or occupancy, or compound disposition. For example, a macrocyclic peptide described herein may be prepared using the radioactive isotope $^{125}I$ and the resulting radiolabeled peptide may be used to develop a binding assay or for metabolism studies. Alternatively, and for the same purpose, a macrocyclic peptide described herein may be converted to a radiolabeled form by catalytic tritiation using methods known to those skilled in the art.

The macrocyclic peptides of the present disclosure can also be used as PET imaging agents by adding a radioactive tracer using methods known to those skilled in the art.

Preferred peptides include at least one of the macrocyclic peptides provided herein and these peptides may be included in pharmaceutical compositions and combinations.

The definitions provided herein apply, without limitation, to the terms as used throughout this specification, unless otherwise limited in specific instances.

Those of ordinary skill in the art of amino acid and peptide chemistry are aware that an amino acid includes a compound represented by the general structure:

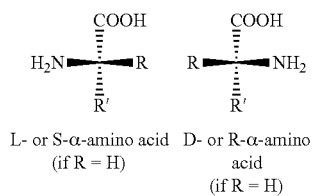

L- or S-α-amino acid (if R = H)    D- or R-α-amino acid (if R = H)

where R and R' are as discussed herein.

Unless otherwise indicated, the term "amino acid" as employed herein, alone or as part of another group, includes, without limitation, an amino group and a carboxyl group linked to the same carbon, referred to as "α" carbon, where R and/or R' can be a natural or an un-natural side chain, including hydrogen. The absolute "S" configuration at the "α" carbon is commonly referred to as the "L" or "natural" configuration. In the case where both the "R" and the "R'" (prime) substituents equal hydrogen, the amino acid is glycine and is not chiral.

The terms "natural amino acid side chain" and "naturally occurring amino acid side chain," as used herein, refer to side chain of any of the naturally occurring amino acids (i.e., alanine, arginine, asparagine, aspartic acid, cysteine, glutamine, glutamic acid, glycine,-histidine, isoleucine, leucine, lysine, methionine, phenylalanine, proline, serine, threonine, tryptophan, tyrosine, and valine) usually in the S-configuration (i.e., the L-amino acid).

The terms "unnatural amino acid side chain" and "non-naturally occurring amino acid side chain," as used herein, refer to a side chain of any naturally occurring amino acid usually in the R-configuration (i.e., the D-amino acid) or to a group other than a naturally occurring amino acid side chain in R- or S-configuration (i.e., the D- or L-amino acid, respectively) selected from:

$C_2$-$C_7$alkenyl, $C_1$-$C_3$alkoxy$C_1$-$C_3$alkyl, $C_1$-$C_6$alkoxycarbonyl$C_1$-$C_3$alkyl, $C_1$-$C_7$alkyl, $C_1$-$C_3$alkylsulfanyl$C_1$-$C_3$alkyl, $C_1$-$C_3$alkylsulfonyl$C_1$-$C_3$alkyl, amido$C_1$-$C_3$alkyl, amino$C_1$-$C_3$alkyl, azaindolyl$C_1$-$C_3$alkyl, benzothiazolyl$C_1$-$C_3$alkyl, benzothienyl$C_1$-$C_3$alkyl, benzyloxy$C_1$-$C_3$alkyl, carboxy$C_1$-$C_3$alkyl, cyano$C_1$-$C_3$alkyl, $C_3$-$C_6$cycloalkyl$C_1$-$C_3$alkyl, diphenylmethyl, furanyl$C_1$-$C_3$alkyl, halo$C_1$-$C_3$alkyl, hydroxy$C_1$-$C_3$alkyl, imidazolyl$C_1$-$C_3$alkyl, naphthyl$C_1$-$C_3$alkyl, pyranyl$C_1$-$C_3$alkyl, pyridinyl$C_1$-$C_3$alkyl, tetrahydrofuryl$C_1$-$C_3$alkyl, thiazolyl$C_1$-$C_3$alkyl, thienyl$C_1$-$C_3$alkyl;

biphenyl$C_1$-$C_3$alkyl wherein the biphenyl is optionally substituted with a group selected from $C_1$-$C_3$alkyl, amino, cyano, halo, hydroxy, and nitro;

indolyl$C_1$-$C_3$alkyl, wherein the indolyl part is optionally substituted with one group selected from $C_1$-$C_3$alkyl, carboxy$C_1$-$C_3$alkyl, cyano, halo, hydroxy, nitro, and phenyl, wherein the phenyl is further optionally substituted by one, two, or three groups independently selected from $C_1$-$C_3$alkoxy, $C_1$-$C_3$alkyl, and halo;

$NR^aR^b(C_1$-$C_7$alkyl), wherein $R^a$ and $R^b$ are independently selected from hydrogen, $C_2$-$C_4$alkenyloxycarbonyl, $C_1$-$C_3$alkoxycarbonyl, $C_1$-$C_3$alkyl, $C_1$-$C_3$alkylcarbonyl, $C_3$-$C_6$cycloalkylcarbonyl, furanylcarbonyl, phenyl$C_1$-$C_3$alkyl, phenylcarbonyl, pyranylcarbonyl, tetrahydrofurylcarbonyl, and thienylcarbonyl. When the alkyl linker contains more than one carbon an additional $NR^aR^b$ group can be on the chain.

$NR^cR^d$carbonyl$C_1$-$C_3$alkyl, wherein $R^c$ and $R^d$ are independently selected from hydrogen, $C_3$-$C_4$alkenyl, $C_1$-$C_3$alkyl, phenyl$C_1$-$C_3$alkyl, and triphenylmethyl;

phenyl$C_1$-$C_3$alkyl wherein the phenyl part is optionally substituted with one, two, three, four, or five groups independently selected from $C_1$-$C_4$alkoxy, $C_1$-$C_4$alkyl, $C_1$-$C_3$alkylsulfonylamino, amido, amino, amino$C_1$-$C_3$alkyl, aminosulfonyl, carboxy, cyano, halo, halo$C_1$-$C_3$alkyl, hydroxy, —$NC(NH_2)_2$, nitro, and —$OP(O)(OH)_2$; and phenoxy$C_1$-$C_3$alkyl wherein the phenyl is optionally substituted with one, two, three, four, or five groups independently selected from $C_1$-$C_4$alkoxy, $C_1$-$C_4$alkyl, $C_1$-$C_3$alkylsulfonylamino, amido, amino, amino$C_1$-$C_3$alkyl, aminosulfonyl, carboxy, cyano, halo, halo$C_1$-$C_3$alkyl, hydroxy, and nitro.

The term "$C_2$-$C_4$alkenyl," as used herein, refers to a straight or branched chain group of two to four carbon atoms containing at least one carbon-carbon double bond.

The term "$C_3$-$C_4$alkenyl," as used herein, refers to a straight or branched chain group of three or four carbon atoms containing at least one carbon-carbon double bond.

The term "$C_2$-$C_7$alkenyl," as used herein, refers to a straight or branched chain group of two to seven carbon atoms containing at least one carbon-carbon double bond.

The term "$C_2$-$C_4$alkenyloxy," as used herein, refers to a $C_2$-$C_4$alkenyl group attached to the parent molecular moiety through an oxygen atom.

The term "$C_1$-$C_3$alkoxy," as used herein, refers to a $C_1$-$C_3$alkyl group attached to the parent molecular moiety through an oxygen atom.

The term "$C_1$-$C_4$alkoxy," as used herein, refers to a $C_1$-$C_4$alkyl group attached to the parent molecular moiety through an oxygen atom.

The term "$C_1$-$C_6$alkoxy," as used herein, refers to a $C_1$-$C_6$alkyl group attached to the parent molecular moiety through an oxygen atom.

The term "$C_1$-$C_3$alkoxy$C_1$-$C_3$alkyl," as used herein, refers to a $C_1$-$C_3$alkoxy group attached to the parent molecular moiety through a $C_1$-$C_3$alkyl group.

The term "$C_1$-$C_3$alkoxycarbonyl," as used herein, refers to a $C_1$-$C_3$alkoxy group attached to the parent molecular moiety through a carbonyl group.

The term "$C_1$-$C_6$alkoxycarbonyl," as used herein, refers to a $C_1$-$C_6$alkoxy group attached to the parent molecular moiety through a carbonyl group.

The term "$C_1$-$C_6$alkoxycarbonyl$C_1$-$C_3$alkyl," as used herein, refers to a $C_1$-$C_6$alkoxycarbonyl group attached to the parent molecular moiety through a $C_1$-$C_3$alkyl group.

The term "$C_1$-$C_3$alkyl," as used herein, refers to a group derived from a straight or branched chain saturated hydrocarbon containing from one to three carbon atoms.

The term "$C_1$-$C_4$alkyl," as used herein, refers to a group derived from a straight or branched chain saturated hydrocarbon containing from one to four carbon atoms.

The term "$C_1$-$C_6$alkyl," as used herein, refers to a group derived from a straight or branched chain saturated hydrocarbon containing from one to six carbon atoms.

The term "$C_1$-$C_3$alkylcarbonyl," as used herein, refers to a $C_1$-$C_3$alkyl group attached to the parent molecular moiety through a carbonyl group.

The term "$C_1$-$C_3$alkylsulfanyl," as used herein, refers to a $C_1$-$C_3$alkyl group attached to the parent molecular moiety through a sulfur atom.

The term "$C_1$-$C_3$alkylsulfanyl$C_1$-$C_3$alkyl," as used herein, refers to a $C_1$-$C_3$alkylsulfanyl group attached to the parent molecular moiety through a $C_1$-$C_3$alkyl group.

The term "$C_1$-$C_3$alkylsulfonyl," as used herein, refers to a $C_1$-$C_3$alkyl group attached to the parent molecular moiety through a sulfonyl group.

The term "$C_1$-$C_3$alkylsulfonyl$C_1$-$C_3$alkyl," as used herein, refers to a $C_1$-$C_3$alkylsulfonyl group attached to the parent molecular moiety through a $C_1$-$C_3$alkyl group.

The term "$C_1$-$C_3$alkylsulfonylamino," as used herein, refers to a $C_1$-$C_3$alkylsulfonyl group attached to the parent molecular moiety through an amino group.

The term "amido," as used herein, refers to —C(O)NH$_2$.

The term "amido$C_1$-$C_3$alkyl," as used herein, refers to an amido group attached to the parent molecular moiety through a $C_1$-$C_3$alkyl group.

The term "amino," as used herein, refers to —NH$_2$.

The term "amino$C_1$-$C_3$alkyl," as used herein, refers to an amino group attached to the parent molecular moiety through a $C_1$-$C_3$alkyl group.

The term "aminosulfonyl," as used herein, refers to an amino group attached to the parent molecular moiety through a sulfonyl group.

The term "azaindolyl$C_1$-$C_3$alkyl," as used herein, refers to an azaindolyl group attached to the parent molecular through a $C_1$-$C_3$alkyl group. The azaindolyl group can be attached to the alkyl moiety through any substitutable atom in the group.

The term "benzothiazolyl$C_1$-$C_3$alkyl," as used herein, refers to an benzothiazolyl group attached to the parent molecular through a $C_1$-$C_3$alkyl group. The benzothiazolyl group can be attached to the alkyl moiety through any substitutable atom in the group.

The term "benzothienyl$C_1$-$C_3$alkyl," as used herein, refers to a benzothienyl group attached to the parent molecular through a $C_1$-$C_3$alkyl group. The benzothienyl group can be attached to the alkyl moiety through any substitutable atom in the group.

The term "benzyloxy," as used herein, refers to a benzyl group attached to the parent molecular moiety through an oxygen atom.

The term "benzyloxy$C_1$-$C_3$alkyl," as used herein, refers to a benzyloxy group attached to the parent molecular moiety through a $C_1$-$C_3$alkyl group.

The term "biphenyl$C_1$-$C_3$alkyl," as used herein, refers to a biphenyl group attached to the parent molecular moiety through a $C_1$-$C_3$alkyl group. The biphenyl group can be attached to the alkyl moiety through any substitutable atom in the group.

The term "carbonyl," as used herein, refers to —C(O)—.

The term "carboxy," as used herein, refers to —CO$_2$H.

The term "carboxy$C_1$-$C_3$alkyl," as used herein, refers to a carboxy group attached to the parent molecular moiety through a $C_1$-$C_3$alkyl group.

The term "cyano," as used herein, refers to —CN.

The term "cyano$C_1$-$C_3$alkyl," as used herein, refers to a cyano group attached to the parent molecular moiety through a $C_1$-$C_3$alkyl group.

The term "$C_3$-$C_6$cycloalkyl," as used herein, refers to a saturated monocyclic, hydrocarbon ring system having three to six carbon atoms and zero heteroatoms.

The term "$C_3$-$C_6$cycloalkyl$C_1$-$C_3$alkyl," as used herein, refers to a $C_3$-$C_6$cycloalkyl group attached to the parent molecular moiety through a $C_1$-$C_3$alkyl group.

The term "$C_3$-$C_6$cycloalkylcarbonyl," as used herein, refers to a $C_3$-$C_6$ cycloalkyl group attached to the parent molecular moiety through a carbonyl group.

The term "furanyl$C_1$-$C_3$alkyl," as used herein, refers to a furanyl group attached to the parent molecular moiety through a $C_1$-$C_3$alkyl group. The furanyl group can be attached to the alkyl moiety through any substitutable atom in the group.

The term "furanylcarbonyl," as used herein, refers to a furanyl group attached to the parent molecular moiety through a carbonyl group.

The terms "halo" and "halogen," as used herein, refer to F, Cl, Br, or I.

The term "halo$C_1$-$C_3$alkyl," as used herein, refers to a $C_1$-$C_3$alkyl group substituted with one, two, or three halogen atoms.

The term "halomethyl," as used herein, refers to a methyl group substituted with one, two, or three halogen atoms.

The term "hydroxy," as used herein, refers to —OH.

The term "hydroxy$C_1$-$C_3$alkyl," as used herein, refers to a hydroxy group attached to the parent molecular moiety through a $C_1$-$C_3$alkyl group.

The term "imidazolyl$C_1$-$C_3$alkyl," as used herein, refers to an imidazolyl group attached to the parent molecular moiety through a $C_1$-$C_3$alkyl group. The imidazolyl group can be attached to the alkyl moiety through any substitutable atom in the group.

The term "indolyl$C_1$-$C_3$alkyl," as used herein, refers to an indolyl group attached to the parent molecular moiety through a $C_1$-$C_3$alkyl group. The indolyl group can be attached to the alkyl moiety through any substitutable atom in the group.

The term "naphthyl$C_1$-$C_3$alkyl," as used herein, refers to a naphthyl group attached to the parent molecular moiety through a $C_1$-$C_3$alkyl group. The naphthyl group can be attached to the alkyl moiety through any substitutable atom in the group.

The term "nitro," as used herein, refers to —NO$_2$.

The term "NR$^a$R$^b$," as used herein, refers to two groups, R$^a$ and R$^b$, which are attached to the parent molecular moiety through a nitrogen atom. R$^a$ and R$^b$ are independently selected from hydrogen, $C_2$-$C_4$alkenyloxycarbonyl, $C_1$-$C_3$alkylcarbonyl, $C_3$-$C_6$cycloalkylcarbonyl, furanylcarbonyl, and phenylcarbonyl.

The term "NR$^a$R$^b$($C_1$-$C_3$)alkyl," as used herein, refers to an NR$^a$R$^b$ group attached to the parent molecular moiety through a $C_1$-$C_3$alkyl group.

The term "NR$^c$R$^d$," as used herein, refers to two groups, R$^c$ and R$^d$, which are attached to the parent molecular moiety through a nitrogen atom. R$^c$ and R$^d$ are independently selected from hydrogen, $C_1$-$C_3$alkyl, and triphenylmethyl.

The term "NR$^c$R$^d$carbonyl," as used herein, refers to an NR$^c$R$^d$ group attached to the parent molecular moiety through a carbonyl group.

The term "NR$^c$R$^d$carbonyl$C_1$-$C_3$alkyl," as used herein, refers to an NR$^c$R$^d$carbonyl group attached to the parent molecular moiety through a $C_1$-$C_3$alkyl group.

The tem "phenoxy," as used herein, refers to a phenyl group attached to the parent molecular moiety through an oxygen atom.

The term "phenoxy$C_1$-$C_3$alkyl," as used herein, refers to a phenoxy group attached to the parent molecular moiety through a $C_1$-$C_3$alkyl group.

The term "phenyl$C_1$-$C_3$alkyl," as used herein, refers to a phenyl group attached to the parent molecular moiety through a $C_1$-$C_3$alkyl group.

The term "phenylcarbonyl," as used herein, refers to a phenyl group attached to the parent molecular moiety through a carbonyl group.

The term "pyranylC$_1$-C$_3$alkyl," as used herein, refers to a pyranyl group attached to the parent molecular moiety through a C$_1$-C$_3$alkyl group. The pyranyl group can be attached to the alkyl moiety through any substitutable atom in the group.

The term "pyranylcarbonyl," as used herein, refers to a pyranyl group attached to the parent molecular moiety through a carbonyl group.

The term "pyridinylC$_1$-C$_3$alkyl," as used herein, refers to a pyridinyl group attached to the parent molecular moiety through a C$_1$-C$_3$alkyl group. The pyridinyl group can be attached to the alkyl moiety through any substitutable atom in the group.

The term "sulfanyl," as used herein, refers to —S—.

The term "sulfonyl," as used herein, refers to —SO$_2$—.

The term "tetrahydrofurylC$_1$-C$_3$alkyl," as used herein, refers to a teterahydrofuryl group attached to the parent molecular moiety through a C$_1$-C$_3$alkyl group. The tetrahydrofuryl group can be attached to the alkyl moiety through any substitutable atom in the group.

The term "tetrahydrofurylcarbonyl," as used herein, refers to a thienyl group attached to the parent molecular moiety through a carbonyl group.

The term "thiazolylC$_1$-C$_3$alkyl," as used herein, refers to a thiazolyl group attached to the parent molecular moiety through a C$_1$-C$_3$alkyl group. The thiazolyl group can be attached to the alkyl moiety through any substitutable atom in the group.

The term "thienylC$_1$-C$_3$alkyl," as used herein, refers to a thienyl group attached to the parent molecular moiety through a C$_1$-C$_3$alkyl group. The thienyl group can be attached to the alkyl moiety through any substitutable atom in the group.

The term "thienylcarbonyl," as used herein, refers to a thienyl group attached to the parent molecular moiety through a carbonyl group.

The term "treating" refers to: (i) preventing a disease, disorder, or condition from occurring in a patient that may be predisposed to the disease, disorder, and/or condition but has not yet been diagnosed as having it; (ii) inhibiting the disease, disorder, or condition, i.e., arresting its development; and (iii) relieving the disease, disorder, or condition, i.e., causing regression of the disease, disorder, and/or condition and/or symptoms associated with the disease, disorder, and/or condition.

Binding of the macrocyclic peptides to PD-L1 can be measured, for example, by methods such as homogeneous time-resolved fluorescence (HTRF), Surface Plasmon Resonance (SPR), isothermal titration calorimetry (ITC), nuclear magnetic resonance spectroscopy (NMR), and the like. Further, binding of the macrocyclic peptides to PD-L1 expressed on the surface of cells can be measured as described herein in cellular binding assays.

Administration of a therapeutic agent described herein includes, without limitation, administration of a therapeutically effective amount of therapeutic agent. The term "therapeutically effective amount" as used herein refers, without limitation, to an amount of a therapeutic agent to treat or prevent a condition treatable by administration of a composition of the PD-1/PD-L1 binding inhibitors described herein. That amount is the amount sufficient to exhibit a detectable therapeutic or preventative or ameliorative effect. The effect may include, for example and without limitation, treatment or prevention of the conditions listed herein. The precise effective amount for a subject will depend upon the subject's size and health, the nature and extent of the condition being treated, recommendations of the treating physician, and therapeutics or combination of therapeutics selected for administration. Thus, it is not useful to specify an exact effective amount in advance.

In another aspect, the disclosure pertains to methods of inhibiting growth of tumor cells in a subject using the macrocyclic peptides of the present disclosure. As demonstrated herein, the macrocyclic peptides of the present disclosure are capable of binding to PD-L1, disrupting the interaction between PD-L1 and PD-1, competing with the binding of PD-L1 with anti-PD-1 monoclonal antibodies that are known to block the interaction with PD-1, enhancing CMV-specific T cell IFNγ secretion, and enhancement of HIV-specific T cell IFNg secretion. As a result, the macrocyclic peptides of the present disclosure are useful for modifying an immune response, treating diseases such as cancer or infectious disease, stimulating a protective autoimmune response or to stimulate antigen-specific immune responses (e.g., by coadministration of PD-L1 blocking peptides with an antigen of interest).

In order that the present disclosure may be more readily understood, certain terms are first defined. Additional definitions are set forth throughout the detailed description.

The terms "Programmed Death Ligand 1", "Programmed Cell Death Ligand 1", "Protein PD-L1", "PD-L1", "PDL1", "PDCDL1", "hPD-L1", "hPD-LI", "CD274" and "B7-H1" are used interchangeably, and include variants, isoforms, species homologs of human PD-L1, and analogs having at least one common epitope with PD-L1. The complete PD-L1 sequence can be found under GENBANK® Accession No. NP_054862.

The terms "Programmed Death 1", "Programmed Cell Death 1", "Protein PD-1", "PD-1", "PD1", "PDCD1", "hPD-1" and "hPD-I" are used interchangeably, and include variants, isoforms, species homologs of human PD-1, and analogs having at least one common epitope with PD-1. The complete PD-1 sequence can be found under GENBANK® Accession No. U64863.

The terms "cytotoxic T lymphocyte-associated antigen-4", "CTLA-4", "CTLA4", "CTLA-4 antigen" and "CD152" (see, e.g., Murata, *Am. J. Pathol.*, 155:453-460 (1999)) are used interchangeably, and include variants, isoforms, species homologs of human CTLA-4, and analogs having at least one common epitope with CTLA-4 (see, e.g., Balzano, *Int. J. Cancer Suppl.*, 7:28-32 (1992)). The complete CTLA-4 nucleic acid sequence can be found under GENBANK® Accession No. L15006.

The term "immune response" refers to the action of, for example, lymphocytes, antigen presenting cells, phagocytic cells, granulocytes, and soluble macromolecules produced by the above cells or the liver (including macrocyclic peptides, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

An "adverse event" (AE) as used herein is any unfavorable and generally unintended, even undesirable, sign (including an abnormal laboratory finding), symptom, or disease associated with the use of a medical treatment. For example, an adverse event may be associated with activation of the immune system or expansion of immune system cells (e.g., T cells) in response to a treatment. A medical treatment may have one or more associated AEs and each AE may have the same or different level of severity. Reference to methods capable of "altering adverse events" means a treatment regime that decreases the incidence and/or severity of one or more AEs associated with the use of a different treatment regime.

As used herein, "hyperproliferative disease" refers to conditions wherein cell growth is increased over normal levels. For example, hyperproliferative diseases or disorders include malignant diseases (e.g., esophageal cancer, colon cancer, biliary cancer) and non-malignant diseases (e.g., atherosclerosis, benign hyperplasia, and benign prostatic hypertrophy).

As used herein, "about" or "comprising essentially of" mean within an acceptable error range for the particular value as determined by one of ordinary skill in the art, which will depend in part on how the value is measured or determined, i.e., the limitations of the measurement system. For example, "about" or "comprising essentially of" can mean within one or more than one standard deviation per the practice in the art. Alternatively, "about" or "comprising essentially of" can mean a range of up to 20%. Furthermore, particularly with respect to biological systems or processes, the terms can mean up to an order of magnitude or up to 5-fold of a value. When particular values are provided in the application and claims, unless otherwise stated, the meaning of "about" or "comprising essentially of" should be assumed to be within an acceptable error range for that particular value.

As described herein, any concentration range, percentage range, ratio range or integer range is to be understood to include the value of any integer within the recited range and, when appropriate, fractions thereof (such as one tenth and one hundredth of an integer), unless otherwise indicated.

Competition Assays

The present disclosure is also directed to macrocyclic peptides that are capable of competing with the binding of a reference anti-PD-L1 antibody (MDX-1105) by at least about 20%, at least about 30%, at least about 40%, at least about 50%, at least about 60%, at least about 70%, at least about 80%, at least about 90%, and at least about 100%. Such macrocyclic peptides may share structural homology with one or more macrocyclic peptides disclosed herein, including mutant, conservative substitution, functional substitution, and deletion forms, provided they specific bind to PD-L1. For example, if a macrocyclic peptide binds substantially to the same region of PD-L1 as a reference anti-PD-L1 antibody, the macrocyclic peptide should bind to an epitope of PD-L1 that at least overlaps with the PD-L1 epitope that the anti-PD-L1 monoclonal antibody binds to. The overlapping region can range from one amino acid residue to several hundred amino acid residues. The macrocyclic peptide should then compete with and/or block the binding of the anti-PD-L1 monoclonal antibody to PD-L1 and thereby decrease the binding of the anti-PD-L1 monoclonal antibody to PD-L1, preferably by at least about 50% in a competition assay.

Anti-PD-L1 antibodies that may be used as reference antibodies for competition assay purposes are known in the art. For example, the following representative anti-PD-L1 antibodies may be used: MDX-1105 (BMS); L01X-C(Serono), L1X3 (Serono), MSB-0010718C (Serono), and PD-L1 Probody (CytomX), and the PD-L1 antibodies disclosed in co-owned WO 2007/005874.

Anti-PD-1 antibodies that may be used as reference antibodies for competition assay purposes are known in the art. For example, the following representative anti-PD-1 antibodies may be used: nivolumab (BMS); 17D8, 2D3, 4H1, 4A11, 7D3 and 5F4 each disclosed in co-owned U.S. Pat. No. 8,008,449 (BMS), MK-3475 (Merck, disclosed in U.S. Pat. No. 8,168,757), and the antibodies disclosed in U.S. Pat. No. 7,488,802.

Pharmaceutical Compositions

In another aspect, the present disclosure provides a composition, e.g., a pharmaceutical composition, containing one or a combination of macrocyclic peptides of the present disclosure, formulated together with a pharmaceutically acceptable carrier. Such compositions may include one or a combination of (e.g., two or more different) macrocyclic peptides, or immunoconjugates or bispecific molecules of the disclosure. For example, a pharmaceutical composition of the disclosure can comprise a combination of macrocyclic peptides (or immunoconjugates or bispecifics) that bind to different epitopes on the target antigen or that have complementary activities.

Pharmaceutical compositions of the disclosure also can be administered in combination therapy, i.e., combined with other agents. For example, the combination therapy can include a macrocyclic peptide combined with at least one other anti-inflammatory or immunosuppressant agent. Examples of therapeutic agents that can be used in combination therapy are described in greater detail below in the section on uses of the macrocyclic peptides of the disclosure.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., a macrocyclic peptide, immunoconjugate, or bispecific molecule, may be coated in a material to protect the compound from the action of acids and other natural conditions that may inactivate the compound.

The pharmaceutical compounds of the disclosure may include one or more pharmaceutically acceptable salts. A "pharmaceutically acceptable salt" or "therapeutically acceptable salt" refers to a salt that retains the desired biological activity of the parent compound and does not impart any undesired toxicological effects (see e.g., Berge, S. M. et al., *J. Pharm. Sci.*, 66:1-19 (1977)). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the disclosure also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the disclosure is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the disclosure are dictated by and directly dependent on (a) the unique characteristics of the active compound and the particular therapeutic effect to be achieved, and (b) the limitations inherent in the art of compounding such an active compound for the treatment of sensitivity in individuals.

For administration of the macrocyclic peptide, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per day, twice per day, bi-weekly, tri-weekly, weekly, once every two weeks, once every three weeks, once every four weeks, once a month, once every 3 months or once every three to 6 months. Preferred dosage regimens for a macrocyclic peptide of the disclosure include 1 mg/kg body weight or 3 mg/kg body weight via intravenous administration, with the macrocycle being given using one of the following dosing schedules: (i) every four weeks for six dosages, then every three months; (ii) every three weeks; (iii) 3 mg/kg body weight once followed by 1 mg/kg body weight every three weeks.

In some methods, two or more macrocyclic peptides with different binding specificities are administered simultaneously, in which case the dosage of each compound administered falls within the ranges indicated. The compounds are usually administered on multiple occasions. Intervals between single dosages can be, for example, weekly, monthly, every three months or yearly. Intervals can also be irregular as indicated by measuring blood levels of macrocyclic peptide to the target antigen in the patient. In some methods, dosage is adjusted to achieve a plasma concentration of about 1-1000 μg/ml and in some methods about 25-300 μg/ml.

Alternatively, the macrocyclic peptide can be administered as a sustained release formulation, in which case less frequent administration is required. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present disclosure may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present disclosure employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of a macrocyclic peptide of the disclosure preferably results in a decrease in severity of disease symptoms, an increase in frequency and duration of disease symptom-free periods, or a prevention of impairment or disability due to the disease affliction. For example, for the treatment of tumors, a "therapeutically effective dosage" preferably inhibits cell growth or tumor growth by at least about 20%, more preferably by at least about 40%, even more preferably by at least about 60%, and still more preferably by at least about 80% relative to untreated subjects. The ability of a compound to inhibit tumor growth and/or HIV can be evaluated in an animal model system predictive of efficacy in human tumors or viral efficacy. Alternatively, this property of a composition can be evaluated by examining the ability of the compound to inhibit, such inhibition in vitro by assays known to the skilled practitioner. A therapeutically effective amount of a therapeutic compound can decrease tumor size, decrease viral load, or otherwise ameliorate symptoms in a subject. One of ordinary skill in the art would be able to determine such amounts based on such factors as the subject's size, the severity of the subject's symptoms, and the particular composition or route of administration selected.

In another aspect, the instant disclosure provides a pharmaceutical kit of parts comprising a macrocyclic peptide and an another immumodulator, as described herein. The kit may also further comprise instructions for use in the treatment of a hyperproliferative disease (such as cancer as described herein) and/or anti-viral disease.

A composition of the present disclosure can be administered via one or more routes of administration using one or more of a variety of methods known in the art. As will be appreciated by the skilled artisan, the route and/or mode of administration will vary depending upon the desired results. Preferred routes of administration for macrocyclic peptides of the disclosure include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, a macrocyclic peptide of the disclosure can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Robinson, J. R., ed., *Sustained and Controlled Release Drug Delivery Systems*, Marcel Dekker, Inc., New York (1978).

Therapeutic compositions can be administered with medical devices known in the art. For example, in a preferred embodiment, a therapeutic composition of the disclosure can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in the present disclosure include: U.S. Pat. No. 4,487,603, which discloses an implantable microinfusion pump for dispensing medication at a controlled rate; U.S. Pat. No. 4,486,194, which discloses a therapeutic device for administering medication through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the macrocyclic peptides of the disclosure can be formulated to ensure proper distribution in vivo. For example, the blood-brain barrier (BBB) excludes many highly hydrophilic compounds. To ensure that therapeutic compounds of the disclosure cross the BBB (if desired), they can be formulated, for example, in liposomes. For methods of manufacturing liposomes, see, e.g., U.S. Pat. Nos. 4,522,811, 5,374,548, and 5,399,331. The liposomes may comprise one or more moieties which are selectively transported into specific cells or organs, thus enhance targeted drug delivery (see, e.g., Ranade, V. V., *J. Clin. Pharmacol.*, 29:685 (1989)). Exemplary targeting moieties include folate or biotin (see, e.g., U.S. Pat. No. 5,416,016 to Low et al.); mannosides (Umezawa et al., *Biochem. Biophys. Res. Commun.*, 153:1038 (1988)); macrocyclic peptides (Bloeman, P. G. et al., *FEBS Lett.*, 357:140 (1995); Owais, M. et al., *Antimicrob. Agents Chemother.*, 39:180 (1995)); surfactant protein A receptor (Briscoe et al., *Am. J. Physiol.*, 1233:134 (1995)); p 120 (Schreier et al., *J. Biol. Chem.*, 269:9090 (1994)); see also Keinanen, K. et al., *FEBS Lett.*, 346:123 (1994); Killion, J. J. et al., *Immunomethods* 4:273 (1994).

Uses and Methods of the Disclosure

The macrocyclic peptides, compositions and methods of the present disclosure have numerous in vitro and in vivo utilities involving, for example, detection of PD-L1 or enhancement of immune response by blockade of PD-L1. For example, these molecules can be administered to cells in culture, in vitro or ex vivo, or to human subjects, e.g., in vivo, to enhance immunity in a variety of situations. Accordingly, in one aspect, the disclosure provides a method of modifying an immune response in a subject comprising administering to the subject the macrocyclic peptide of the disclosure such that the immune response in the subject is modified. Preferably, the response is enhanced, stimulated or up-regulated. In other respects, the macrocyclic peptide may have anti-cyno, anti-mouse, and/or anti-woodchuck binding and therapeutic activity.

As used herein, the term "subject" is intended to include human and non-human animals. Non-human animals includes all vertebrates, e.g., mammals and non-mammals, such as non-human primates, sheep, dogs, cats, cows, horses, chickens, woodchuck, amphibians, and reptiles, although mammals are preferred, such as non-human primates, sheep, dogs, cats, cows and horses. Preferred subjects include human patients in need of enhancement of an immune response. The methods are particularly suitable for treating human patients having a disorder that can be treated by augmenting the T-cell mediated immune response. In a particular embodiment, the methods are particularly suitable for treatment of cancer cells in vivo. To achieve antigen-specific enhancement of immunity, the macrocyclic peptides can be administered together with an antigen of interest. When macrocyclic peptides to PD-L1 are administered together with another agent, the two can be administered in either order or simultaneously.

The disclosure further provides methods for detecting the presence of human, woodchuck, cyno, and/or mouse PD-L1 antigen in a sample, or measuring the amount of human, woodchuck, cyno, and/or mouse PD-L1 antigen, comprising contacting the sample, and a control sample, with a reference macrocyclic peptide which specifically binds to human, woodchuck, cyno, and/or mouse PD-L1, under conditions that allow for formation of a complex between the macrocycle and human, woodchuck, cyno, and/or mouse PD-L1. The formation of a complex is then detected, wherein a difference complex formation between the sample compared to the control sample is indicative the presence of human, woodchuck, cyno, and/or mouse PD-L1 antigen in the sample.

Given the specific binding of the macrocyclic peptides of the disclosure for PD-L1, compared to CD28, ICOS and CTLA-4, the macrocyclic peptides of the disclosure can be used to specifically detect PD-L1 expression on the surface of cells and, moreover, can be used to purify PD-L1 via immunoaffinity purification.

Cancer

Blockade of PD-1 by macrocyclic peptides can enhance the immune response to cancerous cells in the patient. The ligand for PD-1, PD-L1, is not expressed in normal human cells, but is abundant in a variety of human cancers (Dong et al., *Nat. Med.*, 8:787-789 (2002)). The interaction between PD-1 and PD-L1 results in a decrease in tumor infiltrating lymphocytes, a decrease in T-cell receptor mediated proliferation, and immune evasion by the cancerous cells (Dong et al., *J. Mol. Med.*, 81:281-287 (2003); Blank et al., *Cancer Immunol. Immunother.*, 54:307-314 (2005); Konishi et al., *Clin. Cancer Res.*, 10:5094-5100 (2004)). Immune suppression can be reversed by inhibiting the local interaction of PD-1 to PD-L1 and the effect is additive when the interaction of PD-1 to PD-L2 is blocked as well (Iwai et al., *Proc. Natl. Acad. Sci.*, 99:12293-12297 (2002); Brown et al., *J. Immunol.*, 170:1257-1266 (2003)). While previous studies have shown that T-cell proliferation can be restored by inhibiting the interaction of PD-1 to PD-L1, there have been no reports of a direct effect on cancer tumor growth in vivo by blocking the PD-1/PD-L1 interaction. In one aspect, the present disclosure relates to treatment of a subject in vivo using a macrocyclic peptide such that growth of cancerous tumors is inhibited. A macrocyclic peptide may be used alone to inhibit the growth of cancerous tumors. Alternatively, a macrocyclic peptide may be used in conjunction with other immunogenic agents, standard cancer treatments, or other macrocyclic peptides, as described below.

Accordingly, in one embodiment, the disclosure provides a method of inhibiting growth of tumor cells in a subject, comprising administering to the subject a therapeutically effective amount of a macrocyclic peptide.

Preferred cancers whose growth may be inhibited using the macrocyclic peptides of the disclosure include cancers typically responsive to immunotherapy. Non-limiting examples of preferred cancers for treatment include melanoma (e.g., metastatic malignant melanoma), renal cell carcinoma (e.g., clear cell carcinoma), prostate cancer (e.g., hormone refractory prostate adenocarcinoma and castration-resistant prostate cancer), breast cancer, colorectal cancer and lung cancer (e.g., squamous and non-squamous non-small cell lung cancer). Additionally, the disclosure includes refractory or recurrent malignancies whose growth may be inhibited using the macrocyclic peptides of the disclosure.

Examples of other cancers that may be treated using the methods of the disclosure include bone cancer, pancreatic cancer, skin cancer, cancer of the head or neck, cutaneous or intraocular malignant melanoma, uterine cancer, ovarian cancer, colon cancer, rectal cancer, cancer of the anal region, stomach/gastric cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The present disclosure is also useful for treatment of metastatic cancers, especially metastatic cancers that express PD-L1 (Iwai et al., *Int. Immunol.*, 17:133-144 (2005)).

Optionally, macrocyclic peptides to PD-L1 can be combined with an immunogenic agent, such as cancerous cells, purified tumor antigens (including recombinant proteins, peptides, and carbohydrate molecules), cells, and cells transfected with genes encoding immune stimulating cytokines (He et al., *J. Immunol.*, 173:4919-4928 (2004)). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF (discussed further below).

In humans, some tumors have been shown to be immunogenic such as melanomas. It is anticipated that by raising the threshold of T cell activation by PD-L1 blockade, we may expect to activate tumor responses in the host.

PD-L1 blockade is likely to be most effective when combined with a vaccination protocol. Many experimental strategies for vaccination against tumors have been devised (see Rosenberg, S., Development of Cancer Vaccines, ASCO Educational Book Spring: 60-62 (2000); Logothetis, C., ASCO Educational Book Spring: 300-302 (2000); Khayat, D., ASCO Educational Book Spring: 414-428 (2000); Foon, K., ASCO Educational Book Spring: 730-738 (2000); see also Restifo, N. et al., Cancer Vaccines, Chapter 61, pp. 3023-3043, in DeVita, V. et al., eds., *Cancer: Principles and Practice of Oncology*, Fifth Edition (1997)). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al., *Proc. Natl. Acad. Sci. USA*, 90: 3539-3543 (1993)).

The study of gene expression and large scale gene expression patterns in various tumors has led to the definition of so called tumor specific antigens (Rosenberg, S. A., *Immunity*, 10:281-287 (1999)). In many cases, these tumor specific antigens are differentiated antigens expressed in the tumors and in the cell from which the tumor arose, for example melanocyte antigens gp100, MAGE antigens, and Trp-2. More importantly, many of these antigens can be shown to be the targets of tumor specific T cells found in the host. PD-L1 blockade may be used in conjunction with a collection of recombinant proteins and/or peptides expressed in a tumor in order to generate an immune response to these proteins. These proteins are normally viewed by the immune system as self antigens and are therefore tolerant to them. The tumor antigen may also include the protein telomerase, which is required for the synthesis of telomeres of chromosomes and which is expressed in more than 85% of human cancers and in only a limited number of somatic tissues (Kim, N et al., *Science*, 266:2011-2013 (1994)). (These somatic tissues may be protected from immune attack by various means). Tumor antigen may also be "neo-antigens" expressed in cancer cells because of somatic mutations that alter protein sequence or create fusion proteins between two unrelated sequences (i.e., bcr-abl in the Philadelphia chromosome), or idiotype from B cell tumors.

Other tumor vaccines may include the proteins from viruses implicated in human cancers such a Human Papilloma Viruses (HPV), Hepatitis Viruses (HBV and HCV) and Kaposi's Herpes Sarcoma Virus (KHSV). Another form of tumor specific antigen which may be used in conjunction with PD-L1 blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot, R. et al., *Science*, 269:1585-1588 (1995); Tamura, Y. et al., *Science*, 278:117-120 (1997)).

Dendritic cells (DC) are potent antigen presenting cells that can be used to prime antigen-specific responses. DC's can be produced ex vivo and loaded with various protein and peptide antigens as well as tumor cell extracts (Nestle, F. et al., *Nat. Med.*, 4:328-332 (1998)). DCs may also be transduced by genetic means to express these tumor antigens as well. DCs have also been fused directly to tumor cells for the purposes of immunization (Kugler, A. et al., *Nat. Med.*, 6:332-336 (2000)). As a method of vaccination, DC immunization may be effectively combined with PD-L1 blockade to activate more potent anti-tumor responses.

PD-L1 blockade may also be combined with standard cancer treatments. PD-L1 blockade may be effectively combined with chemotherapeutic regimes. In these instances, it may be possible to reduce the dose of chemotherapeutic reagent administered (Mokyr, M. et al., *Cancer Res.*, 58:5301-5304 (1998)). An example of such a combination is a macrocyclic peptide in combination with decarbazine for the treatment of melanoma. Another example of such a combination is a macrocyclic peptide in combination with interleukin-2 (IL-2) for the treatment of melanoma. The scientific rationale behind the combined use of PD-L1 blockade and chemotherapy is that cell death, that is a consequence of the cytotoxic action of most chemotherapeutic compounds, should result in increased levels of tumor antigen in the antigen presentation pathway. Other combination therapies that may result in synergy with PD-L1 blockade through cell death are radiation, surgery, and hormone deprivation. Each of these protocols creates a source of tumor antigen in the host. Angiogenesis inhibitors may also be combined with PD-L1 blockade Inhibition of angiogenesis leads to tumor cell death which may feed tumor antigen into host antigen presentation pathways.

PD-L1 blocking macrocyclic peptides can also be used in combination with bispecific macrocyclic peptides that target Fc alpha or Fc gamma receptor-expressing effectors cells to tumor cells (see, e.g., U.S. Pat. Nos. 5,922,845 and 5,837,243). Bispecific macrocyclic peptides can be used to target two separate antigens. For example anti-Fc receptor/anti tumor antigen (e.g., Her-2/neu) bispecific macrocyclic peptides have been used to target macrophages to sites of tumor. This targeting may more effectively activate tumor specific responses. The T cell arm of these responses would be augmented by the use of PD-L1 blockade. Alternatively, antigen may be delivered directly to DCs by the use of bispecific macrocyclic peptides which bind to tumor antigen and a dendritic cell specific cell surface marker.

Tumors evade host immune surveillance by a large variety of mechanisms. Many of these mechanisms may be overcome by the inactivation of proteins which are expressed by the tumors and which are immunosuppressive. These include among others TGF-beta (Kehrl, J. et al., *J. Exp. Med.*, 163:1037-1050 (1986)), IL-10 (Howard, M. et al., *Immunology Today*, 13:198-200 (1992)), and Fas ligand (Hahne, M. et al., *Science*, 274:1363-1365 (1996)). Macrocyclic peptides to each of these entities may be used in combination with anti-PD-L1 to counteract the effects of the immunosuppressive agent and favor tumor immune responses by the host.

Other macrocyclic peptides which may be used to activate host immune responsiveness can be used in combination with anti-PD-L1. These include molecules on the surface of dendritic cells which activate DC function and antigen presentation. Anti-CD40 macrocyclic peptides are able to substitute effectively for T cell helper activity (Ridge, J. et al., *Nature*, 393:474-478 (1998)) and can be used in conjunction with PD-1 antibodies (Ito, N. et al., *Immunobiology*, 201(5):527-540 (2000)). Activating macrocyclic peptides to T cell costimulatory molecules such as CTLA-4 (e.g., U.S. Pat. No. 5,811,097), OX-40 (Weinberg, A. et al., *Immunol.*, 164:2160-2169 (2000)), 4-1BB (Melero, I. et al., *Nat. Med.*, 3:682-685 (1997), and ICOS (Hutloff, A. et al., *Nature*, 397:262-266 (1999)) may also provide for increased levels of T cell activation.

Bone marrow transplantation is currently being used to treat a variety of tumors of hematopoietic origin. While graft versus host disease is a consequence of this treatment, therapeutic benefit may be obtained from graft vs. tumor responses. PD-L1 blockade can be used to increase the effectiveness of the donor engrafted tumor specific T cells.

There are also several experimental treatment protocols that involve ex vivo activation and expansion of antigen specific T cells and adoptive transfer of these cells into recipients in order to antigen-specific T cells against tumor (Greenberg, R. et al., *Science*, 285:546-551 (1999)). These methods may also be used to activate T cell responses to infectious agents such as CMV. Ex vivo activation in the presence of macrocyclic peptides may be expected to increase the frequency and activity of the adoptively transferred T cells.

Infectious Diseases

Other methods of the disclosure are used to treat patients that have been exposed to particular toxins or pathogens. Accordingly, another aspect of the disclosure provides a method of treating an infectious disease in a subject comprising administering to the subject a macrocyclic peptide of the present disclosure such that the subject is treated for the infectious disease.

Similar to its application to tumors as discussed above, PD-L1 blockade can be used alone, or as an adjuvant, in combination with vaccines, to stimulate the immune response to pathogens, toxins, and self-antigens. Examples of pathogens for which this therapeutic approach may be particularly useful, include pathogens for which there is currently no effective vaccine, or pathogens for which conventional vaccines are less than completely effective. These include, but are not limited to HIV, Hepatitis (A, B, and C), Influenza, Herpes, *Giardia*, Malaria (Butler, N. S. et al., *Nature Immunology* 13, 188-195 (2012); Hafalla, J. C. R., et al. *PLOS Pathogens*; Feb. 2, 2012)), *Leishmania, Staphylococcus aureus, Pseudomonas Aeruginosa*. PD-L1 blockade is particularly useful against established infections by agents such as HIV that present altered antigens over the course of the infections. These novel epitopes are recognized as foreign at the time of anti-human PD-L1 administration, thus provoking a strong T cell response that is not dampened by negative signals through PD-L1.

Some examples of pathogenic viruses causing infections treatable by methods of the disclosure include HIV, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Some examples of pathogenic bacteria causing infections treatable by methods of the disclosure include *chlamydia*, rickettsial bacteria, mycobacteria, staphylococci, streptococci, pneumonococci, meningococci and conococci, *klebsiella, proteus, serratia, pseudomonas, legionella*, diphtheria, *salmonella*, bacilli, cholera, tetanus, botulism, anthrax, plague, leptospirosis, and Lyme disease bacteria.

Some examples of pathogenic fungi causing infections treatable by methods of the disclosure include *Candida* (*albicans, krusei, glabrata, tropicalis*, etc.), *Cryptococcus neoformans, Aspergillus* (*fumigatus, niger*, etc.), Genus *Mucorales* (*mucor, absidia*, rhizophus), *Sporothrix schenkii, Blastomyces dermatitidis, Paracoccidioides brasiliensis, Coccidioides immitis* and *Histoplasma capsulatum*.

Some examples of pathogenic parasites causing infections treatable by methods of the disclosure include *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis*.

In all of the above methods, PD-L1 blockade can be combined with other forms of immunotherapy such as cytokine treatment (e.g., interferons, agents targeting VEGF activity or VEGF-receptors, GM-CSF, G-CSF, IL-2), or bispecific antibody therapy, which provides for enhanced presentation of tumor antigens (see, e.g., Holliger, *Proc. Natl. Acad. Sci. USA*, 90:6444-6448 (1993); Poljak, *Structure*, 2:1121-1123 (1994)).

Autoimmune Reactions

The macrocyclic peptides may provoke and amplify autoimmune responses. Indeed, induction of anti-tumor responses using tumor cell and peptide vaccines reveals that many anti-tumor responses involve anti-self reactivities (depigmentation observed in anti-CTLA-4+GM-CSF-modified B 16 melanoma in van Elsas et al. supra; depigmentation in Trp-2 vaccinated mice (Overwijk, W. et al., *Proc. Natl. Acad. Sci. USA*, 96:2982-2987 (1999)); autoimmune prostatitis evoked by TRAMP tumor cell vaccines (Hurwitz, A., supra (2000)), melanoma peptide antigen vaccination and vitiligo observed in human clinical trials (Rosenberg, S. A. et al., *J. Immunother. Emphasis Tumor Immunol.*, 19(1):81-84 (1996)).

Therefore, it is possible to consider using anti-PD-L1 blockade in conjunction with various self proteins in order to devise vaccination protocols to efficiently generate immune responses against these self proteins for disease treatment. For example, Alzheimer's disease involves inappropriate accumulation of A.beta. peptide in amyloid deposits in the brain; antibody responses against amyloid are able to clear these amyloid deposits (Schenk et al., *Nature*, 400:173-177 (1999)).

Other self proteins may also be used as targets such as IgE for the treatment of allergy and asthma, and TNF.alpha for rheumatoid arthritis. Finally, antibody responses to various hormones may be induced by the use of the macrocycles disclosed herein. Neutralizing antibody responses to reproductive hormones may be used for contraception. Neutralizing antibody response to hormones and other soluble factors that are required for the growth of particular tumors may also be considered as possible vaccination targets.

Analogous methods as described above for the use of anti-PD-L1 macrocycles can be used for induction of therapeutic autoimmune responses to treat patients having an inappropriate accumulation of other self-antigens, such as amyloid deposits, including A.beta. in Alzheimer's disease, cytokines such as TNF.alpha., and IgE.

Vaccines

The macrocyclic peptides may be used to stimulate antigen-specific immune responses by coadministration of an anti-PD-1 macrocycle with an antigen of interest (e.g., a vaccine). Accordingly, in another aspect the disclosure provides a method of enhancing an immune response to an antigen in a subject, comprising administering to the subject: (i) the antigen; and (ii) an anti-PD-1 macrocycle such that an immune response to the antigen in the subject is enhanced. The antigen can be, for example, a tumor antigen, a viral antigen, a bacterial antigen or an antigen from a pathogen. Non-limiting examples of such antigens include those discussed in the sections above, such as the tumor antigens (or tumor vaccines) discussed above, or antigens from the viruses, bacteria or other pathogens described above.

Suitable routes of administering the compositions (e.g., macrocyclic peptides, multispecific and bispecific molecules and immunoconjugates) of the disclosure in vivo and in vitro are well known in the art and can be selected by those of ordinary skill. For example, the compositions can be administered by injection (e.g., intravenous or subcutaneous). Suitable dosages of the molecules used will depend on the age and weight of the subject and the concentration and/or formulation of the composition.

As previously described the macrocyclic peptides of the disclosure can be co-administered with one or other more therapeutic agents, e.g., a cytotoxic agent, a radiotoxic agent or an immunosuppressive agent. The peptide can be linked to the agent (as an immunocomplex) or can be administered separate from the agent. In the latter case (separate administration), the peptide can be administered before, after or concurrently with the agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil, decarbazine and cyclophosphamide hydroxyurea which, by themselves, are only effective at levels which are toxic or subtoxic to a patient. Cisplatin is intravenously administered as a 100 mg/dose once every four weeks and adriamycin is intravenously administered as a 60-75 mg/ml dose once every 21 days. Co-administration of the macrocyclic peptides of the present disclosure with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the peptides.

Also within the scope of the present disclosure are kits comprising the compositions of the disclosure (e.g., macrocyclic peptides, bispecific or multispecific molecules, or immunoconjugates) and instructions for use. The kit can further contain at least one additional reagent, or one or more additional macrocyclic peptides of the disclosure (e.g., a human antibody having a complementary activity which binds to an epitope in PD-L1 antigen distinct from the macrocycle). Kits typically include a label indicating the intended use of the contents of the kit. The term label includes any writing, or recorded material supplied on or with the kit, or which otherwise accompanies the kit.

Combination Therapy

The combination of the macrocyclic peptides of the present disclosure with another PD-L1 antagonist and/or other immunomodulator is useful for enhancement of an immune response against a hyperproliferative disease. For example, these molecules can be administered to cells in culture, in vitro or ex vivo, or to human subjects, e.g., in vivo, to enhance immunity in a variety of situations. Accordingly, in one aspect, the disclosure provides a method of modifying an immune response in a subject comprising administering to the subject a macrocyclic peptide of the disclosure such that the immune response in the subject is modified. Preferably, the response is enhanced, stimulated or up-regulated. In another embodiment, the instant disclosure provides a method of altering adverse events associated with treatment of a hyperproliferative disease with an immuno-stimulatory therapeutic agent, comprising administering a macrocyclic peptide of the present disclosure and a sub-therapeutic dose of another immunomodulator to a subject.

Blockade of PD-L1 by macrocyclic peptides can enhance the immune response to cancerous cells in the patient. Cancers whose growth may be inhibited using the macrocyclic peptides of the instant disclosure include cancers typically responsive to immunotherapy. Representative examples of cancers for treatment with the combination therapy of the instant disclosure include melanoma (e.g., metastatic malignant melanoma), renal cancer, prostate cancer, breast cancer, colon cancer and lung cancer. Examples of other cancers that may be treated using the methods of the instant disclosure include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The present disclosure is also useful for treatment of metastatic cancers.

In certain embodiments, the combination of therapeutic agents containing at least one macrocyclic peptide discussed herein may be administered concurrently as a single composition in a pharmaceutically acceptable carrier, or concurrently as separate compositions wherein each agent can be administered sequentially. For example, a second immunomodulator and a macrocyclic peptide of the present disclosure can be administered sequentially, such as the second immunomodulator administered first and the macrocyclic peptide second, or the macrocyclic peptide being administered first and the second immunomodulator second. Furthermore, if more than one dose of the combination therapy is administered sequentially, the order of the sequential administration can be reversed or kept in the same order at each time point of administration, sequential administrations may be combined with concurrent administrations, or any combination thereof. For example, the first administration of a second immunomodulator and the macrocyclic peptide may be concurrent, the second administration may be sequential with the second immunomodulator first and the macrocyclic peptide second, and the third administration may be sequential with the macrocyclic peptide first and second immunomodulator second, etc. Another representative dosing scheme may involve a first administration that is sequential with the macrocyclic peptide first and the second immunomodulator second, and subsequent administrations may be concurrent.

Optionally, the combination of the macrocyclic peptide and a second immunomodulator can be further combined with an immunogenic agent, such as cancerous cells, purified tumor antigens (including recombinant proteins, peptides, and carbohydrate molecules), cells, and cells transfected with genes encoding immune stimulating cytokines (He et al., *J. Immunol.*, 173:4919-4928 (2004)). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF (discussed further below).

A combined PD-L1 macrocyclic peptide and a second immunomodulator can be further combined with a vaccination protocol. Many experimental strategies for vaccination against tumors have been devised (see Rosenberg, S., Development of Cancer Vaccines, ASCO Educational Book Spring: 60-62 (2000); Logothetis, C., ASCO Educational Book Spring: 300-302 (2000); Khayat, D., ASCO Educational Book Spring: 414-428 (2000); Foon, K., ASCO Educational Book Spring: 730-738 (2000); see also Restifo et al., Cancer Vaccines, Chapter 61, pp. 3023-3043 in DeVita et al., eds., *Cancer: Principles and Practice of Oncology*, Fifth Edition (1997)). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al., *Proc. Natl. Acad. Sci. USA*, 90:3539-3543 (1993)).

The study of gene expression and large scale gene expression patterns in various tumors has led to the definition of so called tumor specific antigens (Rosenberg, *Immunity*, 10:281-287 (1999)). In many cases, these tumor specific antigens are differentiation antigens expressed in the tumors and in the cell from which the tumor arose, for example melanocyte antigens gp100, MAGE antigens, and Trp-2. More importantly, many of these antigens can be shown to be the targets of tumor specific T cells found in the host. In certain embodiments, a combined PD-L1 macrocyclic peptide and a second immunomodulator may be used in conjunction with a collection of recombinant proteins and/or peptides expressed in a tumor in order to generate an immune response to these proteins. These proteins are normally viewed by the immune system as self-antigens and are, therefore, tolerant to them. The tumor antigen may also include the protein telomerase, which is required for the synthesis of telomeres of chromosomes and which is expressed in more than 85% of human cancers and in only a limited number of somatic tissues (Kim et al., *Science*, 266:2011-2013 (1994)). (These somatic tissues may be protected from immune attack by various means). Tumor antigen may also be "neo-antigens" expressed in cancer cells because of somatic mutations that alter protein sequence or create fusion proteins between two unrelated sequences (i.e., bcr-abl in the Philadelphia chromosome), or idiotype from B cell tumors.

Other tumor vaccines may include the proteins from viruses implicated in human cancers such a Human Papilloma Viruses (HPV), Hepatitis Viruses (HBV and HCV) and Kaposi's Herpes Sarcoma Virus (KHSV). Another form of tumor specific antigen which may be used in conjunction with PD-L1 macrocyclic peptide blockade is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot et al., *Science*, 269:1585-1588 (1995); Tamura et al., *Science*, 278:117-120 (1997)).

Dendritic cells (DC) are potent antigen presenting cells that can be used to prime antigen-specific responses. DC's can be produced ex vivo and loaded with various protein and peptide antigens as well as tumor cell extracts (Nestle et al., *Nat. Med.*, 4:328-332 (1998)). DCs may also be transduced by genetic means to express these tumor antigens as well. DCs have also been fused directly to tumor cells for the purposes of immunization (Kugler et al., *Nat. Med.*, 6:332-336 (2000)). As a method of vaccination, DC immunization may be effectively further combined with a combined anti-PD-L1 macrocyclic peptide and a second immunomodulator to activate more potent anti-tumor responses.

A combined anti-PD-L1 macrocyclic peptide and additional immunomodulator may also be further combined with standard cancer treatments. For example, a combination of a macrocyclic peptide and a second immunomodulator may be effectively combined with chemotherapeutic regimes. In these instances, as is observed with the combination of a macrocyclic peptide and a second immunomodulator, it may be possible to reduce the dose of other chemotherapeutic reagent administered with the combination of the instant disclosure (Mokyr et al., *Cancer Res.*, 58:5301-5304 (1998)). An example of such a combination is a combination of a macrocyclic peptide and a second immunomodulator further in combination with decarbazine for the treatment of melanoma. Another example is a combination of a macrocyclic peptide and a second immunomodulatory agent further in combination with interleukin-2 (IL-2) for the treatment of melanoma. The scientific rationale behind the combined use of PD-L1 macrocyclic peptide and another immunomodulator with chemotherapy is that cell death, which is a consequence of the cytotoxic action of most chemotherapeutic compounds, should result in increased levels of tumor antigen in the antigen presentation pathway. Other combination therapies that may result in synergy with a combined anti-PD-L1 macrocyclic peptide and additional immunomodulator through cell death include radiation, surgery, or hormone deprivation. Each of these protocols creates a source of tumor antigen in the host. Angiogenesis inhibitors may also be combined with a combined PD-L1 and second immunomodulator. Inhibition of angiogenesis leads to tumor cell death, which may also be a source of tumor antigen to be fed into host antigen presentation pathways.

A combination of PD-L1 and another immunomodulator can also be used in combination with bispecific macrocyclic peptides that target Fc.alpha. or Fc.gamma. receptor-expressing effector cells to tumor cells (see, e.g., U.S. Pat. Nos. 5,922,845 and 5,837,243). Bispecific macrocyclic peptides can be used to target two separate antigens. For example anti-Fc receptor/anti tumor antigen (e.g., Her-2/neu) bispecific macrocyclic peptides have been used to target macrophages to sites of tumor. This targeting may more effectively activate tumor specific responses. The T cell arm of these responses would be augmented by the use of a combined PD-L1 and a second immunomodulator. Alternatively, antigen may be delivered directly to DCs by the use of bispecific macrocyclic peptides which bind to tumor antigen and a dendritic cell specific cell surface marker.

In another example, a combination of a macrocyclic peptide and a second immunomodulator can be used in conjunction with anti-neoplastic macrocyclic agents, such as RITUXAN® (rituximab), HERCEPTIN® (trastuzumab), BEXXAR® (tositumomab), ZEVALIN® (ibritumomab), CAMPATH® (alemtuzumab), Lymphocide (eprtuzumab), AVASTIN® (bevacizumab), and TARCEVA® (erlotinib), and the like. By way of example and not wishing to be bound by theory, treatment with an anti-cancer antibody or an anti-cancer antibody conjugated to a toxin can lead to cancer cell death (e.g., tumor cells) which would potentiate an immune response mediated by the second immunomodulator target or PD-L1. In an exemplary embodiment, a treatment of a hyperproliferative disease (e.g., a cancer tumor) may include an anti-cancer antibody in combination with a macrocyclic peptide and a second immunomodulator concurrently or sequentially or any combination thereof, which may potentiate an anti-tumor immune responses by the host.

Tumors evade host immune surveillance by a large variety of mechanisms. Many of these mechanisms may be overcome by the inactivation of proteins, which are expressed by the tumors and which are immunosuppressive. These include, among others, TGF-.beta. (Kehrl, J. et al., *J. Exp. Med.*, 163:1037-1050 (1986)), IL-10 (Howard, M. et al., *Immunology Today*, 13:198-200 (1992)), and Fas ligand (Hahne, M. et al., *Science*, 274:1363-1365 (1996)). In another example, antibodies to each of these entities may be further combined with a macrocyclic peptide and another immunomodulator to counteract the effects of immunosuppressive agents and favor anti-tumor immune responses by the host.

Other agents that may be used to activate host immune responsiveness can be further used in combination with a macrocyclic peptide of the present disclosure. These include molecules on the surface of dendritic cells that activate DC function and antigen presentation. Anti-CD40 macrocyclic peptides are able to substitute effectively for T cell helper activity (Ridge, J. et al., *Nature*, 393:474-478 (1998)) and can be used in conjunction with the macrocyclic peptides of the present disclosure, either alone or in combination with an anti-CTLA-4 combination (Ito, N. et al., *Immunobiology*, 201(5):527-540 (2000)). Activating macrocyclic peptides to T cell costimulatory molecules, such as OX-40 (Weinberg, A. et al., *Immunol.*, 164:2160-2169 (2000)), 4-1BB (Melero, I. et al., *Nat. Med.*, 3:682-685 (1997), and ICOS (Hutloff, A. et al., *Nature*, 397:262-266 (1999)) may also provide for increased levels of T cell activation.

Bone marrow transplantation is currently being used to treat a variety of tumors of hematopoietic origin. While graft versus host disease is a consequence of this treatment, therapeutic benefit may be obtained from graft vs. tumor responses. A macrocyclic peptide of the present disclosure, either alone or in combination with another immunomodulator, can be used to increase the effectiveness of the donor engrafted tumor specific T cells.

There are also several experimental treatment protocols that involve ex vivo activation and expansion of antigen specific T cells and adoptive transfer of these cells into recipients in order to antigen-specific T cells against tumor (Greenberg, R. et al., *Science*, 285:546-551 (1999)). These methods may also be used to activate T cell responses to infectious agents such as CMV. Ex vivo activation in the presence a macrocyclic peptide of the present disclosure, either alone or in combination with another immunomodulator, may be expected to increase the frequency and activity of the adoptively transferred T cells.

In certain embodiments, the present disclosure provides a method for altering an adverse event associated with treatment of a hyperproliferative disease with an immunostimulatory agent, comprising administering a macrocyclic peptide of the present disclosure in combination with a subtherapeutic dose of another immunomodulator to a subject. For example, the methods of the present disclosure provide for a method of reducing the incidence of immunostimulatory therapeutic antibody-induced colitis or diarrhea by administering a non-absorbable steroid to the patient. Because any patient who will receive an immunostimulatory therapeutic antibody is at risk for developing colitis or diarrhea induced by such treatment, this entire patient population is suitable for therapy according to the methods of the present disclosure. Although steroids have been administered to treat inflammatory bowel disease (IBD) and prevent exacerbations of IBD, they have not been used to prevent (decrease the incidence of) IBD in patients who have not been diagnosed with IBD. The significant side effects associated with steroids, even non-absorbable steroids, have discouraged prophylactic use.

In further embodiments, a macrocyclic peptide of the present disclosure, either alone or in combination with another immunomodulator, can be further combined with the use of any non-absorbable steroid. As used herein, a "non-absorbable steroid" is a glucocorticoid that exhibits extensive first pass metabolism such that, following metabolism in the liver, the bioavailability of the steroid is low, i.e., less than about 20%. In one embodiment of the disclosure, the non-absorbable steroid is budesonide. Budesonide is a locally-acting glucocorticosteroid, which is extensively metabolized, primarily by the liver, following oral administration. ENTOCORT® EC (Astra-Zeneca) is a pH- and time-dependent oral formulation of budesonide developed to optimize drug delivery to the ileum and throughout the colon. ENTOCORT® EC is approved in the U.S. for the treatment of mild to moderate Crohn's disease involving the ileum and/or ascending colon. The usual oral dosage of ENTOCORT® EC for the treatment of Crohn's disease is 6 to 9 mg/day. ENTOCORT® EC is released in the intestines before being absorbed and retained in the gut mucosa. Once it passes through the gut mucosa target tissue, ENTOCORT® EC is extensively metabolized by the cytochrome P450 system in the liver to metabolites with negligible glucocorticoid activity. Therefore, the bioavailability is low (about 10%). The low bioavailability of budesonide results in an improved therapeutic ratio compared to other glucocorticoids with less extensive first-pass metabolism. Budesonide results in fewer adverse effects, including less hypothalamic-pituitary suppression, than systemically-acting corticosteroids. However, chronic administration of ENTOCORT® EC can result in systemic glucocorticoid effects such as hypercorticism and adrenal suppression. See *Physicians' Desk Reference Supplement*, 58th Edition, 608-610 (2004).

In still further embodiments, a combination PD-L1 and another immunomodulator in conjunction with a non-absorbable steroid can be further combined with a salicylate. Salicylates include 5-ASA agents such as, for example: sulfasalazine (AZULFIDINE®, Pharmacia & Upjohn); olsalazine (DIPENTUM®, Pharmacia & UpJohn); balsalazide (COLAZAL®, Salix Pharmaceuticals, Inc.); and mesalamine (ASACOL®, Procter & Gamble Pharmaceuticals; PENTASA®, Shire US; CANASA®, Axcan Scandipharm, Inc.; ROWASA®, Solvay).

Dosage and Formulation

A suitable peptide of Formula I, or more specifically a macrocyclic peptide described herein, can be administered to patients to treat diabetes and other related diseases as the compound alone and or mixed with an acceptable carrier in the form of pharmaceutical formulations. Those skilled in the art of treating diabetes can easily determine the dosage and route of administration of the compound to mammals, including humans, in need of such treatment. The route of administration may include but is not limited to oral, intraoral, rectal, transdermal, buccal, intranasal, pulmonary, subcutaneous, intramuscular, intradermal, sublingual, intracolonic, intraoccular, intravenous, or intestinal administration. The compound is formulated according to the route of administration based on acceptable pharmacy practice (Fingl et al., in *The Pharmacological Basis of Therapeutics*, Chapter 1, p. 1 (1975); *Remington's Pharmaceutical Sciences*, 18th Edition, Mack Publishing Co., Easton, Pa. (1990)).

The pharmaceutically acceptable peptide compositions described herein can be administered in multiple dosage forms such as tablets, capsules (each of which includes sustained release or timed release formulations), pills, powders, granules, elixirs, in situ gels, microspheres, crystalline complexes, liposomes, micro-emulsions, tinctures, suspensions, syrups, aerosol sprays and emulsions. The compositions described herein can also be administered in oral, intravenous (bolus or infusion), intraperitoneal, subcutaneous, transdermally or intramuscular form, all using dosage forms well known to those of ordinary skill in the pharmaceutical arts. The compositions may be administered alone, but generally will be administered with a pharmaceutical carrier selected on the basis of the chosen route of administration and standard pharmaceutical practice.

The dosage regimen for the compositions described herein will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the disease state.

By way of general guidance, the daily oral dosage of the active ingredient, when used for the indicated effects, will range between about 0.001 to 1000 mg/kg of body weight, preferably between about 0.01 to 100 mg/kg of body weight per day, and most preferably between about 0.6 to 20 mg/kg/day. Intravenously, the daily dosage of the active ingredient when used for the indicated effects will range between 0.001 ng to 100.0 ng per min/per Kg of body weight during a constant rate infusion. Such constant intravenous infusion can be preferably administered at a rate of 0.01 ng to 50 ng per min per Kg body weight and most preferably at 0.01 ng to 10.0 mg per min per Kg body weight. The compositions described herein may be administered in a single daily dose, or the total daily dosage may be administered in divided doses of two, three, or four times daily. The compositions described herein may also be administered by a depot formulation that will allow sustained release of the drug over a period of days/weeks/months as desired.

The compositions described herein can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compositions are typically administered in a mixture with suitable pharmaceutical diluents, excipients, or carriers (collectively referred to herein as pharmaceutical carriers) suitably selected with respect to the intended form of administration, that is, oral tablets, capsules, elixirs, aerosol sprays generated with or without propellant and syrups, and consistent with conventional pharmaceutical practices.

For instance, for oral administration in the form of a tablet or capsule, the active drug component can be combined with an oral, non-toxic, pharmaceutically acceptable, inert carrier such as but not limited to, lactose, starch, sucrose, glucose, methyl cellulose, magnesium stearate, dicalcium phosphate, calcium sulfate, mannitol, and sorbitol; for oral administration in liquid form, the oral drug components can be combined with any oral, non-toxic, pharmaceutically acceptable inert carrier such as, but not limited to, ethanol, glycerol, and water. Moreover, when desired or necessary, suitable binders, lubricants, disintegrating agents, and coloring agents can also be incorporated into the mixture. Suitable binders include, but not limited to, starch, gelatin, natural sugars such as, but not limited to, glucose or beta-lactose, corn sweeteners, natural and synthetic gums such as acacia, tragacanth, or sodium alginate, carboxymethylcellulose, polyethylene glycol, and waxes. Lubricants used in these dosage forms include sodium oleate, sodium stearate, magnesium stearate, sodium benzoate, sodium acetate, and sodium chloride. Disintegrants include, but are not limited to, starch, methyl cellulose, agar, bentonite, and xanthan gum.

The compositions described herein may also be administered in the form of mixed micellar or liposome delivery systems, such as small unilamellar vesicles, large unilamellar vesicles, and multilamellar vesicles. Liposomes can be formed from a variety of phospholipids, such as cholesterol, stearylamine, or phosphatidylcholines. Permeation enhancers may be added to enhance drug absorption.

Since prodrugs are known to enhance numerous desirable qualities of pharmaceuticals (i.e., solubility, bioavailability, manufacturing, etc.) the compounds described herein may be delivered in prodrug form. Thus, the subject matter described herein is intended to cover prodrugs of the presently claimed compounds, methods of delivering the same, and compositions containing the same.

The compositions described herein may also be coupled with soluble polymers as targetable drug carriers. Such polymers can include polyvinyl-pyrrolidone, pyran copolymer, polyhydroxypropyl-methacrylamide-phenol, polyhydroxyethylaspartamidephenol, or polyethyleneoxide-polylysine substituted with palmitoyl residues. Furthermore, the compositions described herein may be combined with a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 0.01 milligram to about 500 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivative, magnesium stearate, and stearic acid. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solution for parenteral administration preferably contains a water-soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington: The Science and Practice of Pharmacy*, Nineteenth Edition, Mack Publishing Company (1995), a standard reference text in this field.

Representative useful pharmaceutical dosage forms for administration of the compounds described herein can be illustrated as follows:

Capsules

A large number of unit capsules can be prepared by filling standard two-piece hard gelatin capsules with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit, for example is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

An injectable formulation of a peptide composition described herein may or may not require the use of excipients such as those that have been approved by regulatory bodies. These excipients include, but are not limited to, solvents and co-solvents, solubilizing, emulsifying or thickening agents, chelating agents, anti-oxidants and reducing agents, antimicrobial preservatives, buffers and pH adjusting agents, bulking agents, protectants and tonicity adjustors and special additives. An injectable formulation has to be sterile, pyrogen free and, in the case of solutions, free of particulate matter.

A parenteral composition suitable for administration by injection may be prepared by stirring for example, 1.5% by weight of active ingredient in a pharmaceutically acceptable buffer that may or may not contain a co-solvent or other excipient. The solution should be made isotonic with sodium chloride and sterilized.

Suspension

An aqueous suspension can be prepared for oral and/or parenteral administration so that, for example, each 5 mL contains 100 mg of finely divided active ingredient, 20 mg of sodium carboxymethyl cellulose, 5 mg of sodium benzoate, 1.0 g of sorbitol solution, U.S.P., and 0.025 mL of vanillin or other palatable flavoring.

Biodegradable Microparticles

A sustained-release parenteral composition suitable for administration by injection may be prepared, for example, by dissolving a suitable biodegradable polymer in a solvent, adding to the polymer solution the active agent to be incorporated, and removing the solvent from the matrix thereby forming the matrix of the polymer with the active agent distributed throughout the matrix.

Peptide Synthesis

Chemical synthesis of a macrocyclic peptide of the present disclosure can be carried out using a variety of art recognized methods, including stepwise solid phase synthesis, semi-synthesis through the conformationally-assisted re-ligation of peptide fragments, enzymatic ligation of cloned or synthetic peptide segments, and chemical ligation. A preferred method to synthesize the macrocyclic peptides and analogs thereof described herein is chemical synthesis using various solid-phase techniques such as those described in Chan, W. C. et al., eds., *Fmoc Solid Phase Synthesis*, Oxford University Press, Oxford (2000); Barany, G. et al., *The Peptides: Analysis, Synthesis, Biology*, Vol. 2: "Special Methods in Peptide Synthesis, Part A", pp. 3-284, Gross, E. et al., eds., Academic Press, New York (1980); and in Stewart, J. M. et al., *Solid-Phase Peptide Synthesis*, 2nd Edition, Pierce Chemical Co., Rockford, Ill. (1984). The preferred strategy is based on the Fmoc (9-Fluorenylmethyl methyl-oxycarbonyl) group for temporary protection of the α-amino group, in combination with the tert-butyl group for temporary protection of the amino acid side chains (see for example Atherton, E. et al., "The Fluorenylmethoxycarbonyl Amino Protecting Group", in *The Peptides: Analysis, Synthesis, Biology*, Vol. 9: "Special Methods in Peptide Synthesis, Part C", pp. 1-38, Undenfriend, S. et al., eds., Academic Press, San Diego (1987).

The peptides can be synthesized in a stepwise manner on an insoluble polymer support (also referred to as "resin") starting from the C-terminus of the peptide. A synthesis is begun by appending the C-terminal amino acid of the peptide to the resin through formation of an amide or ester linkage. This allows the eventual release of the resulting peptide as a C-terminal amide or carboxylic acid, respectively.

The C-terminal amino acid and all other amino acids used in the synthesis are required to have their α-amino groups and side chain functionalities (if present) differentially protected such that the α-amino protecting group may be selectively removed during the synthesis. The coupling of an amino acid is performed by activation of its carboxyl group as an active ester and reaction thereof with the unblocked α-amino group of the N-terminal amino acid appended to the resin. The sequence of α-amino group deprotection and coupling is repeated until the entire peptide sequence is assembled. The peptide is then released from the resin with concomitant deprotection of the side chain functionalities, usually in the presence of appropriate scavengers to limit side reactions. The resulting peptide is finally purified by reverse phase HPLC.

The synthesis of the peptidyl-resins required as precursors to the final peptides utilizes commercially available cross-linked polystyrene polymer resins (Novabiochem, San Diego, Calif.; Applied Biosystems, Foster City, Calif.). Preferred solid supports are: 4-(2',4'-dimethoxyphenyl-Fmoc-aminomethyl)-phenoxyacetyl-p-methyl benzhydrylamine resin (Rink amide MBHA resin); 9-Fmoc-amino-xanthen-3-yloxy-Merrifield resin (Sieber amide resin); 4-(9-

Fmoc)aminomethyl-3,5-dimethoxyphenoxy)valeryl-aminomethyl-Merrifield resin (PAL resin), for C-terminal carboxamides. Coupling of first and subsequent amino acids can be accomplished using HOBt, 6-Cl-HOBt or HOAt active esters produced from DIC/HOBt, HBTU/HOBt, BOP, PyBOP, or from DIC/6-Cl-HOBt, HCTU, DIC/HOAt or HATU, respectively. Preferred solid supports are: 2-Chlorotrityl chloride resin and 9-Fmoc-amino-xanthen-3-yloxy-Merrifield resin (Sieber amide resin) for protected peptide fragments. Loading of the first amino acid onto the 2-chlorotrityl chloride resin is best achieved by reacting the Fmoc-protected amino acid with the resin in dichloromethane and DIEA. If necessary, a small amount of DMF may be added to facilitate dissolution of the amino acid.

The syntheses of the peptide analogs described herein can be carried out by using a single or multi-channel peptide synthesizer, such as an CEM Liberty Microwave synthesizer, or a Protein Technologies, Inc. Prelude (6 channels) or Symphony (12 channels) synthesizer.

The peptidyl-resin precursors for their respective peptides may be cleaved and deprotected using any standard procedure (see, for example, King, D. S. et al., *Int. J. Peptide Protein Res.*, 36:255-266 (1990)). A desired method is the use of TFA in the presence of water and TIS as scavengers. Typically, the peptidyl-resin is stirred in TFA/water/TIS (94:3:3, v:v:v; 1 mL/100 mg of peptidyl resin) for 2-6 hrs at room temperature. The spent resin is then filtered off and the TFA solution is concentrated or dried under reduced pressure. The resulting crude peptide is either precipitated and washed with $Et_2O$ or is redissolved directly into DMSO or 50% aqueous acetic acid for purification by preparative HPLC.

Peptides with the desired purity can be obtained by purification using preparative HPLC, for example, on a Waters Model 4000 or a Shimadzu Model LC-8A liquid chromatograph. The solution of crude peptide is injected into a YMC S5 ODS (20×100 mm) column and eluted with a linear gradient of MeCN in water, both buffered with 0.1% TFA, using a flow rate of 14-20 mL/min with effluent monitoring by UV absorbance at 220 nm. The structures of the purified peptides can be confirmed by electro-spray MS analysis.

Analytical Data:

Mass Spectrometry: "ESI-MS(+)" signifies electrospray ionization mass spectrometry performed in positive ion mode; "ESI-MS(−)" signifies electrospray ionization mass spectrometry performed in negative ion mode; "ESI-HRMS (+)" signifies high-resolution electrospray ionization mass spectrometry performed in positive ion mode; "ESI-HRMS (−)" signifies high-resolution electrospray ionization mass spectrometry performed in negative ion mode. The detected masses are reported following the "m/z" unit designation. Compounds with exact masses greater than 1000 were often detected as double-charged or triple-charged ions.

Analytical Data:

Mass Spectrometry: "ESI-MS(+)" signifies electrospray ionization mass spectrometry performed in positive ion mode; "ESI-MS(−)" signifies electrospray ionization mass spectrometry performed in negative ion mode; "ESI-HRMS (+)" signifies high-resolution electrospray ionization mass spectrometry performed in positive ion mode; "ESI-HRMS (−)" signifies high-resolution electrospray ionization mass spectrometry performed in negative ion mode. The detected masses are reported following the "m/z" unit designation. Compounds with exact masses greater than 1000 were often detected as double-charged or triple-charged ions.

Analysis Condition A:
Column: Waters BEH C18, 2.0×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B, 0-100% B over 3 minutes, then a 0.5-minute hold at 100% B; Flow: 1 mL/min; Detection: UV at 220 nm.

Analysis Condition B:
Column: Waters BEH C18, 2.0×50 mm, 1.7-µm particles; Mobile Phase A: 5:95 methanol:water with 10 mM ammonium acetate; Mobile Phase B: 95:5 methanol:water with 10 mM ammonium acetate; Temperature: 50° C.; Gradient: 0% B, 0-100% B over 3 minutes, then a 0.5-minute hold at 100% B; Flow: 0.5 mL/min; Detection: UV at 220 nm.

Analysis Condition C:
Column: Waters Aquity BEH C18 2.1×50 mm 1.7 µm particles; Mobile Phase A: water with 0.05% TFA; Mobile Phase B: acetonitrile with 0.05% TFA; Temperature: 40° C.; Gradient: 0% B, 0-100% B over 3 minutes, then a 0.5-minute hold at 100% B; Flow: 0.8 mL/min; Detection: UV at 220 nm.

Analysis Condition D:
Column: Waters Aquity BEH C18 2.1×50 mm 1.7 µm particles; Mobile Phase A: water with 0.05% TFA; Mobile Phase B: methanol with 0.05% TFA; Temperature: 40° C.; Gradient: 0% B, 0-100% B over 3 minutes, then a 0.5-minute hold at 100% B; Flow: 0.8 mL/min; Detection: UV at 220 nm.

General Procedures:
Prelude Method A:

All manipulations were performed under automation on a Prelude peptide synthesizer (Protein Technologies). All procedures unless noted were performed in a 10 mL polypropylene tube fitted with a bottom frit; where the scale of the reaction exceeded 0.100 mmol, a 40 mL polypropylene tube fitted with a bottom frit was used. The tube connects to a the Prelude peptide synthesizer through both the bottom and the top of the tube. DMF and DCM can be added through the top of the tube, which washes down the sides of the tube equally. The remaining reagents are added through the bottom of the tube and pass up through the frit to contact the resin. All solutions are removed through the bottom of the tube. "Periodic agitation" describes a brief pulse of $N_2$ gas through the bottom frit; the pulse lasts approximately 5 seconds and occurs every 30 seconds. Amino acid solutions were generally not used beyond three weeks from preparation. HATU solutions were used within 5 days of preparation. DMF=dimethylformamide; HATU=1-[Bis(dimethylamino)methylene]-1H-1,2,3-triazolo[4,5-b]pyridinium 3-oxid hexafluorophosphate; DIPEA=diisopropylethylamine; TIPS=triisopropylsilane; DTT=DL-dithiothreitol. The resin used is 2-Chlorotritylchloride resin (1.42 mmol/g loading). Common amino acids used are listed below with side-chain protecting groups indicated inside parenthesis: Fmoc-Ala-OH; Fmoc-Arg (Pbf)-OH; Fmoc-Asn(Trt)-OH; Fmoc-Asp(OtBu)-OH; Fmoc-Bzt-OH; Fmoc-Cys(Trt)-OH; Fmoc-Dab(Boc)-OH; Fmoc-Dap(Boc)-OH; Fmoc-Gln(Trt)-OH; Fmoc-Gly-OH; Fmoc-His(Trt)-OH; Fmoc-Hyp(tBu)-OH; Fmoc-Ile-OH; Fmoc-Leu-OH; Fmoc-Lys(Boc)-OH; Fmoc-Nle-OH; Fmoc-Met-OH; Fmoc-[N-Me]Ala-OH; Fmoc-[N-Me]Nle-OH; Fmoc-Phe-OH; Fmoc-Pro-OH; Fmoc-Sar-OH; Fmoc-Ser (tBu)-OH; Fmoc-Thr(tBu)-OH; Fmoc-Trp(Boc)-OH; Fmoc-Tyr(tBu)-OH; Fmoc-Val-OH.

The procedures of "Prelude Method A" describe an experiment performed on a 0.100 mmol scale, where the scale is determined by the amount of amino acid used in the "Resin-loading procedure" described below. On a 0.100 mmol scale approximately 100 mg of 2-chlorotritylchloride resin is used. All procedures can be scaled beyond 0.100 mmol scale by adjusting the described volumes by the multiple of the scale.

Prior to amino acid coupling, all peptide synthesis sequences began with loading of the first amino acid onto the resin, described below as "Resin-loading procedure". Coupling of amino acids to a primary amine N-terminus used the "Single-coupling procedure" described below. Coupling of amino acids to a secondary amine N-terminus used the "Double-coupling procedure" described below. procedure" detailed below.

Resin-Loading Procedure:

To a 10 mL polypropylene solid-phase reaction vessel was added 2-Chlorotritylchloride resin (100 mg, 1.42 mmol/g loading). The reaction vessel was placed on the Prelude peptide synthesizer. Manually, to the reaction vessel was added a solution of the Fmoc-protected C-terminus amino acid (0.10 mmol) and diisopropylethylamine (0.65 mmol) in DCM (2.5 mL). Under automation, the mixture was agitated by periodic nitrogen bubbling for 60 minutes. To the reaction vessel was added methanol (0.20 mL). The mixture was agitated by periodic nitrogen bubbling for 15 minutes, then the reaction vessel was drained through the frit. The resin was washed successively three times as follows: for each wash, DCM (2.0 mL) was added to top of the vessel and the resulting mixture was periodically agitated for 90 seconds before the solution was drained through the frit. The resin was washed successively three times as follows: for each wash, DMF (2.0 mL) was added to top of the vessel and the resulting mixture was periodically agitated for 90 seconds before the solution was drained through the frit. The resin was washed successively two times as follows: for each wash, DCM (2.0 mL) was added to top of the vessel and the resulting mixture was periodically agitated for 90 seconds before the solution was drained through the frit. The resin was washed successively three times as follows: for each wash, DMF (2.0 mL) was added to top of the vessel and the resulting mixture was periodically agitated for 90 seconds before the solution was drained through the frit.

Single-Coupling Procedure:

To the reaction vessel containing resin from the previous step was added piperidine:DMF (20:80 v/v, 2.0 mL). The mixture was periodically agitated for 3 minutes and then the solution was drained through the frit. To the reaction vessel was added piperidine:DMF (20:80 v/v, 2.0 mL). The mixture was periodically agitated for 3 minutes and then the solution was drained through the frit. The resin was washed successively six times as follows: for each wash, DMF (2.0 mL) was added through the top of the vessel and the resulting mixture was periodically agitated for 30 seconds before the solution was drained through the frit. To the reaction vessel was added the amino acid (0.2M in DMF, 1.0 mL, 2 eq), then HATU (0.2M in DMF, 1.0 mL, 2 eq), and finally DIPEA (0.8M in DMF, 0.5 mL, 4 eq). The mixture was periodically agitated for 15 minutes, then the reaction solution was drained through the frit. The resin was washed successively four times as follows: for each wash, DMF (2.0 mL) was added through the top of the vessel and the resulting mixture was periodically agitated for 30 seconds before the solution was drained through the frit. An end-capping step was performed as follows: to the reaction vessel was added DMF (0.65 mL), then DIPEA (0.8M in DMF, 0.45 mL), then acetic anhydride (1.0M in DMF, 1.45 mL). The mixture was periodically agitated for 10 minutes, then the solution was drained through the frit. The resin was washed successively four times as follows: for each wash, DMF (2.0 mL) was added through the top of the vessel and the resulting mixture was periodically agitated for 90 seconds before the solution was drained through the frit. The resulting resin was used directly in the next step.

Double-Coupling Procedure:

To the reaction vessel containing resin from the previous step was added piperidine:DMF (20:80 v/v, 2.0 mL). The mixture was periodically agitated for 3 minutes and then the solution was drained through the frit. To the reaction vessel was added piperidine:DMF (20:80 v/v, 2.0 mL). The mixture was periodically agitated for 3 minutes and then the solution was drained through the frit. The resin was washed successively six times as follows: For each wash, DMF (2.0 mL) was added through the top of the vessel and the resulting mixture was periodically agitated for 30 seconds before the solution was drained through the frit. To the reaction vessel was added the amino acid (0.2M in DMF, 1.0 mL, 2 eq), then HATU (0.2M in DMF, 1.0 mL, 2 eq), and finally DIPEA (0.8M in DMF, 0.5 mL, 4 eq). The mixture was periodically agitated for 15 minutes, then the reaction solution was drained through the frit. The resin was twice washed as follows: for each wash, DMF (2.0 mL) was added through the top of the vessel and the resulting mixture was periodically agitated for 30 seconds before the solution was drained through the frit. To the reaction vessel was added the amino acid (0.2M in DMF, 1.0 mL, 2 eq), then HATU (0.2M in DMF, 1.0 mL, 2 eq), and finally DIPEA (0.8M in DMF, 0.5 mL, 4 eq). The mixture was periodically agitated for 15 minutes, then the reaction solution was drained through the frit. The resin was twice washed as follows: for each wash, DMF (2.0 mL) was added through the top of the vessel and the resulting mixture was periodically agitated for 30 seconds before the solution was drained through the frit. An end-capping step was performed as follows: to the reaction vessel was added DMF (0.65 mL), then DIPEA (0.8M in DMF, 0.45 mL), then acetic anhydride (1.0M in DMF, 1.45 mL). The mixture was periodically agitated for 10 minutes, then the solution was drained through the frit. The resin was washed successively four times as follows: for each wash, DMF (2.0 mL) was added through the top of the vessel and the resulting mixture was periodically agitated for 90 seconds before the solution was drained through the frit. The resulting resin was used directly in the next step.

Symphony Method A:

This collection of procedures is identical that of "Prelude Method A" except as noted. For all procedures a Symphony X peptide synthesizer (Protein Technologies) was used instead of a Prelude peptide synthesizer and all reagents were added through the top of the reaction vessel.

Resin-Loading Procedure:

Regardless of the peptide synthesizer used in the peptide coupling steps, the resin-loading step was always performed on the Prelude synthesizer following "Prelude Method A: Resin-loading procedure".

Single-Coupling Procedure:

This procedure is identical to "Prelude Method A: Single-coupling procedure" except that the concentration of DIPEA solution was 0.4M and 1.0 mL of this solution was delivered to the reaction. Also, the reagents used in the end-capping step are neat acetic anhydride (1.0 mL) added to the resin suspended in DIPEA (0.4 M, 1.0 mL).

Double-Coupling Procedure:

This procedure is identical to "Prelude Method A: Double-coupling procedure" except that the concentration of DIPEA solution was 0.4M and 1.0 mL of this solution was delivered to the reaction. Also, the reagents used in the end-capping step are neat acetic anhydride (1.0 mL) added to the resin suspended in DIPEA (0.4 M, 1.0 mL).

General Synthetic Sequence A:

"General Synthetic Sequence A" describes a general sequence of procedures that were used to afford the cyclic peptides described herein. For the purposes of this general procedure, the procedures of "Symphony Method A" are interchangeable with those of "Prelude Method A". The procedure can be scaled beyond 0.100 mmol scale by adjusting the described volumes by the multiple of the scale. "Prelude Method A: Resin-loading procedure" was performed using 0.100 mmol of amino acid. Then a series of amino acids couplings was sequentially performed on the Prelude following "Prelude Method A: Single-coupling procedure" if the N-terminus of the resin-bound peptide was a primary amine or "Prelude Method A: Double-coupling procedure" if the N-terminus of the resin-bound peptide was a secondary amine.

PREPARATION OF EXAMPLE 5001

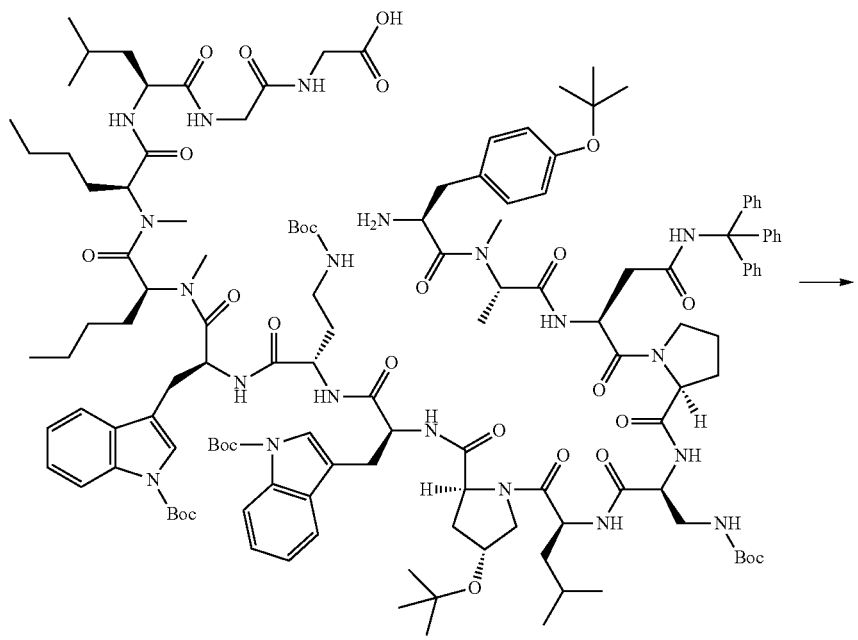

Intermediate 5001A

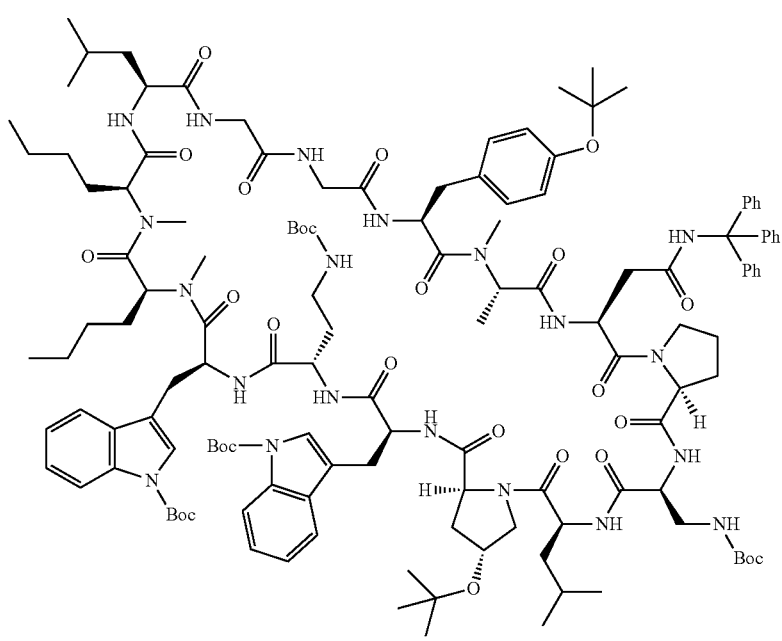

Intermediate 5001B

-continued

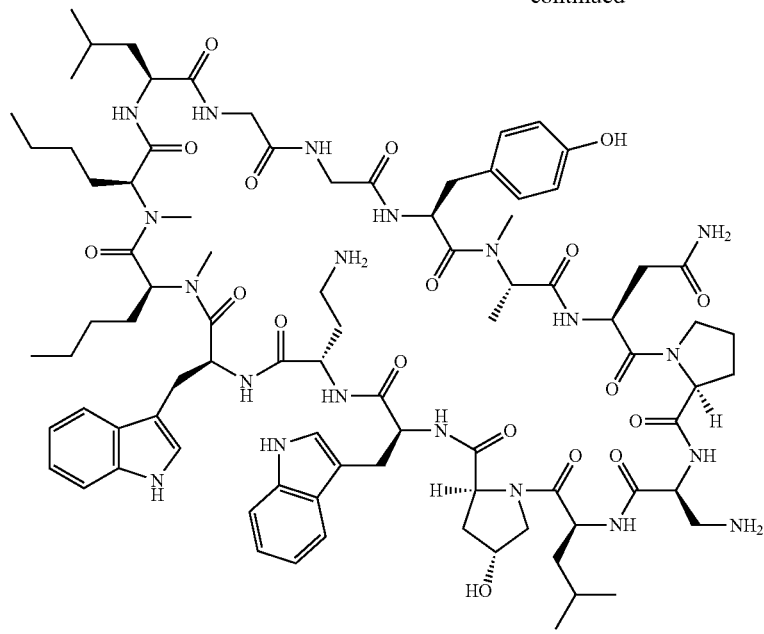

Example 5001

Preparation of Intermediate 5001A

"General Synthetic Sequence A" was followed. To the reaction vessel containing resin from the automated sequence was added piperidine:DMF (20:80 v/v, 2.0 mL). The mixture was periodically agitated for 4 minutes and then the solution was drained through the frit. To the reaction vessel was added piperidine:DMF (20:80 v/v, 2.0 mL). The mixture was periodically agitated for 4 minutes and then the solution was drained through the frit. The resin was washed successively five times as follows: for each wash, DMF (2.0 mL) was added through the top of the vessel and the resulting mixture was periodically agitated for 90 seconds before the solution was drained through the frit. The resin was washed successively five times as follows: for each wash, DCM (2.0 mL) was added through the top of the vessel and the resulting mixture was periodically agitated for 90 seconds before the solution was drained through the frit. The resin was then immediately transferred using DCM (8 mL) to a 15 mL vial. To the solution was added hexafluoroisopropanol (2 mL). The resin immediately turned deep red; the solution remained colorless. The mixture briefly manually agitated, then was allowed to stand at r.t. for 15 minutes, then was filtered. The filtrate was transferred to a 15 mL vial and was concentrated under a $N_2$ stream to afford a solid residue, Intermediate 5001A.

Preparation of Intermediate 5001B

To a 15 mL vial charged with the entirety of Intermediate 5001A prepared above was added DMF (0.50 mL), then HATU (45.6 mg, 0.120 mmol) then DIPEA (0.114 mL, 0.650 mmol). The yellow solution was stirred for 30 minutes. The solution was directly subjected to HPLC purification under the following conditions: Column: Luna C18, 30×100 mm, 5-μm particles; Mobile Phase A: 5:95 acetonitrile:water with 0.1% TFA; Mobile Phase B: 95:5 acetonitrile:water with 0.1% TFA; Gradient: 60-100% B over 10 minutes, then a 10 minute hold at 100% B; Flow: 42 mL/min. Fractions containing the desired product were combined and dried via centrifugal evaporation to afford a white solid, Intermediate 5001B.

PREPARATION OF EXAMPLE 5001

A "deprotection solution" was prepared by combining in a 40 mL glass vial trifluoroacetic acid (22 mL), phenol (1.325 g), water (1.25 mL), TIPS (0.5 mL) and DTT (0.25 g). To a 1 dram vial charged with the entirety of Intermediate 5001B prepared above was added the "deprotection solution" (1.0 mL). The solution was mixed for 1.5 h in a shaker running at 500 rpm, then was poured into a 25 mL test tube charged with $Et_2O$ (20 mL). A small amount of white solid precipitated. The mixture was centrifuged; the liquid was decanted. The solids were suspended in $Et_2O$ (10 mL). The mixture was centrifuged, the liquid was decanted. The resulting residue was dissolved in MeOH, and crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 0.5 mg, and its estimated purity by LCMS analysis was 100%.

Analysis condition A: Retention time=1.49 min; ESI-MS (+) m/z 864.2 (M+2H) Analysis condition B: Retention time=2.73 min; ESI-MS(+) m/z 863.8 (M+2H) ESI-HRMS (+) m/z: Calculated: 863.4774 Found: 863.4768.

PREPARATION OF EXAMPLE 5002
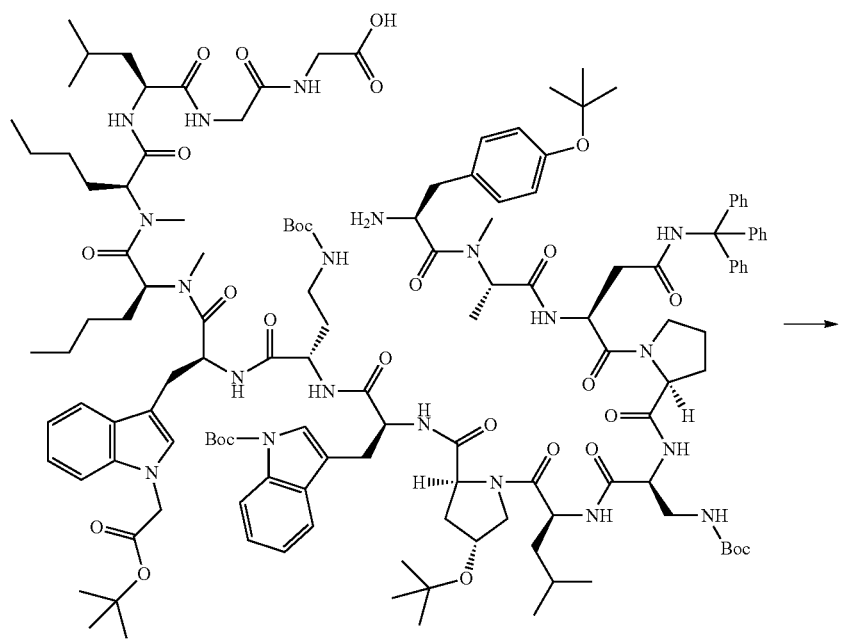
Intermediate 5002A
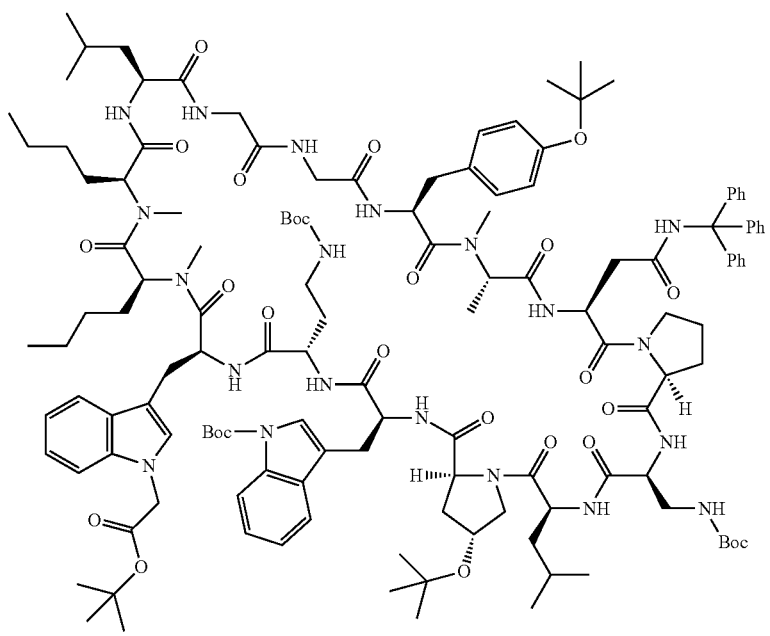
Intermediate 5002B

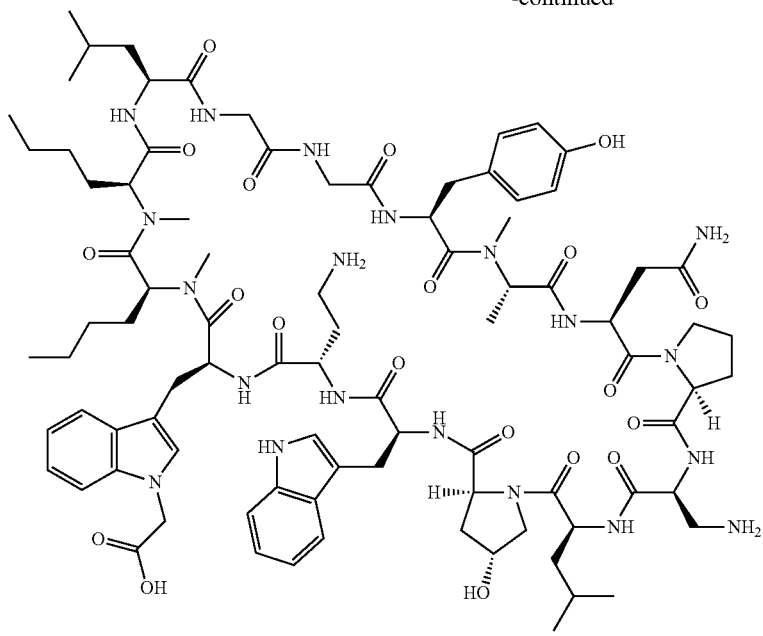

Example 5002

Preparation of Intermediate 5002A

"General Synthetic Sequence A" was followed. To the reaction vessel containing resin from the automated sequence was added piperidine:DMF (20:80 v/v, 2.0 mL). The mixture was periodically agitated for 4 minutes and then the solution was drained through the frit. To the reaction vessel was added piperidine:DMF (20:80 v/v, 2.0 mL). The mixture was periodically agitated for 4 minutes and then the solution was drained through the frit. The resin was washed successively five times as follows: for each wash, DMF (2.0 mL) was added through the top of the vessel and the resulting mixture was periodically agitated for 90 seconds before the solution was drained through the frit. The resin was washed successively five times as follows: for each wash, DCM (2.0 mL) was added through the top of the vessel and the resulting mixture was periodically agitated for 90 seconds before the solution was drained through the frit. The resin was then immediately transferred using DCM (8 mL) to a 15 mL vial. To the solution was added hexafluoroisopropanol (2 mL). The resin immediately turned deep red; the solution remained colorless. The mixture briefly manually agitated, then was allowed to stand at r.t. for 15 minutes, then was filtered. The filtrate was transferred to a 15 mL vial and was concentrated under a $N_2$ stream to afford a solid residue, Intermediate 5002A.

Preparation of Intermediate 5002B

To a 15 mL vial charged with the entirety of Intermediate 5002A prepared above was added DMF (0.50 mL), then HATU (45.6 mg, 0.120 mmol) then DIPEA (0.114 mL, 0.650 mmol). The yellow solution was stirred for 30 minutes. The solution was directly subjected to HPLC purification under the following conditions: Column: Luna C18, 30×100 mm, 5-μm particles; Mobile Phase A: 5:95 acetonitrile:water with 0.1% TFA; Mobile Phase B: 95:5 acetonitrile:water with 0.1% TFA; Gradient: 60-100% B over 10 minutes, then a 10 minute hold at 100% B; Flow: 42 mL/min. Fractions containing the desired product were combined and dried via centrifugal evaporation to afford a white solid, Intermediate 5002B.

PREPARATION OF EXAMPLE 5002

A "deprotection solution" was prepared by combining in a 40 mL glass vial trifluoroacetic acid (22 mL), phenol (1.325 g), water (1.25 mL), TIPS (0.5 mL) and DTT (0.25 g). To a 1 dram vial charged with the entirety of Intermediate 5002B prepared above was added the "deprotection solution" (1.0 mL). The solution was mixed for 1.0 h in a shaker running at 500 rpm, then was poured into a 25 mL test tube charged with $Et_2O$ (15 mL). A small amount of white solid precipitated. The mixture was centrifuged; the liquid was decanted. The solids were suspended in $Et_2O$ (15 mL). The mixture was centrifuged, the liquid was decanted. The resulting residue was dissolved in MeOH, and to the solution was added DIPEA (0.050 mL). The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 1.7 mg, and its estimated purity by LCMS analysis was 95%. Analysis condition A: Retention time=1.69 min; ESI-MS(−) m/z 891.3 (M-2H) ESI-HRMS(+) m/z: Calculated: 892.4801 Found: 892.4796.

PREPARATION OF EXAMPLE 5003
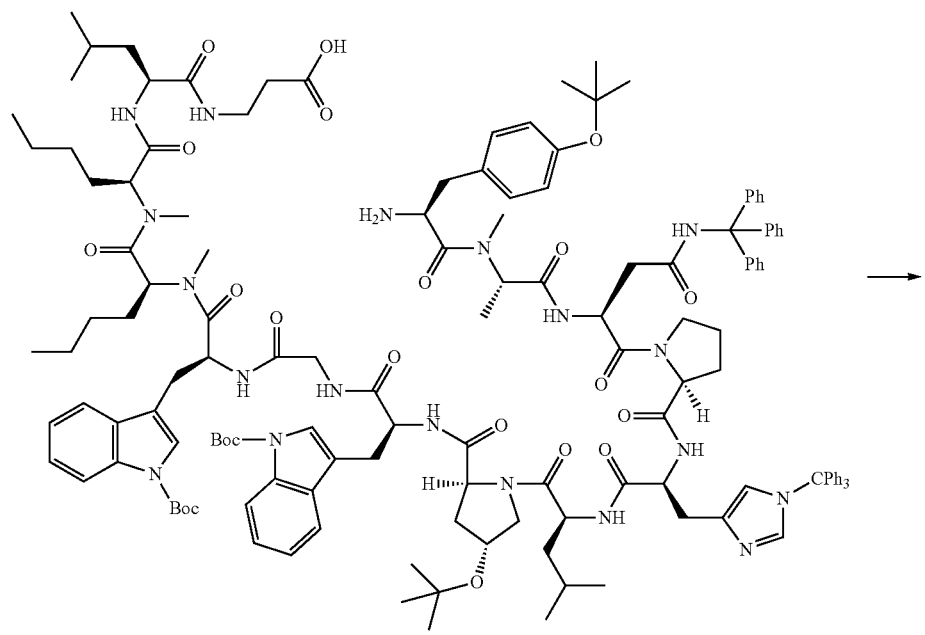
Intermediate 5003A
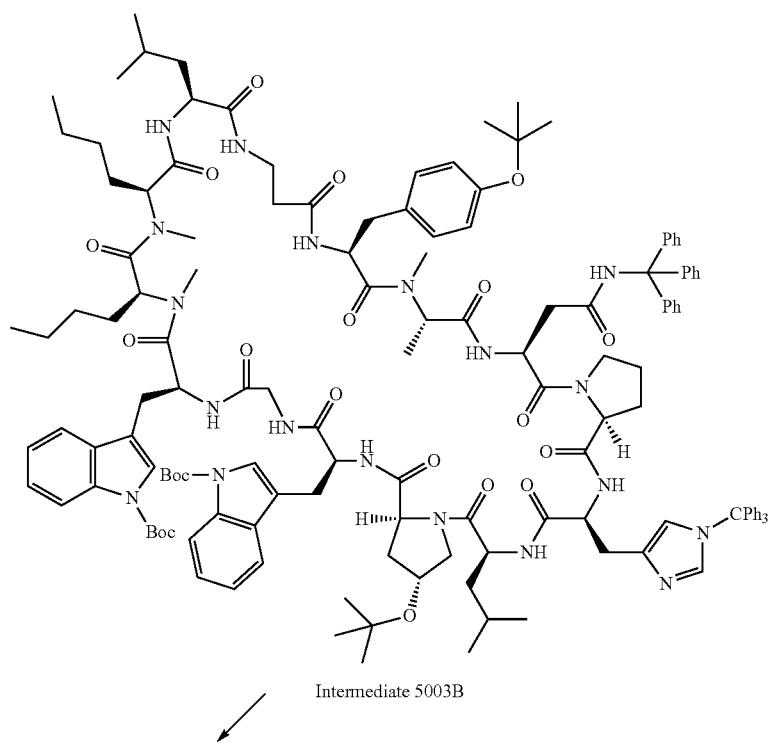
Intermediate 5003B -continued

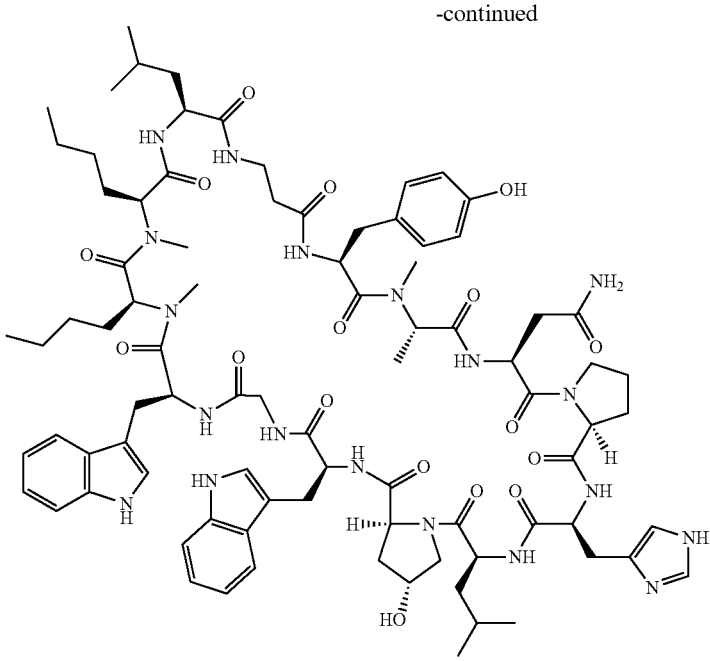

Intermediate 5003

Preparation of Intermediate 5003A

"General Synthetic Sequence A" was followed on a 0.200 mmol scale using a 45 mL reaction vessel (RV). To the reaction vessel containing resin from the automated sequence was added piperidine:DMF (20:80 v/v, 4.0 mL). The mixture was periodically agitated for 4 minutes and then the solution was drained through the frit. To the reaction vessel was added piperidine:DMF (20:80 v/v, 4.0 mL). The mixture was periodically agitated for 4 minutes and then the solution was drained through the frit. The resin was washed successively five times as follows: for each wash, DMF (4.0 mL) was added through the top of the vessel and the resulting mixture was periodically agitated for 90 seconds before the solution was drained through the frit. The resin was washed successively five times as follows: for each wash, DCM (4.0 mL) was added through the top of the vessel and the resulting mixture was periodically agitated for 90 seconds before the solution was drained through the frit. To the RV was added DCM (16 mL) followed by hexafluoroisopropanol (4 mL). The mixture was briefly manually agitated, then was allowed to stand at r.t. for 15 minutes, then was filtered through the bottom frit of the RV. The filtrate was transferred to a 25 mL test and was concentrated via centrifugal evaporation to afford Intermediate 5003A.

Preparation of Intermediate 5003B

To the 25 mL test tube charged with the entirety of Intermediate 5003A prepared above was added DMF (2.0 mL), then HATU (84 mg, 0.220 mmol) then DIPEA (0.350 mL, 2.00 mmol). The test tube was placed in a shaker running at 500 rpm for 30 minutes. The solution was then diluted with PhMe to a volume of 20 mL and the solution was then concentrated via centrifugal evaporation to afford a solid residue, crude Intermediate 5003B.

PREPARATION OF EXAMPLE 5003

A "deprotection solution" was prepared by combining in a 40 mL glass vial trifluoroacetic acid (22 mL), phenol (1.325 g), water (1.25 mL), TIPS (0.5 mL) and DTT (0.25 g). To the 25 mL test tube charged with the entirety of crude Intermediate 5003B prepared above was added the "deprotection solution" (2.0 mL). The solution was mixed for 1.0 h in a shaker running at 500 rpm, then was diluted via the addition of Et$_2$O (15 mL). A white precipitate was formed as the mixture was thoroughly mixed. The mixture was centrifuged; the liquid was decanted. The solids were suspended in Et$_2$O (15 mL). The mixture was centrifuged, the liquid was decanted. The resulting residue was dissolved in water: MeOH:MeCN (1 mL:1 mL:1 mL), and to the solution was added ammonium bicarbonate (app. 25 mg). The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 3-minute hold at 100% B; Flow: 20 mL/min. Fractions containing the desired product were combined and dried via centrifugal evaporation. The yield of the product was 1.0 mg, and its estimated purity by LCMS analysis was 100%. Analysis condition A: Retention time=1.93 min; ESI-MS(+) m/z 846.7 (M+2H); ESI-HRMS (+) m/z: Calculated: 845.9588 Found: 845.9576.

PREPARATION OF EXAMPLE 5004
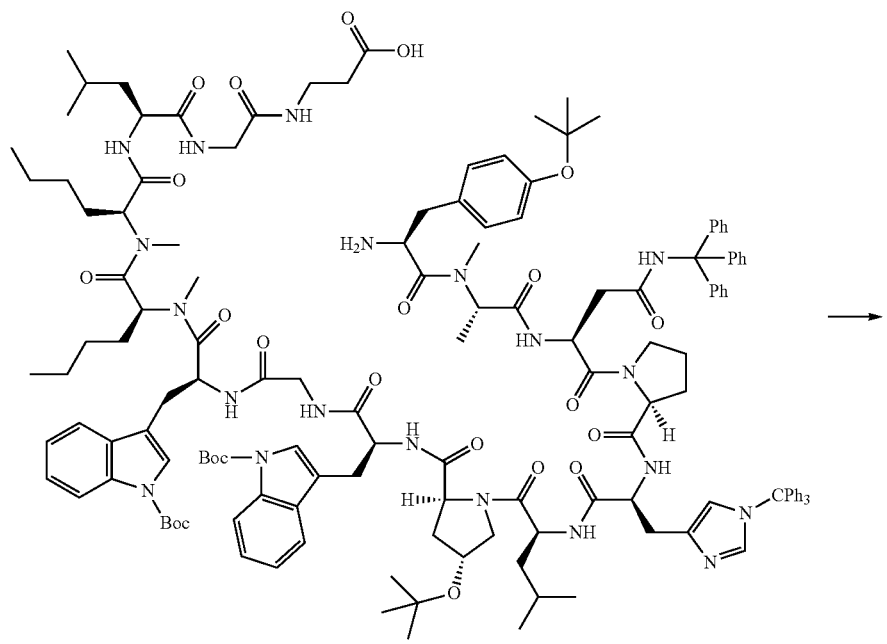
Intermediate 5004A
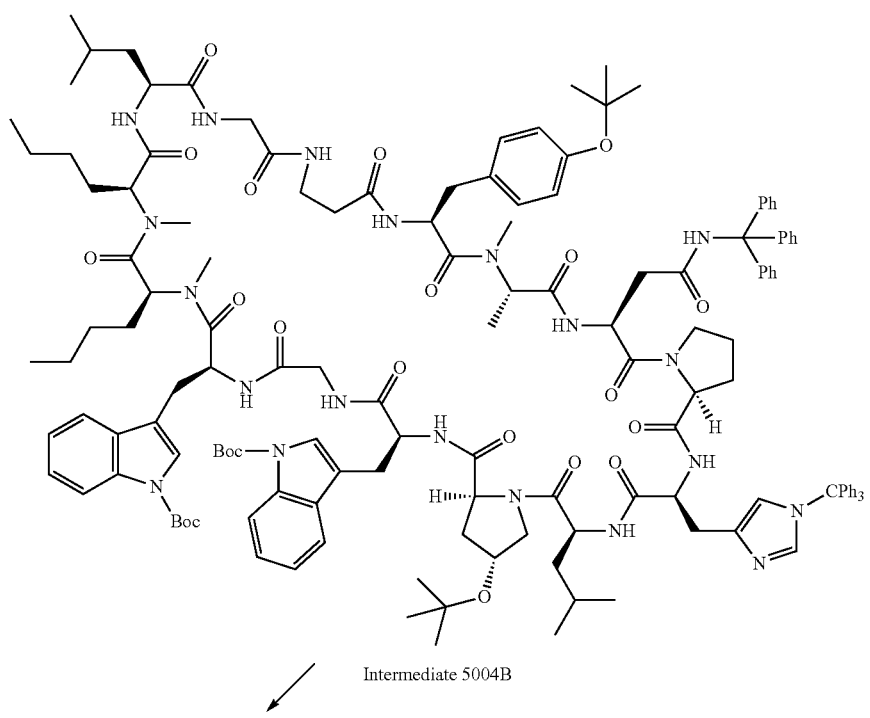
Intermediate 5004B -continued

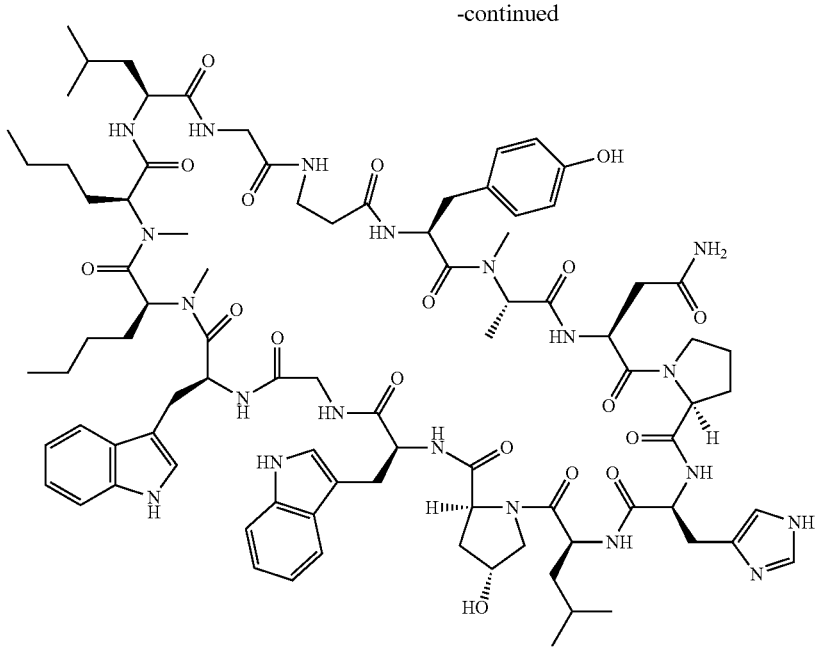

Example 5004

Preparation of Intermediate 5004A

"General Synthetic Sequence A" was followed on a 0.200 mmol scale using a 45 mL reaction vessel (RV). To the reaction vessel containing resin from the automated sequence was added piperidine:DMF (20:80 v/v, 4.0 mL). The mixture was periodically agitated for 4 minutes and then the solution was drained through the frit. To the reaction vessel was added piperidine:DMF (20:80 v/v, 4.0 mL). The mixture was periodically agitated for 4 minutes and then the solution was drained through the frit. The resin was washed successively five times as follows: for each wash, DMF (4.0 mL) was added through the top of the vessel and the resulting mixture was periodically agitated for 90 seconds before the solution was drained through the frit. The resin was washed successively five times as follows: for each wash, DCM (4.0 mL) was added through the top of the vessel and the resulting mixture was periodically agitated for 90 seconds before the solution was drained through the frit. To the RV was added DCM (16 mL) followed by hexafluoroisopropanol (4 mL). The mixture was briefly manually agitated, then was allowed to stand at r.t. for 15 minutes, then was filtered through the bottom frit of the RV. The filtrate was transferred to a 25 mL test and was concentrated via centrifugal evaporation to afford Intermediate 5004A.

Preparation of Intermediate 5004B

To the 25 mL test tube charged with the entirety of Intermediate 5004A prepared above was added DMF (2.0 mL), then DIPEA (0.350 mL, 2.00 mmol), then a solution of HATU (84 mg, 0.220 mmol) in DMF (0.5 mL). The test tube was placed in a shaker running at 500 rpm for 2 h. The solution was then diluted with PhMe to a volume of 20 mL and the solution was then concentrated via centrifugal evaporation to afford a solid residue, crude Intermediate 5004B.

PREPARATION OF EXAMPLE 5004

A "deprotection solution" was prepared by combining in a 40 mL glass vial trifluoroacetic acid (22 mL), phenol (1.325 g), water (1.25 mL), TIPS (0.5 mL) and DTT (0.25 g). To the 25 mL test tube charged with the entirety of crude Intermediate 5004B prepared above was added the "deprotection solution" (2.0 mL). The solution was mixed for 1.0 h in a shaker running at 500 rpm, then was diluted via the addition of $Et_2O$ (15 mL). A white precipitate was formed as the mixture was thoroughly mixed. The mixture was centrifuged; the liquid was decanted. The solids were suspended in $Et_2O$ (15 mL). The mixture was centrifuged, the liquid was decanted. The resulting residue was dissolved in water:MeOH:MeCN (1 mL:1 mL:1 mL), and to the solution was added ammonium bicarbonate (app. 100 mg). The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 5.5 mg, and its estimated purity by LCMS analysis was 100%. Analysis condition A: Retention time=1.84 min; ESI-MS(+) m/z 874.4 (M+2H)

ESI-HRMS(+) m/z: Calculated: 874.4696 Found: 874.4679.

PREPARATION OF EXAMPLE 5005
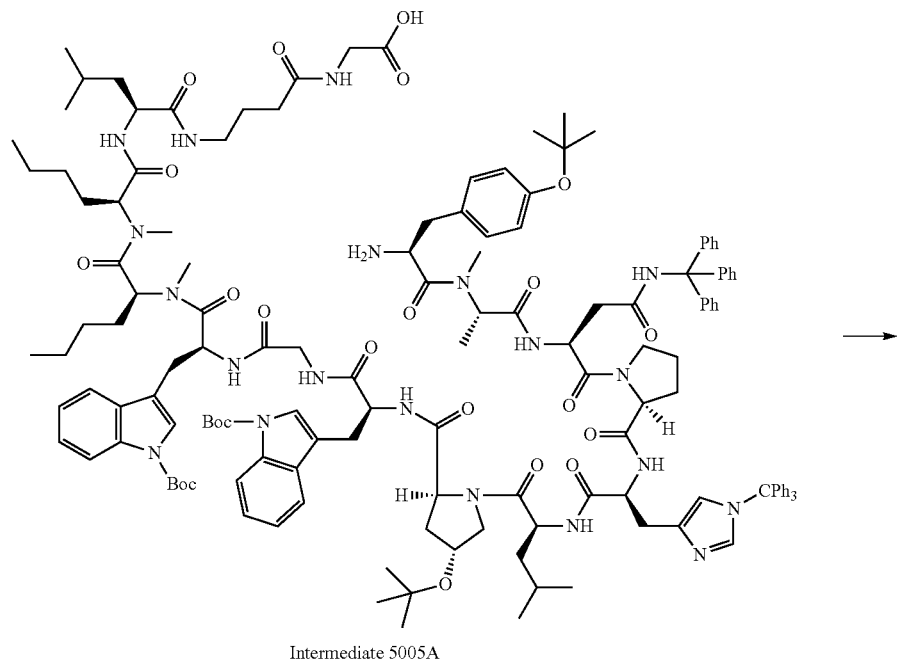
Intermediate 5005A
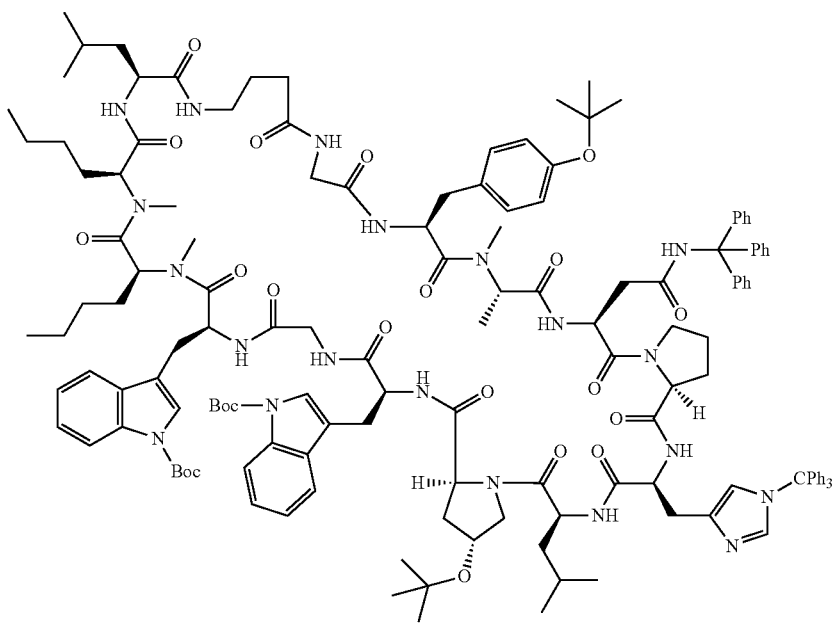
Intermediate 5005B

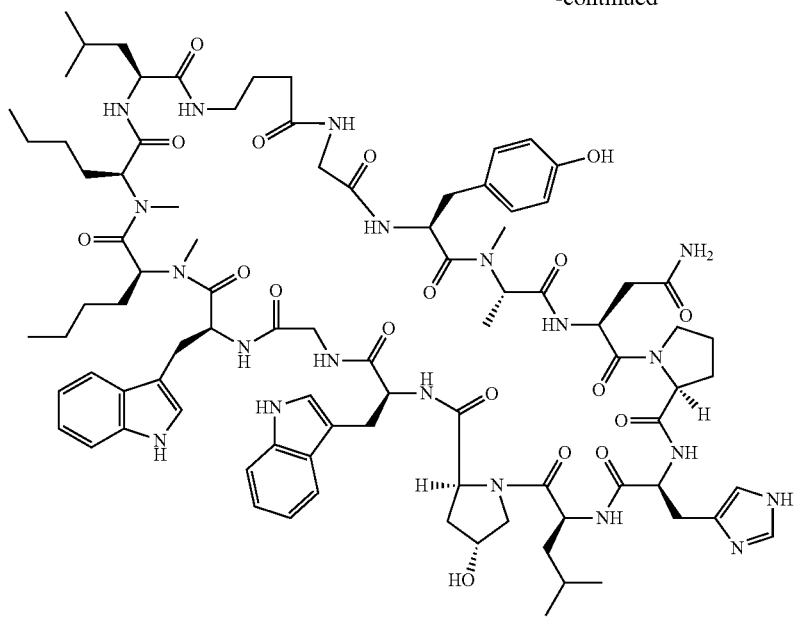

Example 5005

Preparation of Intermediate 5005A

"General Synthetic Sequence A" was followed on a 0.200 mmol scale using a 45 mL reaction vessel (RV). To the reaction vessel containing resin from the automated sequence was added piperidine:DMF (20:80 v/v, 4.0 mL). The mixture was periodically agitated for 4 minutes and then the solution was drained through the frit. To the reaction vessel was added piperidine:DMF (20:80 v/v, 4.0 mL). The mixture was periodically agitated for 4 minutes and then the solution was drained through the frit. The resin was washed successively five times as follows: for each wash, DMF (4.0 mL) was added through the top of the vessel and the resulting mixture was periodically agitated for 90 seconds before the solution was drained through the frit. The resin was washed successively five times as follows: for each wash, DCM (4.0 mL) was added through the top of the vessel and the resulting mixture was periodically agitated for 90 seconds before the solution was drained through the frit. To the RV was added DCM (16 mL) followed by hexafluoroisopropanol (4 mL). The mixture was briefly manually agitated, then was allowed to stand at r.t. for 15 minutes, then was filtered through the bottom frit of the RV. The filtrate was transferred to a 25 mL test and was concentrated via centrifugal evaporation to afford Intermediate 5005A.

Preparation of Intermediate 5005B

To the 25 mL test tube charged with the entirety of Intermediate 5005A prepared above was added DMF (2.0 mL), then DIPEA (0.350 mL, 2.00 mmol), then a solution of HATU (84 mg, 0.220 mmol) in DMF (0.5 mL). The test tube was placed in a shaker running at 500 rpm for 2 h. The solution was then diluted with PhMe to a volume of 20 mL and the solution was then concentrated via centrifugal evaporation to afford a solid residue, crude Intermediate 5005B.

PREPARATION OF EXAMPLE 5005

A "deprotection solution" was prepared by combining in a 40 mL glass vial trifluoroacetic acid (22 mL), phenol (1.325 g), water (1.25 mL), TIPS (0.5 mL) and DTT (0.25 g). To the 25 mL test tube charged with the entirety of crude Intermediate 5005B prepared above was added the "deprotection solution" (2.0 mL). The solution was mixed for 1.0 h in a shaker running at 500 rpm, then was diluted via the addition of $Et_2O$ (15 mL). A white precipitate was formed as the mixture was thoroughly mixed. The mixture was centrifuged; the liquid was decanted. The solids were suspended in $Et_2O$ (15 mL). The mixture was centrifuged, the liquid was decanted. The resulting residue was dissolved in water:MeOH:MeCN (1 mL:1 mL:1 mL), and to the solution was added ammonium bicarbonate (app. 100 mg). The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 30 minutes, then a 5-minute hold at 100% B; Flow: 20 mL/min. Fractions containing the desired product were combined and dried via centrifugal evaporation. The yield of the product was 4.5 mg, and its estimated purity by LCMS analysis was 95%. Analysis condition A: Retention time=1.84 min; ESI-MS(+) m/z 881.5 (M+2H); ESI-HRMS(+) m/z: Calculated: 881.4774 Found: 881.4761.

PREPARATION OF EXAMPLE 5006
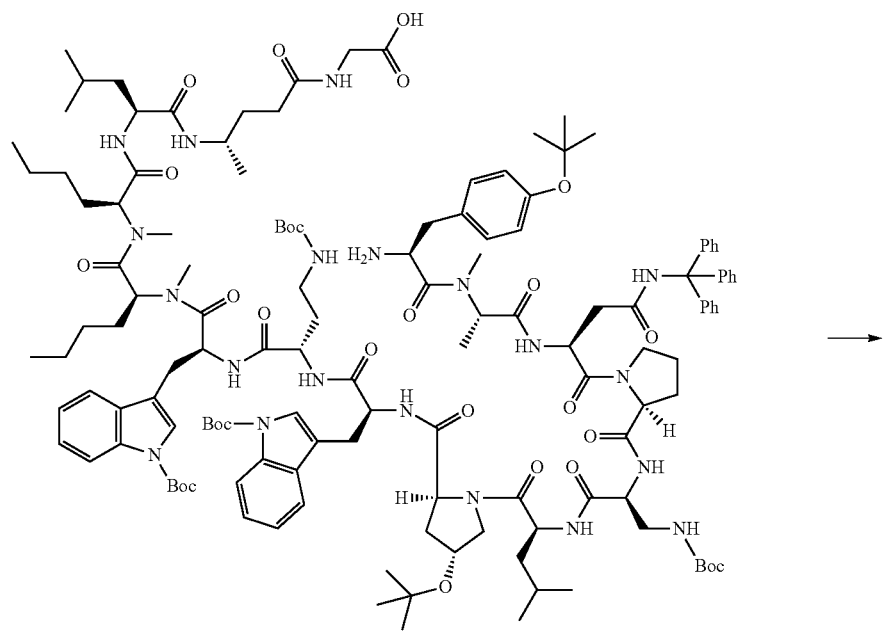
Intermediate 5006A
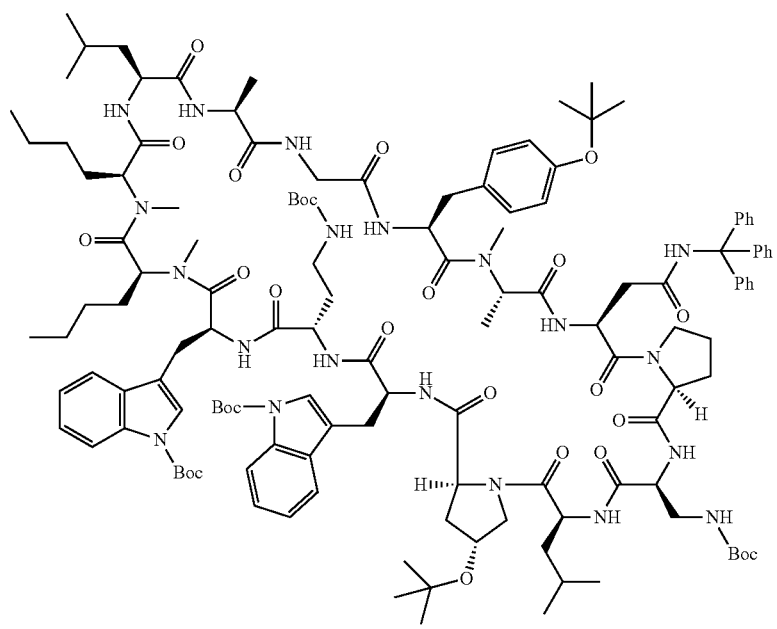
Intermediate 5006B

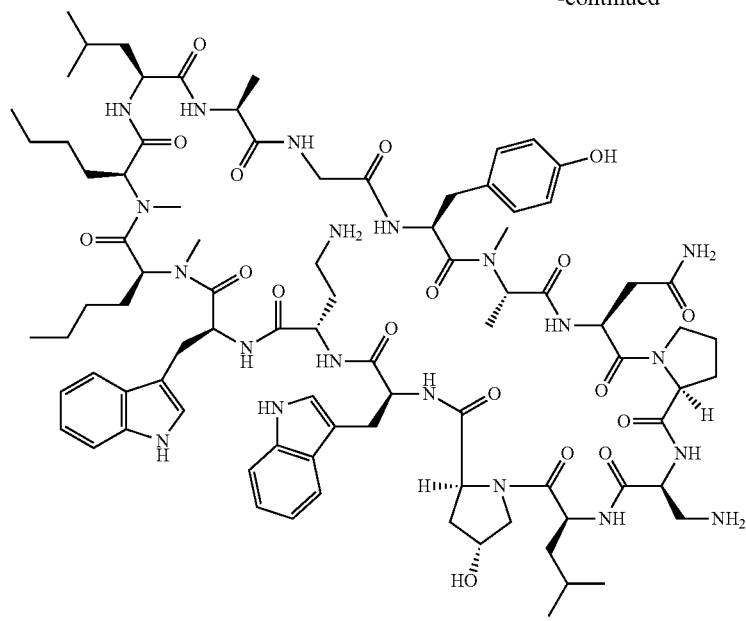

Example 5006

Preparation of Intermediate 5006A

"General Synthetic Sequence A" was followed on a 0.200 mmol scale using a 45 mL reaction vessel (RV). To the reaction vessel containing resin from the automated sequence was added piperidine:DMF (20:80 v/v, 4.0 mL). The mixture was periodically agitated for 4 minutes and then the solution was drained through the frit. To the reaction vessel was added piperidine:DMF (20:80 v/v, 4.0 mL). The mixture was periodically agitated for 4 minutes and then the solution was drained through the frit. The resin was washed successively five times as follows: for each wash, DMF (4.0 mL) was added through the top of the vessel and the resulting mixture was periodically agitated for 90 seconds before the solution was drained through the frit. The resin was washed successively five times as follows: for each wash, DCM (4.0 mL) was added through the top of the vessel and the resulting mixture was periodically agitated for 90 seconds before the solution was drained through the frit. To the RV was added DCM (16 mL) followed by hexafluoroisopropanol (4 mL). The mixture was briefly manually agitated, then was allowed to stand at r.t. for 15 minutes, then was filtered through the bottom frit of the RV. The filtrate was reserved. To the RV containing the resin was added DCM (16 mL) followed by hexafluoroisopropanol (4 mL). The mixture was briefly manually agitated, then was allowed to stand at r.t. for 15 minutes, then was filtered through the bottom frit of the RV. The filtrates were combined concentrated via centrifugal evaporation to afford Intermediate 5006A.

Preparation of Intermediate 5006B

To a 7 mL vial with the entirety of Intermediate 5006A prepared above was added DMF (2.0 mL), then DIPEA (0.350 mL, 2.00 mmol), then a HATU (84 mg, 0.220 mmol). The test tube was placed in a shaker running at 500 rpm for 1 h. The solution was concentrated under a $N_2$ stream, then was further concentrated under high vacuum to afford and amber solid, crude Intermediate 5006B.

PREPARATION OF EXAMPLE 5006

A "deprotection solution" was prepared by combining in a 40 mL glass vial trifluoroacetic acid (22 mL), phenol (1.325 g), water (1.25 mL), TIPS (0.5 mL) and DTT (0.25 g). To the vial charged with the entirety of crude Intermediate 5006B prepared above was added the "deprotection solution" (2.0 mL). The solution was mixed for 1.0 h in a shaker running at 500 rpm, then was diluted via the addition of $Et_2O$ (15 mL). A white precipitate was formed as the mixture was thoroughly mixed. The mixture was centrifuged; the liquid was decanted. The solids were suspended in $Et_2O$ (15 mL). The mixture was centrifuged, the liquid was decanted. The resulting residue was dissolved in water: MeOH:MeCN (1 mL:1 mL:1 mL), and to the solution was added ammonium bicarbonate (app. 25 mg). The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 6.4 mg, and its estimated purity by LCMS analysis was 100%. Analysis condition A: Retention time=1.77 min; ESI-MS(+) m/z 870.1 (M+2H); Analysis condition C: Retention time=1.44 min; ESI-MS(+) m/z 871.2 (M+2H).

PREPARATION OF EXAMPLE 5007
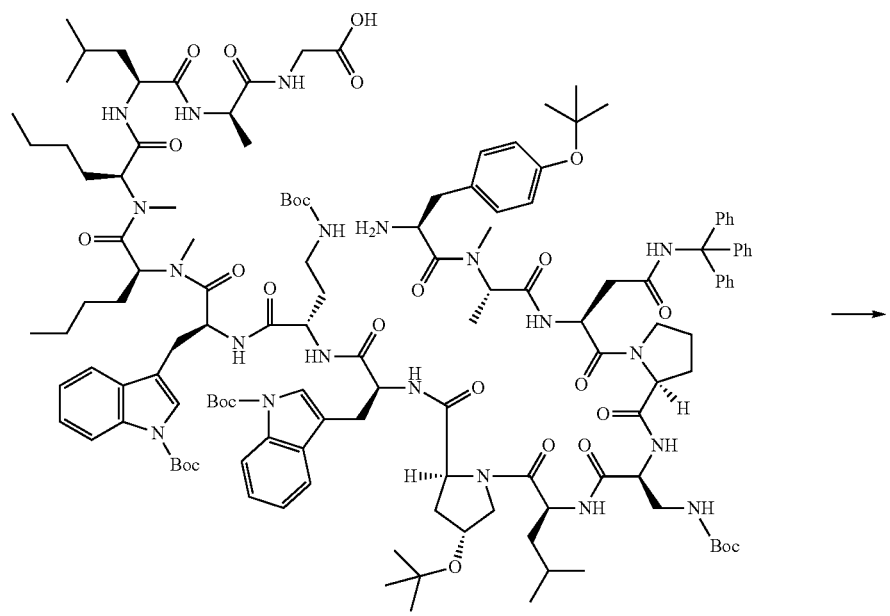
Intermediate 5007A
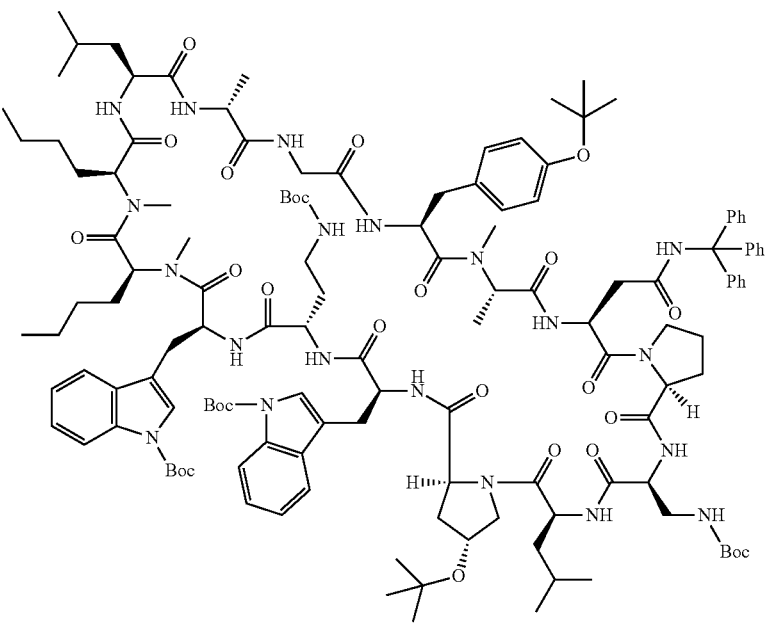
Intermediate 5007B

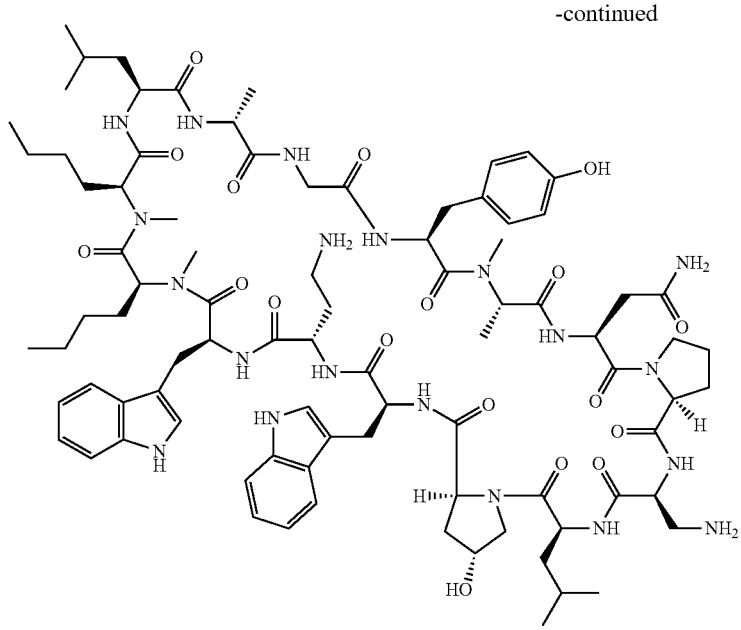

Example 5007

Preparation of Intermediate 5007A

"General Synthetic Sequence A" was followed on a 0.200 mmol scale using a 45 mL reaction vessel (RV). To the reaction vessel containing resin from the automated sequence was added piperidine:DMF (20:80 v/v, 4.0 mL). The mixture was periodically agitated for 4 minutes and then the solution was drained through the frit. To the reaction vessel was added piperidine:DMF (20:80 v/v, 4.0 mL). The mixture was periodically agitated for 4 minutes and then the solution was drained through the frit. The resin was washed successively five times as follows: for each wash, DMF (4.0 mL) was added through the top of the vessel and the resulting mixture was periodically agitated for 90 seconds before the solution was drained through the frit. The resin was washed successively five times as follows: for each wash, DCM (4.0 mL) was added through the top of the vessel and the resulting mixture was periodically agitated for 90 seconds before the solution was drained through the frit. To the RV was added DCM (16 mL) followed by hexafluoroisopropanol (4 mL). The mixture was briefly manually agitated, then was allowed to stand at r.t. for 15 minutes, then was filtered through the bottom frit of the RV. The filtrate was reserved. To the RV containing the resin was added DCM (16 mL) followed by hexafluoroisopropanol (4 mL). The mixture was briefly manually agitated, then was allowed to stand at r.t. for 15 minutes, then was filtered through the bottom frit of the RV. The filtrates were combined concentrated via centrifugal evaporation to afford Intermediate 5007A.

Preparation of Intermediate 5007B

To a 7 mL vial with the entirety of Intermediate 5007A prepared above was added DMF (2.0 mL), then DIPEA (0.350 mL, 2.00 mmol), then a HATU (84 mg, 0.220 mmol). The test tube was placed in a shaker running at 500 rpm for 1 h. The solution was concentrated under a $N_2$ stream, then was further concentrated under high vacuum to afford and amber solid, crude Intermediate 5007B.

PREPARATION OF EXAMPLE 5007

A "deprotection solution" was prepared by combining in a 40 mL glass vial trifluoroacetic acid (22 mL), phenol (1.325 g), water (1.25 mL), TIPS (0.5 mL) and DTT (0.25 g). To the vial charged with the entirety of crude Intermediate 5007B prepared above was added the "deprotection solution" (2.0 mL). The solution was mixed for 1.0 h in a shaker running at 500 rpm, then was diluted via the addition of $Et_2O$ (15 mL). A white precipitate was formed as the mixture was thoroughly mixed. The mixture was centrifuged; the liquid was decanted. The solids were suspended in $Et_2O$ (15 mL). The mixture was centrifuged, the liquid was decanted. The resulting residue was dissolved in water: MeOH:MeCN (1 mL:1 mL:1 mL), and to the solution was added ammonium bicarbonate (app. 25 mg). The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 6.5 mg, and its estimated purity by LCMS analysis was 97%. Analysis condition A: Retention time=1.70 min; ESI-MS(+) m/z 871.0 (M+2H).

PREPARATION OF EXAMPLE 5008
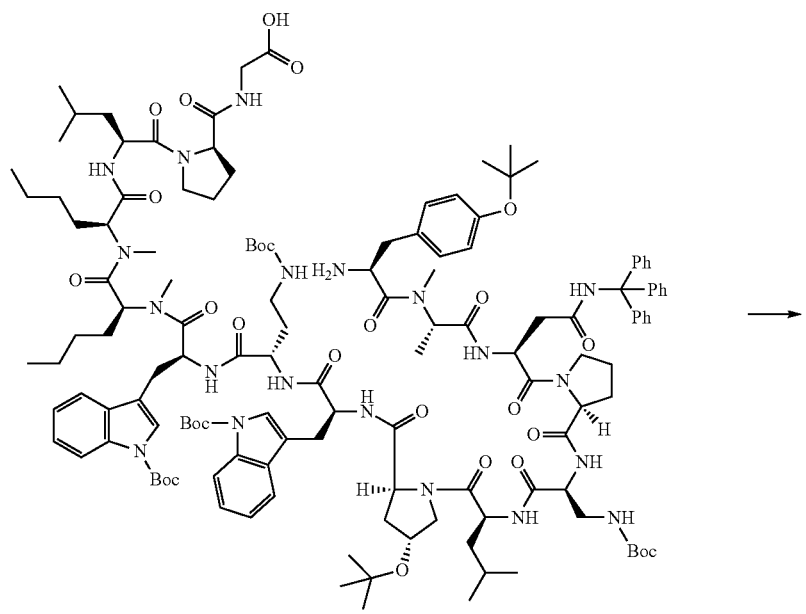
Intermediate 5008A
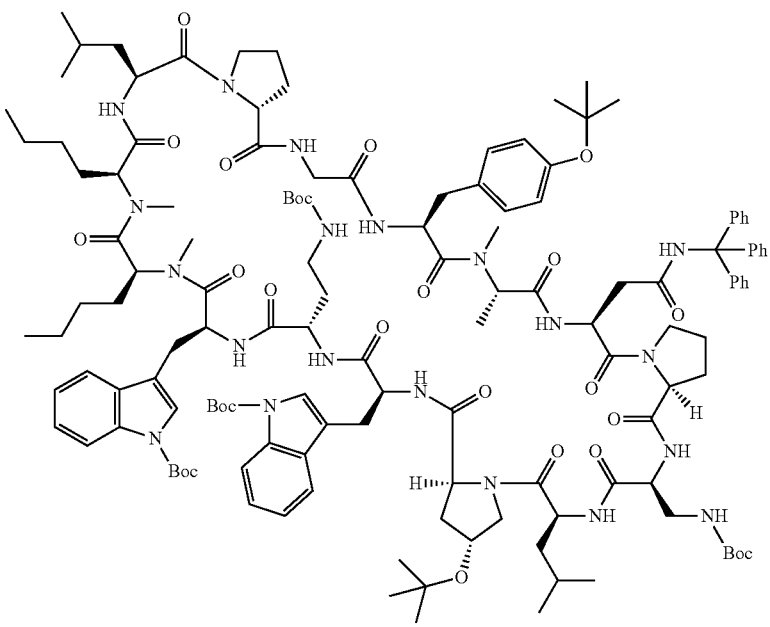
Intermediate 5008B

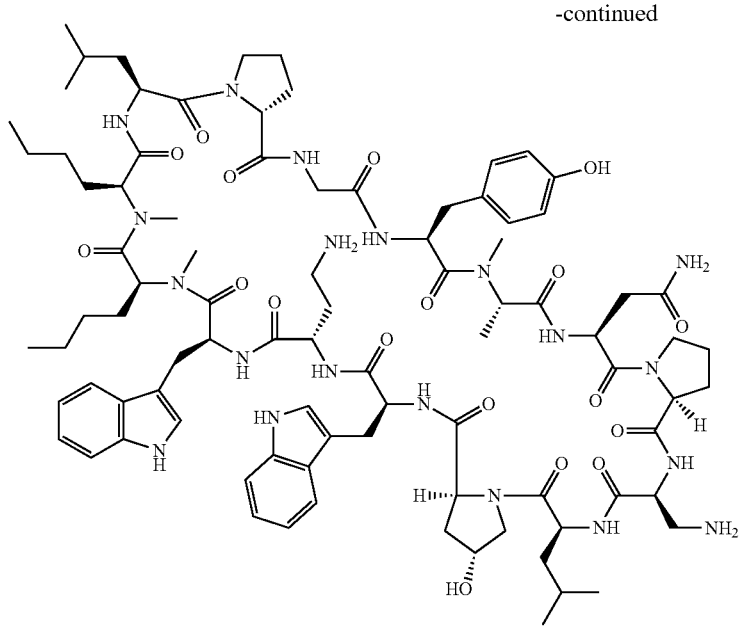

Example 5008

Preparation of Intermediate 5008A

"General Synthetic Sequence A" was followed on a 0.200 mmol scale using a 45 mL reaction vessel (RV). To the reaction vessel containing resin from the automated sequence was added piperidine:DMF (20:80 v/v, 4.0 mL). The mixture was periodically agitated for 4 minutes and then the solution was drained through the frit. To the reaction vessel was added piperidine:DMF (20:80 v/v, 4.0 mL). The mixture was periodically agitated for 4 minutes and then the solution was drained through the frit. The resin was washed successively five times as follows: for each wash, DMF (4.0 mL) was added through the top of the vessel and the resulting mixture was periodically agitated for 90 seconds before the solution was drained through the frit. The resin was washed successively five times as follows: for each wash, DCM (4.0 mL) was added through the top of the vessel and the resulting mixture was periodically agitated for 90 seconds before the solution was drained through the frit. To the RV was added DCM (16 mL) followed by hexafluoroisopropanol (4 mL). The mixture was briefly manually agitated, then was allowed to stand at r.t. for 15 minutes, then was filtered through the bottom frit of the RV. The filtrate was reserved. To the RV containing the resin was added DCM (16 mL) followed by hexafluoroisopropanol (4 mL). The mixture was briefly manually agitated, then was allowed to stand at r.t. for 15 minutes, then was filtered through the bottom frit of the RV. The filtrates were combined concentrated via centrifugal evaporation to afford Intermediate 5008A.

Preparation of Intermediate 5008B

To a 7 mL vial with the entirety of Intermediate 5008A prepared above was added DMF (2.0 mL), then DIPEA (0.350 mL, 2.00 mmol), then a HATU (84 mg, 0.220 mmol). The test tube was placed in a shaker running at 500 rpm for 1 h. The solution was concentrated under a $N_2$ stream, then was further concentrated under high vacuum to afford and amber solid, crude Intermediate 5008B.

PREPARATION OF EXAMPLE 5008

A "deprotection solution" was prepared by combining in a 40 mL glass vial trifluoroacetic acid (22 mL), phenol (1.325 g), water (1.25 mL), TIPS (0.5 mL) and DTT (0.25 g). To the vial charged with the entirety of crude Intermediate 5008B prepared above was added the "deprotection solution" (2.0 mL). The solution was mixed for 1.0 h in a shaker running at 500 rpm, then was diluted via the addition of $Et_2O$ (15 mL). A white precipitate was formed as the mixture was thoroughly mixed. The mixture was centrifuged; the liquid was decanted. The solids were suspended in $Et_2O$ (15 mL). The mixture was centrifuged, the liquid was decanted. The resulting residue was dissolved in water:MeOH:MeCN (1 mL:1 mL:1 mL), and to the solution was added ammonium bicarbonate (app. 25 mg). The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 30 minutes, then a 4-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The yield of the product was 5.1 mg, and its estimated purity by LCMS analysis was 98%. Analysis condition A: Retention time=1.75 min; ESI-MS(+) m/z 883.7 (M+2H); Analysis condition B: Retention time=2.73 min; ESI-MS(+) m/z 884.3 (M+2H).

PREPARATION OF EXAMPLE 5009
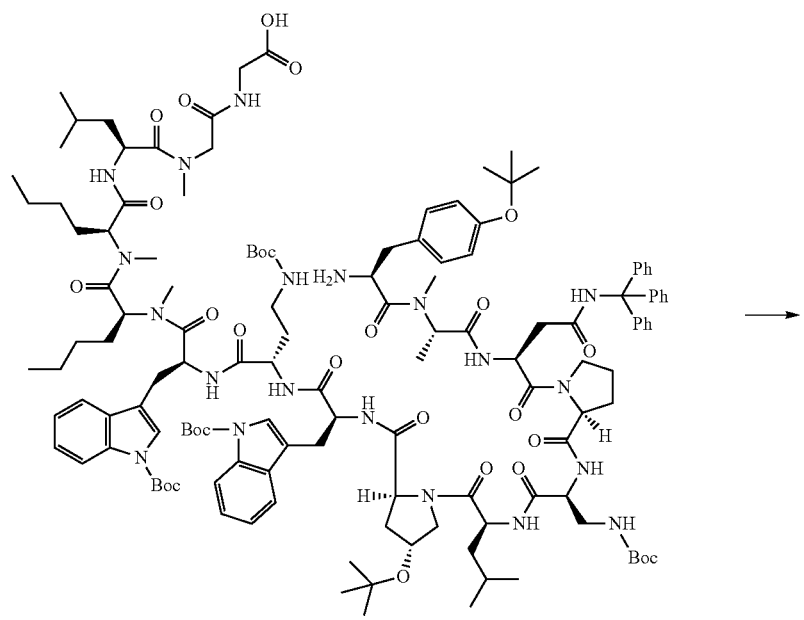
Intermediate 5009A
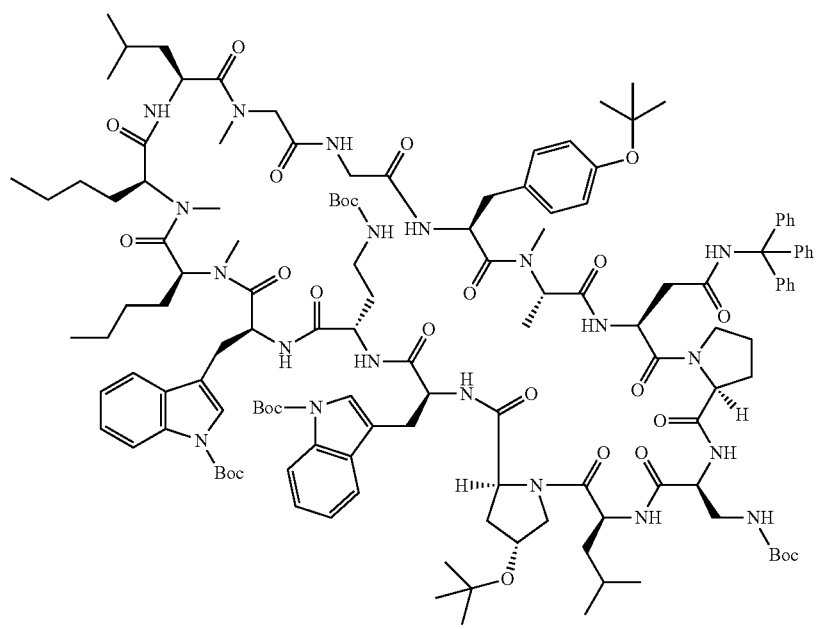
Intermediate 5009B

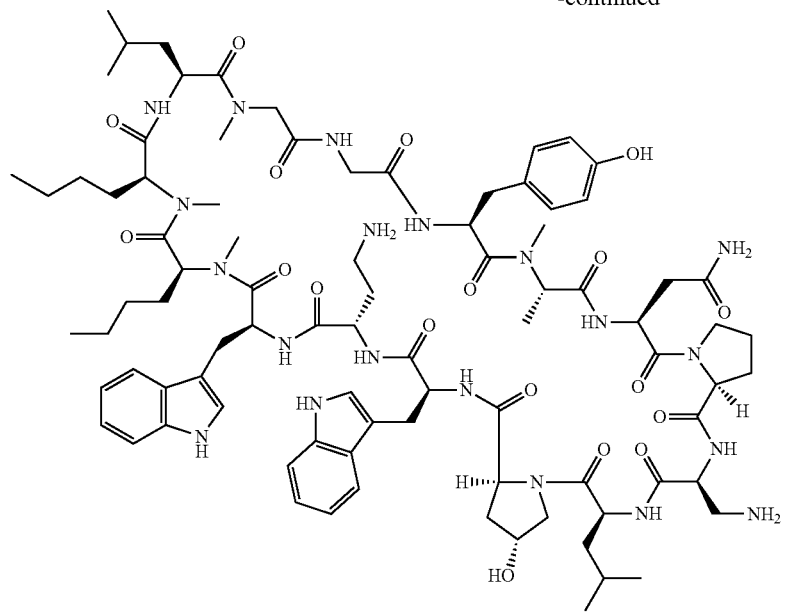

Example 5009

Preparation of Intermediate 5009A

"General Synthetic Sequence A" was followed on a 0.200 mmol scale using a 45 mL reaction vessel (RV). To the reaction vessel containing resin from the automated sequence was added piperidine:DMF (20:80 v/v, 4.0 mL). The mixture was periodically agitated for 4 minutes and then the solution was drained through the frit. To the reaction vessel was added piperidine:DMF (20:80 v/v, 4.0 mL). The mixture was periodically agitated for 4 minutes and then the solution was drained through the frit. The resin was washed successively five times as follows: for each wash, DMF (4.0 mL) was added through the top of the vessel and the resulting mixture was periodically agitated for 90 seconds before the solution was drained through the frit. The resin was washed successively five times as follows: for each wash, DCM (4.0 mL) was added through the top of the vessel and the resulting mixture was periodically agitated for 90 seconds before the solution was drained through the frit. To the RV was added DCM (16 mL) followed by hexafluoroisopropanol (4 mL). The mixture was briefly manually agitated, then was allowed to stand at r.t. for 15 minutes, then was filtered through the bottom frit of the RV. The filtrate was reserved. To the RV containing the resin was added DCM (16 mL) followed by hexafluoroisopropanol (4 mL). The mixture was briefly manually agitated, then was allowed to stand at r.t. for 15 minutes, then was filtered through the bottom frit of the RV. The filtrates were combined concentrated via centrifugal evaporation to afford Intermediate 5009A.

Preparation of Intermediate 5009B

To a 7 mL vial with the entirety of Intermediate 5009A prepared above was added DMF (2.0 mL), then DIPEA (0.350 mL, 2.00 mmol), then a HATU (84 mg, 0.220 mmol). The test tube was placed in a shaker running at 500 rpm for 1 h. The solution was concentrated under a $N_2$ stream, then was further concentrated under high vacuum to afford and amber solid, crude Intermediate 5009B.

PREPARATION OF EXAMPLE 5009

A "deprotection solution" was prepared by combining in a 40 mL glass vial trifluoroacetic acid (22 mL), phenol (1.325 g), water (1.25 mL), TIPS (0.5 mL) and DTT (0.25 g). To the vial charged with the entirety of crude Intermediate 5009B prepared above was added the "deprotection solution" (2.0 mL). The solution was mixed for 1.0 h in a shaker running at 500 rpm, then was diluted via the addition of $Et_2O$ (15 mL). A white precipitate was formed as the mixture was thoroughly mixed. The mixture was centrifuged; the liquid was decanted. The solids were suspended in $Et_2O$ (15 mL). The mixture was centrifuged, the liquid was decanted. The resulting residue was dissolved in water:MeOH:MeCN (1 mL:1 mL:1 mL), and to the solution was added ammonium bicarbonate (app. 25 mg). The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 45-85% B over 30 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 6.2 mg, and its estimated purity by LCMS analysis was 100%. Analysis condition A: Retention time=1.72 min; ESI-MS(+) m/z 869.1 (M+2H); Analysis condition C: Retention time=1.47 min; ESI-MS(+) m/z 1852.5 (M+TFA).

General Procedures for Symphony X Method E/F/G

General Coupling Procedures:

All manipulations were performed under automation on a Symphony X peptide synthesizer (Protein Technologies). All procedures unless noted were performed in a 10 mL polypropylene tube fitted with a bottom frit; where the scale of the reaction exceeded 0.100 mmol, a 40 mL polypropylene tube fitted with a bottom frit was used. The tube connects to a the Symphony X peptide synthesizer through both the bottom and the top of the tube. DMF and DCM can be added through the top of the tube, which washes down the sides of the tube equally. The remaining reagents are added through the top of the tube and pass up through the frit to contact the resin. All solutions are removed through the bottom of the tube. "Periodic agitation" describes a brief pulse of N2 gas through the bottom frit; the pulse lasts approximately 5 seconds and occurs every 30 seconds. Chloroacetyl chloride solutions in DMF were used within 24 h of preparation. Amino acid solutions were generally not used beyond three weeks from preparation. HATU solutions were used within 5 days of preparation. DMF=dimethylformamide; HATU=1-[Bis(dimethylamino) methylene]-1H-1,2,3-triazolo[4,5-b]pyridinium 3-oxid hexafluorophosphate; DIPEA=diisopropylethylamine; Rink resin: 4-((2,4-dimethoxyphenyl)(Fmocamino) methyl)phenoxymethylpolystyrene.

Resin-Swelling Procedure:

To a 10 mL polypropylene solid-phase reaction vessel was added resin (0.100 mmol). The resin was washed (swelled) three times as follows: to the reaction vessel was added DMF (2.0 mL), upon which the mixture was periodically agitated for 10 minutes before the solvent was drained through the frit.

Single-Coupling Procedure:

To the reaction vessel containing resin from the previous step was added piperidine:DMF (20:80 v/v, 2.0 mL). The mixture was periodically agitated for 3 minutes and then the solution was drained through the frit. To the reaction vessel was added piperidine:DMF (20:80 v/v, 2.0 mL). The mixture was periodically agitated for 3 minutes and then the solution was drained through the frit. The resin was washed successively six times as follows: for each wash, DMF (2.0 mL) was added through the top of the vessel and the resulting mixture was periodically agitated for 30 seconds before the solution was drained through the frit. To the reaction vessel was added the amino acid (0.2M in DMF, 1.0 mL, 2 eq), then HATU (0.2M in DMF, 1.0 mL, 2 eq), and finally DIPEA (0.4M in DMF, 1.0 mL, 4 eq). The mixture was periodically agitated for 15 minutes, then the reaction solution was drained through the frit. The resin was washed successively four times as follows: for each wash, DMF (2.0 mL) was added through the top of the vessel and the resulting mixture was periodically agitated for 30 seconds before the solution was drained through the frit. To the reaction vessel was added acetic anhydride (2.0 mL). The mixture was periodically agitated for 10 minutes, then the solution was drained through the frit. The resin was washed successively four times as follows: for each wash, DMF (2.0 mL) was added through the top of the vessel and the resulting mixture was periodically agitated for 90 seconds before the solution was drained through the frit. The resulting resin was used directly in the next step.

Single-Coupling 1 h Procedure:

To the reaction vessel containing resin from the previous step was added piperidine:DMF (20:80 v/v, 2.0 mL). The mixture was periodically agitated for 3 minutes and then the solution was drained through the frit. To the reaction vessel was added piperidine:DMF (20:80 v/v, 2.0 mL). The mixture was periodically agitated for 3 minutes and then the solution was drained through the frit. The resin was washed successively six times as follows: for each wash, DMF (2.0 mL) was added through the top of the vessel and the resulting mixture was periodically agitated for 30 seconds before the solution was drained through the frit. To the reaction vessel was added the amino acid (0.2M in DMF, 1.0 mL, 2 eq), then HATU (0.2M in DMF, 1.0 mL, 2 eq), and finally DIPEA (0.4M in DMF, 1.0 mL, 4 eq). The mixture was periodically agitated for 60 minutes, then the reaction solution was drained through the frit. The resin was washed successively four times as follows: for each wash, DMF (2.0 mL) was added through the top of the vessel and the resulting mixture was periodically agitated for 30 seconds before the solution was drained through the frit. To the reaction vessel was added acetic anhydride (2.0 mL). The mixture was periodically agitated for 10 minutes, then the solution was drained through the frit. The resin was washed successively four times as follows: for each wash, DMF (2.0 mL) was added through the top of the vessel and the resulting mixture was periodically agitated for 90 seconds before the solution was drained through the frit. The resulting resin was used directly in the next step.

Double-Coupling Procedure:

To the reaction vessel containing resin from the previous step was added piperidine:DMF (20:80 v/v, 2.0 mL). The mixture was periodically agitated for 3 minutes and then the solution was drained through the frit. To the reaction vessel was added piperidine:DMF (20:80 v/v, 2.0 mL). The mixture was periodically agitated for 3 minutes and then the solution was drained through the frit. The resin was washed successively six times as follows: for each wash, DMF (2.0 mL) was added through the top of the vessel and the resulting mixture was periodically agitated for 30 seconds before the solution was drained through the frit. To the reaction vessel was added the amino acid (0.2M in DMF, 1.0 mL, 2 eq), then HATU (0.2M in DMF, 1.0 mL, 2 eq), and finally DIPEA (0.4M in DMF, 1.0 mL, 4 eq). The mixture was periodically agitated for 15 minutes, then the reaction solution was drained through the frit. The resin was twice washed as follows: for each wash, DMF (2.0 mL) was added through the top of the vessel and the resulting mixture was periodically agitated for 30 seconds before the solution was drained through the frit. To the reaction vessel was added the amino acid (0.2M in DMF, 1.0 mL, 2 eq), then HATU (0.2M in DMF, 1.0 mL, 2 eq), and finally DIPEA (0.4M in DMF, 1.0 mL, 4 eq). The mixture was periodically agitated for 15 minutes, then the reaction solution was drained through the frit. The resin was twice washed as follows: for each wash, DMF (2.0 mL) was added through the top of the vessel and the resulting mixture was periodically agitated for 30 seconds before the solution was drained through the frit. To the reaction vessel was added acetic anhydride (2.0 mL). The mixture was periodically agitated for 10 minutes, then the solution was drained through the frit. The resin was washed successively four times as follows: for each wash, DMF (2.0 mL) was added through the top of the vessel and the resulting mixture was periodically agitated for 90 seconds before the solution was drained through the frit. The resulting resin was used directly in the next step.

Chloroacetyl Chloride Coupling Procedure:

To the reaction vessel containing the resin from the previous step was added piperidine:DMF (20:80 v/v, 2.0 mL). The mixture was periodically agitated for 3 minutes and then the solution was drained through the frit. To the reaction vessel was added piperidine:DMF (20:80 v/v, 2.0 mL). The mixture was periodically agitated for 3 minutes and then the solution was drained through the frit. The resin was washed successively six times as follows: for each wash, DMF (2.0 mL) was added through the top of the vessel and the resulting mixture was periodically agitated for 30 seconds before the solution was drained through the frit. To the reaction vessel was added DIPEA (0.8M in DMF, 3.0 mL, 24 eq), then chloroacetyl chloride (0.8M in DMF, 1.65 mL, 13.2 eq). The mixture was periodically agitated for 30 minutes, then the solution was drained through the frit. The resin was washed successively three times as follows: for each wash, DMF (2.0 mL) was added to top of the vessel and the resulting mixture was periodically agitated for 90 seconds before the solution was drained through the frit. The resin was washed successively four times as follows: for each wash, $CH_2Cl_2$ (2.0 mL) was added to top of the vessel and the resulting mixture was periodically agitated for 90 seconds before the solution was drained through the frit. The resulting resin was placed under a $N_2$ stream for 15 minutes.

Deprotection Method:

All manipulations were performed manually unless noted. The procedure of "Deprotection Method" describes an experiment performed on a 0.100 mmol scale. The procedure can be scaled beyond 0.100 mmol scale by adjusting the described volumes by the multiple of the scale. A "deprotection solution" was prepared by combining in a 40 mL glass vial trifluoroacetic acid (38 mL), DTT (1 g) and triisopropylsilane (1 mL). The resin was removed from the reaction vessel and transferred to a 4 mL glass vial. To the vial was added the "deprotection solution" (2.0 mL). The mixture was vigorously mixed in a shaker (1000 RPM for 30-90 minutes). The mixture was filtered through a 0.2 micron syringe filter and the solids were extracted with the "deprotection solution" (1.0 mL). To a 24 mL test tube charged with the combined filtrates was added $Et_2O$ (15 mL). The mixture was vigorously mixed upon which a significant amount of a white solid precipitated. The mixture was centrifuged for 3 minutes, then the solution was decanted away from the solids and discarded. The solids were suspended in $Et_2O$ (20 mL); then the mixture was centrifuged for 3 minutes; and the solution was decanted away from the solids and discarded. For a final time, the solids were suspended in $Et_2O$ (20 mL); the mixture was centrifuged for 3 minutes; and the solution was decanted away from the solids and discarded to afford the crude peptide as a white to off-white solid.

Cyclization Method E:

All manipulations were performed manually unless noted. The procedure of "Cyclization Method E" describes an experiment performed on a 0.100 mmol scale. The procedure can be scaled beyond 0.100 mmol scale by adjusting the described volumes by the multiple of the scale. The crude peptide solids were dissolved in 20 mL DMF, and the solution was added 0.5 mL of DIEA then 50 mg of KI. The solution was heated to 65° C. for overnight. The reaction solution was concentrated and the residue was subjected to reverse-phase HPLC purification to afford the desired cyclic peptide.

General Procedures for Symphony X Method E:

"General procedures for Symphony X Method E" describes a general sequence of procedures that were used to afford the cyclic peptides described herein. To a 10 mL polypropylene solid-phase reaction vessel was added Rink resin, and the reaction vessel was placed on the Symphony X peptide synthesizer. "General coupling Procedures E": Resin-swelling procedure was followed. Then a series of amino acids couplings was sequentially performed on the Symphony X peptide synthesizer following "Single-coupling procedure" if the N-terminus of the resin-bound peptide was a primary amine or "Double-coupling procedure" if the N-terminus of the resin-bound peptide was a secondary amine. "Single-coupling 1 h" procedure was used with the amino acid (S)-2-((((9H-fluoren-9-yl)methoxy)carbonyl)amino)-3-(1-(2-(tert-butoxy)-2-oxoethyl)-1H-indol-3-yl)propanoic acid was coupled onto the resin. Chloroacetyl chloride coupling procedure was followed; then Deprotection Method was followed; then Cyclization Method E was followed.

Cyclization Method F:

All manipulations were performed manually unless noted. The procedure of "Cyclization Method F" describes an experiment performed on a 0.100 mmol scale. The procedure can be scaled beyond 0.100 mmol scale by adjusting the described volumes by the multiple of the scale. The crude peptide solids were dissolved in 20 mL DMF, and the solution was added 0.2 mL of DIEA. The reaction mixture was stirred for 5 minutes before cooling down to 0° C. 0.5 mL 0.2M CDI in DMF solution was added to the reaction mixture dropwise. The solution was stirred at rt for overnight. The reaction solution was concentrated and the residue was subjected to reverse-phase HPLC purification to afford the desired cyclic peptide.

General Procedures for Symphony X Method F:

"General procedures for Symphony X Method F" describes a general sequence of procedures that were used to afford the cyclic peptides described herein. To a 10 mL polypropylene solid-phase reaction vessel was added Rink resin, and the reaction vessel was placed on the Symphony X peptide synthesizer. "General coupling Procedures": Resin-swelling procedure was followed. Then a series of amino acids couplings was sequentially performed on the Symphony X peptide synthesizer following "Single-coupling procedure" if the N-terminus of the resin-bound peptide was a primary amine or "Double-coupling procedure" if the N-terminus of the resin-bound peptide was a secondary amine. "Single-coupling 1 h" procedure was used with the amino acid (S)-2-((((9H-fluoren-9-yl)methoxy)carbonyl)amino)-3-(1-(2-(tert-butoxy)-2-oxoethyl)-1H-indol-3-yl)propanoic acid was coupled onto the resin. After the last amino acid was coupled on the peptide, the reaction vessel was added piperidine:DMF (20:80 v/v, 2.0 mL). The mixture was shaked for 30 minutes on the shaker. The solution was drained through the frit. The resin was washed successively with DMF then DCM. Deprotection Method was followed; then Cyclization Method F was followed.

Cyclization Method G:

All manipulations were performed manually unless noted. The procedure of "Cyclization Method G" describes an experiment performed on a 0.100 mmol scale. The procedure can be scaled beyond 0.100 mmol scale by adjusting the described volumes by the multiple of the scale. The crude peptide solids were dissolved in 20 mL THF, and the solution was added 0.2 mL of DIEA. The reaction mixture was stirred for 5 minutes before cooling down to 0° C. 0.5 mL 0.2M oxalyl dichloride in THF solution was added to the reaction mixture dropwise. The solution was stirred at rt for overnight. The reaction solution was concentrated and the residue was subjected to reverse-phase HPLC purification to afford the desired cyclic peptide.

General Procedures for Symphony X Method G:

"General procedures for Symphony X Method G" describes a general sequence of procedures that were used to afford the cyclic peptides described herein. To a 10 mL polypropylene solid-phase reaction vessel was added Rink resin, and the reaction vessel was placed on the Symphony X peptide synthesizer. "General coupling Procedures": Resin-swelling procedure was followed. Then a series of amino acids couplings was sequentially performed on the Symphony X peptide synthesizer following "Single-coupling procedure" if the N-terminus of the resin-bound peptide was a primary amine or "Double-coupling procedure" if the N-terminus of the resin-bound peptide was a secondary amine. "Single-coupling 1 h" procedure was used with the amino acid (S)-2-((((9H-fluoren-9-yl)methoxy)carbonyl)amino)-3-(1-(2-(tert-butoxy)-2-oxoethyl)-1H-indol-3-yl)propanoic acid was coupled onto the resin. After the last amino acid was coupled on the peptide, the reaction vessel was added piperidine:DMF (20:80 v/v, 2.0 mL). The mixture was shaked for 30 minutes on the shaker. The solution was drained through the frit. The resin was washed successively with DMF then DCM. Deprotection Method was followed; then Cyclization Method G was followed.

Example 10001-10028 were prepared by following the "General procedures for Symphony X Method E".

PREPARATION OF EXAMPLE 10001

Example 10001

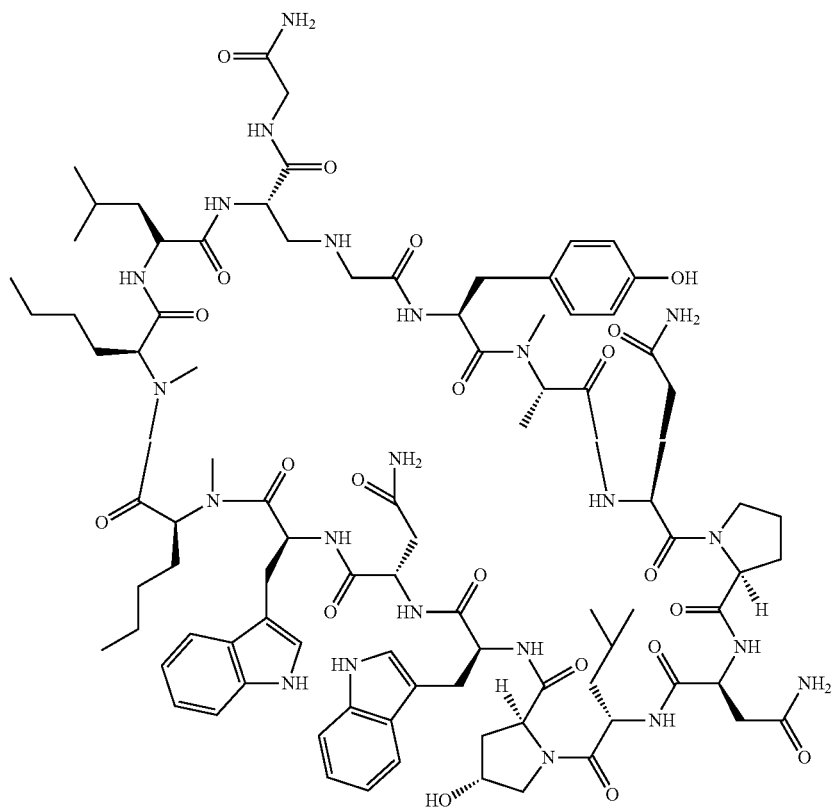

The crude material of Example 10001 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 20.9 mg, and its estimated purity by LCMS analysis was 100%.

Analysis condition A: Retention time=1.64 min; ESI-MS (+) m/z 927.55 (M+2H). Analysis condition B: Retention time=3.14 min; ESI-MS(+) m/z 927.75 (M+2H). ESI-HRMS(+) m/z: Calculated: 927.4885 (M+2H). Found: 927.4877 (M+2H).

PREPARATION OF EXAMPLE 10002

Example 10002

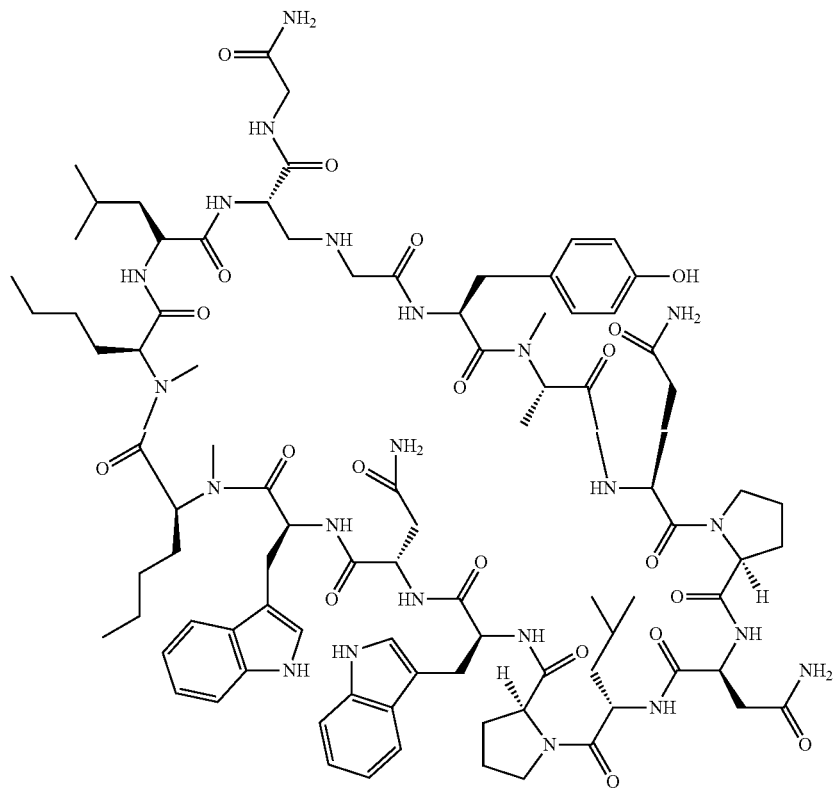

The crude material of Example 10002 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 14.9 mg, and its estimated purity by LCMS analysis was 96%.

Analysis condition A: Retention time=1.70 min; ESI-MS (+) m/z 919.75 (M+2H). Analysis condition B: Retention time=3.19 min; ESI-MS(+) m/z 919.75 (M+2H). ESI-HRMS(+) m/z: Calculated: 919.4910 (M+2H). Found: 919.4897 (M+2H).

PREPARATION OF EXAMPLE 10003

Example 10003

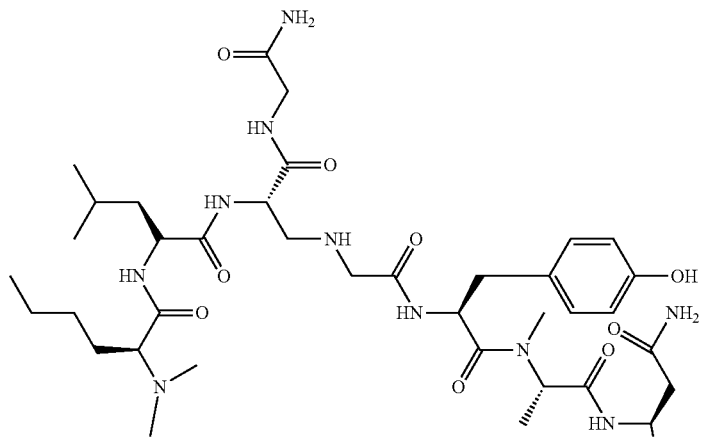

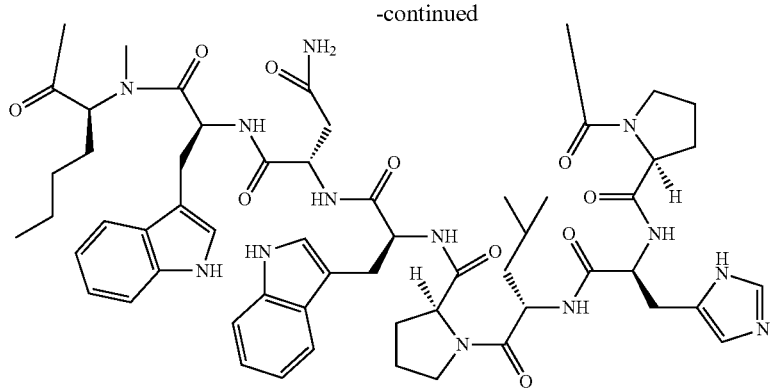

The crude material of Example 10003 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 14.2 mg, and its estimated purity by LCMS analysis was 98%.

Analysis condition A: Retention time=1.71 min; ESI-MS (+) m/z 931.30 (M+2H). Analysis condition B: Retention time=3.21 min; ESI-MS(+) m/z 931.30 (M+2H). ESI-HRMS(+) m/z: Calculated: 930.9990 (M+2H). Found: 930.9985 (M+2H).

PREPARATION OF EXAMPLE 10004

Example 10004

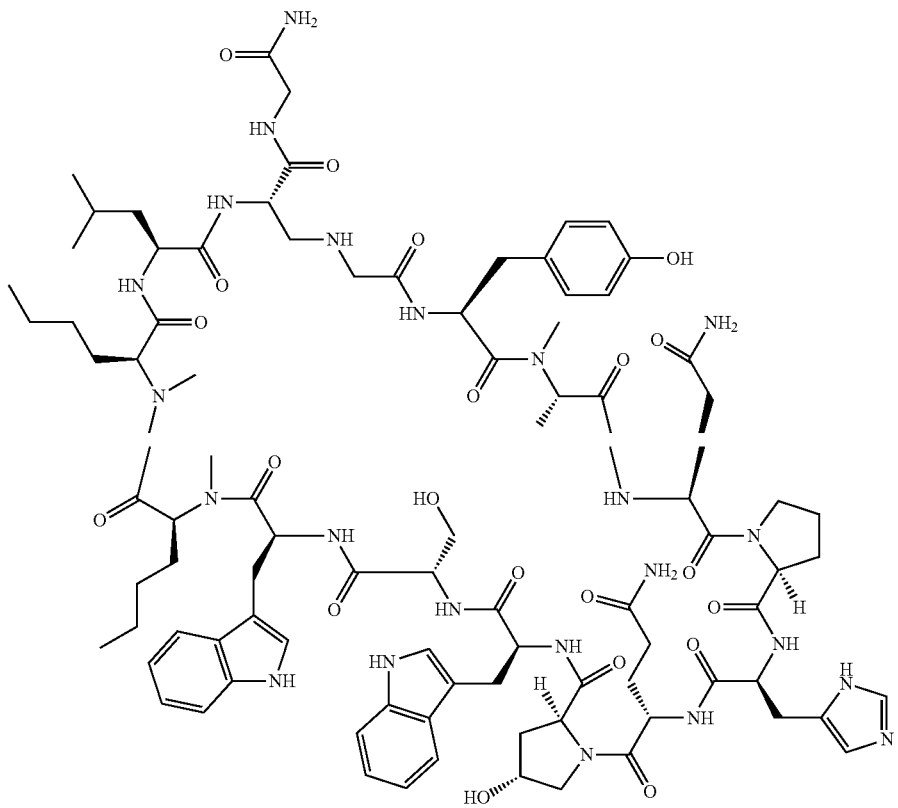

The crude material of Example 10004 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 2.7 mg, and its estimated purity by LCMS analysis was 100%.

Analysis condition A: Retention time=1.64 min; ESI-MS (+) m/z 933.20 (M+2H). Analysis condition B: Retention time=3.14 min; ESI-MS(+) m/z 933.25 (M+2H). ESI-HRMS(+) m/z: Calculated: 932.9783 (M+2H). Found: 932.9775 (M+2H).

PREPARATION OF EXAMPLE 10005

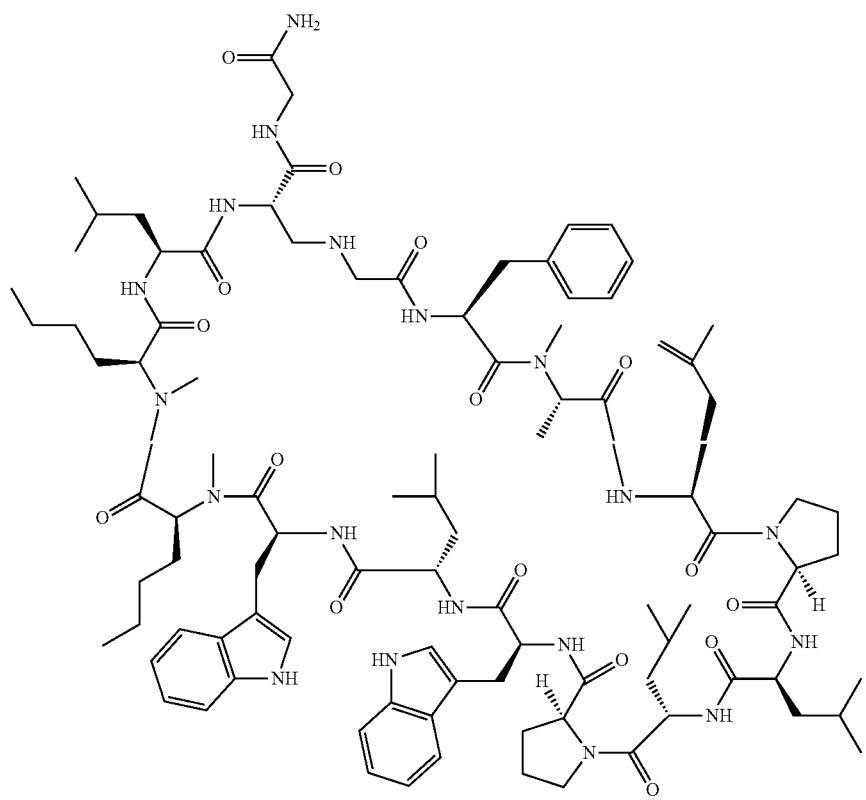

Example 10005

The crude material of Example 10005 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 20.3 mg, and its estimated purity by LCMS analysis was 100%.

Analysis condition A: Retention time=2.46 min; ESI-MS (+) m/z 910.50 (M+2H). Analysis condition B: Retention time=3.29 min; ESI-MS(+) m/z 910.50 (M+2H). ESI-HRMS(+) m/z: Calculated: 910.0553 (M+2H). Found: 910.0541 (M+2H).

PREPARATION OF EXAMPLE 10006

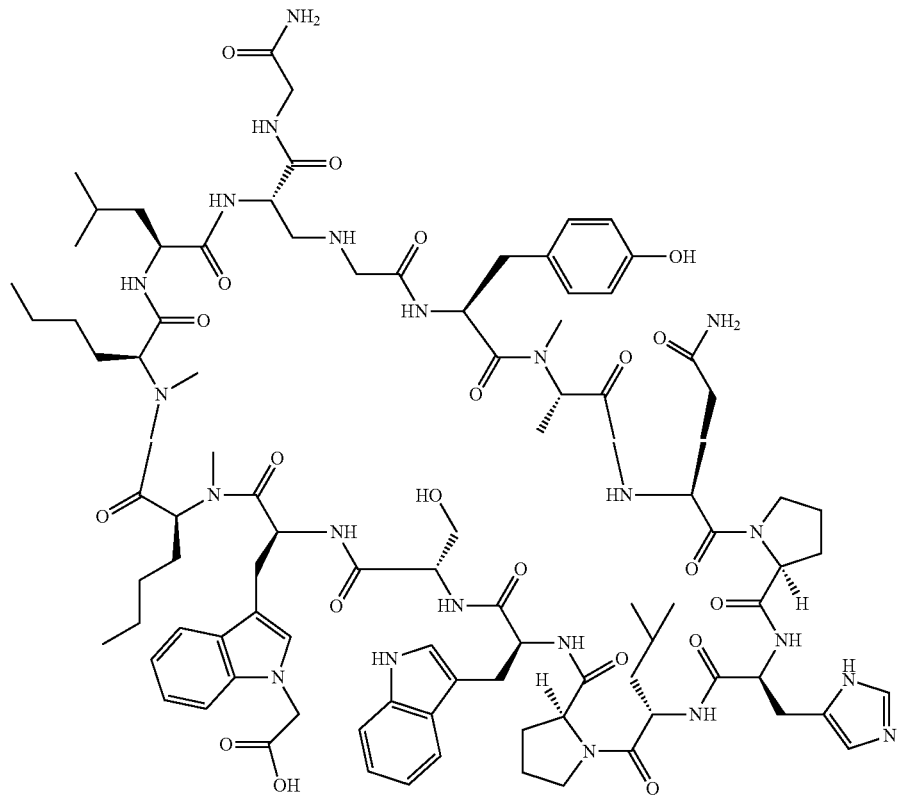

Example 10006

The crude material of Example 10006 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 8.4 mg, and its estimated purity by LCMS analysis was 98%.

Analysis condition A: Retention time=1.44 min; ESI-MS (+) m/z 947.40 (M+2H). Analysis condition B: Retention time=2.56 min; ESI-MS(+) m/z 946.80 (M+2H). ESI-HRMS(+) m/z: Calculated: 946.4963 (M+2H). Found: 946.4941 (M+2H).

PREPARATION OF EXAMPLE 10007

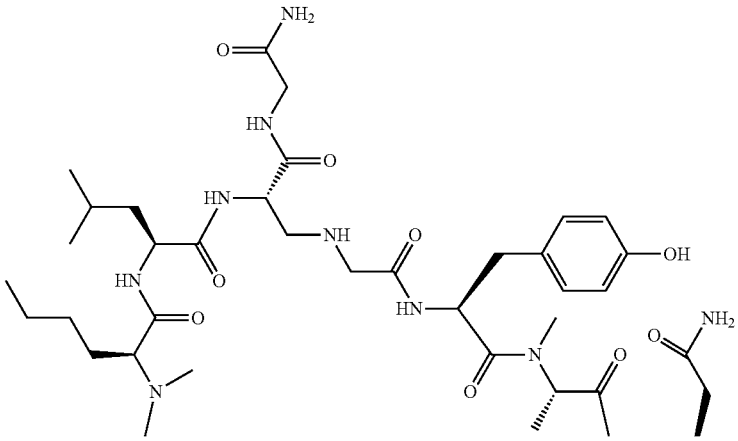

Example 10007

-continued

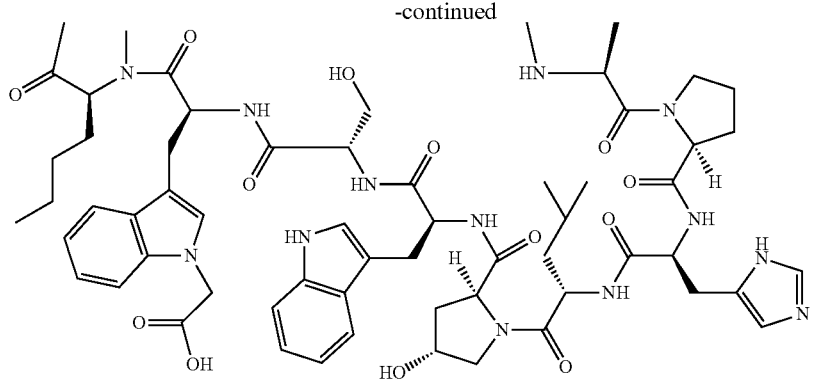

The crude material of Example 10007 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 1.5 mg, and its estimated purity by LCMS analysis was 97%.

Analysis condition A: Retention time=1.38 min; ESI-MS (+) m/z 954.70 (M+2H). Analysis condition B: Retention time=2.52 min; ESI-MS(+) m/z 954.40 (M+2H). ESI-HRMS(+) m/z: Calculated: 954.4938 (M+2H). Found: 954.4915 (M+2H).

PREPARATION OF EXAMPLE 10008

Example 10008

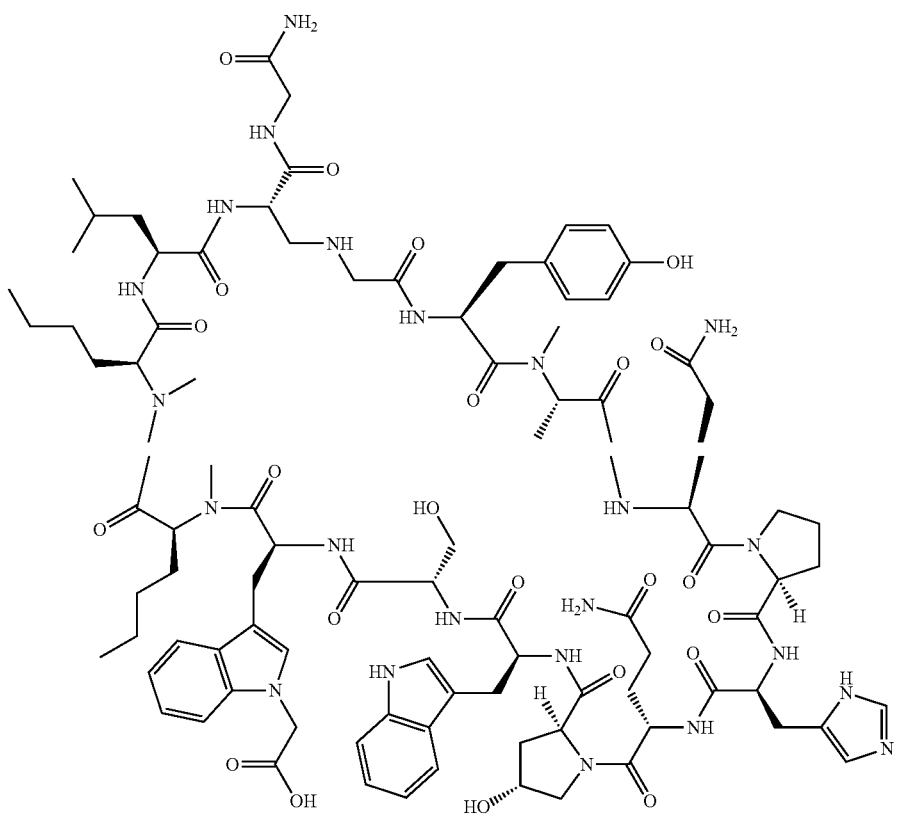

The crude material of Example 10008 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 5.6 mg, and its estimated purity by LCMS analysis was 97%.

Analysis condition A: Retention time=1.40 min; ESI-MS (+) m/z 962.30 (M+2H). Analysis condition B: Retention time=2.92 min; ESI-MS(+) m/z 962.25 (M+2H). ESI-HRMS(+) m/z: Calculated: 961.9810 (M+2H). Found: 961.9804 (M+2H).

PREPARATION OF EXAMPLE 10009

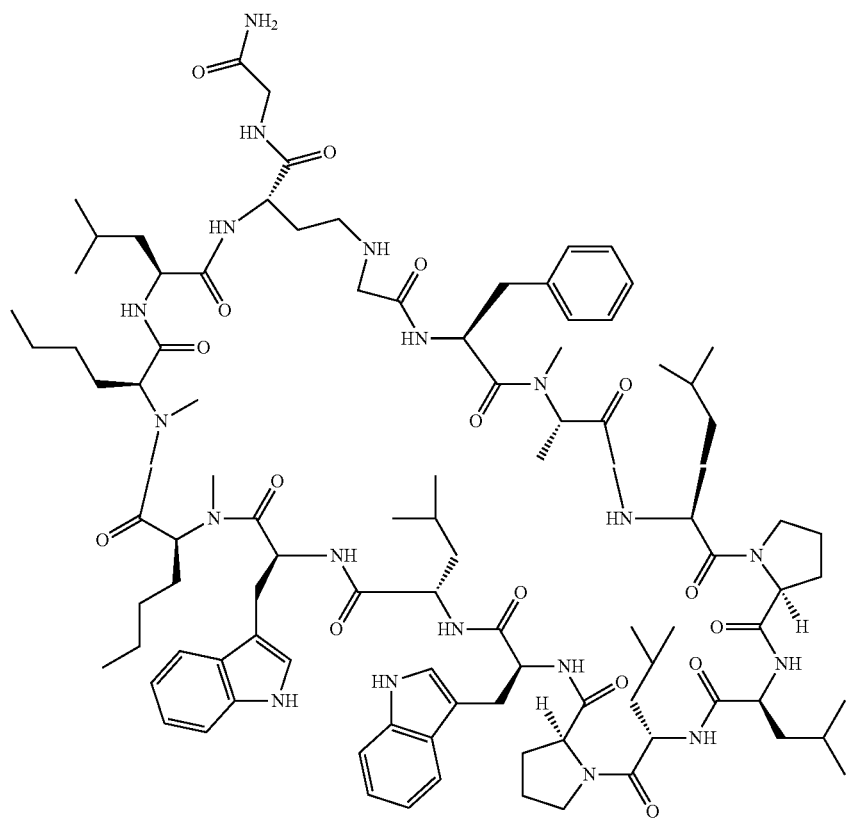

Example 10009

The crude material of Example 10009 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 35.8 mg, and its estimated purity by LCMS analysis was 100%.

Analysis condition A: Retention time=2.38 min; ESI-MS (+) m/z 917.50 (M+2H). ESI-HRMS(+) m/z: Calculated: 917.0631 (M+2H). Found: 917.0618 (M+2H).

PREPARATION OF EXAMPLE 10010

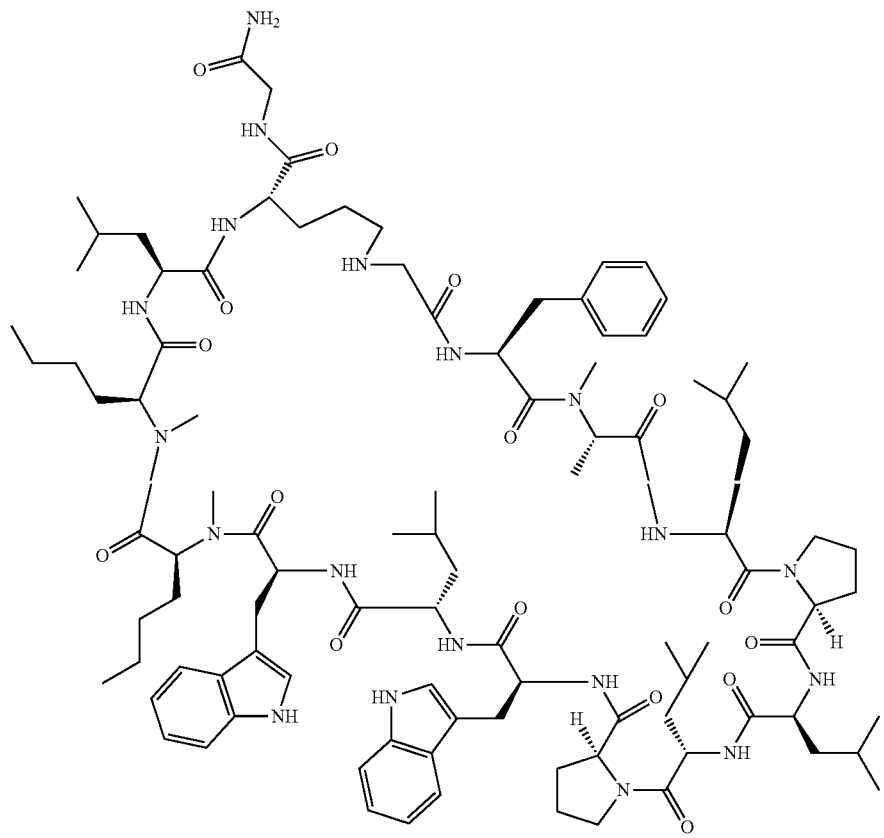

Example 10010

The crude material of Example 10010 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 24.5 mg, and its estimated purity by LCMS analysis was 100%.

Analysis condition A: Retention time=2.36 min; ESI-MS (+) m/z 924.55 (M+2H). ESI-HRMS(+) m/z: Calculated: 924.0709 (M+2H). Found: 924.0700 (M+2H).

PREPARATION OF EXAMPLE 10011

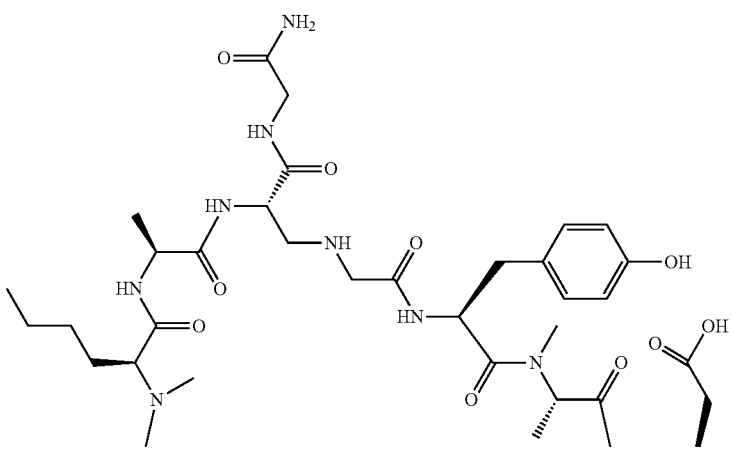

Example 10011

-continued

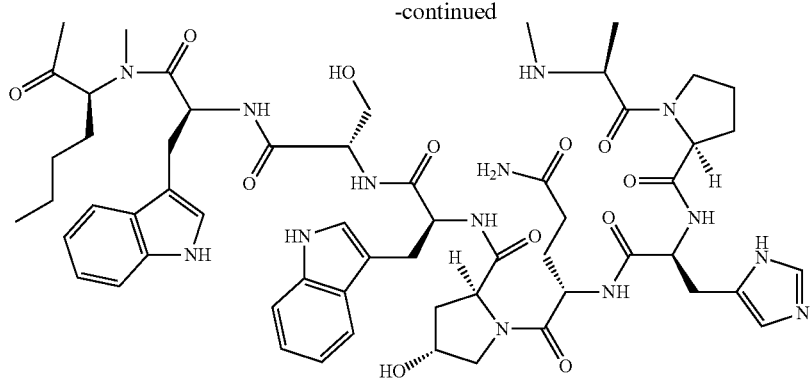

The crude material of Example 10011 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 2.4 mg, and its estimated purity by LCMS analysis was 100%.

Analysis condition A: Retention time=1.33 min; ESI-MS (+) m/z 912.90 (M+2H). Analysis condition B: Retention time=2.78 min; ESI-MS(+) m/z 912.85 (M+2H). ESI-HRMS(+) m/z: Calculated: 912.4468 (M+2H). Found: 912.4468 (M+2H).

PREPARATION OF EXAMPLE 10012

Example 10012

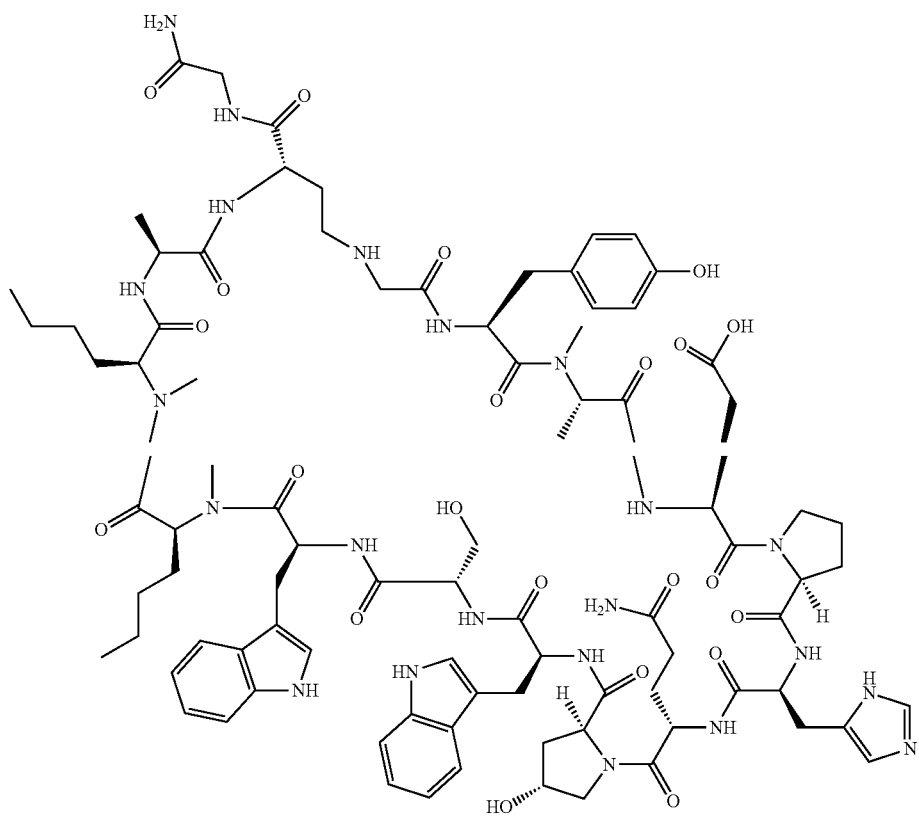

The crude material of Example 10012 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 11.7 mg, and its estimated purity by LCMS analysis was 100%.

Analysis condition A: Retention time=1.50 min; ESI-MS (+) m/z 919.90 (M+2H). Analysis condition B: Retention time=2.97 min; ESI-MS(+) m/z 919.90 (M+2H). ESI-HRMS(+) m/z: Calculated: 919.4547 (M+2H). Found: 919.4549 (M+2H).

PREPARATION OF EXAMPLE 10013

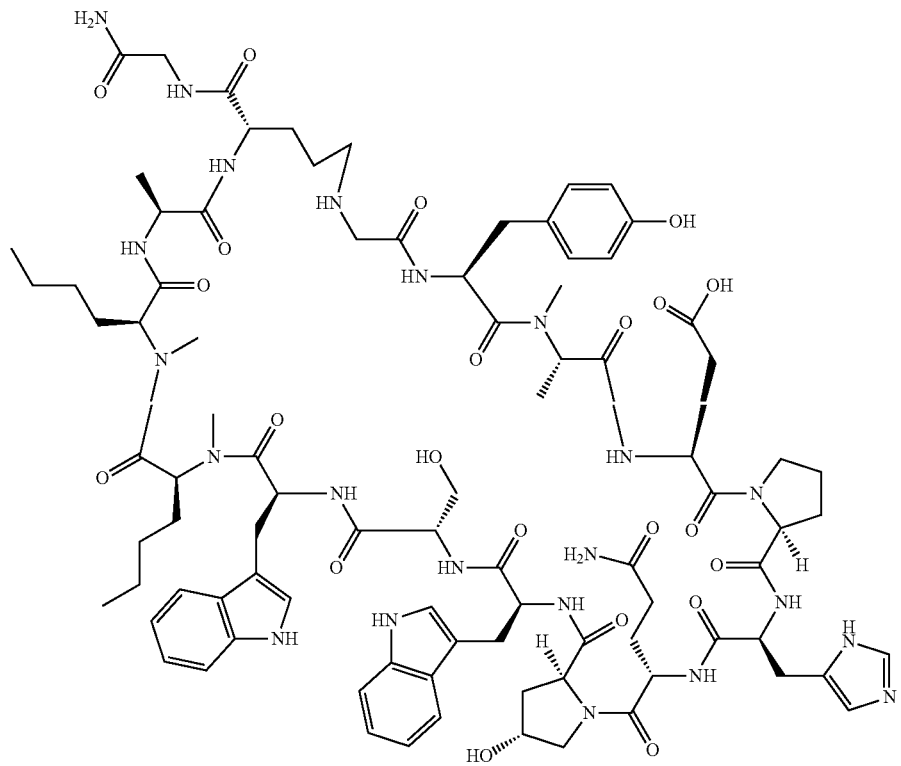

Example 10013

The crude material of Example 10013 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 6.4 mg, and its estimated purity by LCMS analysis was 100%.

Analysis condition A: Retention time=1.38 min; ESI-MS (+) m/z 927.00 (M+2H). Analysis condition B: Retention time=2.73 min; ESI-MS(+) m/z 926.95 (M+2H).

PREPARATION OF EXAMPLE 10014

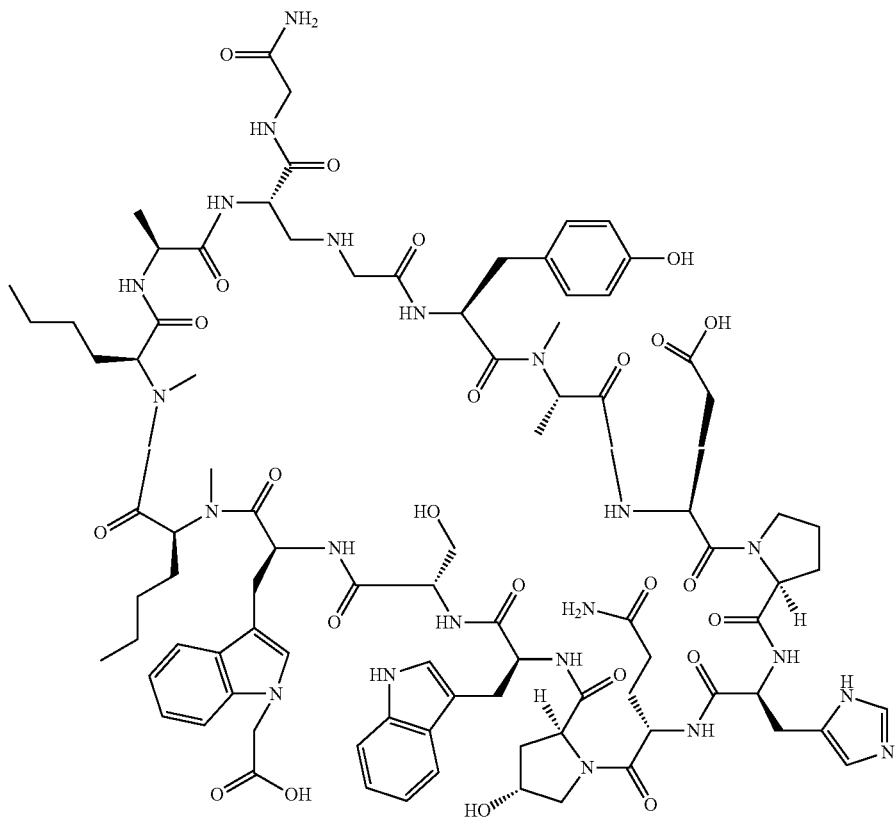

Example 10014

The crude material of Example 10014 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 1.1 mg, and its estimated purity by LCMS analysis was 100%.

Analysis condition A: Retention time=1.28 min; ESI-MS (+) m/z 941.90 (M+2H). Analysis condition B: Retention time=2.71 min; ESI-MS(+) m/z 941.90 (M+2H).

PREPARATION OF EXAMPLE 10015

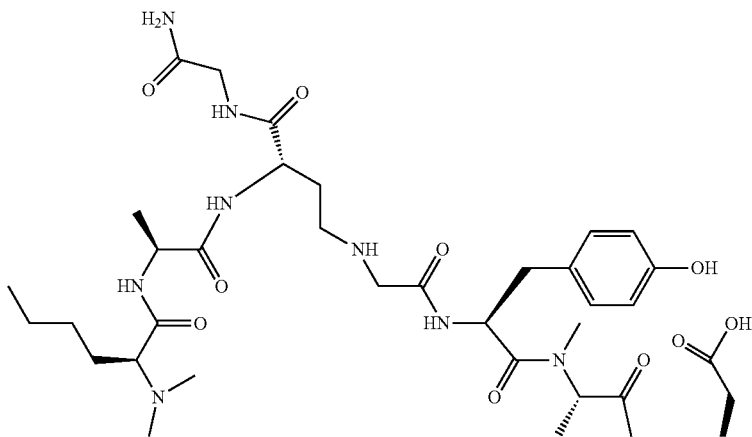

Example 10015

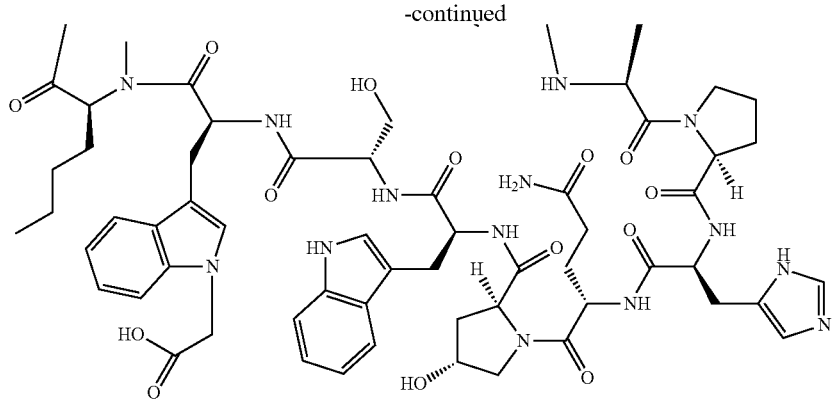

The crude material of Example 10015 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 4.3 mg, and its estimated purity by LCMS analysis was 100%.

Analysis condition A: Retention time=1.32 min; ESI-MS (+) m/z 948.90 (M+2H). Analysis condition B: Retention time=2.80 min; ESI-MS(+) m/z 948.80 (M+2H).

PREPARATION OF EXAMPLE 10016

The crude material of Example 10016 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 5.3 mg, and its estimated purity by LCMS analysis was 100%.

Analysis condition A: Retention time=1.31 min; ESI-MS (+) m/z 955.90 (M+2H). Analysis condition B: Retention time=2.82 min; ESI-MS(+) m/z 955.90 (M+2H).

Example 10016

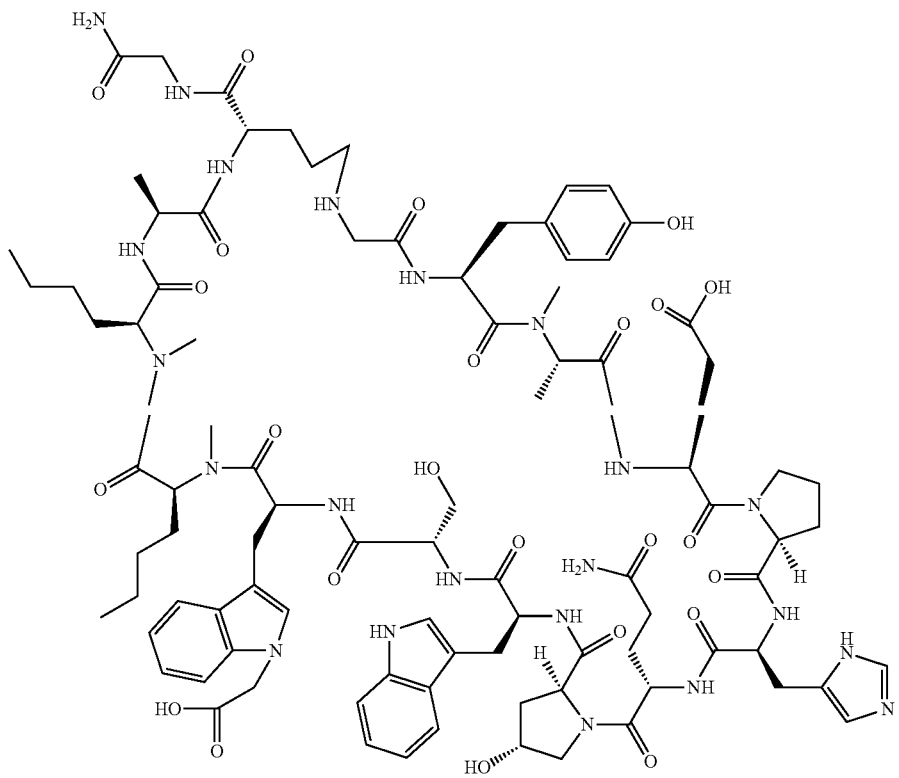

PREPARATION OF EXAMPLE 10017

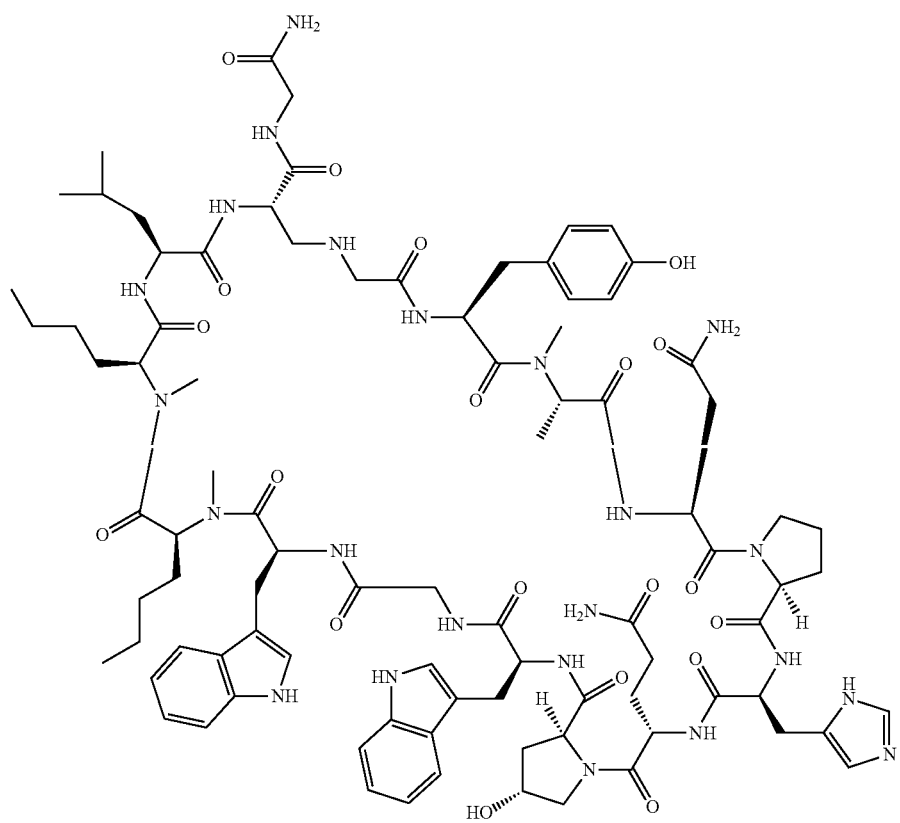

Example 10017

The crude material of Example 10017 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 28.9 mg, and its estimated purity by LCMS analysis was 98%.

Analysis condition A: Retention time=1.64 min; ESI-MS (+) m/z 918.40 (M+2H). Analysis condition B: Retention time=3.16 min; ESI-MS(+) m/z 918.40 (M+2H). ESI-HRMS(+) m/z: Calculated: 917.9730 (M+2H). Found: 917.9720 (M+2H).

PREPARATION OF EXAMPLE 10018

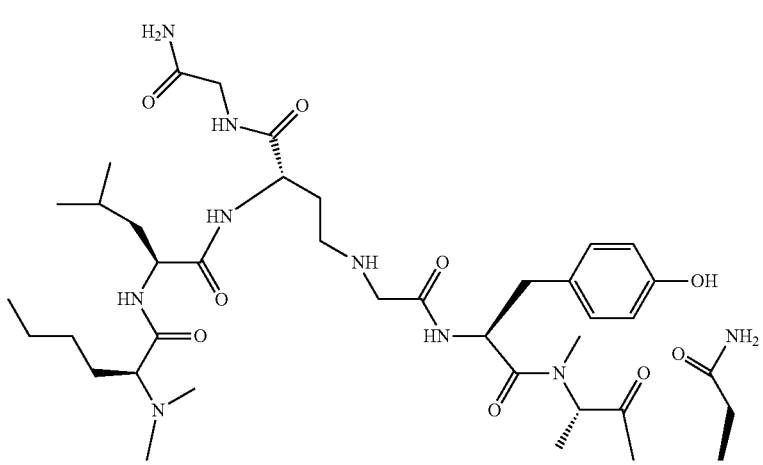

Example 10018

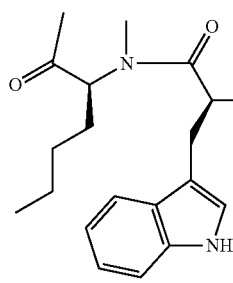
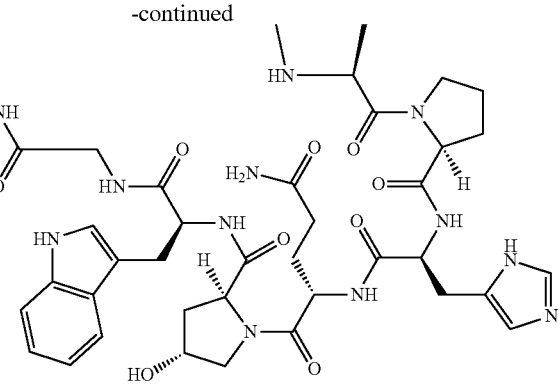

The crude material of Example 10018 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 31.3 mg, and its estimated purity by LCMS analysis was 98%.

Analysis condition A: Retention time=1.61 min; ESI-MS (+) m/z 924.45 (M+2H). Analysis condition B: Retention time=3.15 min; ESI-MS(+) m/z 925.40 (M+2H). ESI-HRMS(+) m/z: Calculated: 924.9808 (M+2H). Found: 924.9808 (M+2H).

PREPARATION OF EXAMPLE 10019

Example 10019

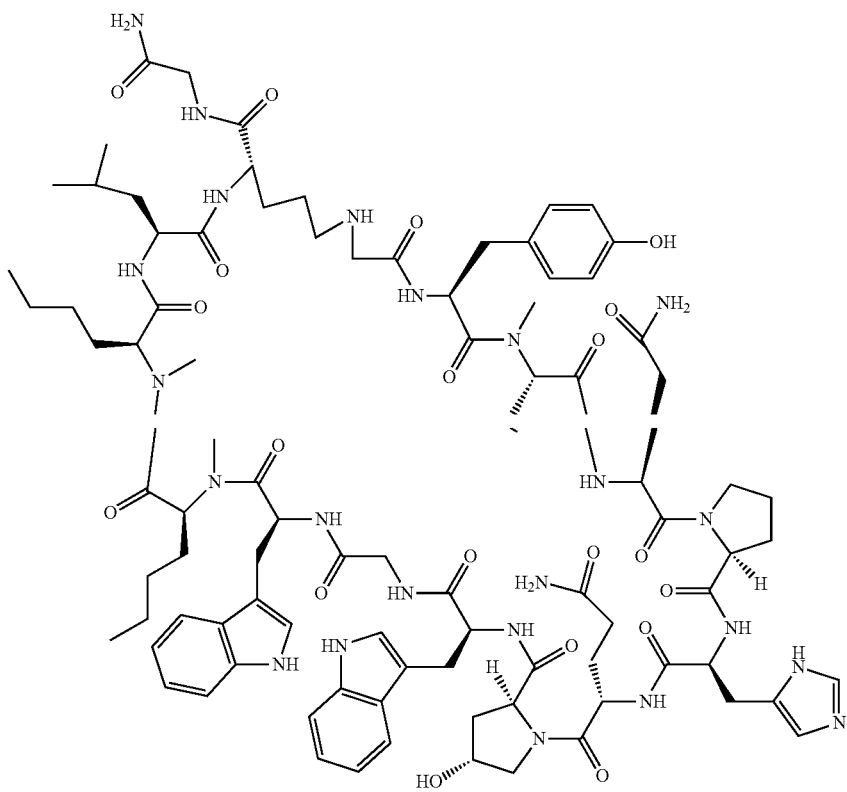

The crude material of Example 10019 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 15.0 mg, and its estimated purity by LCMS analysis was 100%.

Analysis condition A: Retention time=1.61 min; ESI-MS (+) m/z 932.45 (M+2H). Analysis condition B: Retention time=3.15 min; ESI-MS(+) m/z 932.40 (M+2H). ESI-HRMS(+) m/z: Calculated: 931.9887 (M+2H). Found: 931.9878 (M+2H).

PREPARATION OF EXAMPLE 10020

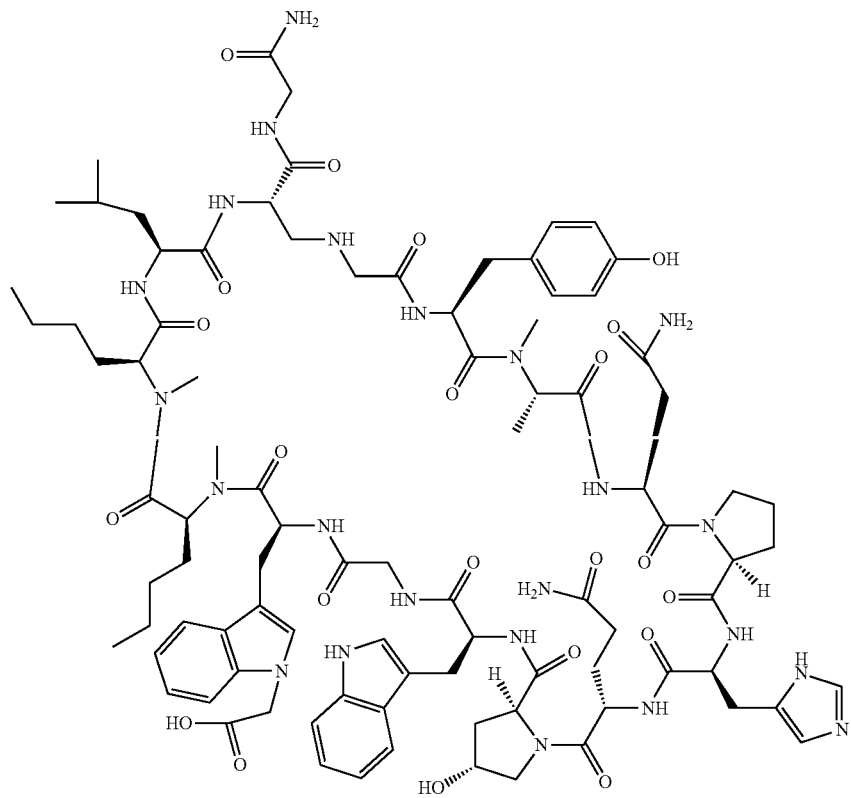

Example 10020

The crude material of Example 10020 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 11.1 mg, and its estimated purity by LCMS analysis was 100%.

Analysis condition A: Retention time=1.42 min; ESI-MS (+) m/z 947.40 (M+2H). Analysis condition B: Retention time=2.95 min; ESI-MS(+) m/z 947.40 (M+2H). ESI-HRMS(+) m/z: Calculated: 946.9758 (M+2H). Found: 946.9756 (M+2H).

PREPARATION OF EXAMPLE 10021

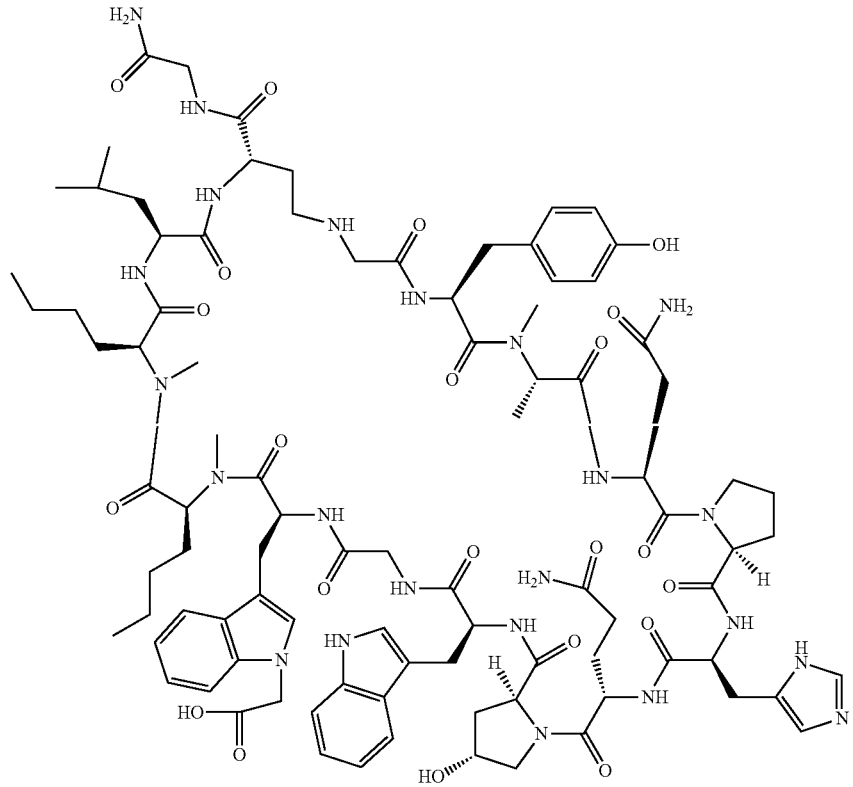

Example 10021

The crude material of Example 10021 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 11.1 mg, and its estimated purity by LCMS analysis was 99%.

Analysis condition A: Retention time=1.44 min; ESI-MS (+) m/z 954.40 (M+2H). Analysis condition B: Retention time=2.99 min; ESI-MS(+) m/z 954.35 (M+2H).

PREPARATION OF EXAMPLE 10022

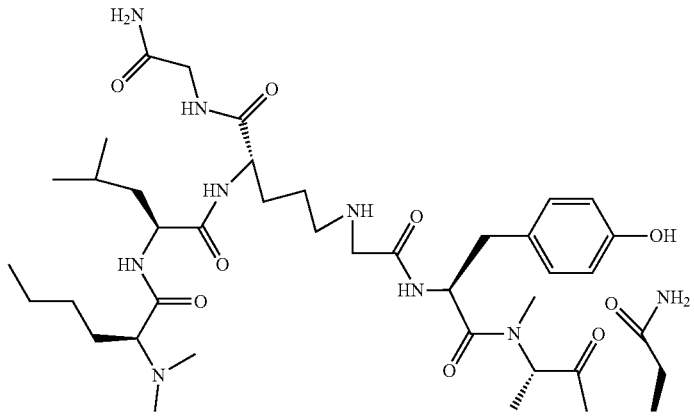

Example 10022

-continued

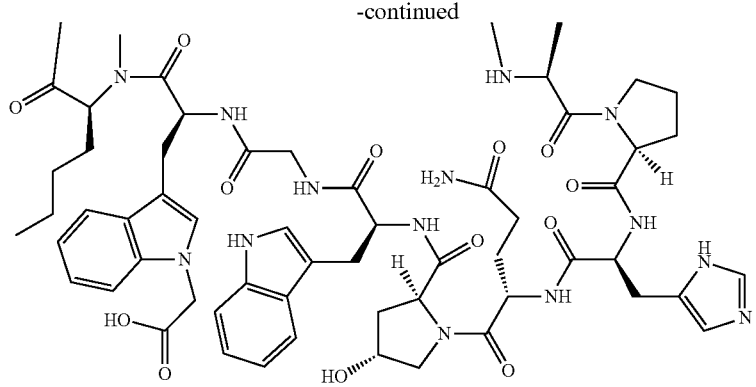

The crude material of Example 10022 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 5.0 mg, and its estimated purity by LCMS analysis was 95%.

Analysis condition A: Retention time=1.46 min; ESI-MS (+) m/z 961.45 (M+2H).

PREPARATION OF EXAMPLE 10023

The crude material of Example 10023 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 3.5 mg, and its estimated purity by LCMS analysis was 100%.

Analysis condition A: Retention time=1.52 min; ESI-MS (+) m/z 949.00 (M+2H). Analysis condition B: Retention time=2.80 min; ESI-MS(+) m/z 948.85 (M+2H).

Example 10023

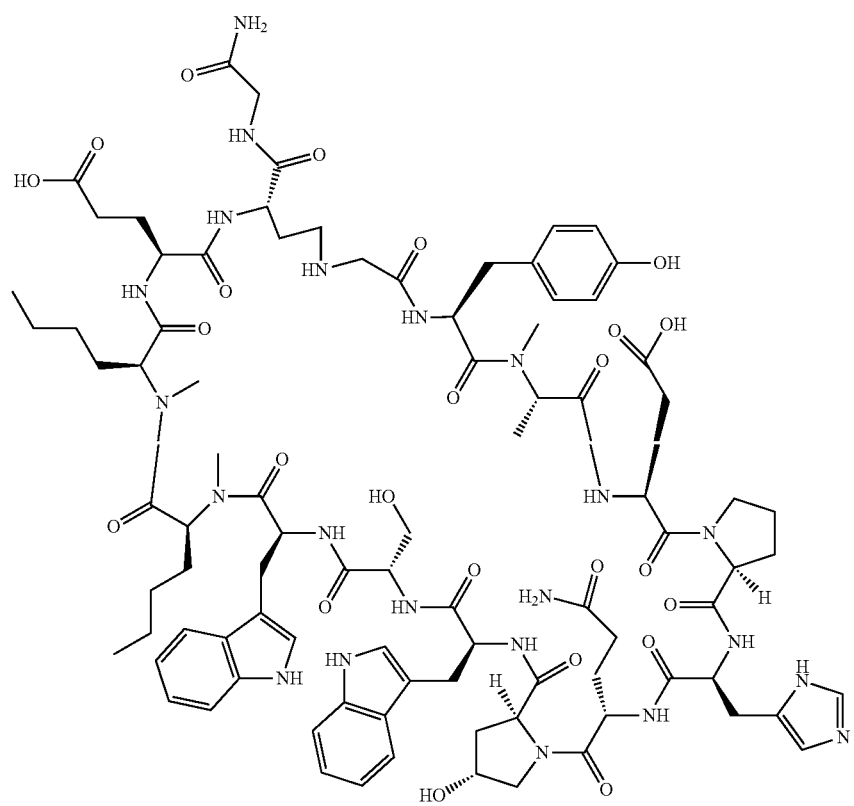

PREPARATION OF EXAMPLE 10024

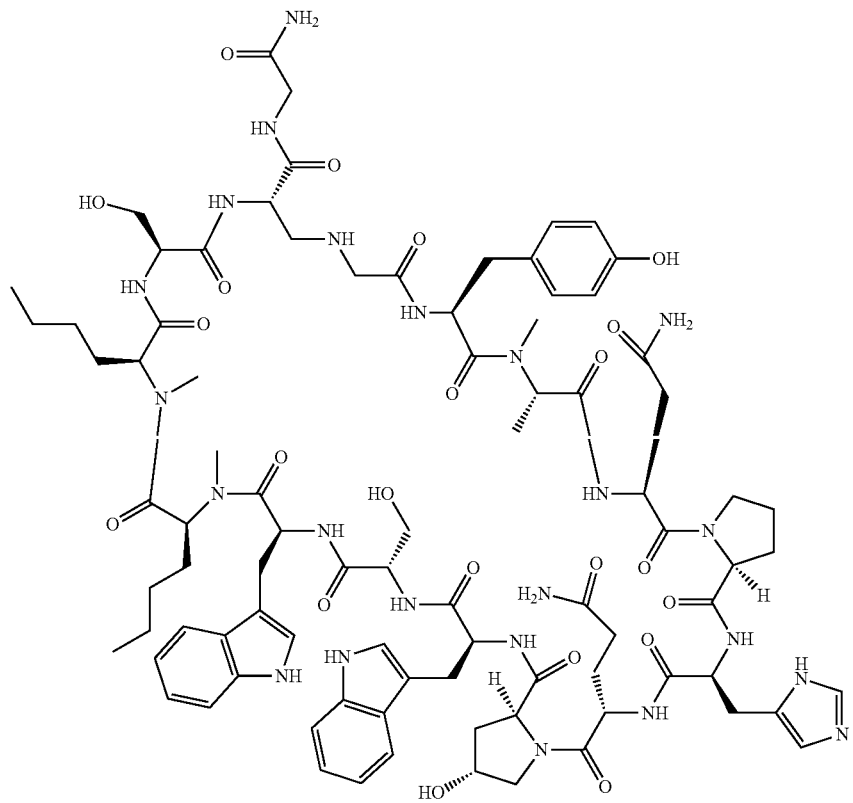

Example 10024

The crude material of Example 10024 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 5.0 mg, and its estimated purity by LCMS analysis was 100%.

Analysis condition A: Retention time=1.56 min; ESI-MS (+) m/z 920.30 (M+2H). Analysis condition B: Retention time=3.05 min; ESI-MS(+) m/z 920.30 (M+2H).

PREPARATION OF EXAMPLE 10025

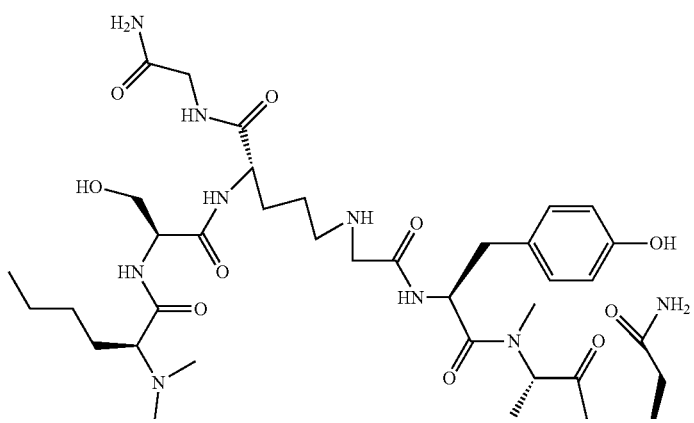

Example 10025

-continued

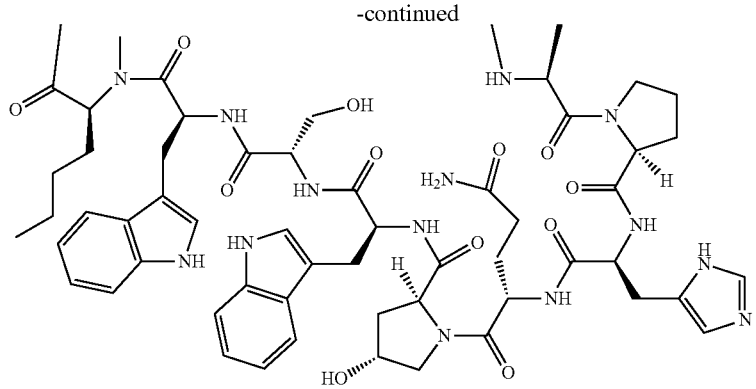

The crude material of Example 10025 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 4.1 mg, and its estimated purity by LCMS analysis was 100%.

Analysis condition A: Retention time=1.43 min; ESI-MS (+) m/z 934.60 (M+2H). Analysis condition B: Retention time=2.97 min; ESI-MS(+) m/z 934.35 (M+2H).

PREPARATION OF EXAMPLE 10026

Example 10026

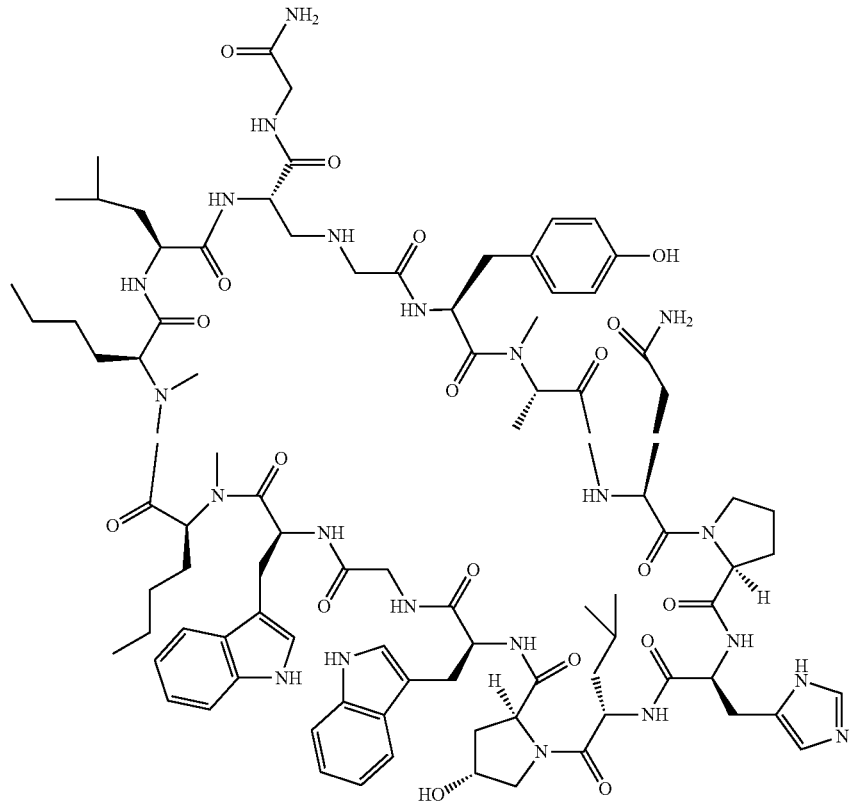

The crude material of Example 10026 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 19.7 mg, and its estimated purity by LCMS analysis was 97%.

Analysis condition A: Retention time=1.69 min; ESI-MS (+) m/z 910.85 (M+2H). Analysis condition B: Retention time=3.18 min; ESI-MS(+) m/z 910.85 (M+2H).

PREPARATION OF EXAMPLE 10027

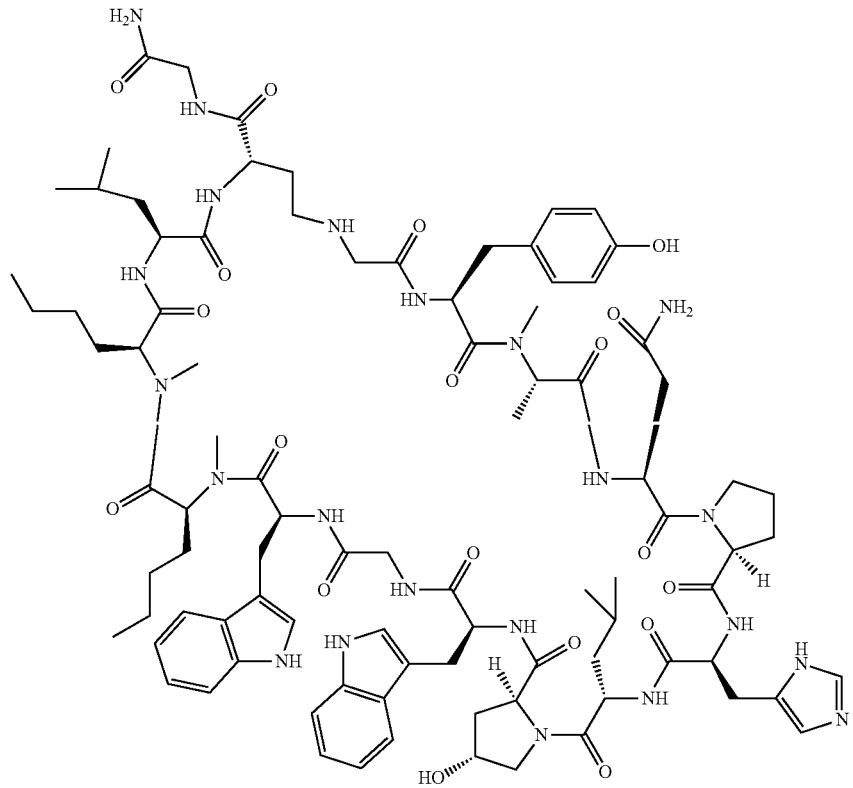

Example 10027

The crude material of Example 10027 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 21.0 mg, and its estimated purity by LCMS analysis was 99%.

Analysis condition A: Retention time=1.66 min; ESI-MS (+) m/z 917.85 (M+2H). Analysis condition B: Retention time=3.18 min; ESI-MS(+) m/z 917.90 (M+2H).

PREPARATION OF EXAMPLE 10028

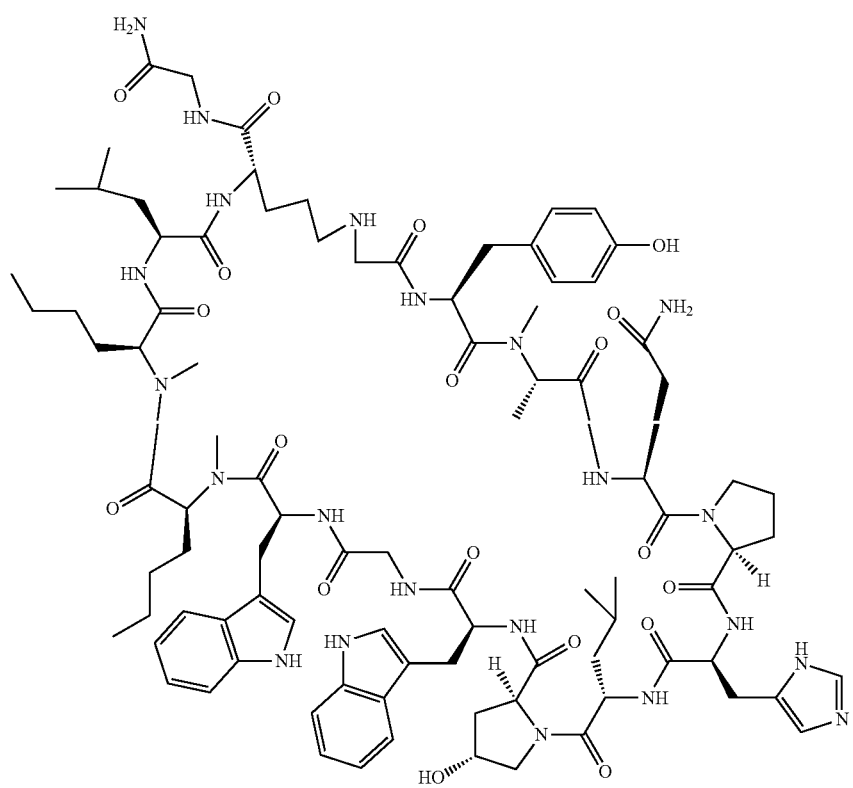

Example 10028

The crude material of Example 10028 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 20.1 mg, and its estimated purity by LCMS analysis was 100%.

Analysis condition A: Retention time=1.65 min; ESI-MS (+) m/z 924.90 (M+2H). Analysis condition B: Retention time=3.17 min; ESI-MS(+) m/z 924.90 (M+2H).

PREPARATION OF EXAMPLE 10500

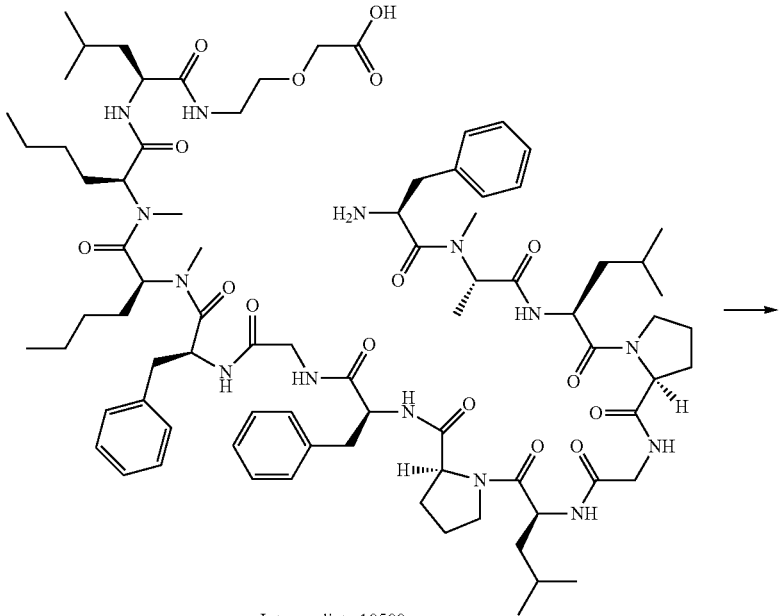

Intermediate 10500

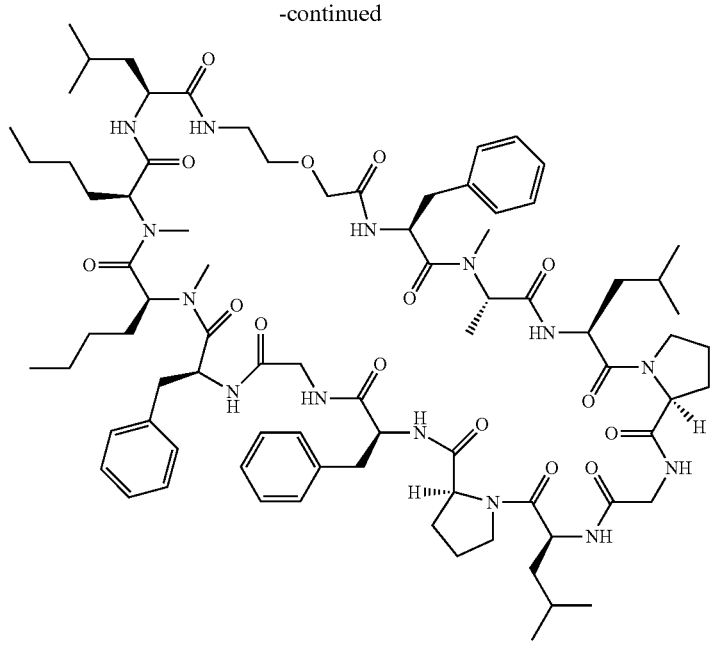

Example 10500

Preparation of Intermediate 10500

"General Synthetic Sequence A" was followed. 2-(2-((((9H-fluoren-9-yl)methoxy)carbonyl)amino)ethoxy)acetic acid was used in the "Resin Loading Procedure". To the reaction vessel containing resin from the automated sequence was added piperidine:DMF (20:80 v/v, 2.0 mL). The mixture was periodically agitated for 4 minutes and then the solution was drained through the frit. To the reaction vessel was added piperidine:DMF (20:80 v/v, 2.0 mL). The mixture was periodically agitated for 4 minutes and then the solution was drained through the frit. The resin was washed successively five times as follows: for each wash, DMF (2.0 mL) was added through the top of the vessel and the resulting mixture was periodically agitated for 90 seconds before the solution was drained through the frit. The resin was washed successively five times as follows: for each wash, DCM (2.0 mL) was added through the top of the vessel and the resulting mixture was periodically agitated for 90 seconds before the solution was drained through the frit. The resin was then immediately transferred using DCM (8 mL) to a 15 mL vial. To the solution was added hexafluoroisopropanol (2 mL). The resin immediately turned deep red; the solution remained colorless. The mixture briefly manually agitated, then was allowed to stand at r.t. for 15 minutes, then was filtered. The filtrate was transferred to a 15 mL vial and was concentrated under a N2 stream to afford a solid residue, Intermediate 10500.

PREPARATION OF EXAMPLE 10500

A "deprotection solution" was prepared by combining in a 40 mL glass vial trifluoroacetic acid (23.75 mL), 1,4-Dithio-DL-threitol (625 mg), triisopropylsilane (0.625 mL). To a 1 dram vial charged with the entirety of Intermediate 10500 prepared above was added the "deprotection solution" (1.0 mL). The solution was mixed for 1.5 h in a shaker running at 500 rpm, then was poured into a 25 mL test tube charged with Et$_2$O (20 mL). A small amount of white solid precipitated. The mixture was centrifuged; the liquid was decanted. The solids were suspended in Et$_2$O (10 mL). The mixture was centrifuged, the liquid was decanted. The crude material was purified via preparative LC/MS with the following conditions: Column: XBridge C18, 19×200 mm, 5-μm particles;

Mobile Phase A: 5:95 acetonitrile:water with 10-mM ammonium acetate; Mobile Phase B: 95:5 acetonitrile:water with 10-mM ammonium acetate; Gradient: 40-80% B over 20 minutes, then a 5-minute hold at 100% B; Flow: 20 mL/min. Fractions containing the desired product were combined and dried via centrifugal evaporation. The yield of the product was 7.3 mg, and its estimated purity by LCMS analysis was 100%.

Analysis condition A: Retention time=2.57 min; ESI-MS (+) m/z 764.9 (M+2H). Analysis condition E: Retention time=2.57 min; ESI-MS(+) m/z 765.4 (M+2H). ESI-HRMS (+) m/z: Calculated: 765.4602 Found: 765.4581.

PREPARATION OF EXAMPLE 10501
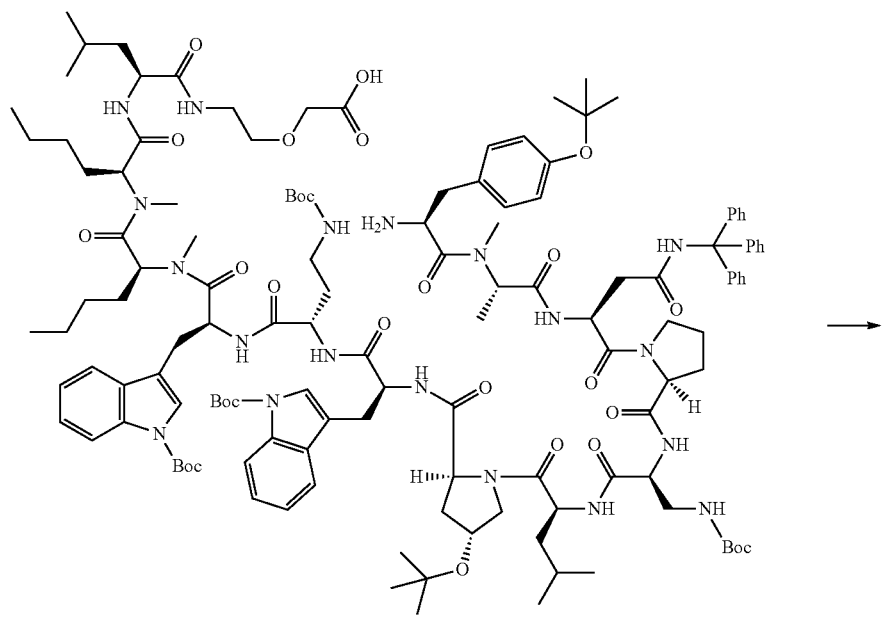
Intermediate 10501A
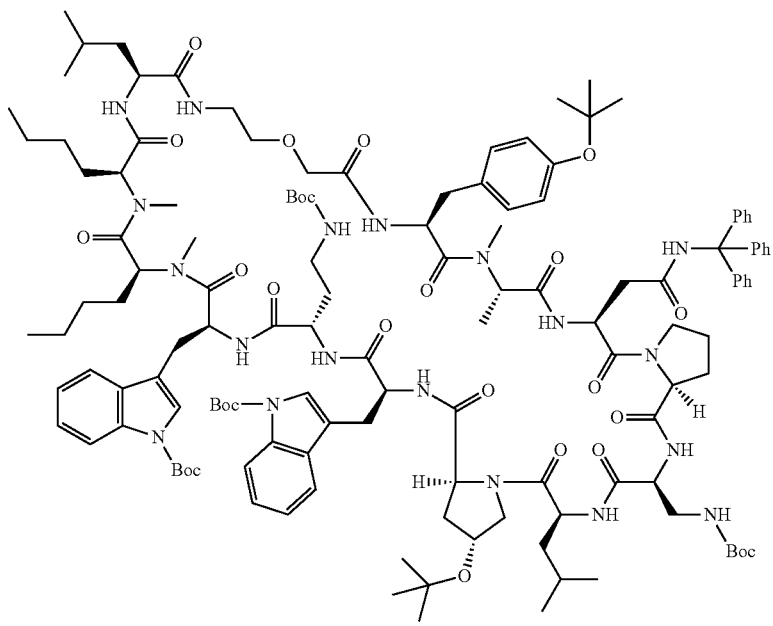
Intermediate 10501B

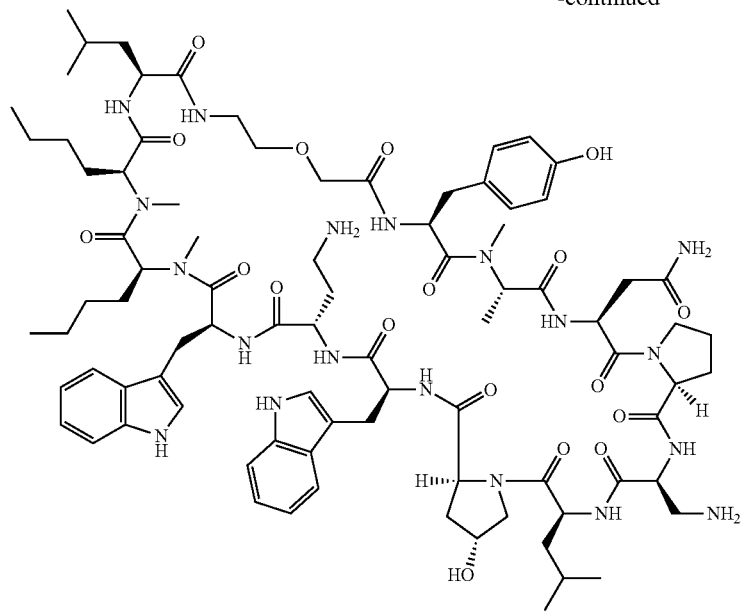

Example 10501

Preparation of Intermediate 10501A

"General Synthetic Sequence A" was followed. 2-(2-(((((9H-fluoren-9-yl)methoxy)carbonyl)amino)ethoxy)acetic acid was used in the "Resin Loading Procedure". To the reaction vessel containing resin from the automated sequence was added piperidine:DMF (20:80 v/v, 2.0 mL). The mixture was periodically agitated for 4 minutes and then the solution was drained through the frit. To the reaction vessel was added piperidine:DMF (20:80 v/v, 2.0 mL). The mixture was periodically agitated for 4 minutes and then the solution was drained through the frit. The resin was washed successively five times as follows: for each wash, DMF (2.0 mL) was added through the top of the vessel and the resulting mixture was periodically agitated for 90 seconds before the solution was drained through the frit. The resin was washed successively five times as follows: for each wash, DCM (2.0 mL) was added through the top of the vessel and the resulting mixture was periodically agitated for 90 seconds before the solution was drained through the frit. The resin was then immediately transferred using DCM (8 mL) to a 15 mL vial. To the solution was added hexafluoroisopropanol (2 mL). The resin immediately turned deep red; the solution remained colorless. The mixture briefly manually agitated, then was allowed to stand at r.t. for 15 minutes, then was filtered. The filtrate was transferred to a 15 mL vial and was concentrated under a N2 stream to afford a solid residue, Intermediate 10501A.

Preparation of Intermediate 10501B

To a 15 mL vial charged with the entirety of Intermediate 10501A prepared above was added DCM (2 mL), then HATU (38 mg, 0.10 mmol) then DIPEA (0.114 mL, 0.650 mmol). The solution was stirred for 2 h. The solution was dried under vacuum to afford Intermediate 10501B.

PREPARATION OF EXAMPLE 10501

A "deprotection solution" was prepared by combining in a 40 mL glass vial trifluoroacetic acid (23.75 mL), 1,4-Dithio-DL-threitol (625 mg), triisopropylsilane (0.625 mL). To a 1 dram vial charged with the entirety of Intermediate 10501A prepared above was added the "deprotection solution" (1.0 mL). The solution was mixed for 1.0 h in a shaker running at 500 rpm, then was poured into a 25 mL test tube charged with Et₂O (15 mL). A small amount of white solid precipitated. The mixture was centrifuged; the liquid was decanted. The solids were suspended in Et₂O (15 mL). The mixture was centrifuged, the liquid was decanted. The resulting residue was dissolved in MeOH, and to the solution was added DIPEA (0.050 mL). The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 4-minute hold at 100% B; Flow: 20 mL/min. Fractions containing the desired product were combined and dried via centrifugal evaporation. The yield of the product was 1.0 mg, and its estimated purity by LCMS analysis was 95%.

Analysis condition A: Retention time=1.65 min; ESI-MS (−) m/z 856.8 (M+2H). Analysis condition B: Retention time=2.72 min; ESI-MS(−) m/z 857.2 (M+2H). ESI-HRMS (+) m/z: Calculated: 856.9798 Found: 856.9790.

PREPARATION OF EXAMPLE 10502
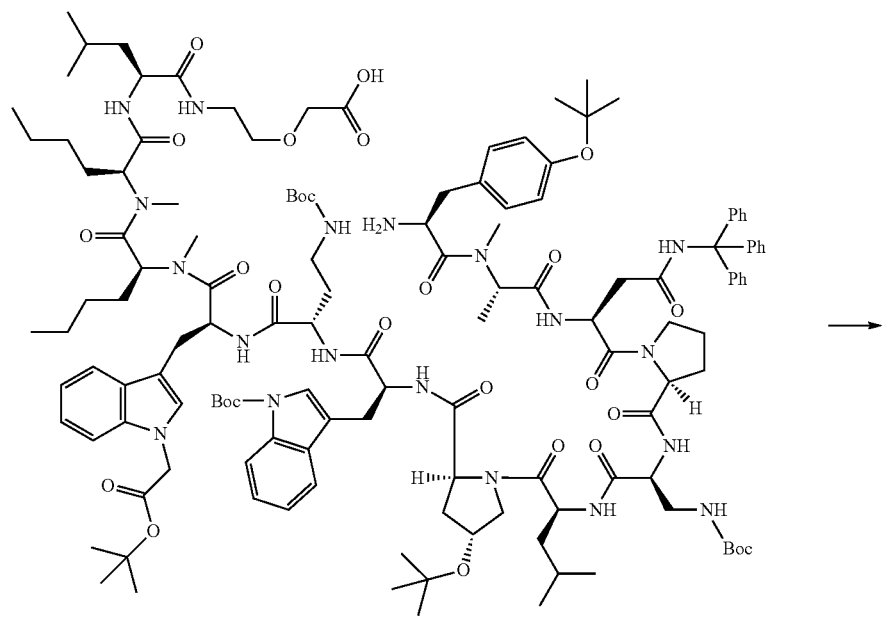
Intermediate 10502A
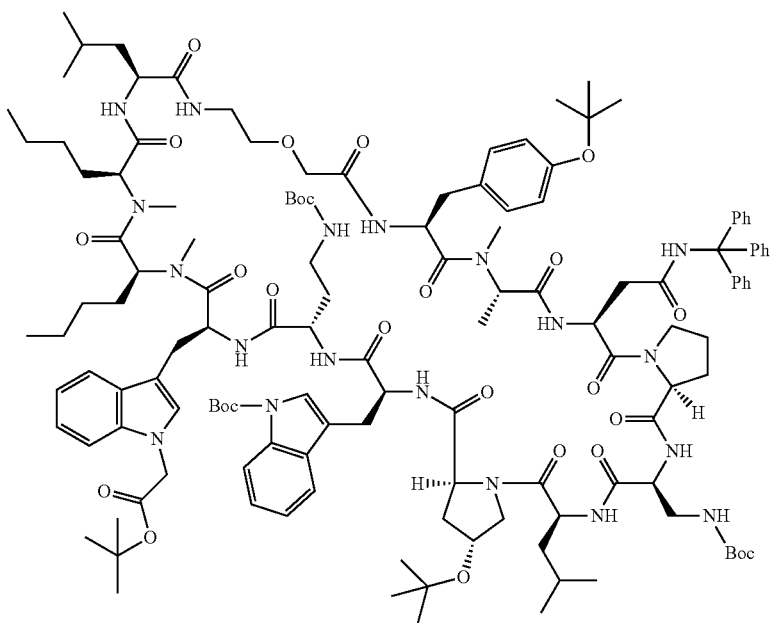
Intermediate 10502B

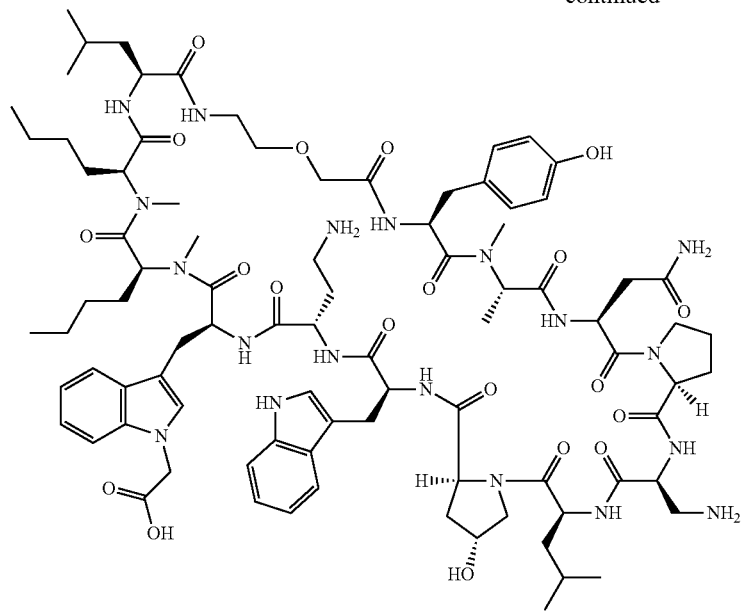

Example 10502

Preparation of Intermediate 10502A

"General Synthetic Sequence A" was followed. 2-(2-((((9H-fluoren-9-yl)methoxy)carbonyl)amino)ethoxy)acetic acid was used in the "Resin Loading Procedure". To the reaction vessel containing resin from the automated sequence was added piperidine:DMF (20:80 v/v, 2.0 mL). The mixture was periodically agitated for 4 minutes and then the solution was drained through the frit. To the reaction vessel was added piperidine:DMF (20:80 v/v, 2.0 mL). The mixture was periodically agitated for 4 minutes and then the solution was drained through the frit. The resin was washed successively five times as follows: for each wash, DMF (2.0 mL) was added through the top of the vessel and the resulting mixture was periodically agitated for 90 seconds before the solution was drained through the frit. The resin was washed successively five times as follows: for each wash, DCM (2.0 mL) was added through the top of the vessel and the resulting mixture was periodically agitated for 90 seconds before the solution was drained through the frit. The resin was then immediately transferred using DCM (8 mL) to a 15 mL vial. To the solution was added hexafluoroisopropanol (2 mL). The resin immediately turned deep red; the solution remained colorless. The mixture briefly manually agitated, then was allowed to stand at r.t. for 15 minutes, then was filtered. The filtrate was transferred to a 15 mL vial and was concentrated under a N2 stream to afford a solid residue, Intermediate 10502A.

Preparation of Intermediate 10502B

To a 15 mL vial charged with the entirety of Intermediate 10501A prepared above was added DCM (2 mL), then HATU (38 mg, 0.10 mmol) then DIPEA (0.114 mL, 0.650 mmol). The solution was stirred for 2 h. The solution was dried under vacuum to afford redissolved in MeOH then subjected to HPLC purification under the following conditions: Column: Waters XBridge C18, 30×100 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 55-100% B over 15 minutes, then a 15-minute hold at 100% B; Flow: 30 mL/min. Fractions containing the desired product were combined and dried via centrifugal evaporation to afford a white solid, Intermediate 10502B.

PREPARATION OF EXAMPLE 10502

A "deprotection solution" was prepared by combining in a 40 mL glass vial trifluoroacetic acid (23.75 mL), 1,4-Dithio-DL-threitol (625 mg), triisopropylsilane (0.625 mL). To a 1 dram vial charged with the entirety of Intermediate 10501A prepared above was added the "deprotection solution" (1.0 mL). The solution was mixed for 1.0 h in a shaker running at 500 rpm, then was poured into a 25 mL test tube charged with $Et_2O$ (15 mL). A small amount of white solid precipitated. The mixture was centrifuged; the liquid was decanted. The solids were suspended in $Et_2O$ (15 mL). The mixture was centrifuged, the liquid was decanted. The resulting residue was dissolved in MeOH, and to the solution was added DIPEA (0.050 mL). The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-100% B over 30 minutes, then a 5-minute hold at 100% B; Flow: 20 mL/min. Fractions containing the desired product were combined and dried via centrifugal evaporation. The yield of the product was 0.1 mg, and its estimated purity by LCMS analysis was 83%. Analysis condition A: Retention time=1.79 min; ESI-MS(−) m/z 886.1 (M+2H).

PREPARATION OF EXAMPLE 10503
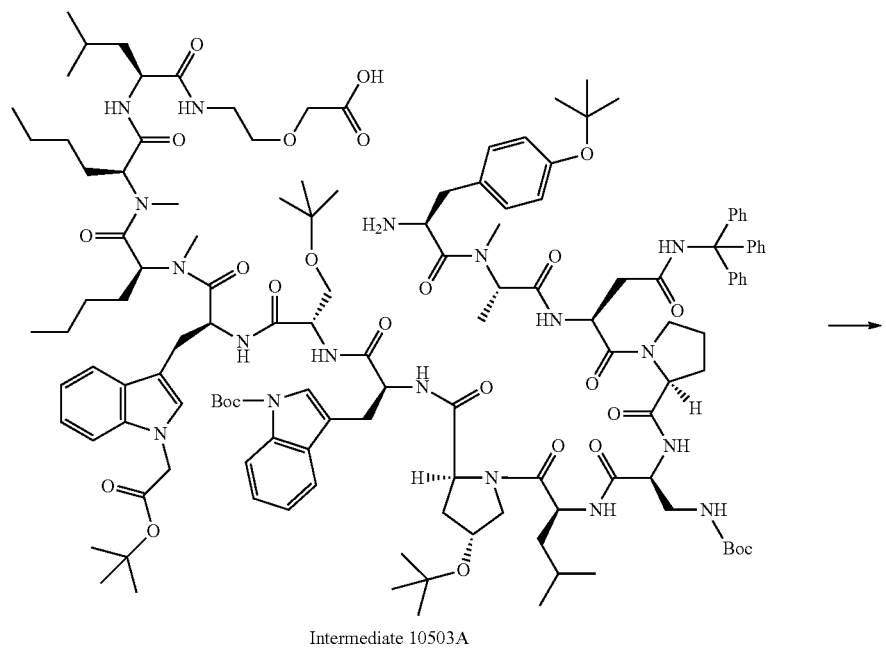
Intermediate 10503A
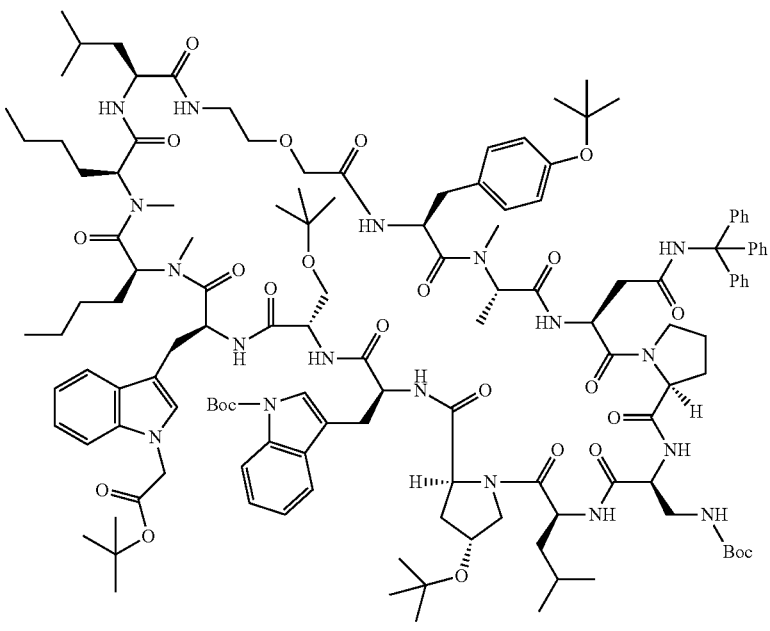
Intermediate 10503B

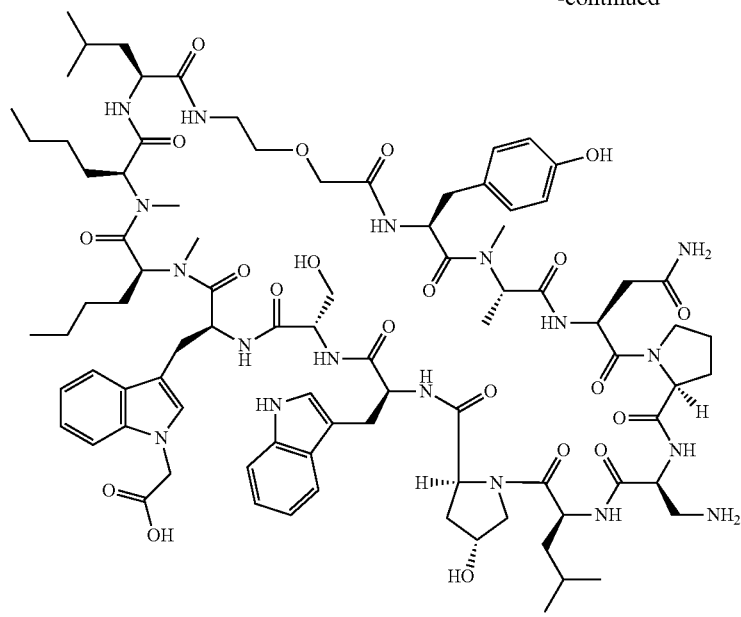

Example 10503

Preparation of Intermediate 10503A

"General Synthetic Sequence A" was followed. 2-(2-((((9H-fluoren-9-yl)methoxy)carbonyl)amino)ethoxy)acetic acid was used in the "Resin Loading Procedure". To the reaction vessel containing resin from the automated sequence was added piperidine:DMF (20:80 v/v, 2.0 mL). The mixture was periodically agitated for 4 minutes and then the solution was drained through the frit. To the reaction vessel was added piperidine:DMF (20:80 v/v, 2.0 mL). The mixture was periodically agitated for 4 minutes and then the solution was drained through the frit. The resin was washed successively five times as follows: for each wash, DMF (2.0 mL) was added through the top of the vessel and the resulting mixture was periodically agitated for 90 seconds before the solution was drained through the frit. The resin was washed successively five times as follows: for each wash, DCM (2.0 mL) was added through the top of the vessel and the resulting mixture was periodically agitated for 90 seconds before the solution was drained through the frit. The resin was then immediately transferred using DCM (8 mL) to a 15 mL vial. To the solution was added hexafluoroisopropanol (2 mL). The resin immediately turned deep red; the solution remained colorless. The mixture briefly manually agitated, then was allowed to stand at r.t. for 15 minutes, then was filtered. The filtrate was transferred to a 15 mL vial and was concentrated under a N2 stream to afford a solid residue, Intermediate 10503A.

Preparation of Intermediate 10503B

To a 15 mL vial charged with the entirety of Intermediate 10501A prepared above was added DCM (2 mL), then HATU (38 mg, 0.10 mmol) then DIPEA (0.114 mL, 0.650 mmol). The solution was stirred for 2 h. The solution was dried under vacuum to afford Intermediate 10503B.

PREPARATION OF EXAMPLE 10503

A "deprotection solution" was prepared by combining in a 40 mL glass vial trifluoroacetic acid (23.75 mL), 1,4-Dithio-DL-threitol (625 mg), triisopropylsilane (0.625 mL). To a 1 dram vial charged with the entirety of Intermediate 10501A prepared above was added the "deprotection solution" (1.0 mL). The solution was mixed for 1.0 h in a shaker running at 500 rpm, then was poured into a 25 mL test tube charged with Et$_2$O (15 mL). A small amount of white solid precipitated. The mixture was centrifuged; the liquid was decanted. The solids were suspended in Et$_2$O (15 mL). The mixture was centrifuged, the liquid was decanted. The resulting residue was dissolved in MeOH, and to the solution was added DIPEA (0.050 mL). The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-90% B over 30 minutes, then a 5-minute hold at 100% B; Flow: 20 mL/min. Fractions containing the desired product were combined and dried via centrifugal evaporation. The material was further purified via preparative LC/MS with the following conditions: Column: waters CSH c-18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 30 minutes, then a 5-minute hold at 100% B; Flow: 20 mL/min. Fractions containing the desired product were combined and dried via centrifugal evaporation. The yield of the product was 0.8 mg, and its estimated purity by LCMS analysis was 99%.

Analysis condition A: Retention time=1.81 min; ESI-MS (−) m/z 879.3 (M+2H). Analysis condition E: Retention time=1.81 min; ESI-MS(−) m/z 1758.1 (M−H).

PREPARATION OF EXAMPLE 9005

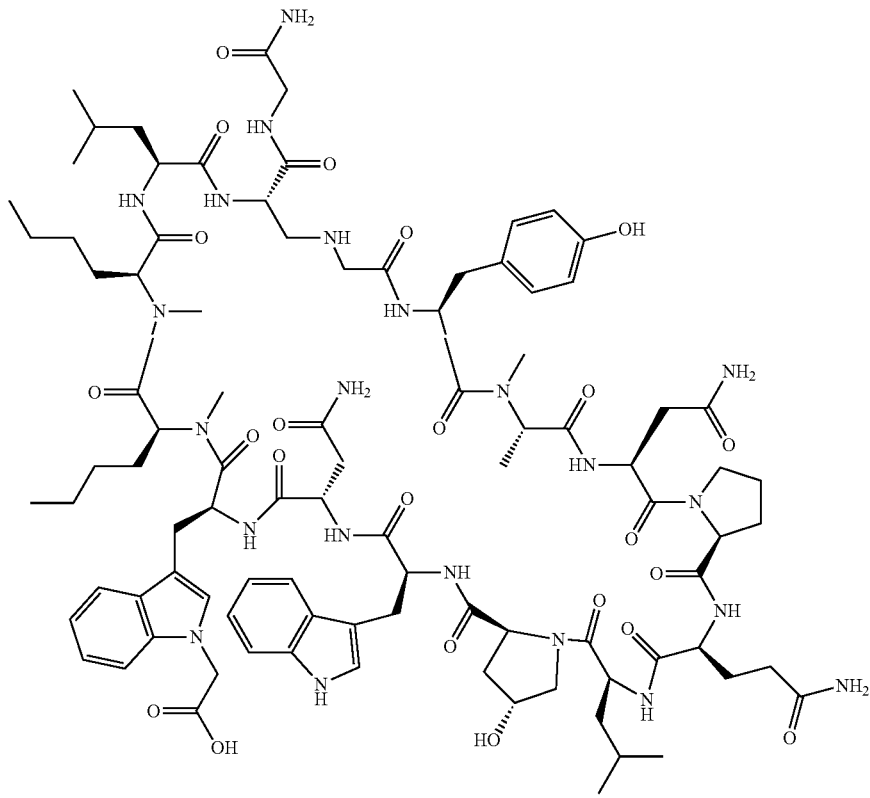

Example 9005

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 3-minute hold at 100% B; Flow: 20 mL/min. Fractions containing the desired product were combined and dried via centrifugal evaporation. The yield of the product was 4.5 mg, and its estimated purity by LCMS analysis was 100%. ESI-MS(+) m/z 964.1 (M+2H).

PREPARATION OF EXAMPLE 9006

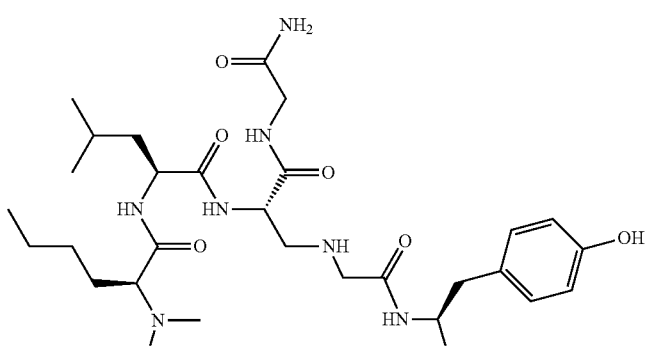

Example 9006

-continued

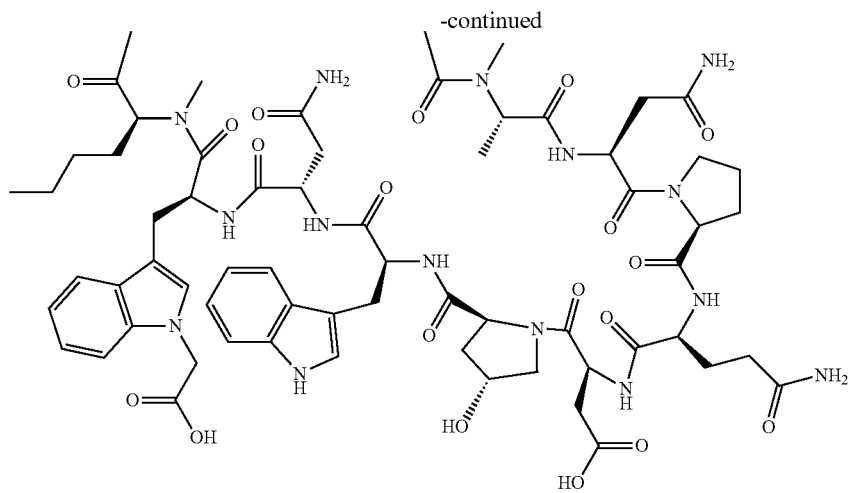

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-40% B over 30 minutes, then a 5-minute hold at 100% B; Flow: 20 mL/min. Fractions containing the desired product were combined and dried via centrifugal evaporation. The yield of the product was 8.7 mg, and its estimated purity by LCMS analysis was 97%. ESI-MS(+) m/z 964.5 (M+2H).

PREPARATION OF EXAMPLE 9007

Example 9007

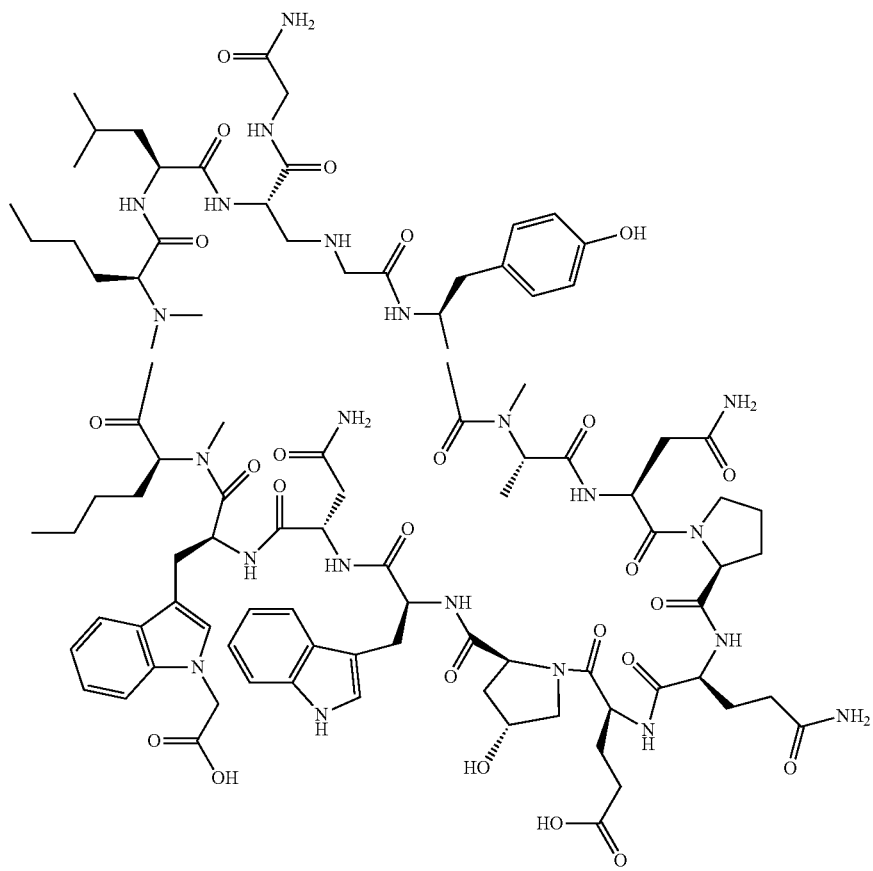

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 30-70% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-40% B over 30 minutes, then a 5-minute hold at 100% B; Flow: 20 mL/min. Fractions containing the desired product were combined and dried via centrifugal evaporation. The yield of the product was 2.7 mg, and its estimated purity by LCMS analysis was 100%. ESI-MS(+) m/z 971.5 (M+2H).

PREPARATION OF EXAMPLE 9008

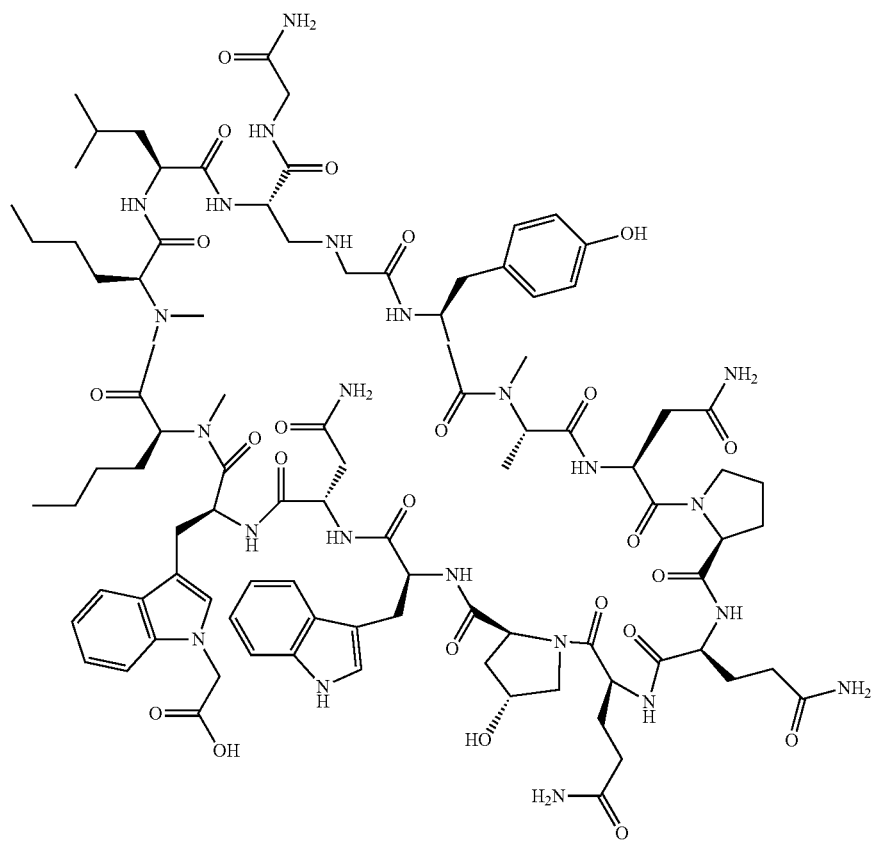

Example 9008

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 40-80% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 3-minute hold at 100% B; Flow: 20 mL/min. Fractions containing the desired product were combined and dried via centrifugal evaporation. The yield of the product was 5.7 mg, and its estimated purity by LCMS analysis was 100%. ESI-MS(+) m/z 971.1 (M+2H).

PREPARATION OF EXAMPLE 9009

Example 9009

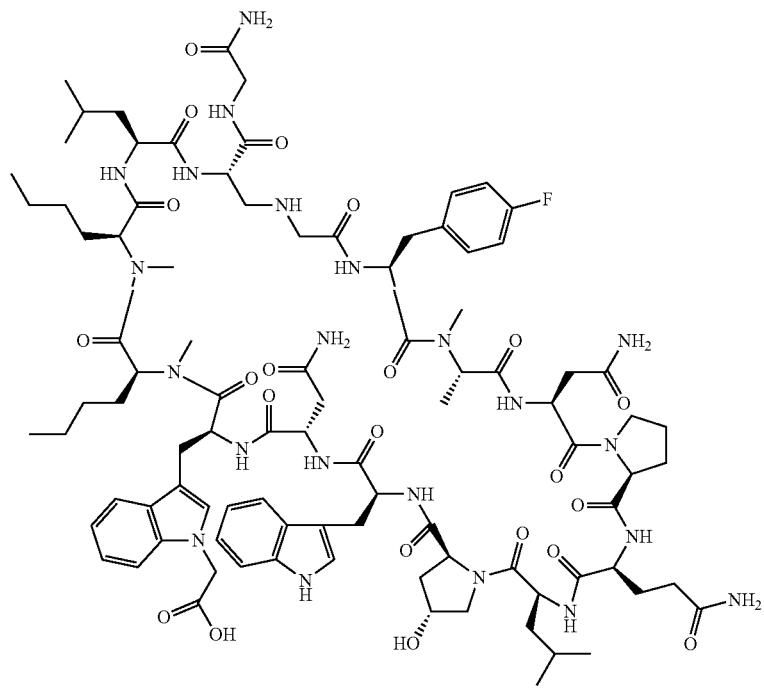

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 9.5 mg, and its estimated purity by LCMS analysis was 97%. ESI-MS(+) m/z 964.9 (M+2H).

PREPARATION OF EXAMPLE 9010

Example 9010

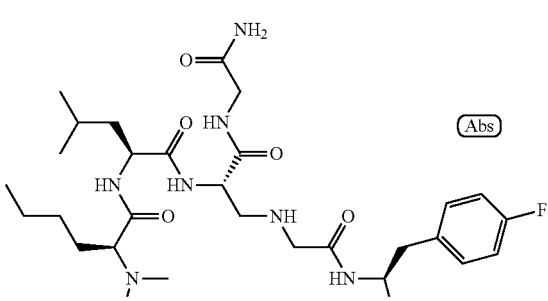

-continued

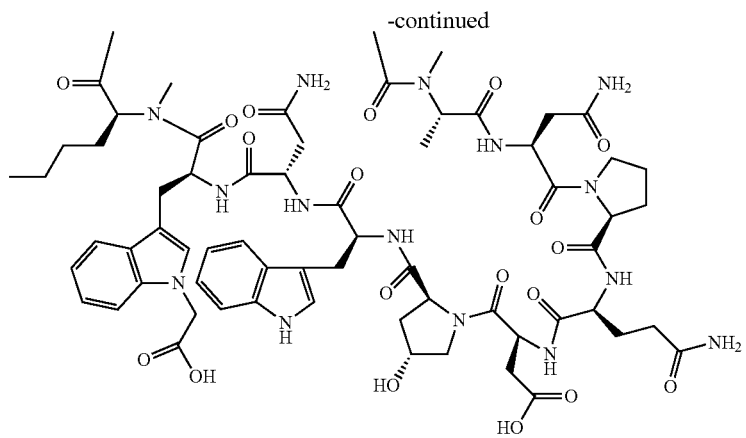

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 10.7 mg, and its estimated purity by LCMS analysis was 97%. ESI-MS(+) m/z 966.1 (M+2H).

PREPARATION OF EXAMPLE 9011

Example 9011

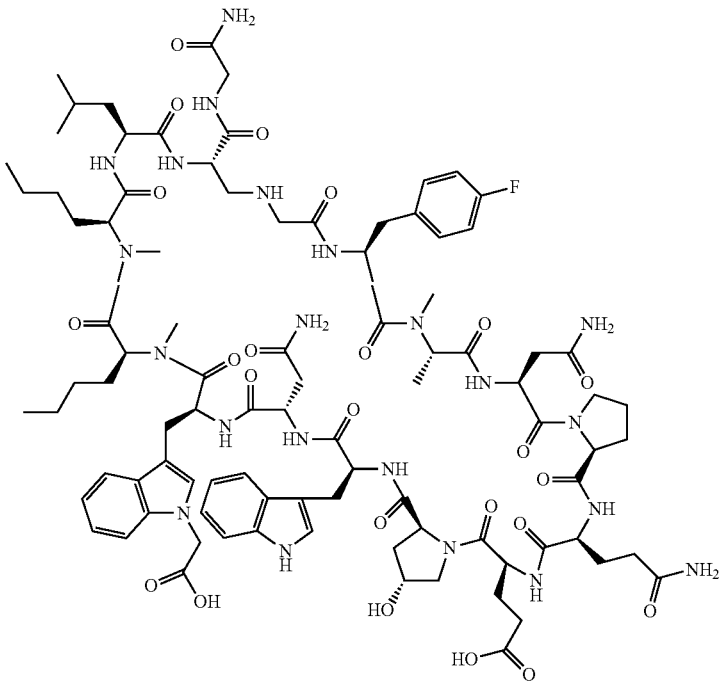

The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-60% B over 30 minutes, then a 5-minute hold at 100% B; Flow: 20 mL/min. Fractions containing the desired product were combined and dried via centrifugal evaporation. The yield of the product was 15.6 mg, and its estimated purity by LCMS analysis was 82%. ESI-MS(+) m/z 973.2 (M+2H).

PREPARATION OF EXAMPLE 9012

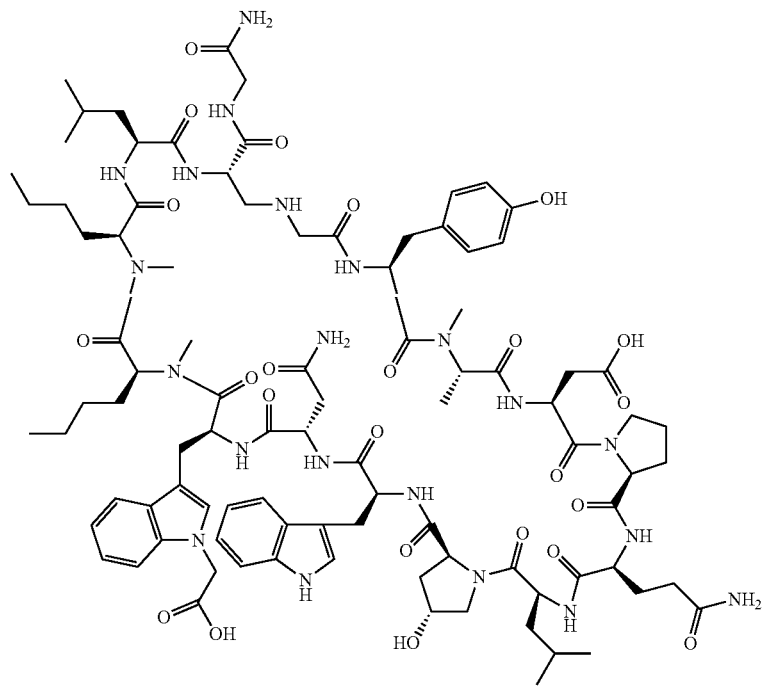

Example 9012

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The yield of the product was 7.3 mg, and its estimated purity by LCMS analysis was 96%. ESI-MS(+) m/z 964.0 (M+2H).

PREPARATION OF EXAMPLE 9013

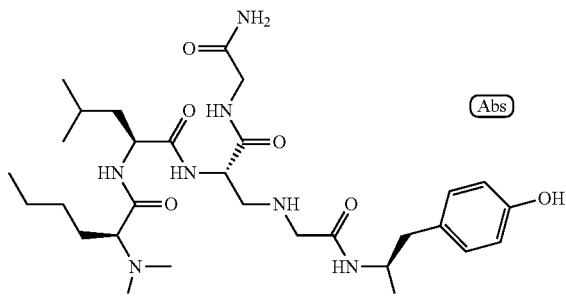

Example 9013

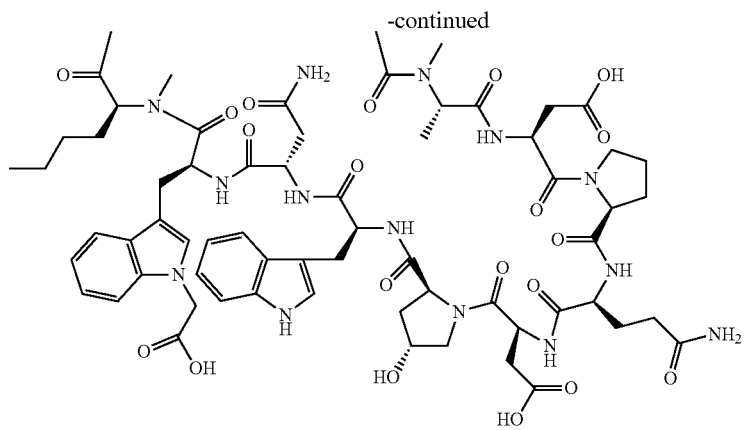

-continued

The crude material was purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 30-70% B over 30 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The yield of the product was 10.7 mg, and its estimated purity by LCMS analysis was 97%. ESI-MS(+) m/z 965.1 (M+2H).

PREPARATION OF EXAMPLE 9014

Example 9014

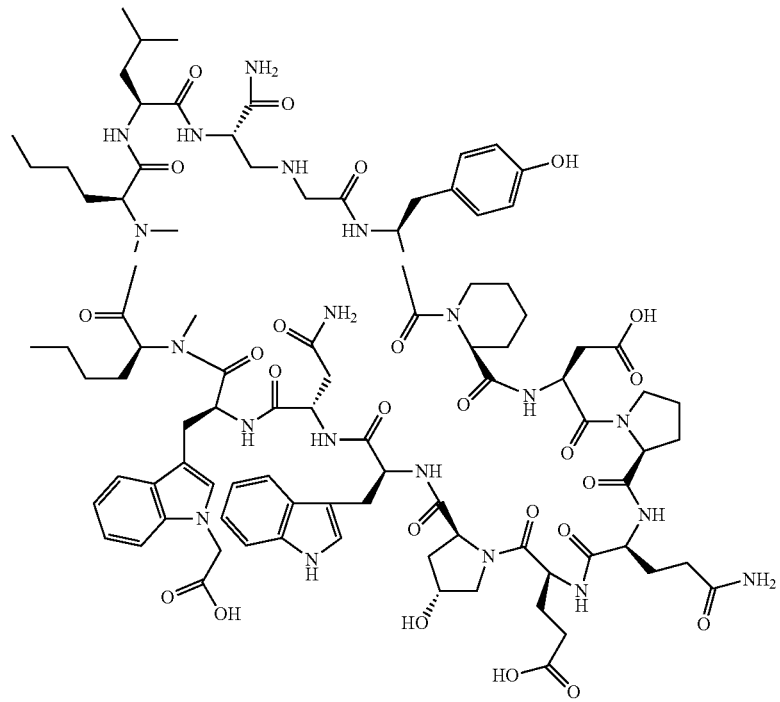

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 30 minutes, then a 5-minute hold at 100% B; Flow: 20 mL/min. Fractions containing the desired product were combined and dried via centrifugal evaporation. The yield of the product was 2.4 mg, and its estimated purity by LCMS analysis was 97%. ESI-MS(+) m/z 972.1 (M+2H).

PREPARATION OF EXAMPLE 9015

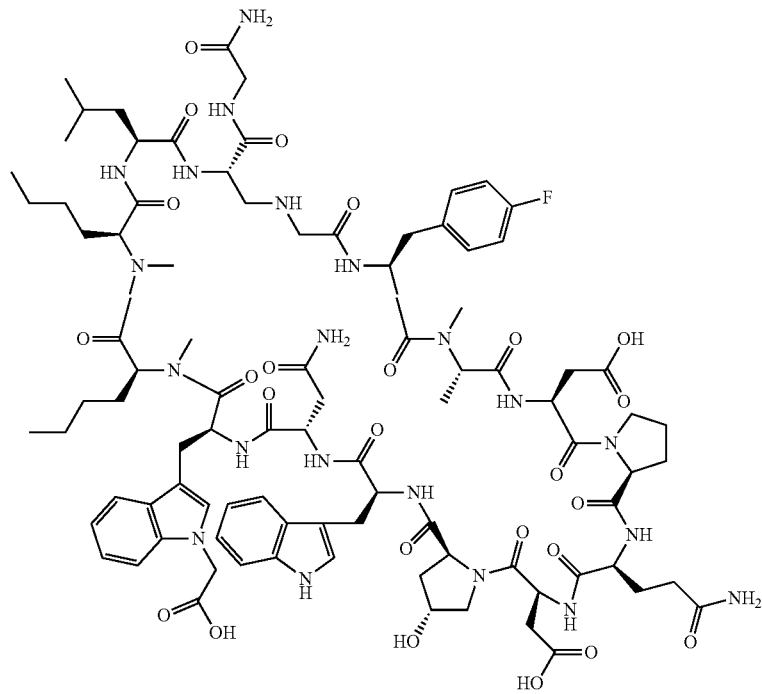

Example 9015

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 8.6 mg, and its estimated purity by LCMS analysis was 96%. ESI-MS(+) m/z 966.2 (M+2H).

PREPARATION OF EXAMPLE 9016

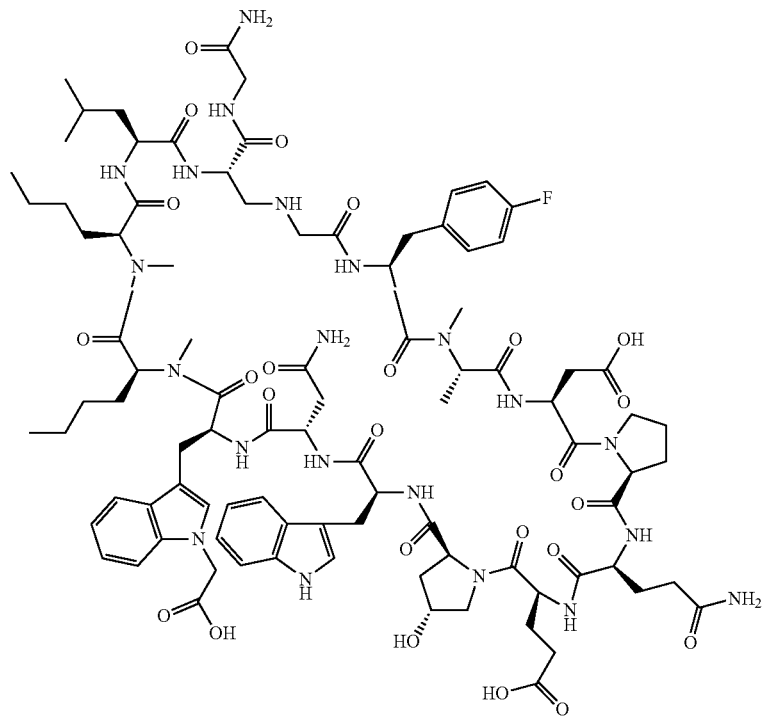

Example 9016

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 2.1 mg, and its estimated purity by LCMS analysis was 95%. ESI-MS(+) m/z 973.2 (M+2H).

PREPARATION OF EXAMPLE 9017

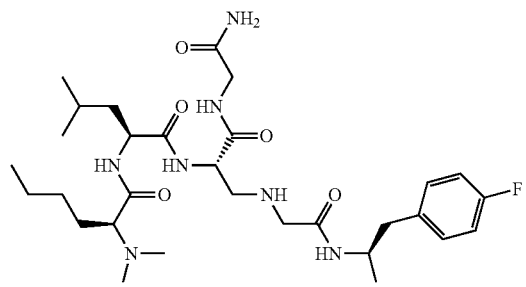

Example 9017

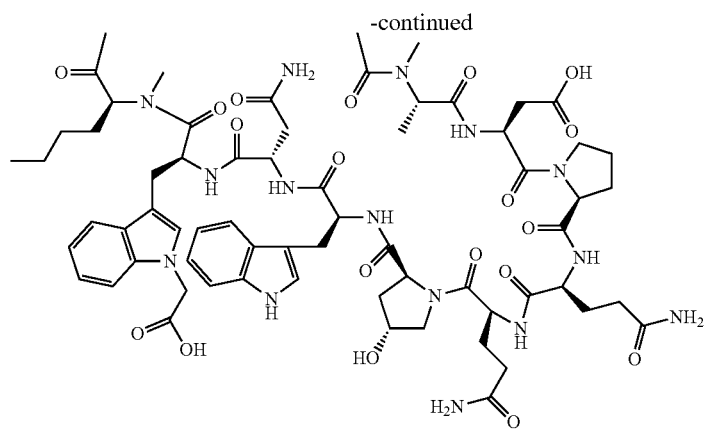

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 3.2 mg, and its estimated purity by LCMS analysis was 92%. ESI-MS(+) m/z 973.1 (M+2H).

PREPARATION OF EXAMPLE 9018

Example 9018

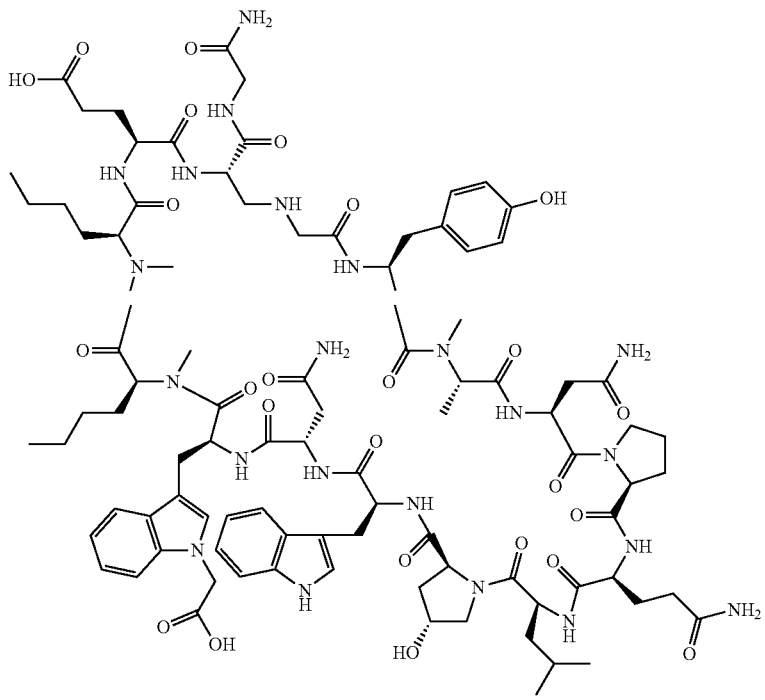

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The yield of the product was 4.5 mg, and its estimated purity by LCMS analysis was 100%. ESI-MS(+) m/z 972.1 (M+2H).

PREPARATION OF EXAMPLE 9019

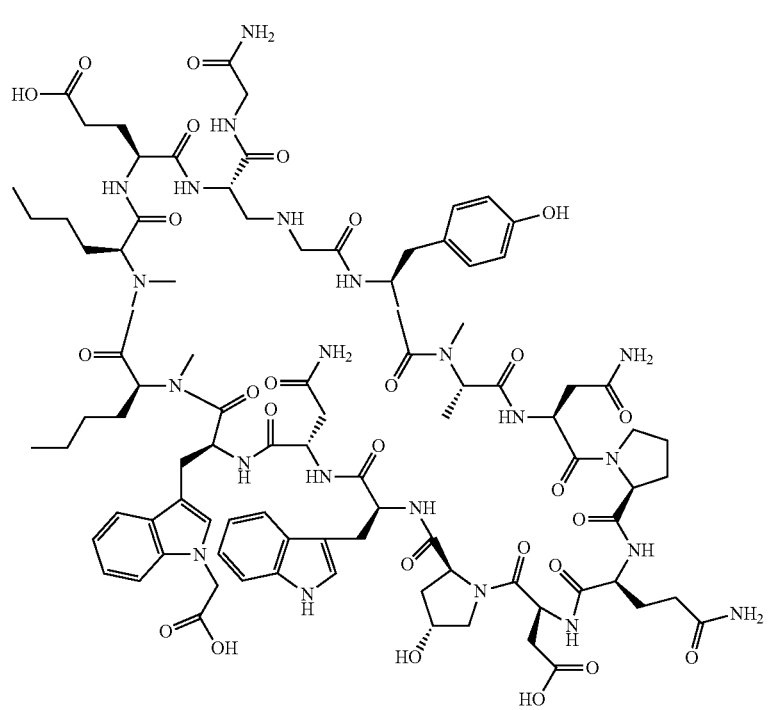

Example 9019

The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 30 minutes, then a 5-minute hold at 100% B; Flow: 20 mL/min. Fractions containing the desired product were combined and dried via centrifugal evaporation. The yield of the product was 6.6 mg, and its estimated purity by LCMS analysis was 95%. ESI-MS(+) m/z 972.4 (M+2H).

PREPARATION OF EXAMPLE 9020

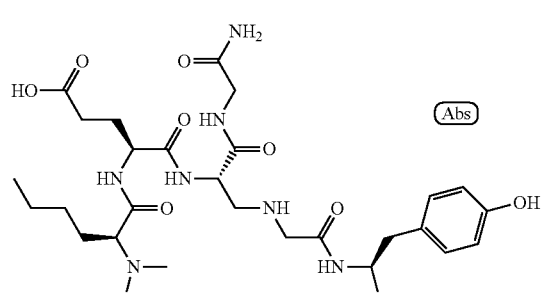

Example 9020

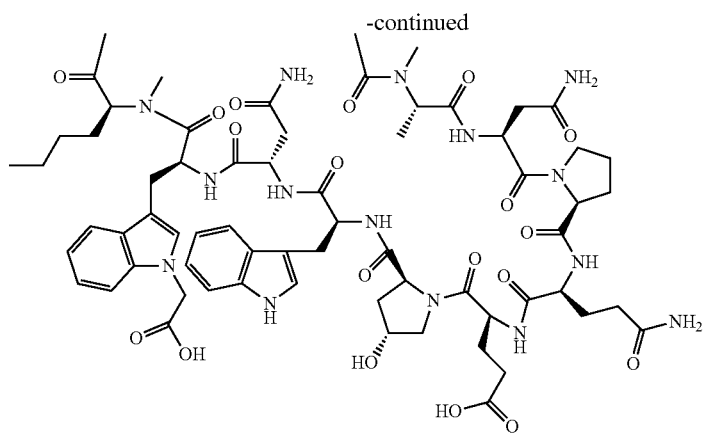

The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 30 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The yield of the product was 4.5 mg, and its estimated purity by LCMS analysis was 94%. ESI-MS(+) m/z 980.2 (M+2H).

PREPARATION OF EXAMPLE 9021

Example 9021

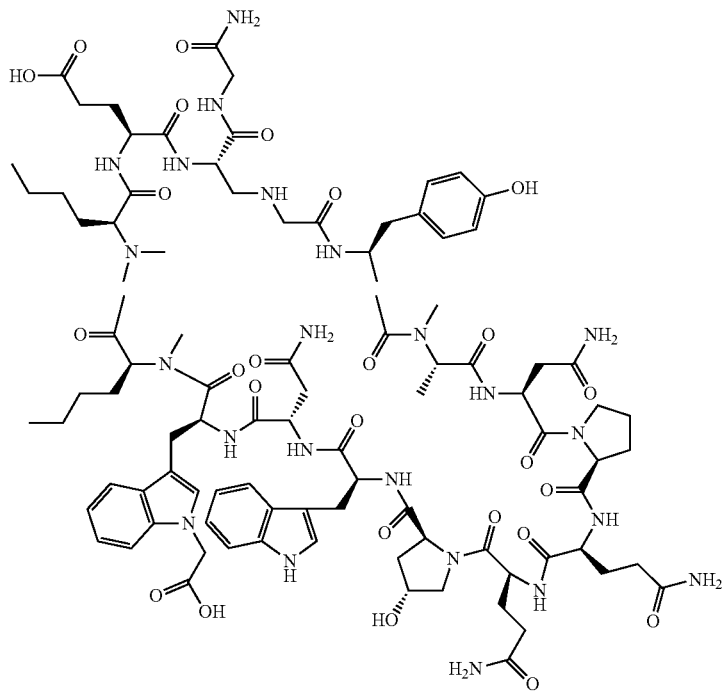

The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 30 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 0-45% B over 50 minutes, then a 5-minute hold at 100% B; Flow: 20 mL/min. Fractions containing the desired product were combined and dried via centrifugal evaporation. The yield of the product was 4.7 mg, and its estimated purity by LCMS analysis was 97%. ESI-MS(+) m/z 979.1 (M+2H).

PREPARATION OF EXAMPLE 9022

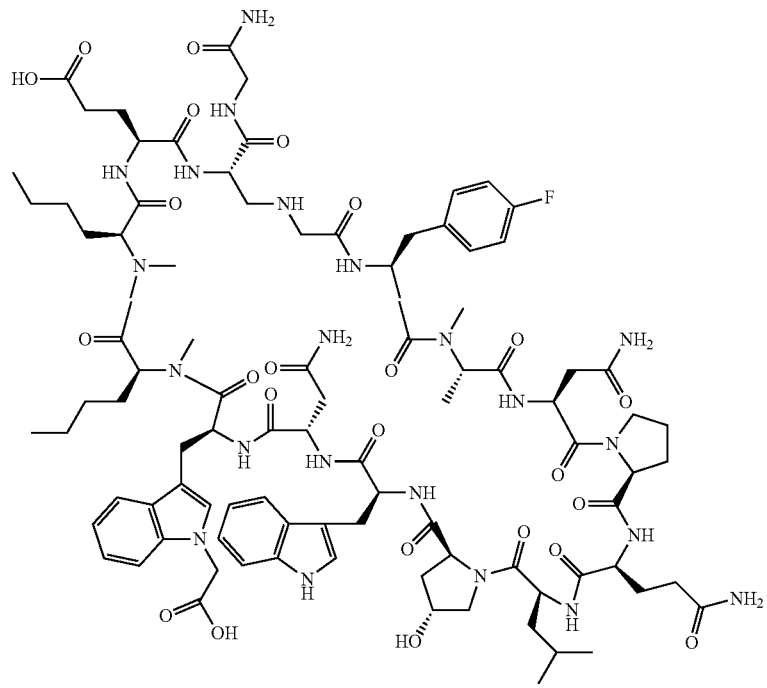

Example 9022

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 33 minutes, then a 5-minute hold at 100% B; Flow: 20 mL/min. Fractions containing the desired product were combined and dried via centrifugal evaporation. The yield of the product was 2.1 mg, and its estimated purity by LCMS analysis was 100%. ESI-MS(+) m/z 972.2 (M+2H).

PREPARATION OF EXAMPLE 9023

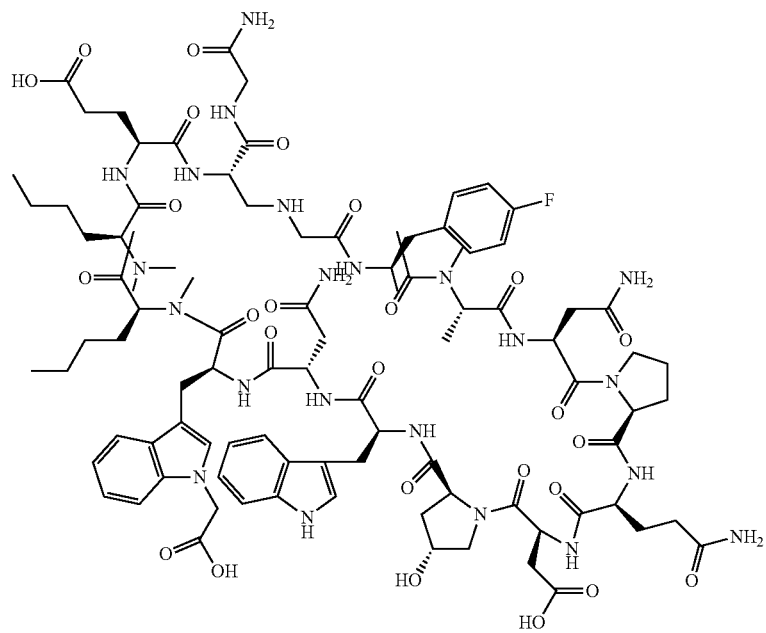

Example 9023

The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-85% B over 30 minutes, then a 5-minute hold at 100% B; Flow: 20 mL/min. Fractions containing the desired product were combined and dried via centrifugal evaporation. The yield of the product was 9.5 mg, and its estimated purity by LCMS analysis was 95%. ESI-MS(+) m/z 974.0 (M+2H).

PREPARATION OF EXAMPLE 9024

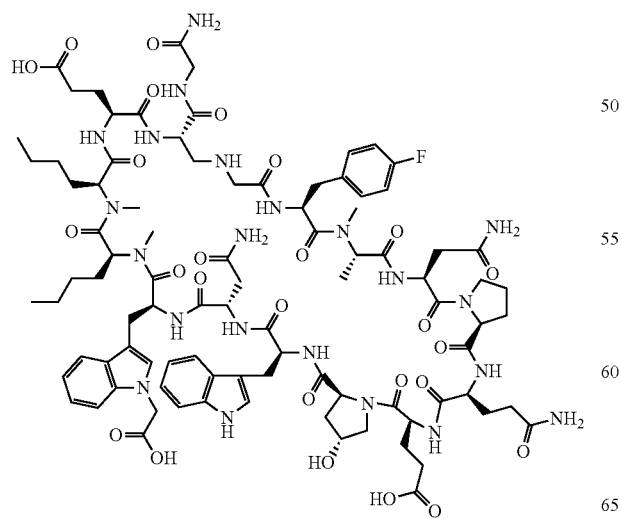

Example 9024

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The yield of the product was 3.4 mg, and its estimated purity by LCMS analysis was 99%. ESI-MS(+) m/z 980.6 (M+2H).

PREPARATION OF EXAMPLE 9025

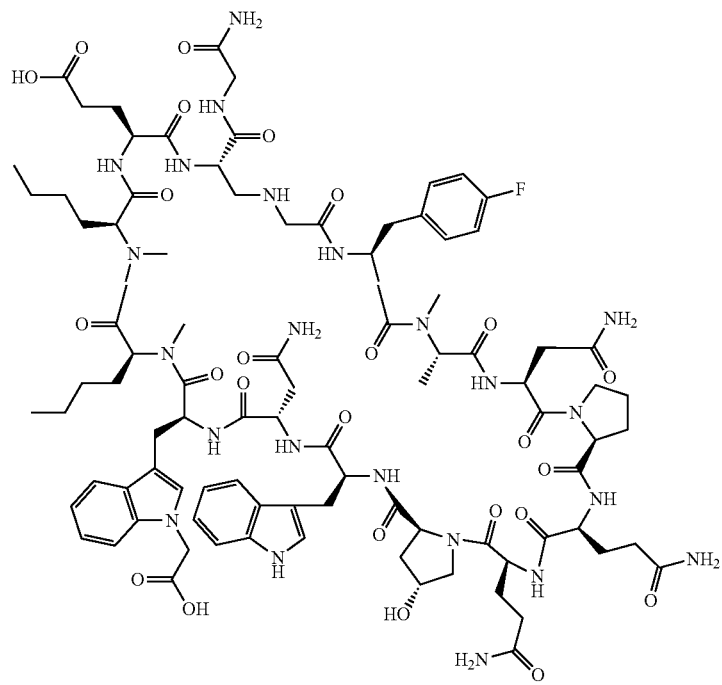

Example 9025

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 0-minute hold at 100% B; Flow: 20 mL/min. Fractions containing the desired product were combined and dried via centrifugal evaporation. The material was further purified via preparative LC/MS with the following conditions: Column: Waters CSH C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The yield of the product was 7.4 mg, and its estimated purity by LCMS analysis was 95%. ESI-MS(+) m/z 980.0 (M+2H).

PREPARATION OF EXAMPLE 9026

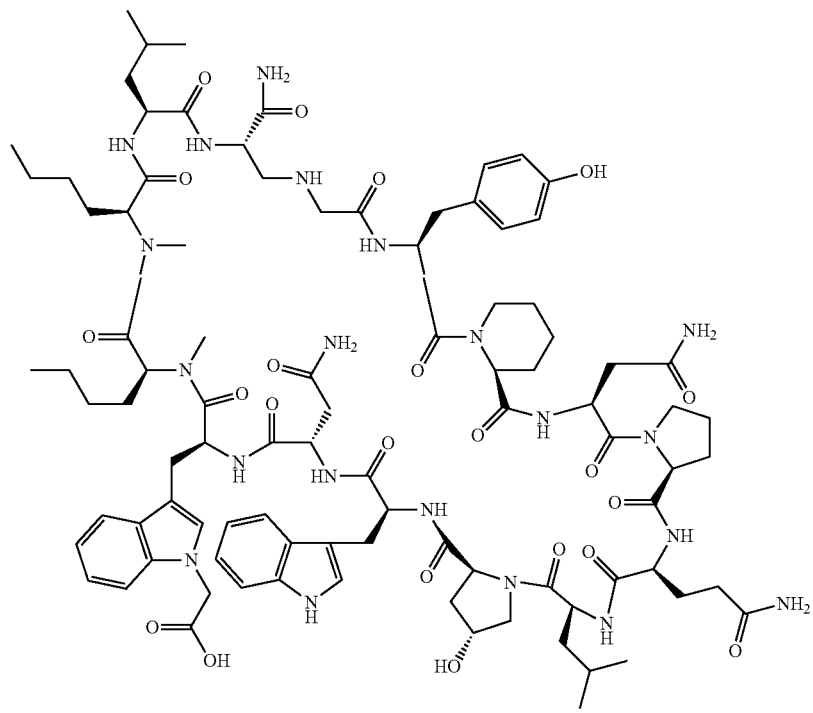

Example 9026

The crude material was purified via preparative LC/MS with the following conditions: Column: waters xbridge c-18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 4.0 mg, and its estimated purity by LCMS analysis was 97%. ESI-MS(+) m/z 948.2 (M+2H).

PREPARATION OF EXAMPLE 9027

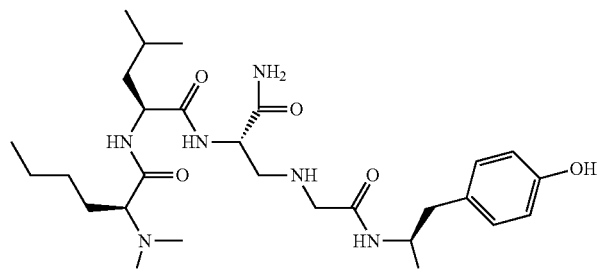

Example 9027

-continued

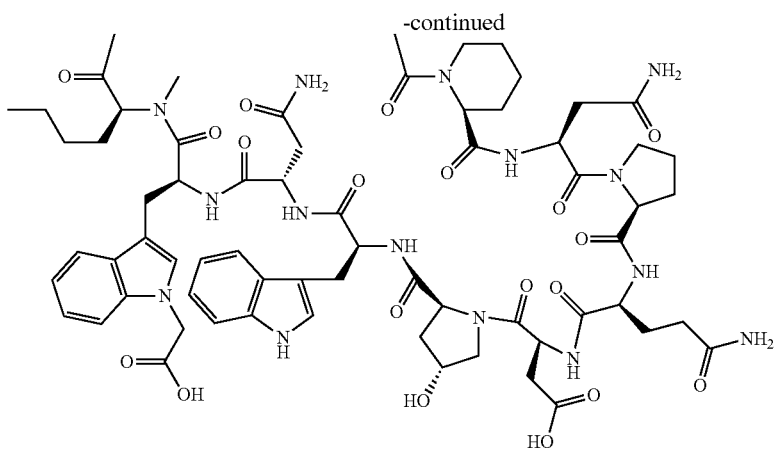

The crude material was purified via preparative LC/MS with the following conditions: Column: waters CSH c-18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The yield of the product was 3.7 mg, and its estimated purity by LCMS analysis was 100%. ESI-MS(+) m/z 949.3 (M+2H).

PREPARATION OF EXAMPLE 9028

Example 9028

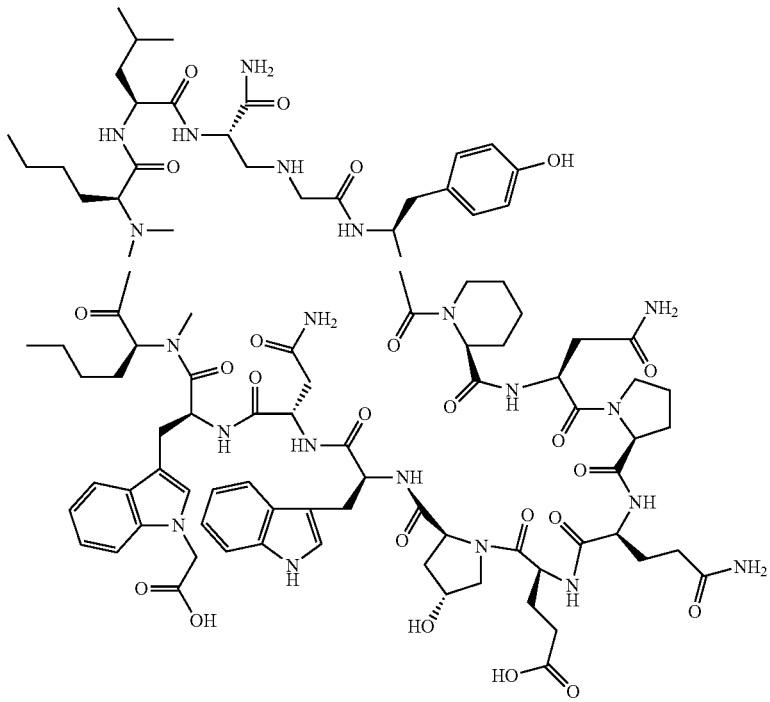

The crude material was purified via preparative LC/MS with the following conditions: Column: waters xbridge c-18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 3.9 mg, and its estimated purity by LCMS analysis was 90%. ESI-MS(+) m/z 956.1 (M+2H).

PREPARATION OF EXAMPLE 9029

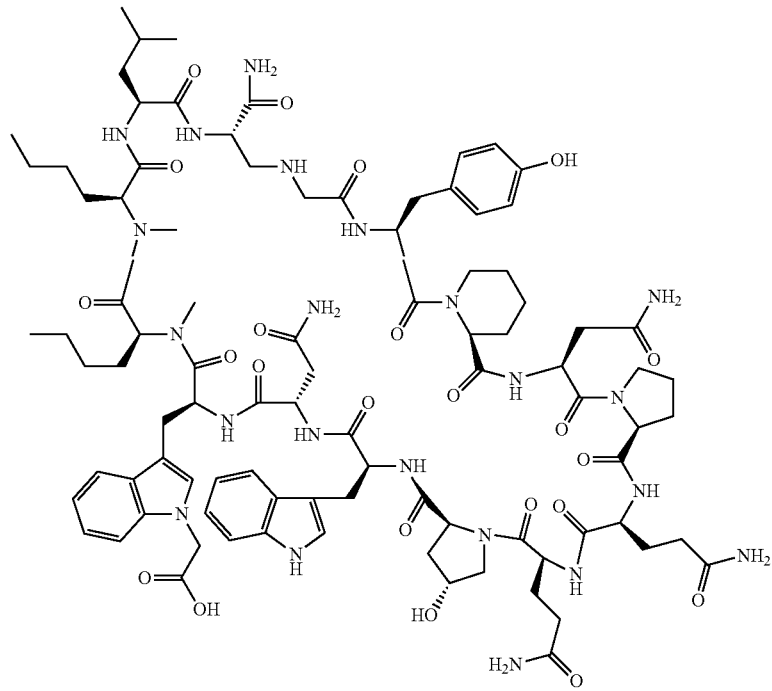

Example 9029

The crude material was purified via preparative LC/MS with the following conditions: Column: waters xbridge c-18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 4.3 mg, and its estimated purity by LCMS analysis was 99%. ESI-MS(+) m/z 956.2 (M+2H).

PREPARATION OF EXAMPLE 9030

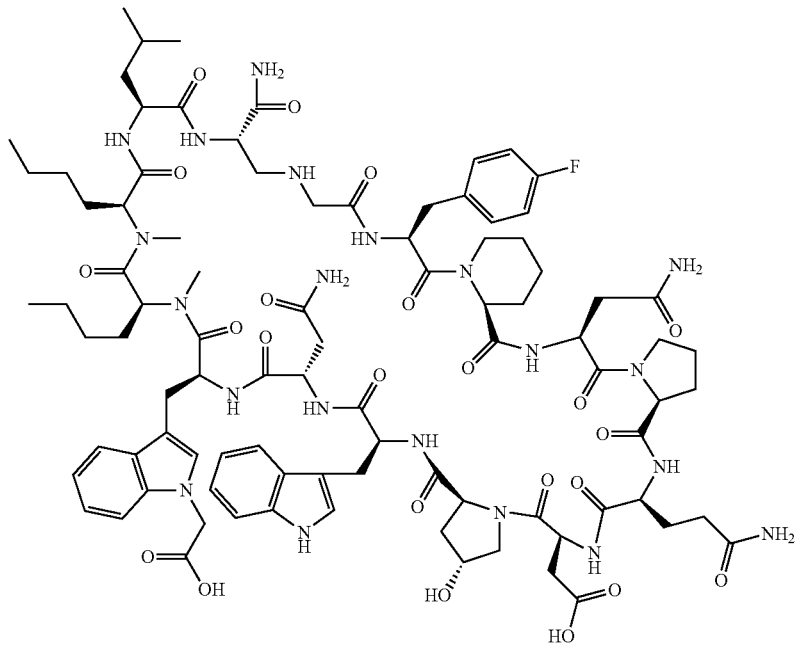

Example 9030

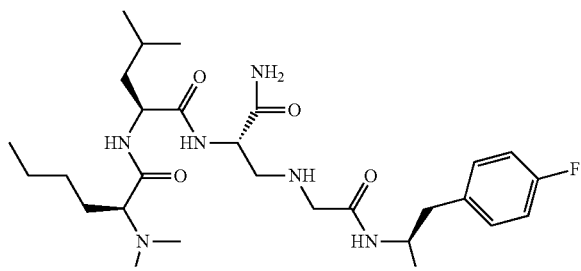

The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 5.8 mg, and its estimated purity by LCMS analysis was 98%. ESI-MS(+) m/z 949.2 (M+2H).

PREPARATION OF EXAMPLE 9031

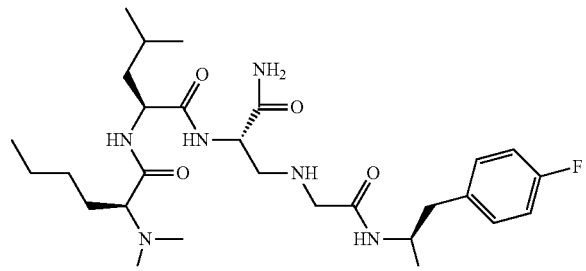

Example 9031

-continued

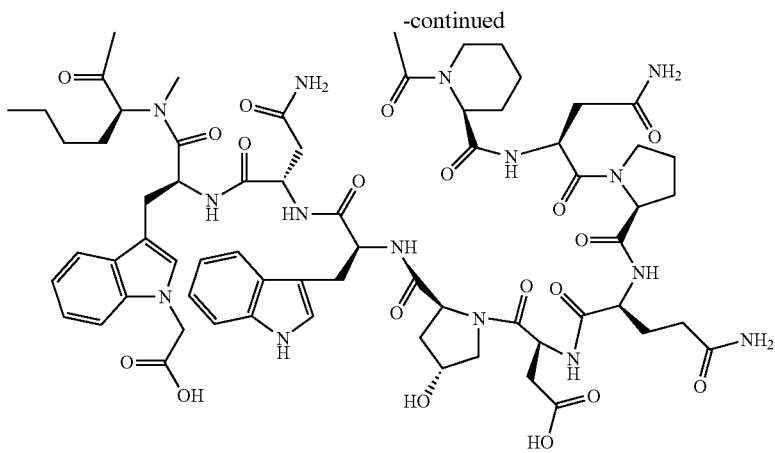

The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-30% B over 30 minutes, then a 5-minute hold at 100% B; Flow: 20 mL/min. Fractions containing the desired product were combined and dried via centrifugal evaporation. The yield of the product was 2.5 mg, and its estimated purity by LCMS analysis was 97%. ESI-MS(+) m/z 950.1 (M+2H).

PREPARATION OF EXAMPLE 9032

Example 9032

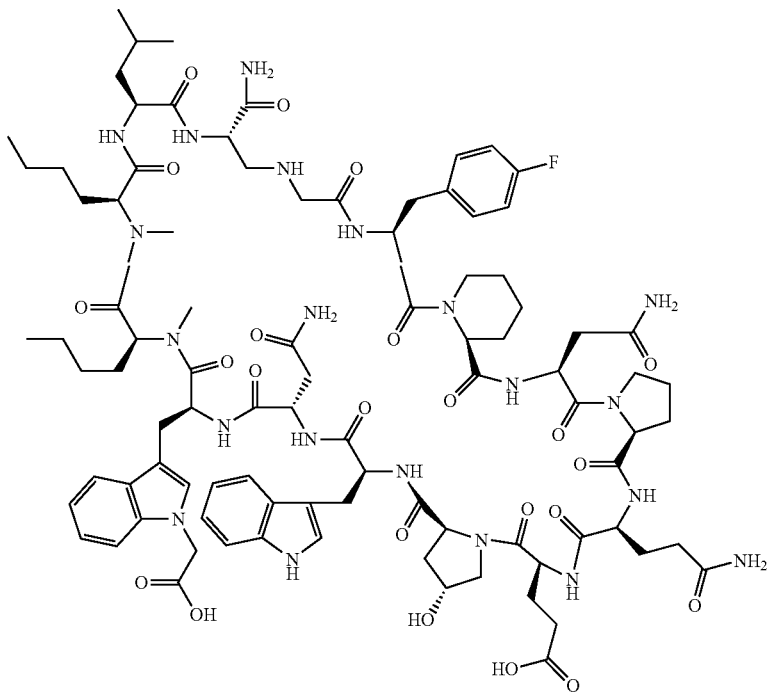

The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 30 minutes, then a 5-minute hold at 100% B; Flow: 20 mL/min. Fractions containing the desired product were combined and dried via centrifugal evaporation. The material was further purified via LC/MS with the following conditions: Column: Waters CSH C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 5.9 mg, and its estimated purity by LCMS analysis was 82%. ESI-MS(+) m/z 957.1 (M+2H).

PREPARATION OF EXAMPLE 9033

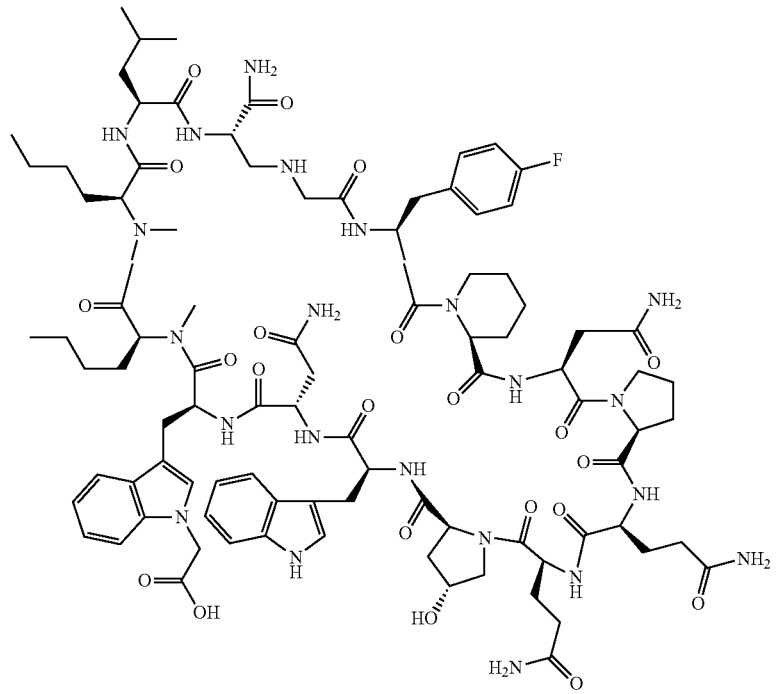

Example 9033

The crude material was purified via preparative LC/MS with the following conditions: Column: XBridge C18, 19×mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 30 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 7.0 mg, and its estimated purity by LCMS analysis was 99%. ESI-MS(+) m/z 956.2 (M+2H).

PREPARATION OF EXAMPLE 9034

Example 9034

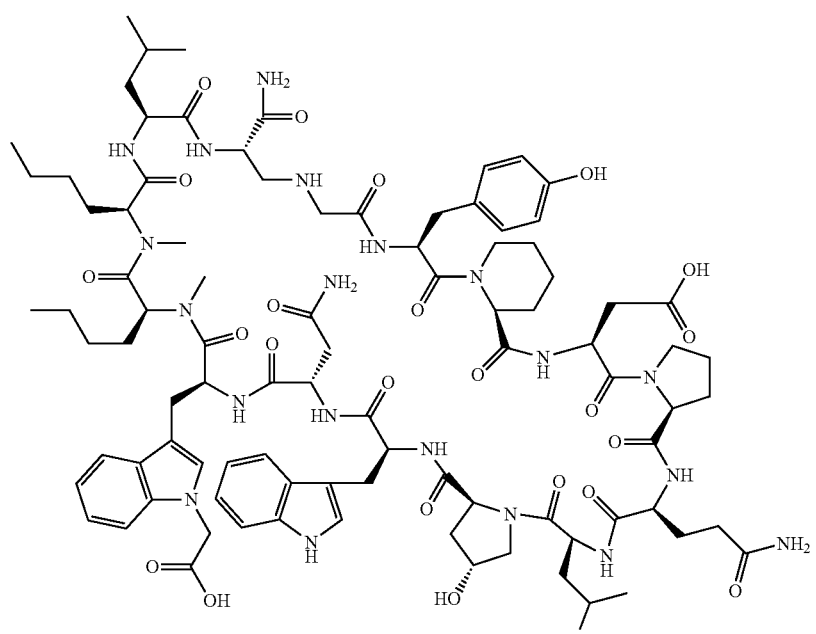

The crude material was purified via preparative LC/MS with the following conditions: Column: XBridge C18, 19×mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 30 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 30 minutes, then a 5-minute hold at 100% B; Flow: 20 mL/min. Fractions containing the desired product were combined and dried via centrifugal evaporation. The yield of the product was 3.3 mg, and its estimated purity by LCMS analysis was 100%. ESI-MS(+) m/z 948.4 (M+2H).

PREPARATION OF EXAMPLE 9035

Example 9035

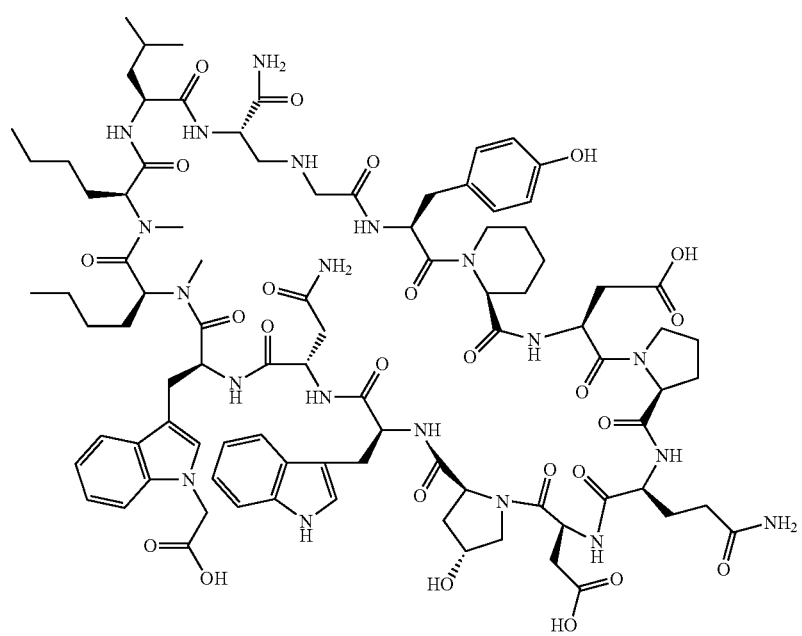

The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The yield of the product was 2.1 mg, and its estimated purity by LCMS analysis was 100%. ESI-MS(+) m/z 950.2 (M+2H).

PREPARATION OF EXAMPLE 9036

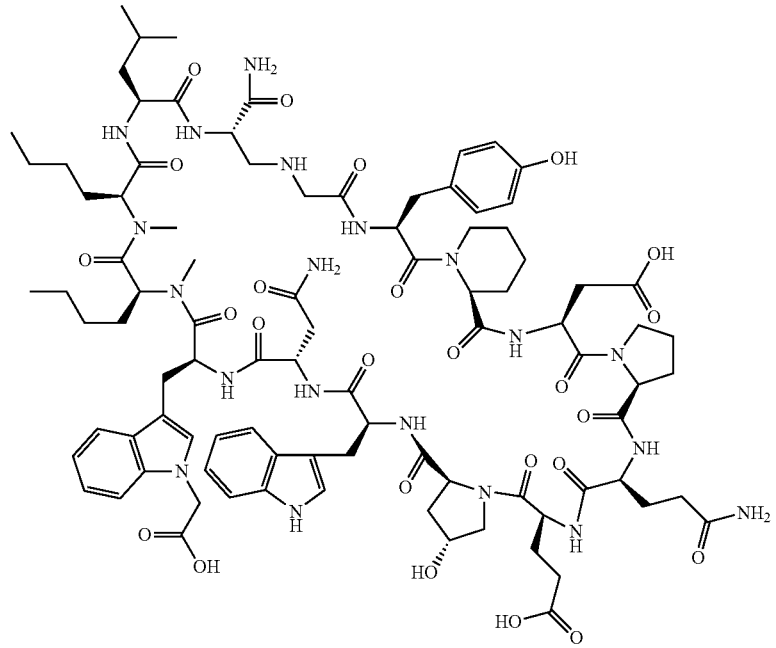

Example 9036

The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The yield of the product was 0.7 mg, and its estimated purity by LCMS analysis was 96%. ESI-MS(+) m/z 956.3 (M+2H).

PREPARATION OF EXAMPLE 9037

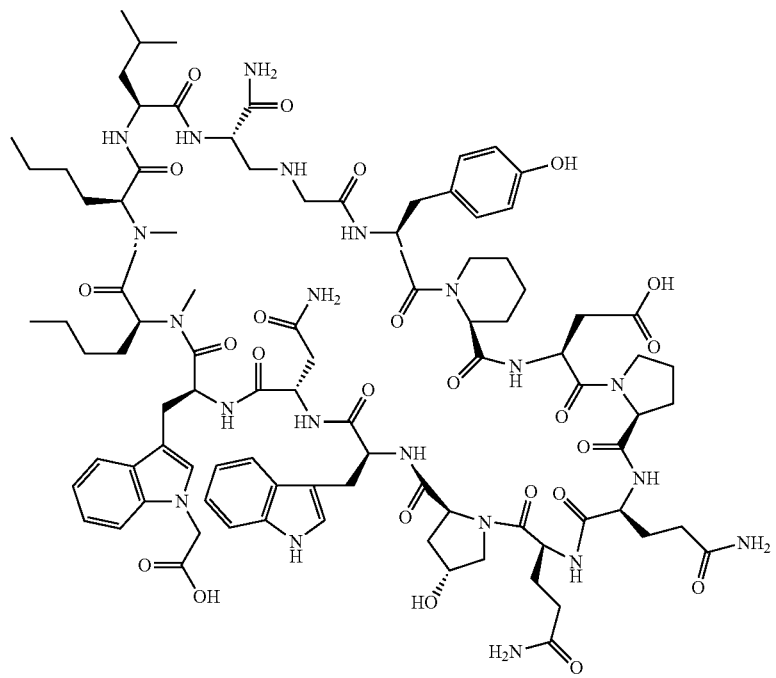

Example 9037

The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 15-55% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute hold at 100% B; Flow: 20 mL/min. Fractions containing the desired product were combined and dried via centrifugal evaporation. The yield of the product was 0.9 mg, and its estimated purity by LCMS analysis was 100%. ESI-MS(+) m/z 956.2 (M+2H).

PREPARATION OF EXAMPLE 9038

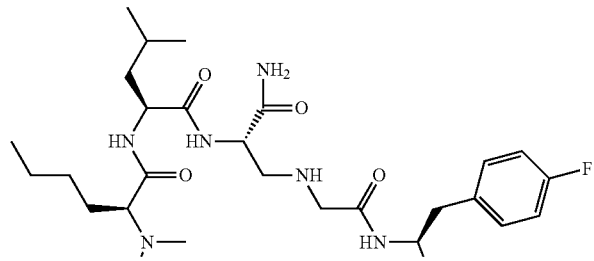

Example 9038

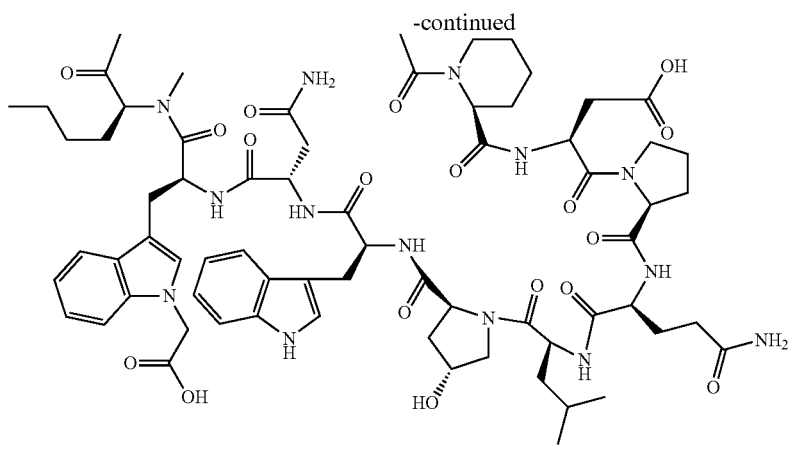

The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-60% B over 30 minutes, then a 5-minute hold at 100% B; Flow: 20 mL/min. Fractions containing the desired product were combined and dried via centrifugal evaporation. The yield of the product was 0.5 mg, and its estimated purity by LCMS analysis was 100%. ESI-MS(+) m/z 949.2 (M+2H).

PREPARATION OF EXAMPLE 9039

Example 9039

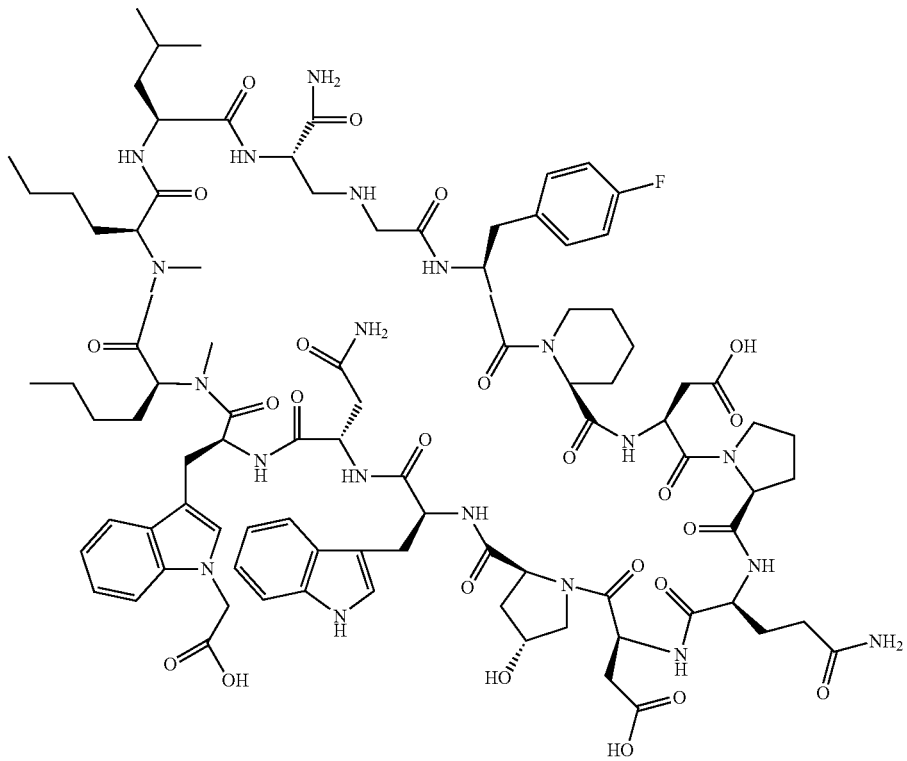

product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-45% B over 30 minutes, then a 5-minute The crude material was purified via preparative LC/MS with the following conditions: Column: XBridge C18, 19×mm, 5-μm particles; Mobile Phase A: 5:95 methanol:water with 10-mM ammonium acetate; Mobile Phase B: 95:5 methanol:water with 10-mM ammonium acetate; Gradient: 20-100% B over 20 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 4.7 mg, and its estimated purity by LCMS analysis was 100%. ESI-MS(+) m/z 951.1 (M+2H).

PREPARATION OF EXAMPLE 9040

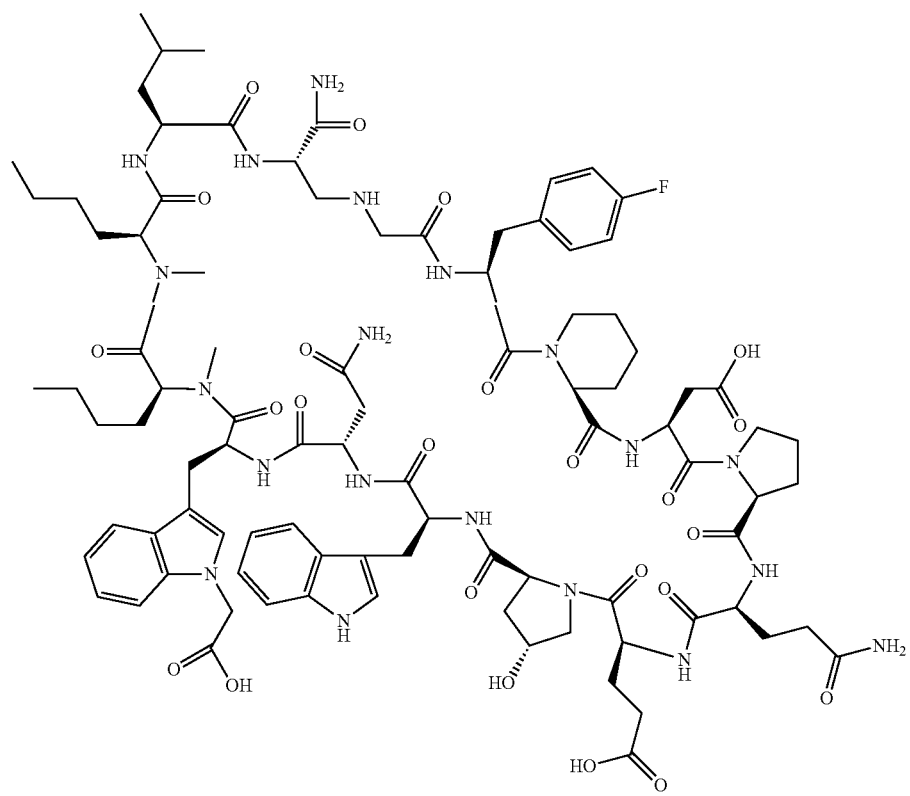

Example 9040

The crude material was purified via preparative LC/MS with the following conditions: Column: XBridge C18, 19×mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 3.3 mg, and its estimated purity by LCMS analysis was 98%. ESI-MS(+) m/z 957.4 (M+2H).

PREPARATION OF EXAMPLE 9041

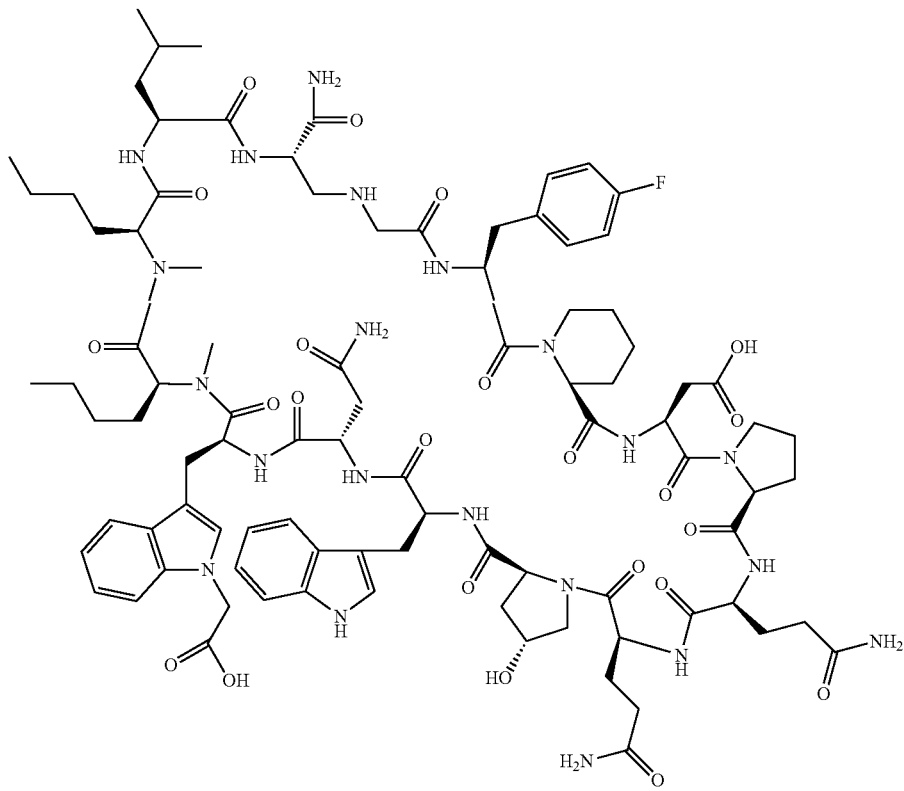

Example 9041

The crude material was purified via preparative LC/MS with the following conditions: Column: XBridge C18, 19×mm, 5-μm particles; Mobile Phase A: 5:95 methanol:water with 10-mM ammonium acetate; Mobile Phase B: 95:5 methanol:water with 10-mM ammonium acetate; Gradient: 25-65% B over 30 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 1.7 mg, and its estimated purity by LCMS analysis was 100%. ESI-MS(+) m/z 957.1 (M+2H).

PREPARATION OF EXAMPLE 9042

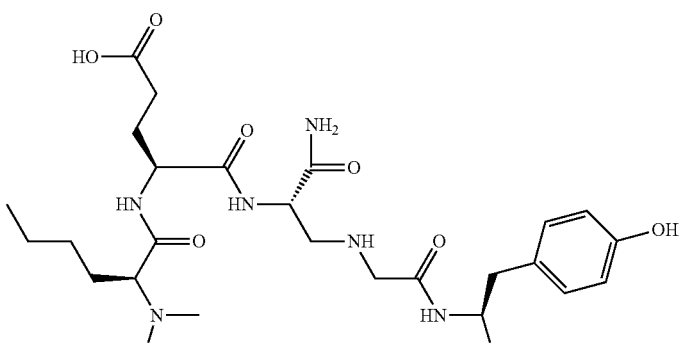

Example 9042

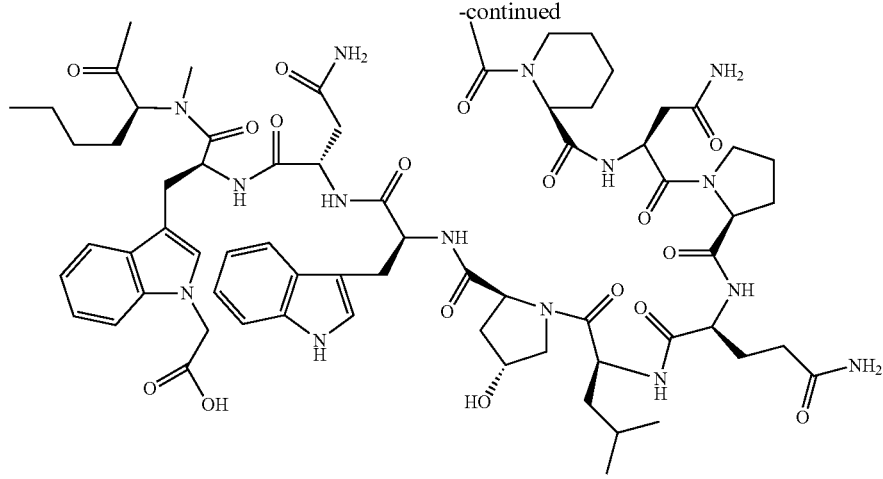

The crude material was purified via preparative LC/MS with the following conditions: Column: XBridge C18, 19×mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 4.5 mg, and its estimated purity by LCMS analysis was 100%. ESI-MS(+) m/z 956.2 (M+2H).

PREPARATION OF EXAMPLE 9043

Example 9043

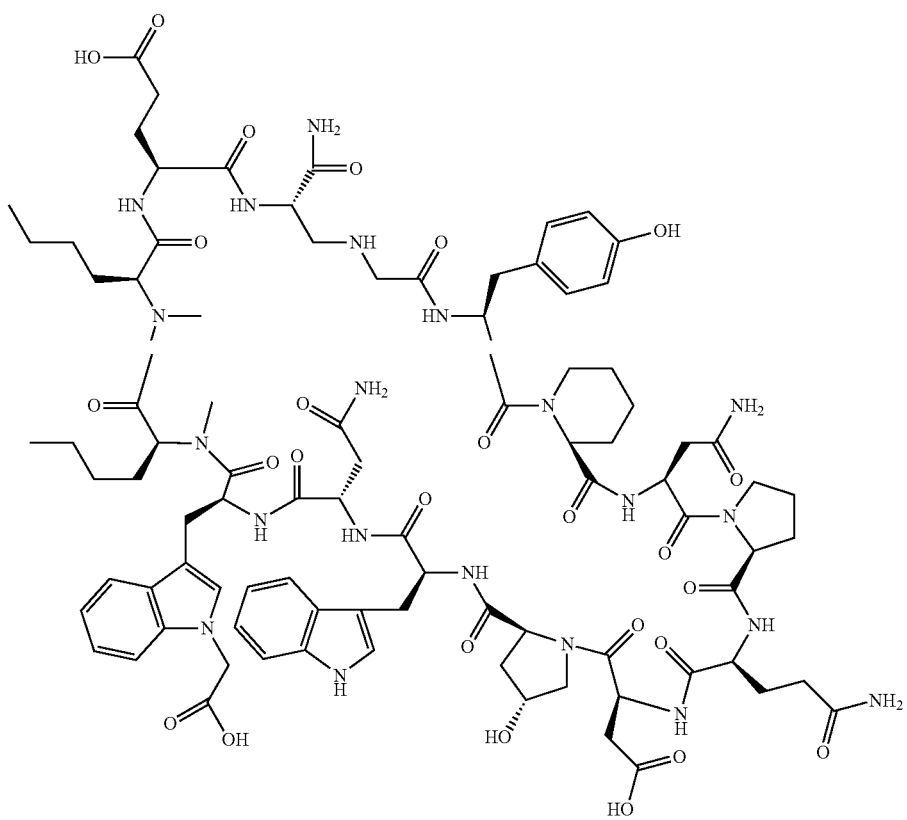

The crude material was purified via preparative LC/MS with the following conditions: Column: XBridge C18, 19×mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 3.3 mg, and its estimated purity by LCMS analysis was 100%. ESI-MS(+) m/z 957.1 (M+2H).

PREPARATION OF EXAMPLE 9044

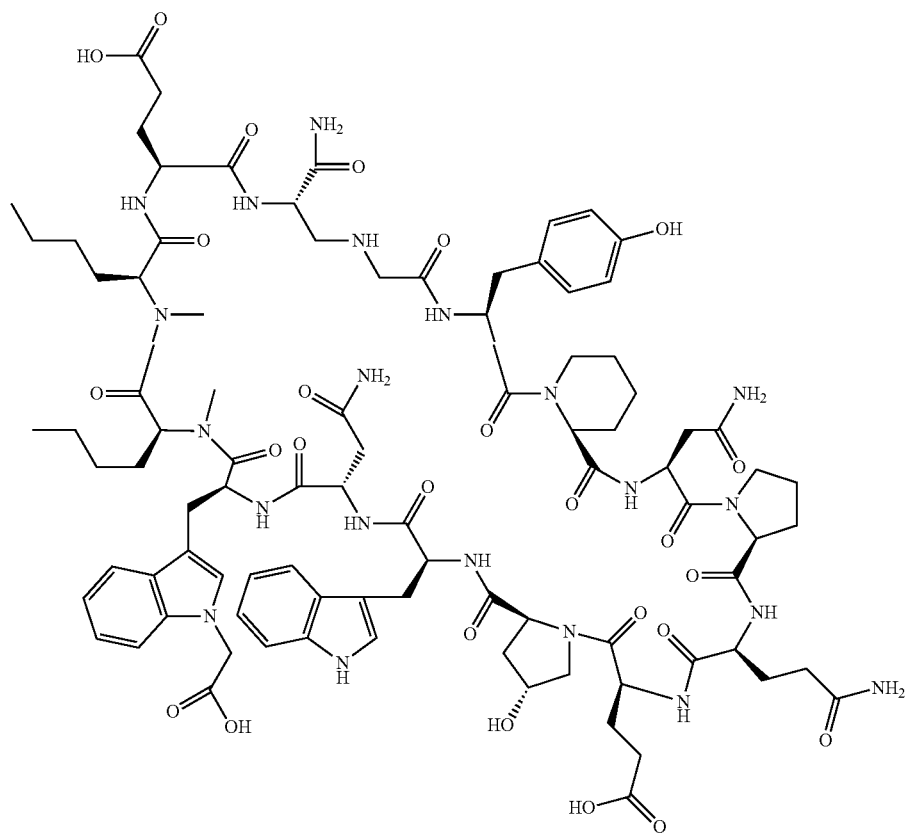

Example 9044

The crude material was purified via preparative LC/MS with the following conditions: Column: XBridge C18, 19×mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 6.3 mg, and its estimated purity by LCMS analysis was 99%. ESI-MS(+) m/z 964.1 (M+2H).

PREPARATION OF EXAMPLE 9045

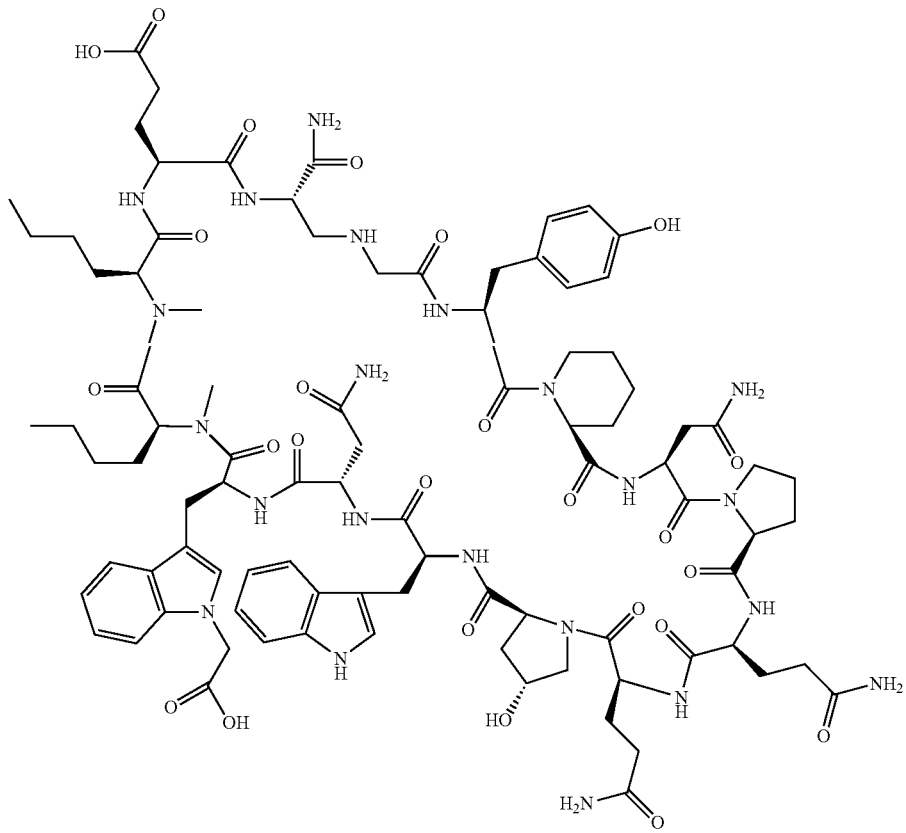

Example 9045

The crude material was purified via preparative LC/MS with the following conditions: Column: XBridge C18, 19×mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 5.5 mg, and its estimated purity by LCMS analysis was 99%. ESI-MS(+) m/z 963.4 (M+2H).

PREPARATION OF EXAMPLE 9046

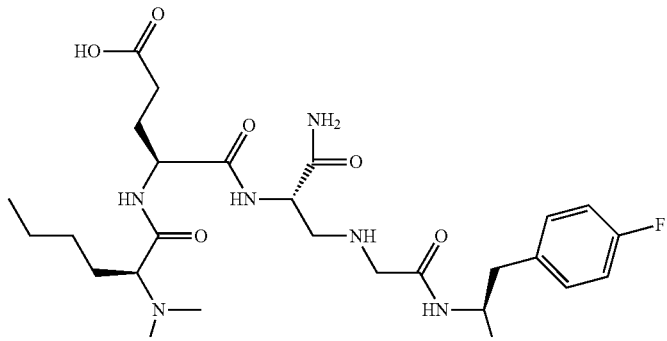

Example 9046

-continued

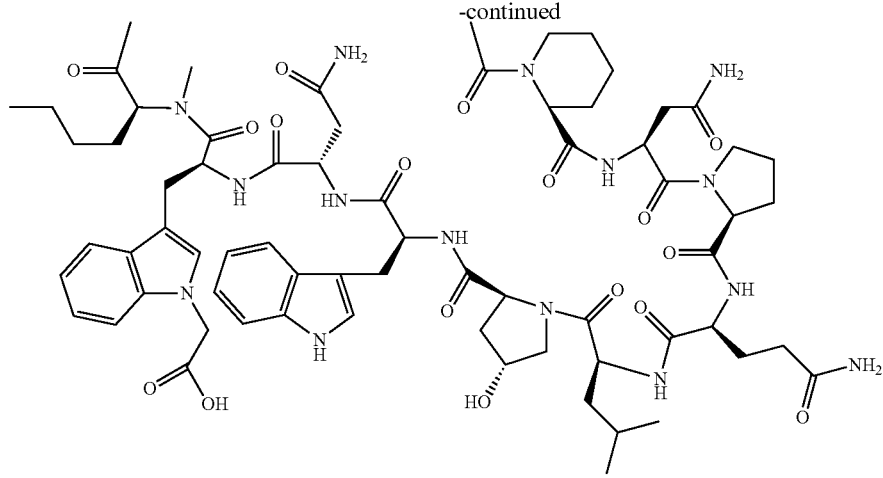

The crude material was purified via preparative LC/MS with the following conditions: Column: XBridge C18, 19×mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 5.2 mg, and its estimated purity by LCMS analysis was 98%. ESI-MS(+) m/z 957.2 (M+2H).

PREPARATION OF EXAMPLE 9047

Example 9047

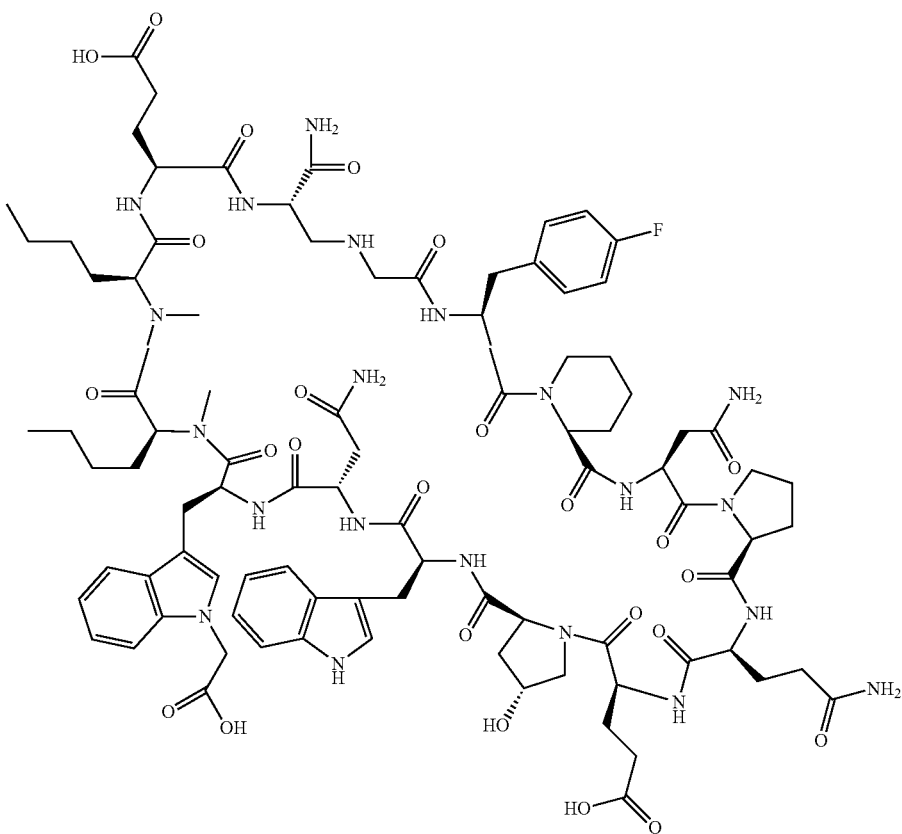

The crude material was purified via preparative LC/MS with the following conditions: Column: XBridge C18, 19×mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 4.9 mg, and its estimated purity by LCMS analysis was 100%. ESI-MS(+) m/z 965.1 (M+2H).

PREPARATION OF EXAMPLE 9048

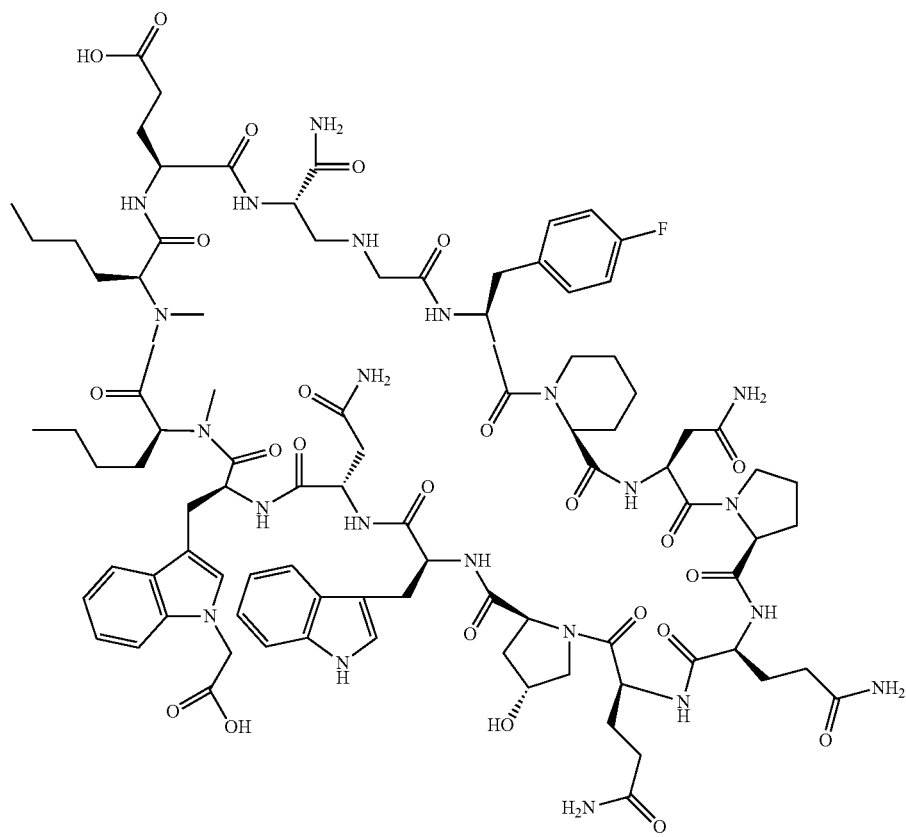

Example 9048

The crude material was purified via preparative LC/MS with the following conditions: Column: XBridge C18, 19×mm, 5-μm particles; Mobile Phase A: 5:95 methanol:water with 10-mM ammonium acetate; Mobile Phase B: 95:5 methanol:water with 10-mM ammonium acetate; Gradient: 35-75% B over 30 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The yield of the product was 6.1 mg, and its estimated purity by LCMS analysis was 96%. ESI-MS(+) m/z 965.1 (M+2H).

PREPARATION OF EXAMPLE 9049

Example 9049

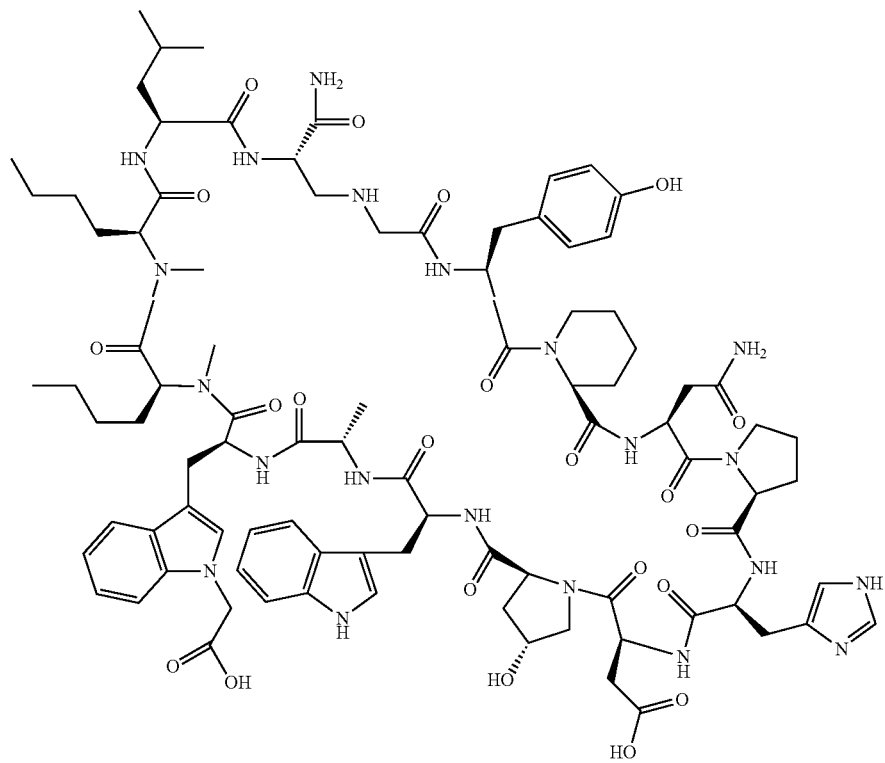

The crude material was purified via preparative LC/MS with the following conditions: Column: XBridge C18, 19×mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-100% B over 20 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 18-58% B over 20 minutes, then a 5-minute hold at 100% B; Flow: 20 mL/min. Fractions containing the desired product were combined and dried via centrifugal evaporation. The yield of the product was 4.4 mg, and its estimated purity by LCMS analysis was 90%. ESI-MS(+) m/z 932.1 (M+2H).

PREPARATION OF EXAMPLE 9050

Example 9050

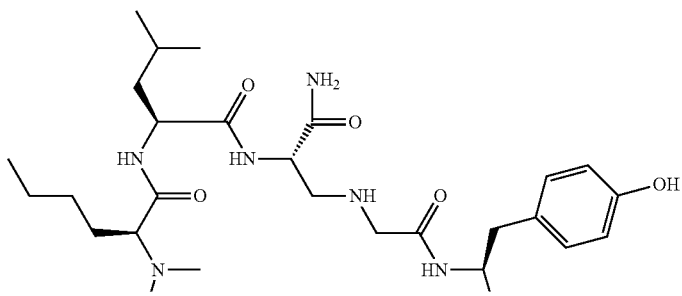

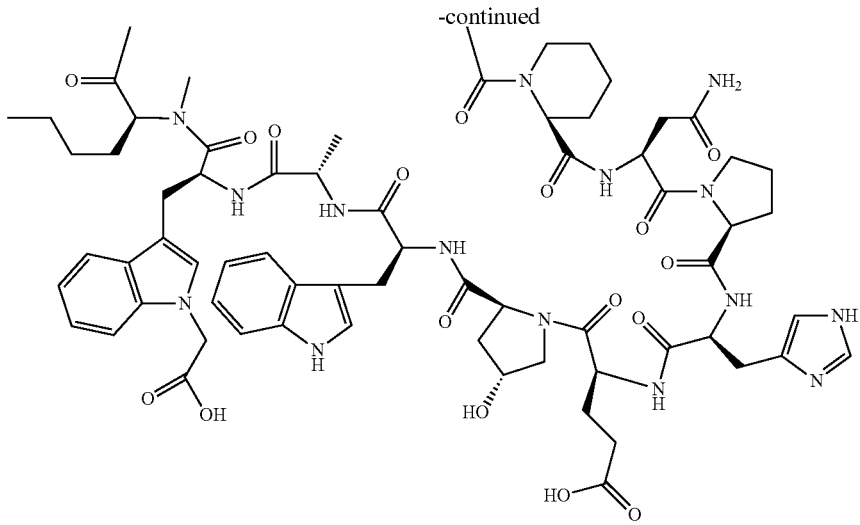

The crude material was purified via preparative LC/MS with the following conditions: Column: XBridge C18, 19×mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-100% B over 20 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 18-58% B over 20 minutes, then a 5-minute hold at 100% B; Flow: 20 mL/min. Fractions containing the desired product were combined and dried via centrifugal evaporation. The yield of the product was 3.9 mg, and its estimated purity by LCMS analysis was 94%. ESI-MS(+) m/z 938.7 (M+2H).

PREPARATION OF EXAMPLE 9051

Example 9051

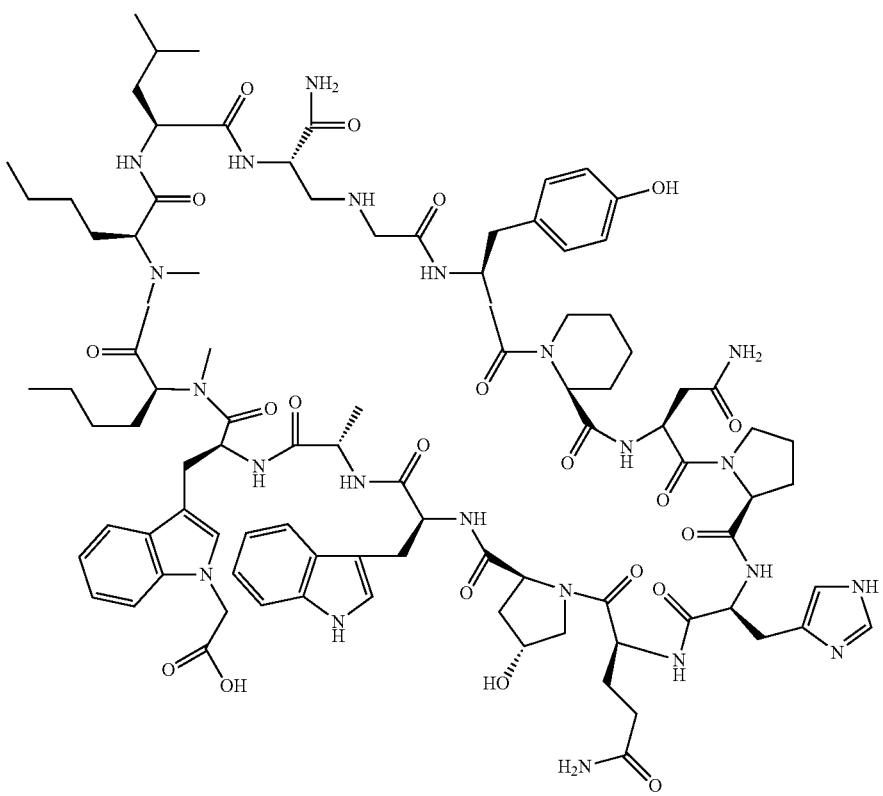

The crude material was purified via preparative LC/MS with the following conditions: Column: XBridge C18, 19×mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-100% B over 20 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 18-58% B over 20 minutes, then a 5-minute hold at 100% B; Flow: 20 mL/min. Fractions containing the desired product were combined and dried via centrifugal evaporation. The yield of the product was 3.9 mg, and its estimated purity by LCMS analysis was 97%. ESI-MS(+) m/z 938.5 (M+2H).

PREPARATION OF EXAMPLE 9052

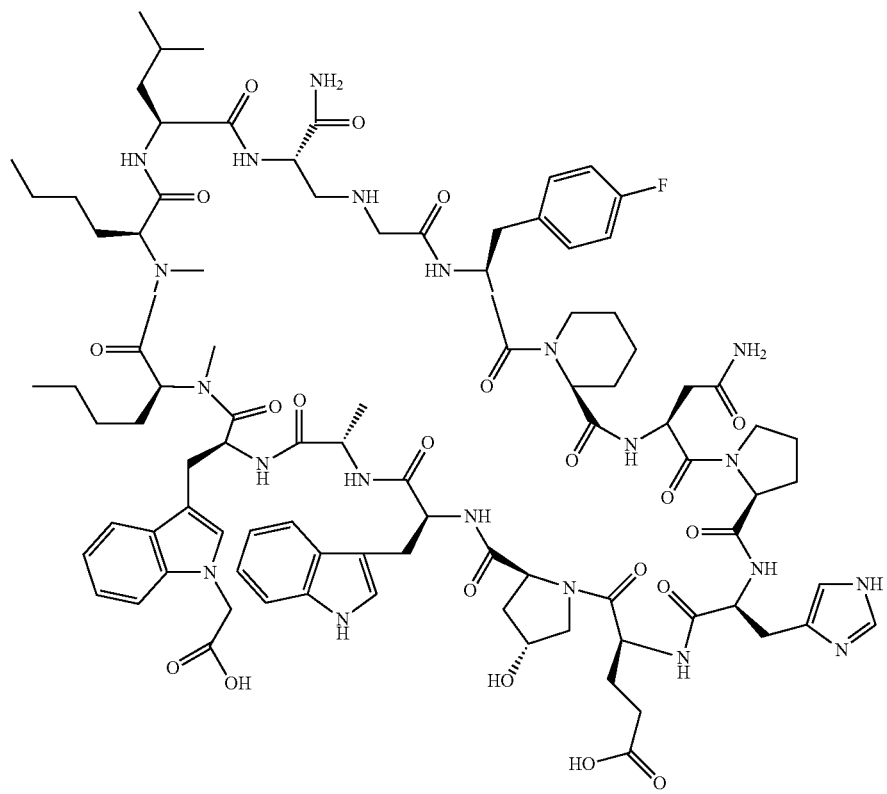

Example 9052

The crude material was purified via preparative LC/MS with the following conditions: Column: XBridge C18, 19×mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-100% B over 15 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-60% B over 20 minutes, then a 5-minute hold at 100% B; Flow: 20 mL/min. Fractions containing the desired product were combined and dried via centrifugal evaporation. The yield of the product was 5.9 mg, and its estimated purity by LCMS analysis was 86%. ESI-MS(+) m/z 940.1 (M+2H).

PREPARATION OF EXAMPLE 9053

Example 9053

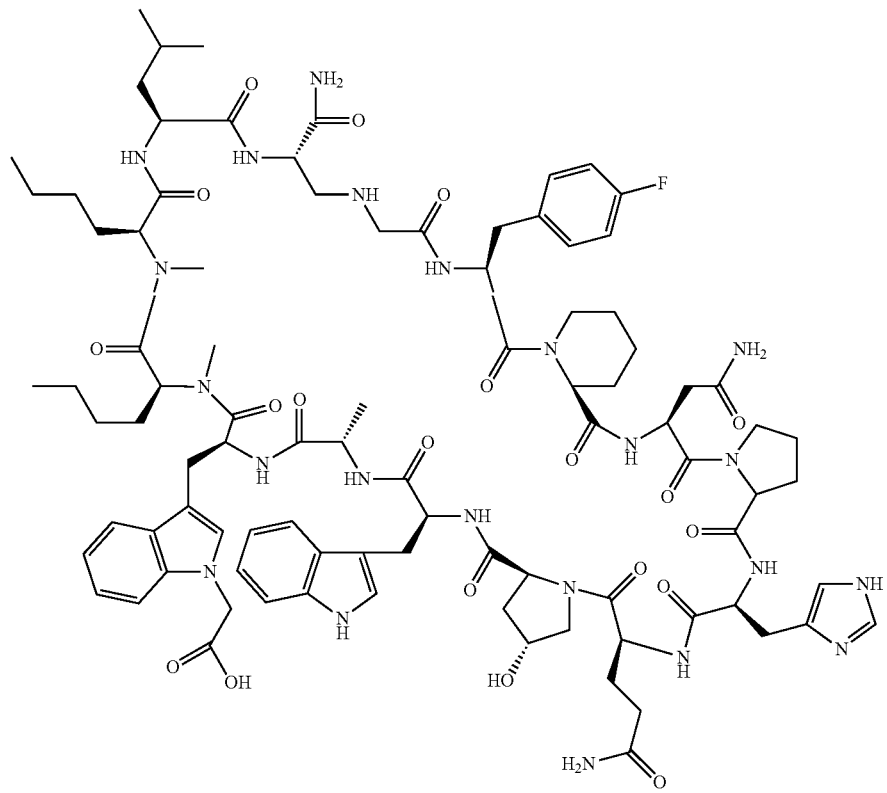

The crude material was purified via preparative LC/MS with the following conditions: Column: XBridge C18, 19×mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-100% B over 15 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-60% B over 20 minutes, then a 5-minute hold at 100% B; Flow: 20 mL/min. Fractions containing the desired product were combined and dried via centrifugal evaporation. The yield of the product was 8.0 mg, and its estimated purity by LCMS analysis was 96%. ESI-MS(+) m/z 940.4 (M+2H).

PREPARATION OF EXAMPLE 9054

Example 9054

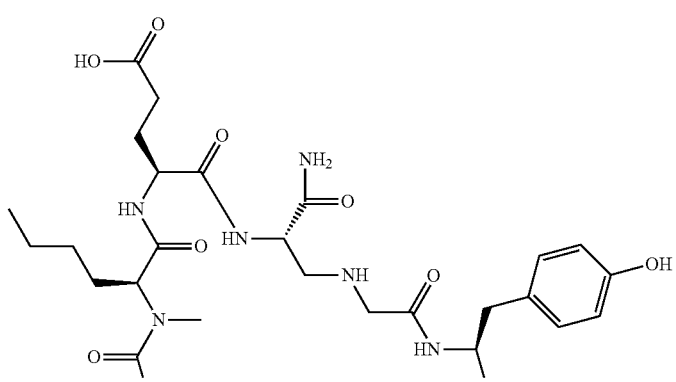

-continued

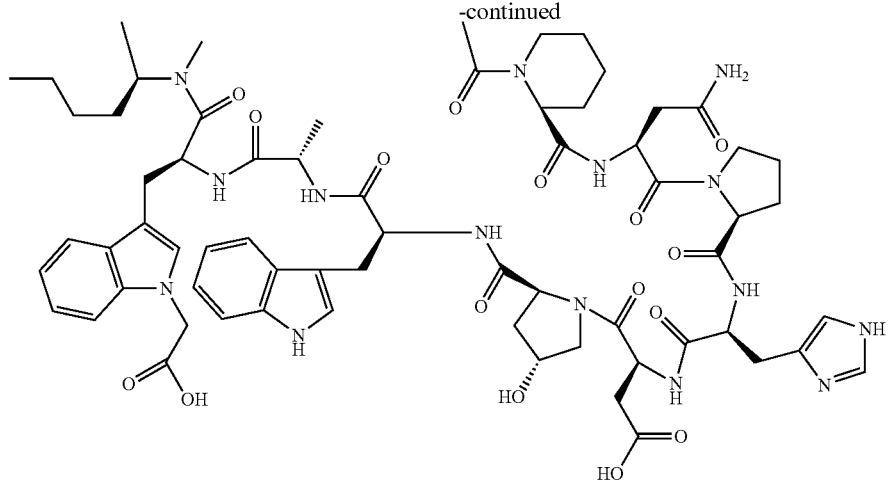

The crude material was purified via preparative LC/MS with the following conditions: Column: XBridge C18, 19×mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-100% B over 15 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 20 minutes, then a 5-minute hold at 100% B; Flow: 20 mL/min. Fractions containing the desired product were combined and dried via centrifugal evaporation. The yield of the product was 3.8 mg, and its estimated purity by LCMS analysis was 98%. ESI-MS(+) m/z 940.2 (M+2H).

PREPARATION OF EXAMPLE 9055

Exqample 9055

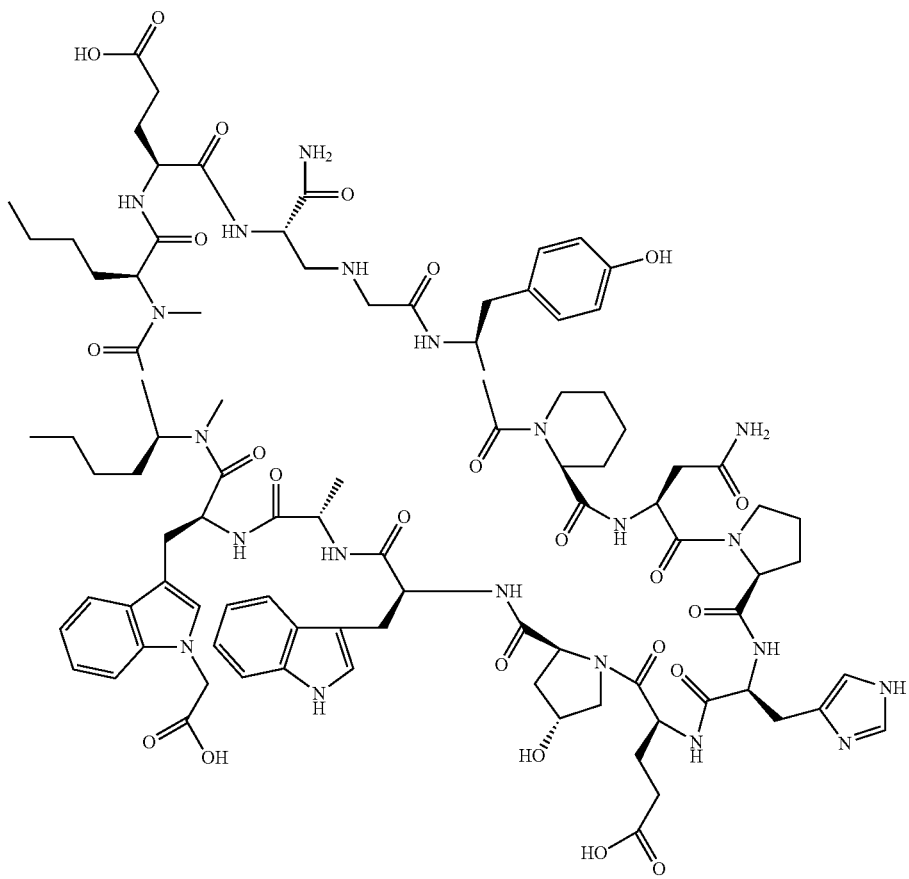

The crude material was purified via preparative LC/MS with the following conditions: Column: XBridge C18, 19×mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-100% B over 15 minutes, then a 5-minute hold at 100% B; Flow: 20 mL/min. Fractions containing the desired product were combined and dried via centrifugal evaporation. The yield of the product was 3.6 mg, and its estimated purity by LCMS analysis was 84%. ESI-MS(+) m/z 947.2 (M+2H).

PREPARATION OF EXAMPLE 9056

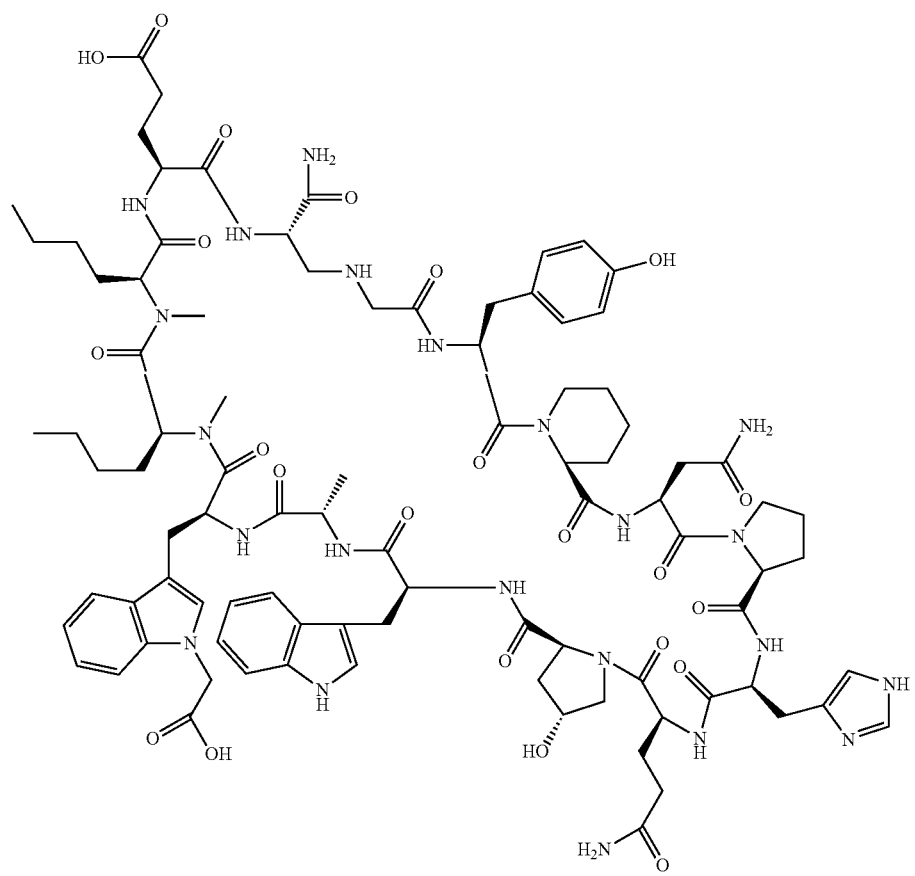

Exqample 9056

The crude material was purified via preparative LC/MS with the following conditions: Column: XBridge C18, 19×mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-100% B over 15 minutes, then a 5-minute hold at 100% B; Flow: 20 mL/min. Fractions containing the desired product were combined and dried via centrifugal evaporation. The yield of the product was 4.0 mg, and its estimated purity by LCMS analysis was 90%. ESI-MS(+) m/z 946.2 (M+2H).

PREPARATION OF EXAMPLE 9057

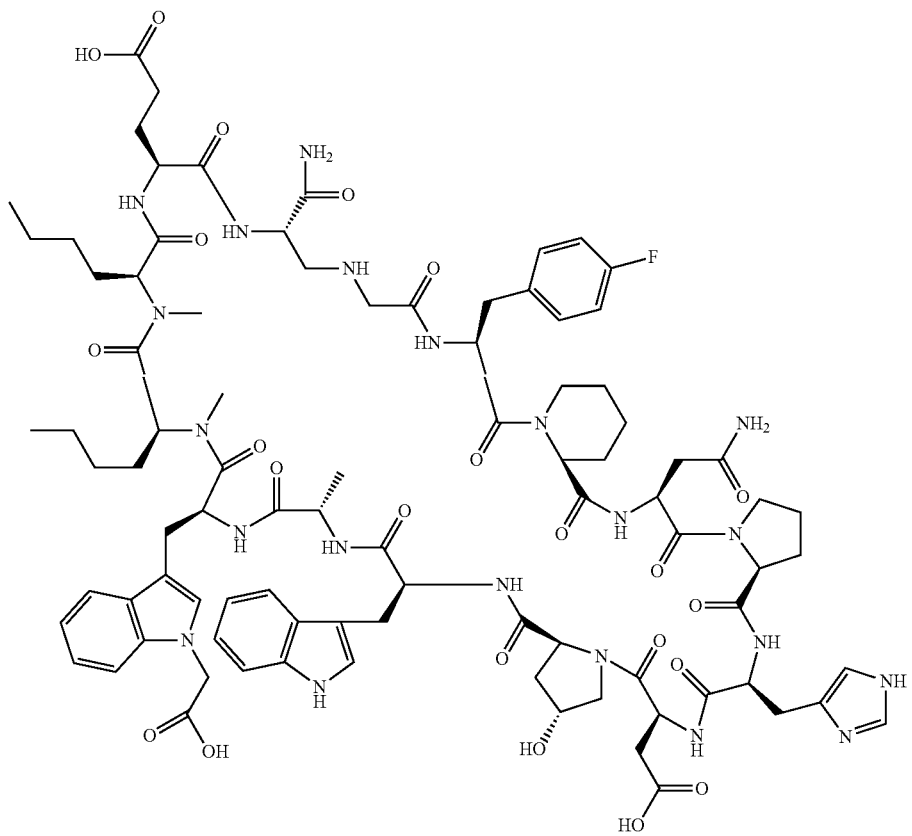

Exqample 9057

The crude material was purified via preparative LC/MS with the following conditions: Column: XBridge C18, 19×mm, 5-μm particles; Mobile Phase A: 5:95 methanol:water with 10-mM ammonium acetate; Mobile Phase B: 95:5 methanol:water with 10-mM ammonium acetate; Gradient: 30-100% B over 20 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 20 minutes, then a 5-minute hold at 100% B; Flow: 20 mL/min. Fractions containing the desired product were combined and dried via centrifugal evaporation. The yield of the product was 4.1 mg, and its estimated purity by LCMS analysis was 92%. ESI-MS(+) m/z 941.4 (M+2H).

PREPARATION OF EXAMPLE 9058

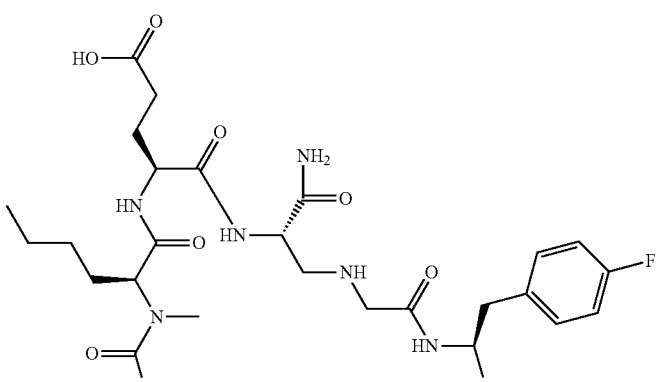

Exqample 9058

-continued

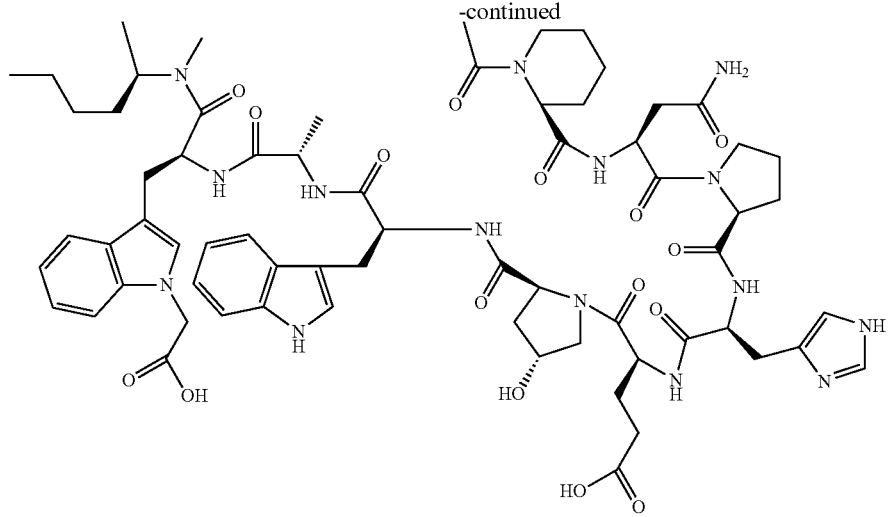

The crude material was purified via preparative LC/MS with the following conditions: Column: XBridge C18, 19×mm, 5-μm particles; Mobile Phase A: 5:95 methanol:water with 10-mM ammonium acetate; Mobile Phase B: 95:5 methanol:water with 10-mM ammonium acetate; Gradient: 30-100% B over 20 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 20 minutes, then a 5-minute hold at 100% B; Flow: 20 mL/min. Fractions containing the desired product were combined and dried via centrifugal evaporation. The yield of the product was 4.2 mg, and its estimated purity by LCMS analysis was 98%. ESI-MS(+) m/z 947.6 (M+2H).

PREPARATION OF EXAMPLE 9059

Exqample 9059

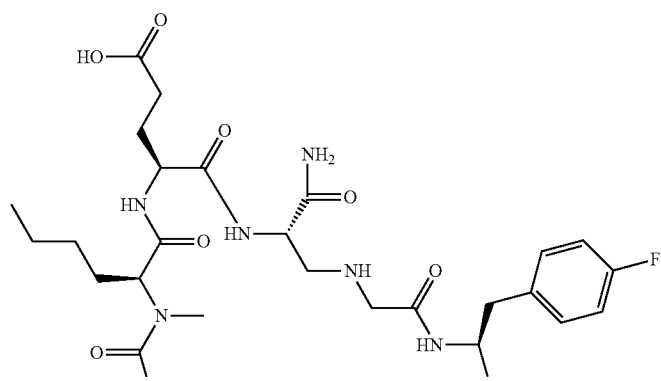

-continued

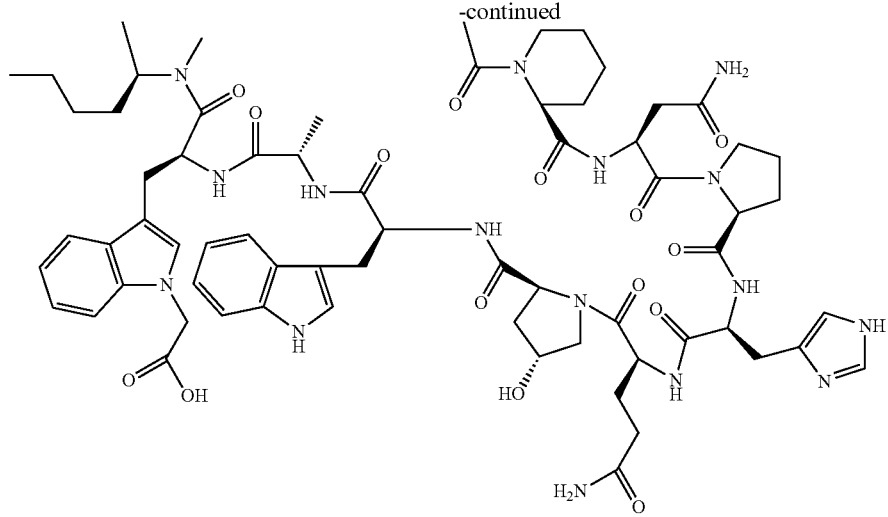

Mobile Phase A: 5:95 methanol:water with 10-mM ammonium acetate; Mobile Phase B: 95:5 methanol:water with 10-mM ammonium acetate; Gradient: 30-100% B over 20 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 20 minutes, then a 5-minute hold at 100% B; Flow: 20 mL/min. Fractions containing the desired product were combined and dried via centrifugal evaporation. The yield of the product was 3.5 mg, and its estimated purity by LCMS analysis was 98%. ESI-MS(+) m/z 947.2 (M+2H).

PREPARATION OF EXAMPLE 10029

Example 10029

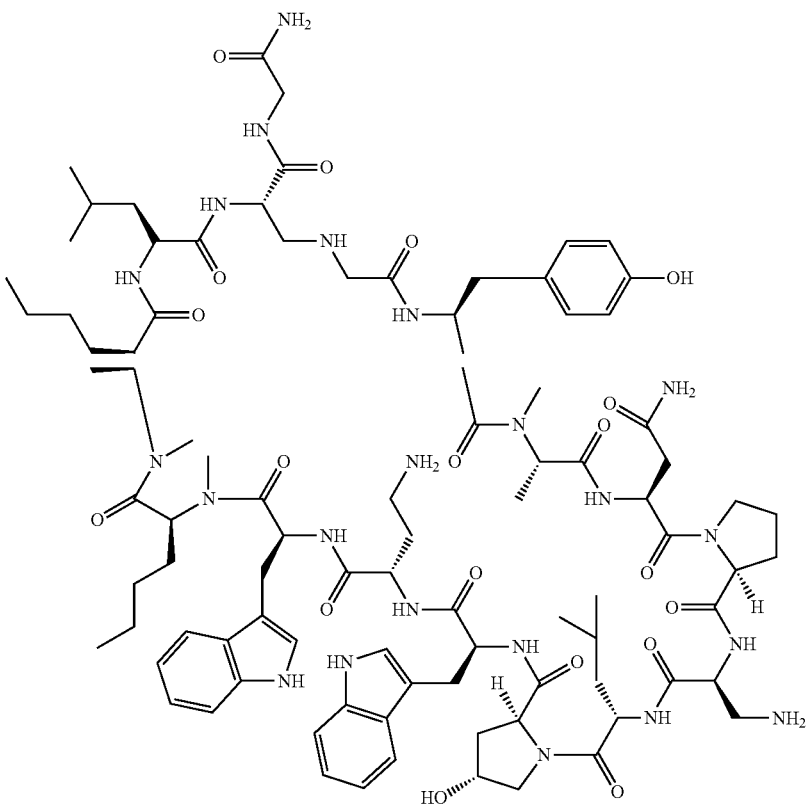

The crude material of Example 10029 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 8.4 mg, and its estimated purity by LCMS analysis was 100%.

Analysis condition A: Retention time=1.24 min; ESI-MS (+) m/z 907.2 (M+2H). Analysis condition B: Retention time=1.67 min; ESI-MS(+) m/z 906.9 (M+2H). ESI-HRMS (+) m/z: Calculated: 906.5014 (M+2H). Found: 906.4994 (M+2H).

PREPARATION OF EXAMPLE 10030

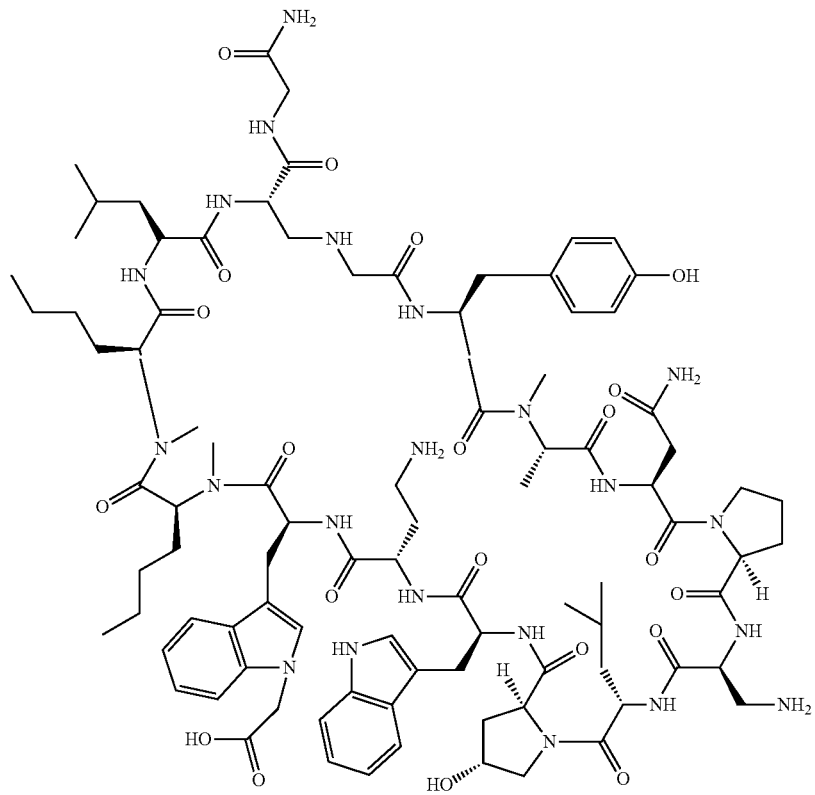

Example 10030

The crude material of Example 10030 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 8.4 mg, and its estimated purity by LCMS analysis was 97%.

Analysis condition A: Retention time=1.65 min; ESI-MS (+) m/z 935.75 (M+2H). Analysis condition B: Retention time=1.70 min; ESI-MS(+) m/z 935.80 (M+2H). ESI-HRMS(+) m/z: Calculated: 935.5041 (M+2H). Found: 935.5024 (M+2H).

PREPARATION OF EXAMPLE 10031

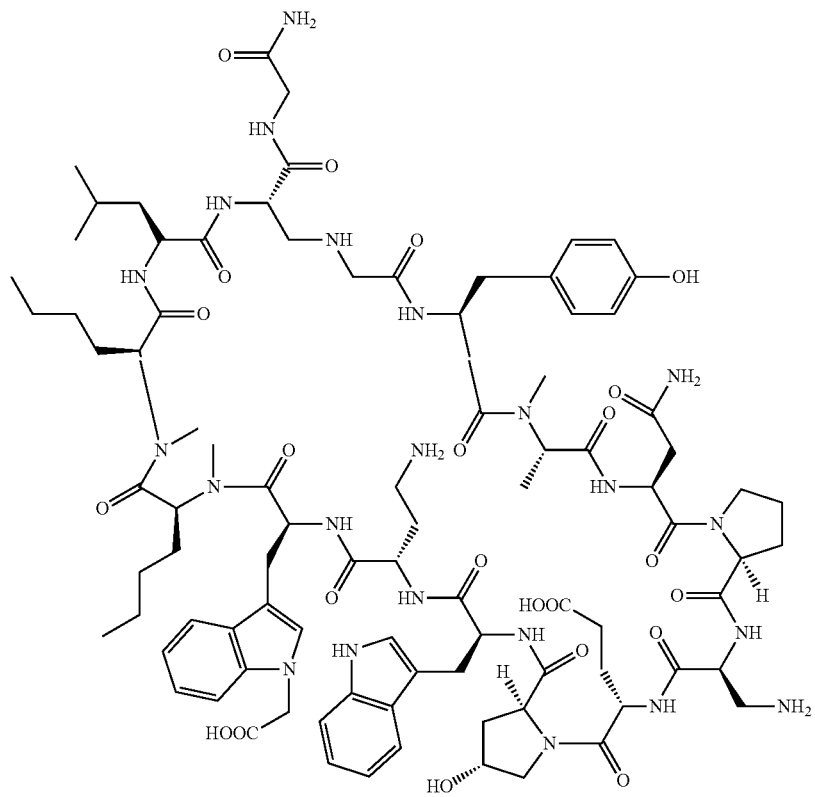

Example 10031

The crude material of Example 10031 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 3.0 mg, and its estimated purity by LCMS analysis was 95%.

Analysis condition A: Retention time=1.14 min; ESI-MS (+) m/z 944.20 (M+2H). Analysis condition B: Retention time=1.59 min; ESI-MS(+) m/z 94350 (M+2H). ESI-HRMS (+) m/z: Calculated: 943.4834 (M+2H). Found: 943.4808 (M+2H).

PREPARATION OF EXAMPLE 10032

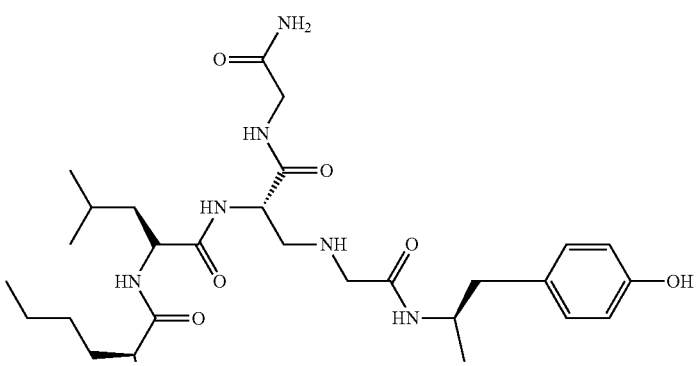

Example 10032

-continued

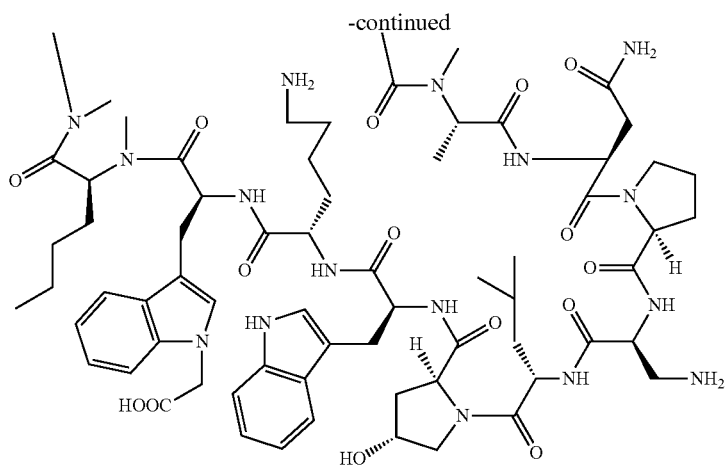

The crude material of Example 10032 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 3.9 mg, and its estimated purity by LCMS analysis was 100%.

Analysis condition A: Retention time=1.15 min; ESI-MS (+) m/z 950.2 (M+2H). Analysis condition B: Retention time=1.47 min; ESI-MS(+) m/z 950.3 (M+2H). ESI-HRMS (+) m/z: Calculated: 949.5198 (M+2H). Found: 949.5158 (M+2H).

PREPARATION OF EXAMPLE 10033

Example 10033

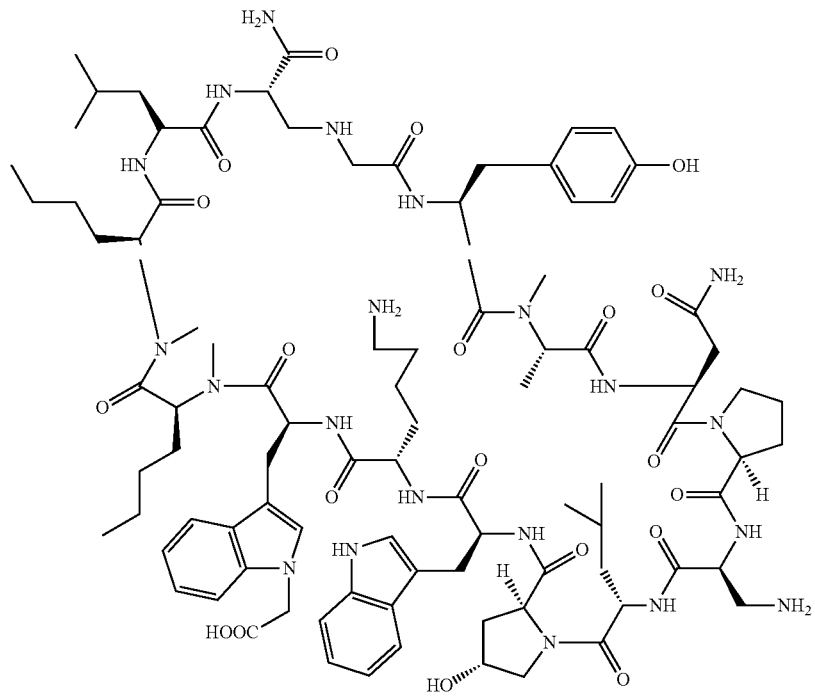

The crude material of Example 10033 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 1.8 mg, and its estimated purity by LCMS analysis was 100%.

Analysis condition A: Retention time=1.17 min; ESI-MS (+) m/z 921.2 (M+2H). Analysis condition B: Retention time=1.48 min; ESI-MS(+) m/z 920.9 (M+2H). ESI-HRMS (+) m/z: Calculated: 921.0091 (M+2H). Found: 921.0053 (M+2H).

PREPARATION OF EXAMPLE 10034

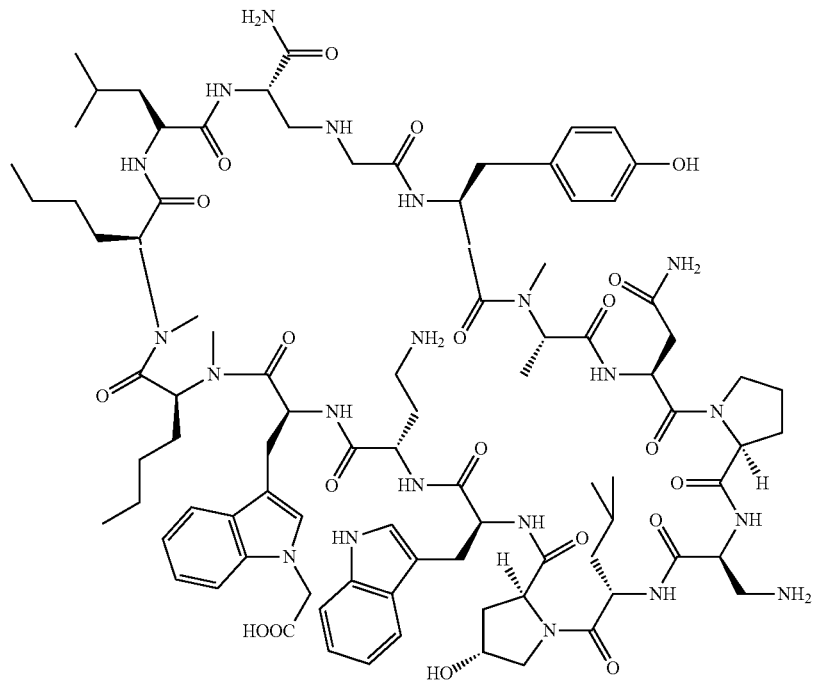

Example 10034

The crude material of Example 10034 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 0.6 mg, and its estimated purity by LCMS analysis was 100%.

Analysis condition A: Retention time=1.17 min; ESI-MS (+) m/z 906.9 (M+2H). Analysis condition B: Retention time=1.56 min; ESI-MS(+) m/z 907.1 (M+2H).

PREPARATION OF EXAMPLE 10035

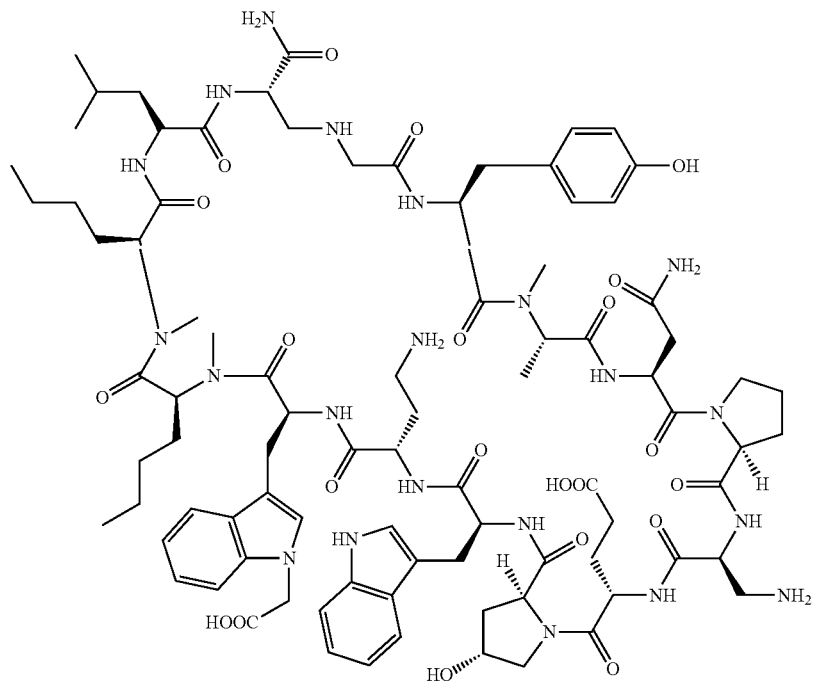

Example 10035

The crude material of Example 10035 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 0.3 mg, and its estimated purity by LCMS analysis was 100%.

Analysis condition A: Retention time=1.15 min; ESI-MS (+) m/z 915.0 (M+2H). Analysis condition B: Retention time=1.48 min; ESI-MS(+) m/z 915.2 (M+2H). ESI-HRMS (+) m/z: 914.9724 (M+2H).

PREPARATION OF EXAMPLE 10036

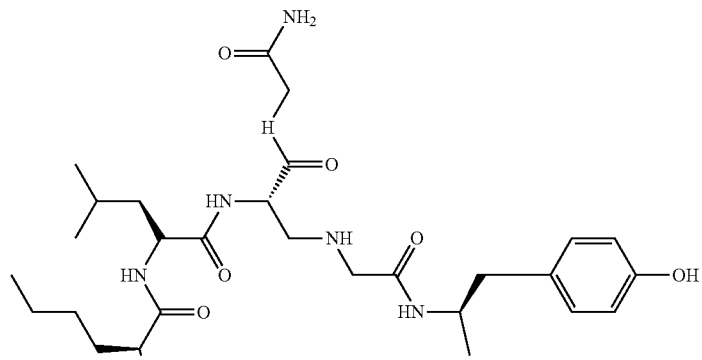

Example 10036

-continued

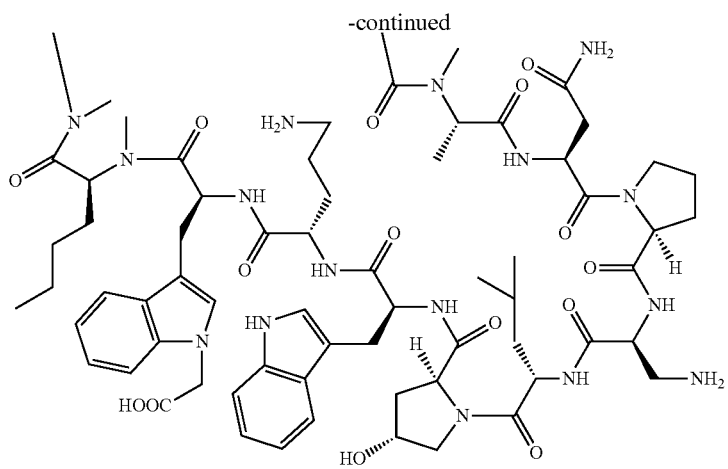

The crude material of Example 10036 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 3.5 mg, and its estimated purity by LCMS analysis was 100%.

Analysis condition A: Retention time=1.16 min; ESI-MS (+) m/z 943.0 (M+2H). Analysis condition B: Retention time=1.51 min; ESI-MS(+) m/z 942.6 (M+2H). ESI-HRMS (+) m/z: 942.5112 (M+2H).

PREPARATION OF EXAMPLE 10037

Example 10037

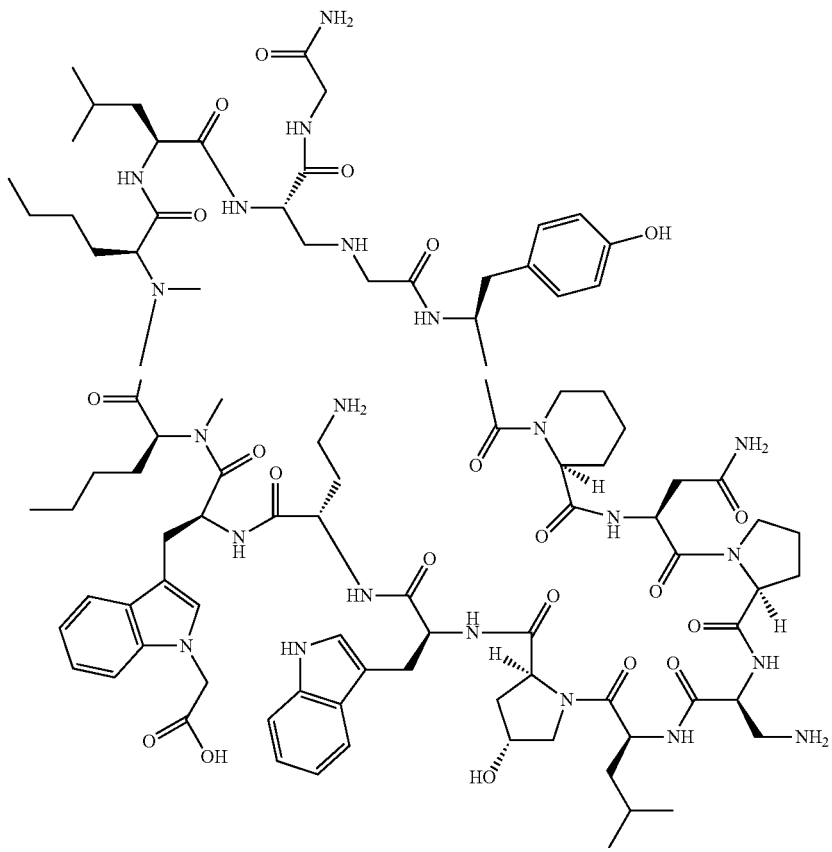

The crude material of Example 10037 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 20.8 mg, and its estimated purity by LCMS analysis was 100%.

Analysis condition A: Retention time=1.17 min; ESI-MS (+) m/z 949.1 (M+2H). Analysis condition B: Retention time=1.57 min; ESI-MS(+) m/z 949.1 (M+2H). ESI-HRMS (+) m/z: 948.5098 (M+2H).

PREPARATION OF EXAMPLE 10038

Example 10038

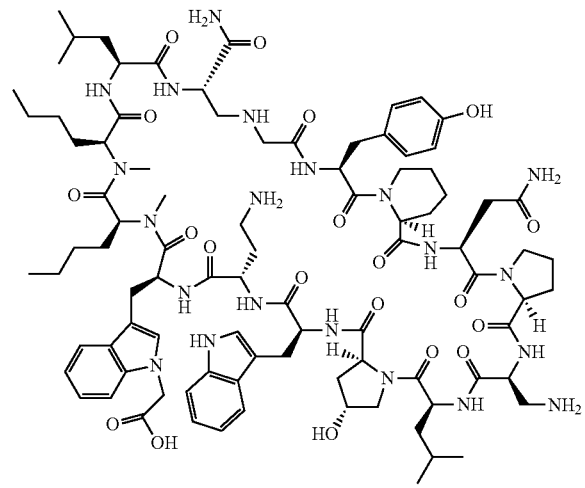

The crude material of Example 10038 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 2.4 mg, and its estimated purity by LCMS analysis was 100%.

Analysis condition A: Retention time=1.20 min; ESI-MS (+) m/z 920.1 (M+2H). Analysis condition B: Retention time=1.60 min; ESI-MS(+) m/z 921.0 (M+2H). ESI-HRMS (+) m/z: 919.9986 (M+2H).

PREPARATION OF EXAMPLE 10039

Example 10039

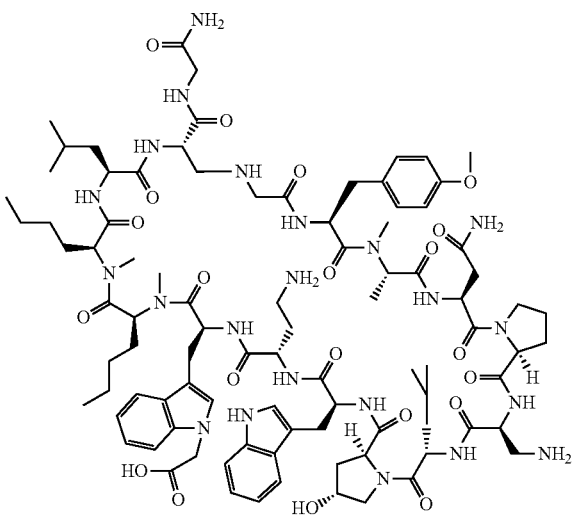

The crude material of Example 10039 was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 8.4 mg, and its estimated purity by LCMS analysis was 100%.

Analysis condition A: Retention time=1.24 min; ESI-MS (+) m/z 943.1 (M+2H). Analysis condition B: Retention time=1.73 min; ESI-MS(+) m/z 943.1 (M+2H). ESI-HRMS (+) m/z: 942.5096 (M+2H).

PREPARATION OF EXAMPLE 10040

Example 10040

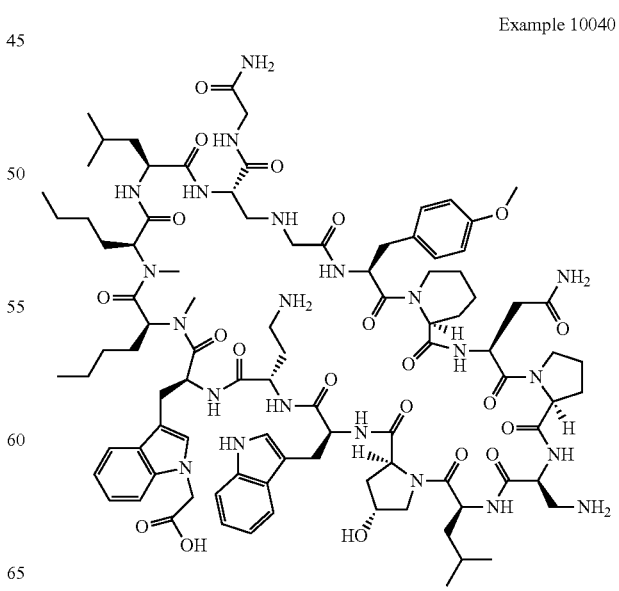

The crude material of Example 10040 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 8.6 mg, and its estimated purity by LCMS analysis was 100%.

Analysis condition A: Retention time=1.28 min; ESI-MS (+) m/z 956.1 (M+2H). Analysis condition B: Retention time=1.80 min; ESI-MS(+) m/z 956.1 (M+2H). ESI-HRMS (+) m/z: 955.5169 (M+2H).

PREPARATION OF EXAMPLE 10041

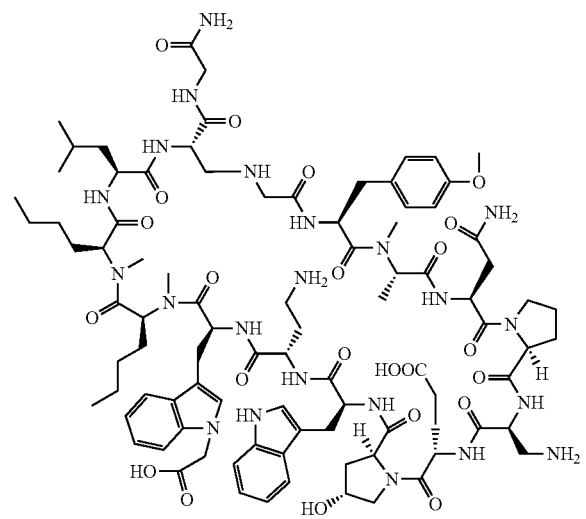

Example 10041

The crude material of Example 10041 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 2.6 mg, and its estimated purity by LCMS analysis was 97%.

Analysis condition A: Retention time=1.23 min; ESI-MS (+) m/z 950.4 (M+2H). Analysis condition B: Retention time=1.64 min; ESI-MS(+) m/z 950.4 (M+2H). ESI-HRMS (+) m/z: 950.4883 (M+2H).

PREPARATION OF EXAMPLE 10042

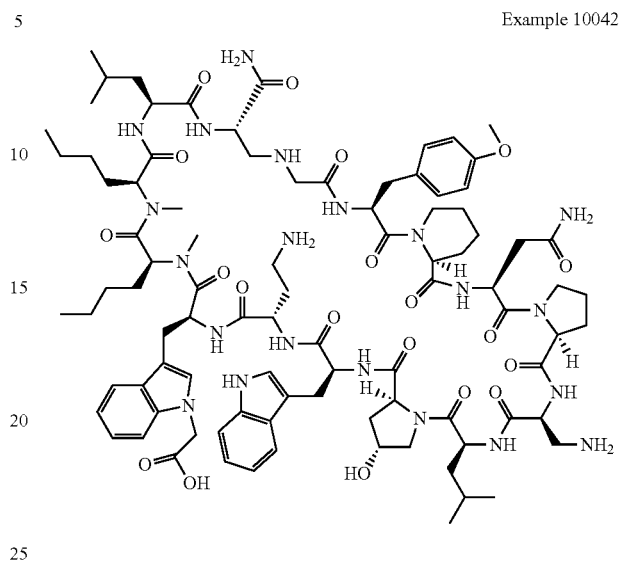

Example 10042

The crude material of Example 10042 was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 minutes, then a 5-minute hold at 100% B; Flow: 20 mL/min. Fractions containing the desired product were combined and dried via centrifugal evaporation. The yield of the product was 14.5 mg, and its estimated purity by LCMS analysis was 95%.

Analysis condition A: Retention time=1.47 min; ESI-MS (+) m/z 926.9 (M+2H). Analysis condition B: Retention time=1.83 min; ESI-MS(+) m/z 926.2 (M+2H). ESI-HRMS (+) m/z: 927.0048 (M+2H).

Preparation of (S)-2-(2-((((9H-fluoren-9-yl)methoxy)carbonyl)amino)-3-((2-amino-2-oxoethyl)amino)-3-oxopropoxy)acetic acid Scheme:

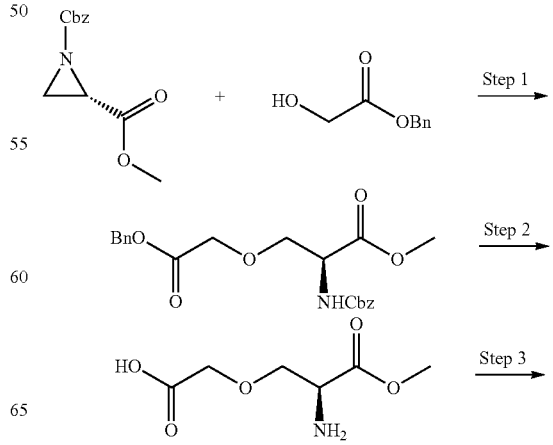

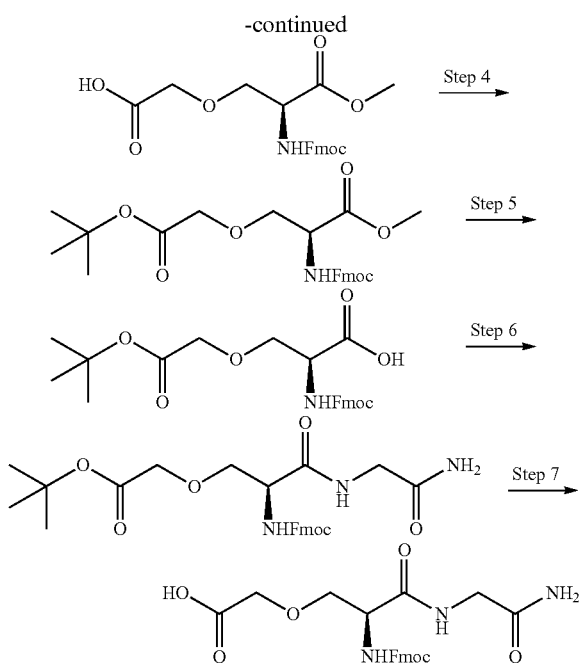

Step 1:

(S)-1-benzyl 2-methyl aziridine-1,2-dicarboxylate (5.105 g, 21.70 mmol), and benzyl 2-hydroxyacetate (6.16 ml, 43.4 mmol) were dissolved in DCM (43.4 ml) and cooled to 0° C. followed by the addition of BF3.OEt2 (0.275 ml, 2.170 mmol). The reaction was stirred for 2 h. TLC showed the aziridine starting material to be consumed. The reaction was stirred for and additional 14 h. Saturated sodium bicarbonate solution was added to the reaction and the biphasic mixture was vigorously stirred for 20 min. The reaction was diluted with DCM and separated from the aquious phase. The organic layer was washed with brine, dried over sodium sulfate and concentrated under vacuum. The crude material was purified by flash chromatography using 10-40% EtOAc/Hexanes. The product fractions were collected and the solvent removed under vacuum to give methyl O-(2-(benzyloxy)-2-oxoethyl)-N-((benzyloxy)carbonyl)-L-serinate, 3.0 (34%). ESI-MS(+) m/z 402.1 (M+1). $^1$H NMR (400 MHz, CHLOROFORM-d) d 7.43-7.30 (m, 10H), 5.95 (d, J=8.0 Hz, 1H), 5.18 (s, 2H), 5.15 (s, 2H), 4.50 (dt, J=8.4, 3.1 Hz, 1H), 4.12 (d, J=2.8 Hz, 2H), 4.10-4.04 (m, 1H), 3.81 (dd, J=9.4, 3.1 Hz, 1H), 3.77 (s, 3H).

Step 2:

(S)-methyl 3-(2-(benzyloxy)-2-oxoethoxy)-2-(((benzyloxy)carbonyl)amino)propanoate (3 g, 7.47 mmol) was dissolved in MeOH (37.4 ml) and placed under an atmosphere of N$_2$. Pd—C(0.398 g, 0.374 mmol) was added to the solution with vigorous stirring. The reaction was placed under an atmosphere of H$_2$ and stirred for 16 h. The reaction was filtered through celite and concentrated under vacuum to give (S)-2-(2-amino-3-methoxy-3-oxopropoxy)acetic acid, 1.32 g, (100%), which was used in step 3 without further purification. ESI-MS(+) m/z 178.1 (M+1).

Step 3:

(S)-2-(2-amino-3-methoxy-3-oxopropoxy)acetic acid (1.323 g, 7.47 mmol) was dissolved in THF (29.9 ml) followed by the addition of Water (29.9 ml). SODIUM BICARBONATE (1.255 g, 14.94 mmol) was then added followed by the addition of (9H-fluoren-9-yl)methyl (2,5-dioxopyrrolidin-1-yl) carbonate (2.52 g, 7.47 mmol). The reaction was stirred for 2 h. Most of the THF was removed under vacuum then Et$_2$O was added. The organic layer was discarded and the aqueous layer was again washed with Et2O. The aqueous phase was collected, acidified with 1 N HCl, and extracted with EtOAc. The organic layer was collected, dried over sodium sulfate, and concentrated under vacuum to give (S)-2-(2-((((9H-fluoren-9-yl)methoxy)carbonyl)amino)-3-methoxy-3-oxopropoxy)acetic acid, 2.76 g (93%), which was not purified further. ESI-MS(+) m/z 400.1 (M+1).

Step 4:

To a solution of (S)-2-(2-((((9H-fluoren-9-yl)methoxy)carbonyl)amino)-3-methoxy-3-oxopropoxy)acetic acid (3.78 g, 9.46 mmol) in Ethyl acetate (40.6 ml) and hexanes (15.05 ml) was added TERT-BUTYL 2,2,2-TRICHLOROACETIMIDATE (1.692 ml, 9.46 mmol) dropwise. After 15 min, BF3.OEt2 (0.060 ml, 0.473 mmol) was added and the reaction was stirred for 1 h. Additional TERT-BUTYL 2,2,2-TRICHLOROACETIMIDATE (1.692 ml, 9.46 mmol) was added followed by BF3.OEt2 (0.060 ml, 0.473 mmol) and stirred for an 1 h. The process was repeated one additional time, TERT-BUTYL 2,2,2-TRICHLOROACETIMIDATE (1.692 ml, 9.46 mmol) addition followed by BF3.OEt2 (0.060 ml, 0.473 mmol) and stirring for 1 h. Sat bicarbonate was added to the reaction and allowed to stir for 15 min. The organic phase was collected, washed with brine, dried over sodium sulfate, and concentrated under vacuum to give crude product which was purified further by flash chromatography using 20-30% EtOAc/Hexanes as eluent. The product fractions were collected and solvent removed under vacuum to give methyl N-(((9H-fluoren-9-yl)methoxy)carbonyl)-O-(2-(tert-butoxy)-2-oxoethyl)-L-serinate, 3.9 g, (90%). ESI-MS(+) m/z 478.1 (M+Na).

Step 5:

(S)-methyl 2-((((9H-fluoren-9-yl)methoxy)carbonyl)amino)-3-(2-(tert-butoxy)-2-oxoethoxy)propanoate (3.9 g, 8.56 mmol) was dissolved in DCE (42.8 ml) followed by the addition of trimethylstannanol (3.10 g, 17.12 mmol). The reaction was heated to 80° C. for 5 h. The solvent was removed under vacuum and the residue was redissolved in EtOAc and washed with 1 N HCl 3x, then brine. The organic layer was collected, dried over sodium sulfate and concentrated under vacuum to give the desired product. The NMR showed some remaining Tin. The material was redissolved in EtOAc and washed with 0.1 M KHSO4, 3x followed by brine. The organic layer was collected, dried over sodium sulfate, and concentrated under vacuum to give N-(((9H-fluoren-9-yl)methoxy)carbonyl)-O-(2-(tert-butoxy)-2-oxoethyl)-L-serine, 3.36 g (89%). ESI-MS(+) m/z 464.0 (M+Na). $^1$H NMR (400 MHz, CHLOROFORM-d) d 7.78 (d, J=7.5 Hz, 2H), 7.66 (t, J=7.4 Hz, 2H), 7.45-7.38 (m, 2H), 7.36-7.29 (m, 2H), 6.44 (d, J=7.0 Hz, 1H), 4.55-4.33 (m, 3H), 4.26 (t, J=7.3 Hz, 1H), 4.12-4.01 (m, 3H), 3.82 (dd, J=9.7, 4.4 Hz, 1H), 1.52 (s, 9H).

Step 6:

(S)-2-((((9H-fluoren-9-yl)methoxy)carbonyl)amino)-6-(tert-butoxy)-6-oxohexanoic acid (850 mg, 1.934 mmol), 2-aminoacetamide, HCl (278 mg, 2.51 mmol), were suspended in DCM (9670 µl) followed by the addition of Hunig's Base (1013 µl, 5.80 mmol) then HATU (809 mg, 2.127 mmol). The reaction was stirred for 2 h. The reaction was diluted with DCM and washed with 1 N HCl, then brine. The organic later was collected, dried over sodium sulfate and concentrated under vacuum. The crude material was purified by flash chromatography using 20-60% Acetone/DCM. The product fractions were collected and the solvent removed under vacuum to give the desired product, 789 mg (82%). ESI-MS(+) m/z 498.1 (M+H).

Step 7:

(S)-tert-butyl 2-(2-((((9H-fluoren-9-yl)methoxy)carbonyl)amino)-3-((2-amino-2-oxoethyl)amino)-3-oxopropoxy)acetate (1.25 g, 2.51 mmol) was dissolved in HCl (4 N in Dioxane) (15 ml, 60.0 mmol). The reaction was stirred for 4 h. The solvent was removed under vacuum to give (S)-2-(2-((((9H-fluoren-9-yl)methoxy)carbonyl)amino)-3-((2-amino-2-oxoethyl)amino)-3-oxopropoxy)acetic acid, 1.11 g (100%). ESI-MS(+) m/z 442.0 (M+H).

Preparation of (S)-2-(2-((((9H-fluoren-9-yl)methoxy)carbonyl)amino)-3-amino-3-oxopropoxy) acetic acid Scheme:

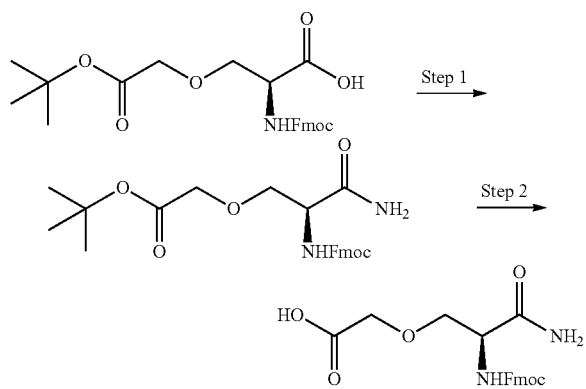

Step 1:

(S)-2-((((9H-fluoren-9-yl)methoxy)carbonyl)amino)-3-(2-(tert-butoxy)-2-oxoethoxy)propanoic acid (1.875 g, 4.25 mmol)(synthesis described elsewhere), AMMONIUM CHLORIDE (0.568 g, 10.62 mmol), were suspended in DMF (21.24 ml) followed by the addition of Hunig's Base (2.225 ml, 12.74 mmol) then HATU (1.776 g, 4.67 mmol). The reaction was stirred for 2 h. The reaction was diluted with DCM and washed with 1 N HCl, then brine. The organic later was collected, dried over sodium sulfate and concentrated under vacuum. The crude material was purified by flash chromatography using 20-40% Acetone/DCM. The product fraction were collected and the solvent removed under vacuum to give tert-butyl (S)-2-(2-((((9H-fluoren-9-yl)methoxy)carbonyl)amino)-3-amino-3-oxopropoxy)acetate, 1.43 g (76%). ESI-MS(+) m/z 441.0 (M+1). $^1$H NMR (400 MHz, CHLOROFORM-d) d 7.78 (d, J=7.5 Hz, 2H), 7.65 (d, J=7.5 Hz, 2H), 7.46-7.38 (m, 2H), 7.36-7.30 (m, 2H), 6.99 (d, J=17.3 Hz, 1H), 6.44 (br. s., 1H), 5.46 (br. s., 1H), 4.43 (d, J=6.3 Hz, 2H), 4.31 (br. s., 1H), 4.27-4.21 (m, 1H), 4.16-3.95 (m, 3H), 3.73-3.64 (m, 1H), 1.51 (s, 9H).

Step 2:

(S)-tert-butyl 2-(2-((((9H-fluoren-9-yl)methoxy)carbonyl)amino)-3-amino-3-oxopropoxy)acetate (1.432 g, 3.25 mmol) was dissolved in HCl (4 N in Dioxane) (15 ml, 60.0 mmol). The reaction was stirred for 4 h. The solvent was removed under vacuum to give (S)-2-(2-((((9H-fluoren-9-yl)methoxy)carbonyl)amino)-3-amino-3-oxopropoxy)acetic acid, 1.25 g, (100. ESI-MS(+) m/z 385.0 (M+1).

Preparation of (S)-5-((((9H-fluoren-9-yl)methoxy)carbonyl)amino)-6-((2-amino-2-oxoethyl)amino)-6-oxohexanoic acid Scheme:

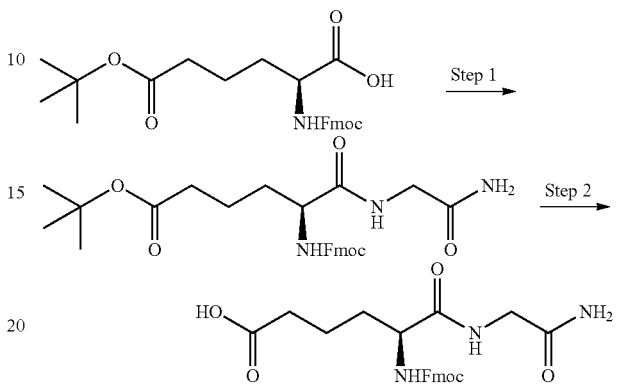

Step 1:

(S)-2-((((9H-fluoren-9-yl)methoxy)carbonyl)amino)-6-(tert-butoxy)-6-oxohexanoic acid (850 mg, 1.934 mmol), 2-aminoacetamide, HCl (278 mg, 2.51 mmol), were suspended in DCM (9670 μl) followed by the addition of Hunig's Base (1013 μl, 5.80 mmol) then HATU (809 mg, 2.127 mmol). The reaction was stirred for 2 h. The reaction was diluted with DCM and washed with 1 N HCl, then brine. The organic later was collected, dried over sodium sulfate and concentrated under vacuum. The crude material was purified by flash chromatography using 20-60% Acetone/DCM. The product fractions were collected and the solvent removed under vacuum to give tert-butyl (S)-5-((((9H-fluoren-9-yl)methoxy)carbonyl)amino)-6-((2-amino-2-oxoethyl)amino)-6-oxohexanoate, 789 mg (82%). ESI-MS(+) m/z 496.1 (M+1). $^1$H NMR (400 MHz, CHLOROFORM-d) d 7.78 (d, J=7.5 Hz, 2H), 7.60 (d, J=7.5 Hz, 2H), 7.45-7.39 (m, 2H), 7.35-7.30 (m, 2H), 6.78 (br. s., 1H), 6.42 (br. s., 1H), 5.71 (d, J=6.0 Hz, 1H), 5.45 (br. s., 1H), 4.44 (d, J=6.8 Hz, 2H), 4.25-4.19 (m, 1H), 4.10 (d, J=6.0 Hz, 1H), 3.97 (d, J=5.5 Hz, 2H), 2.36-2.24 (m, 2H), 1.90 (br. s., 1H), 1.76-1.55 (m, 3H), 1.46 (s, 9H)

Step 2:

(S)-tert-butyl 5-((((9H-fluoren-9-yl)methoxy)carbonyl)amino)-6-((2-amino-2-oxoethyl)amino)-6-oxohexanoate (0.789 g, 1.593 mmol) was dissolved in HCl (4 N in Dioxane) (15 ml, 60.0 mmol). The reaction was stirred for 6 h. The solvent was removed under vacuum to give (S)-5-((((9H-fluoren-9-yl)methoxy)carbonyl)amino)-6-((2-amino-2-oxoethyl)amino)-6-oxohexanoic acid, 700 mg (100%). ESI-MS(+) m/z 440.0 (M+1).

Preparation of (S)-5-((((9H-fluoren-9-yl)methoxy)carbonyl)amino)-6-amino-6-oxohexanoic acid Scheme:

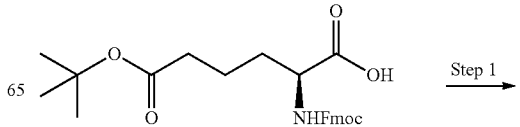

243

-continued

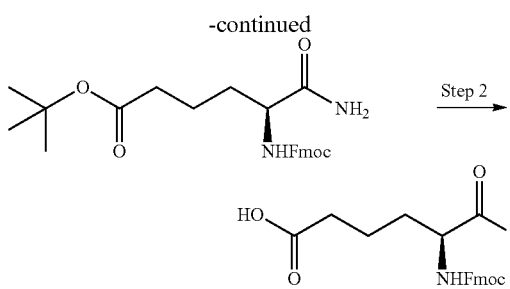

Step 1:
(S)-2-((((9H-fluoren-9-yl)methoxy)carbonyl)amino)-6-(tert-butoxy)-6-oxohexanoic acid (2.5 g, 5.69 mmol), AMMONIUM CHLORIDE (0.761 g, 14.22 mmol), were suspended in DMF (28.4 ml) followed by the addition of Hunig's Base (2.98 ml, 17.06 mmol) then HATU (2.379 g, 6.26 mmol). The reaction was stirred for 2 h. The reaction was diluted with Et$_2$O and washed with 1 N HCl, then brine. The organic later was collected, dried over sodium sulfate and concentrated under vacuum. The crude material was purified by flash chromatography using 0-20% Acetone/DCM. The product fractions were collected and the solvent removed under vacuum to give tert-butyl (S)-5-((((9H-fluoren-9-yl)methoxy)carbonyl)amino)-6-amino-6-oxohexanoate, 1.89 g (76%). ESI-MS(+) m/z 439.0 (M+1).

Step 2:
(S)-tert-butyl 5-((((9H-fluoren-9-yl)methoxy)carbonyl)amino)-6-amino-6-oxohexanoate (1.89 g, 4.31 mmol) was dissolved in HCl (4 N in Dioxane) (15 ml, 60.0 mmol). The reaction was stirred for 4 h. The solvent was removed under vacuum to give (S)-5-((((9H-fluoren-9-yl)methoxy)carbonyl)amino)-6-amino-6-oxohexanoic acid, 1.65 g, (100. ESI-MS(+) m/z 385.0 (M+1). $^1$H NMR (400 MHz, METHANOL-d$_4$) d 7.80 (d, J=7.5 Hz, 2H), 7.71-7.65 (m, 2H), 7.43-7.36 (m, 2H), 7.35-7.29 (m, 2H), 4.47-4.35 (m, 2H), 4.26-4.21 (m, 1H), 4.09 (d, J=7.8 Hz, 1H), 2.32 (t, J=6.4 Hz, 2H), 1.88-1.57 (m, 4H).

244

Preparation of (R)-5-((((9H-fluoren-9-yl)methoxy)carbonyl)amino)-2-((tert-butoxycarbonyl)amino)pentanoic acid Scheme:

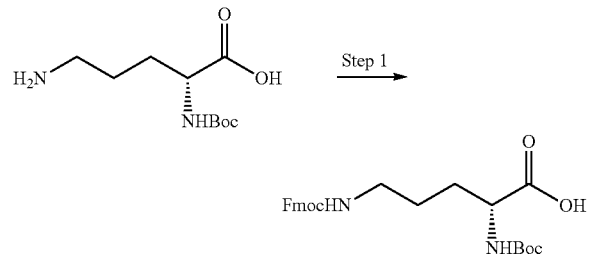

Step 1:
(R)-5-amino-2-((tert-butoxycarbonyl)amino)pentanoic acid (4.77 g, 20.54 mmol) was dissolved in THF (82 ml) followed by the addition of Water (82 ml). SODIUM BICARBONATE (3.45 g, 41.1 mmol) was then added followed by the addition of (9H-fluoren-9-yl)methyl (2,5-dioxopyrrolidin-1-yl) carbonate (6.93 g, 20.54 mmol). The reaction was stirred for 2 h. Most of the THF was removed under vacuum then Et2O was added. The organic layer was discarded and the aqueous layer was again washed with Et2O. The aqueous phase was collected, acidified with 1 N HCl, and extracted with EtOAc. The organic layer was collected, dried over sodium sulfate, and concentrated under vacuum to give (R)-5-((((9H-fluoren-9-yl)methoxy)carbonyl)amino)-2-((tert-butoxycarbonyl)amino)pentanoic acid, 8.76 g (94%). ESI-MS(+) m/z 454.9 (M+1).

PREPARATION OF EXAMPLE 10504

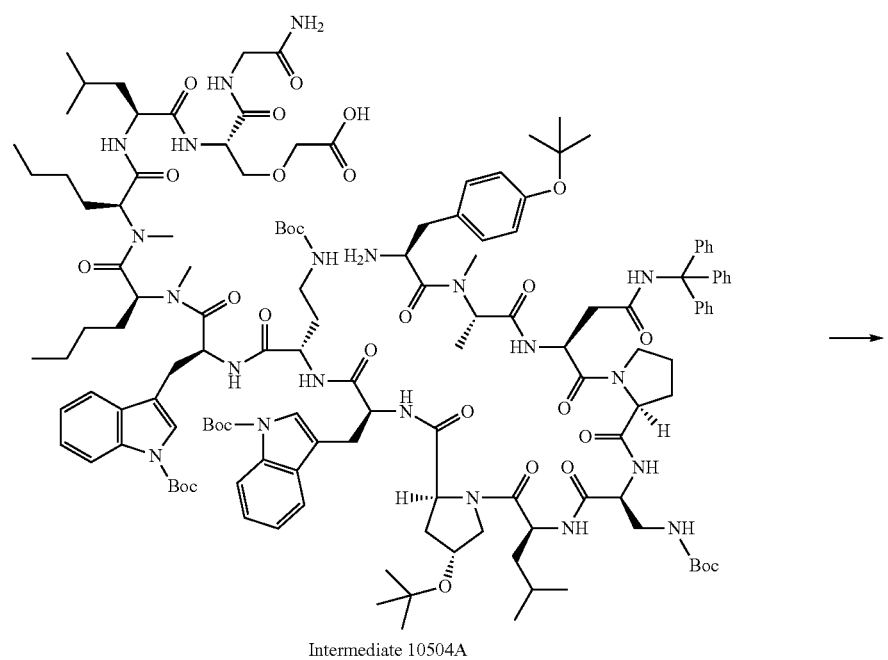

Intermediate 10504A

-continued

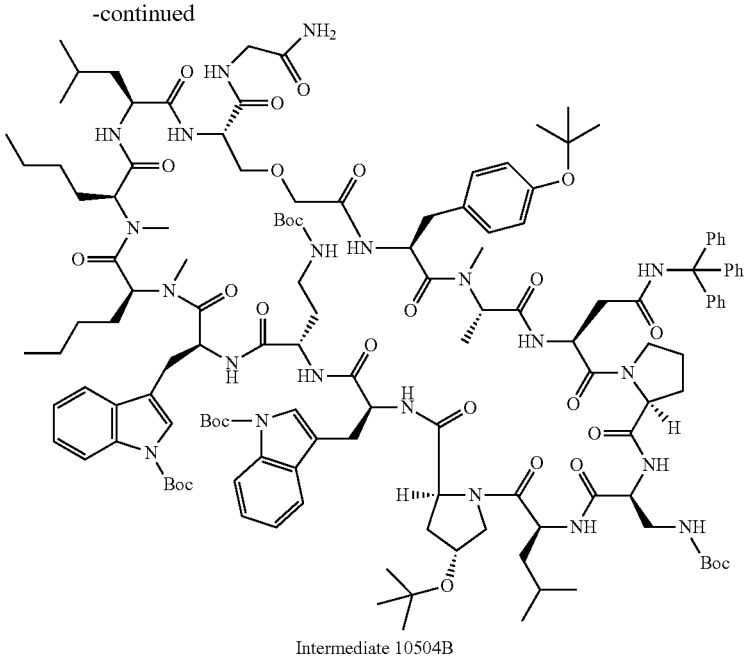

Intermediate 10504B

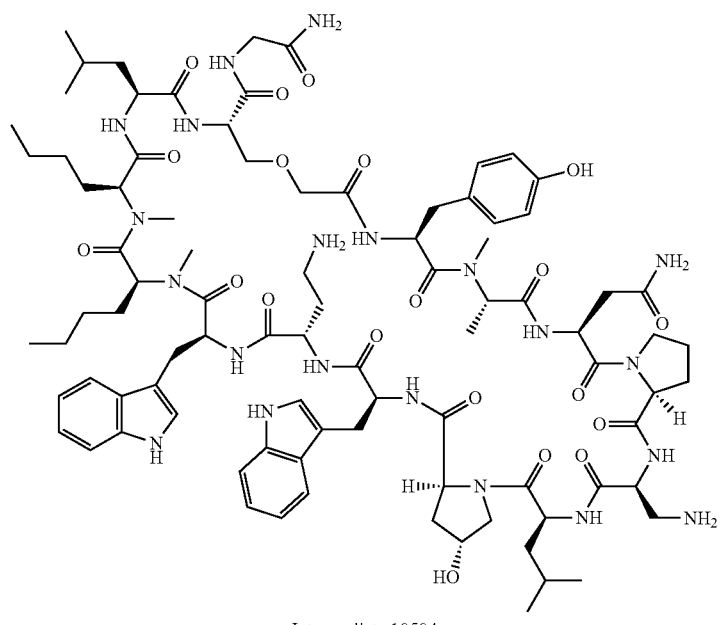

Intermediate 10504

Preparation of Intermediate 10504A

"General Synthetic Sequence A" was followed. (S)-2-(2-((((9H-fluoren-9-yl)methoxy)carbonyl)amino)-3-((2-amino-2-oxoethyl)amino)-3-oxopropoxy)acetic acid was used in the "Resin Loading Procedure". To the reaction vessel containing resin from the automated sequence was added piperidine:DMF (20:80 v/v, 2.0 mL). The mixture was periodically agitated for 4 minutes and then the solution was drained through the frit. To the reaction vessel was added piperidine:DMF (20:80 v/v, 2.0 mL). The mixture was periodically agitated for 4 minutes and then the solution was drained through the frit. The resin was washed successively five times as follows: for each wash, DMF (2.0 mL) was added through the top of the vessel and the resulting mixture was periodically agitated for 90 seconds before the solution was drained through the frit. The resin was washed successively five times as follows: for each wash, DCM (2.0 mL) was added through the top of the vessel and the resulting mixture was periodically agitated for 90 seconds before the solution was drained through the frit. The resin was then immediately transferred using DCM (8 mL) to a 15 mL vial. To the solution was added hexafluoroisopropanol (2 mL). The resin immediately turned deep red; the solution remained colorless. The mixture briefly manually agitated, then was allowed to stand at r.t. for 15 minutes, then was filtered. The filtrate was transferred to a 15 mL vial and was concentrated under a N2 stream to afford a solid residue, Intermediate 10501A.

Preparation of Intermediate 10504B

To a 40 mL vial charged with the entirety of Intermediate 10504A prepared above was added DCM (20 mL), then HATU (38 mg, 0.10 mmol) then DIPEA (0.114 mL, 0.650 mmol). The solution was stirred for 2 h. The solution was dried under vacuum to afford Intermediate 10504B.

PREPARATION OF EXAMPLE 10504

A "deprotection solution" was prepared by combining in a 40 mL glass vial trifluoroacetic acid (23.75 mL), 1,4-Dithio-DL-threitol (625 mg), triisopropylsilane (0.625 mL). To a 5 dram vial charged with the entirety of Intermediate 10504A prepared above was added the "deprotection solution" (2.0 mL). The solution was mixed for 20 minutes in a shaker running at 500 rpm, then was poured into a 25 mL test tube charged with Et$_2$O (15 mL). A small amount of white solid precipitated. The mixture was centrifuged; the liquid was decanted. The solids were suspended in Et$_2$O (15 mL). The mixture was centrifuged, the liquid was decanted. The crude material was purified via preparative LC/MS with the following conditions: Column: XBridge C18, 19×200 mm, 5-μm particles; Mobile Phase A: 5:95 cetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 0-40% B over 30 minutes, then a 5-minute hold at 100% B; Flow: 20 mL/min. Fractions containing the desired product were combined and dried via centrifugal evaporation. The yield of the product was 7.3 mg, and its estimated purity by LCMS analysis was 93%.

Analysis condition A: Retention time=1.58 min; ESI-MS (+) m/z 936.1 (M+2H). Analysis condition B: Retention time=2.70 min; ESI-MS(+) m/z 935.9 (M+2H).

PREPARATION OF EXAMPLE 10505

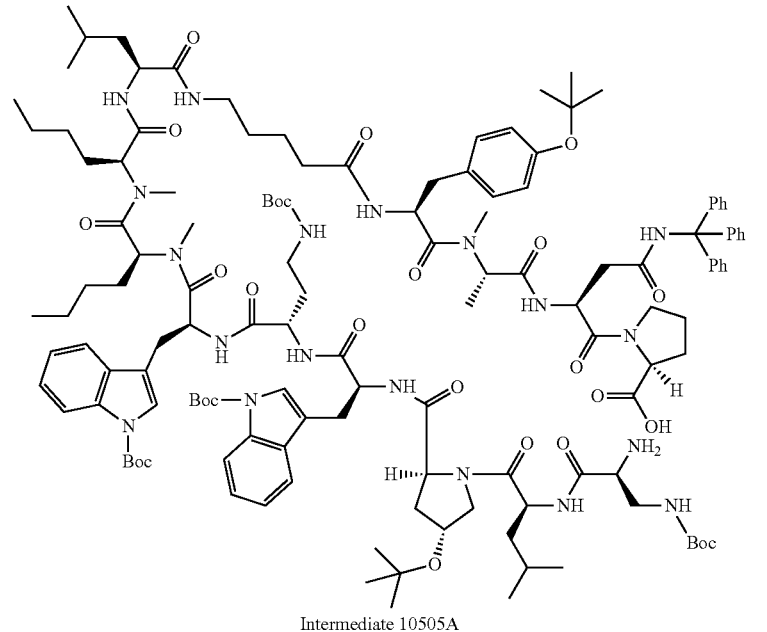

Intermediate 10505A

-continued

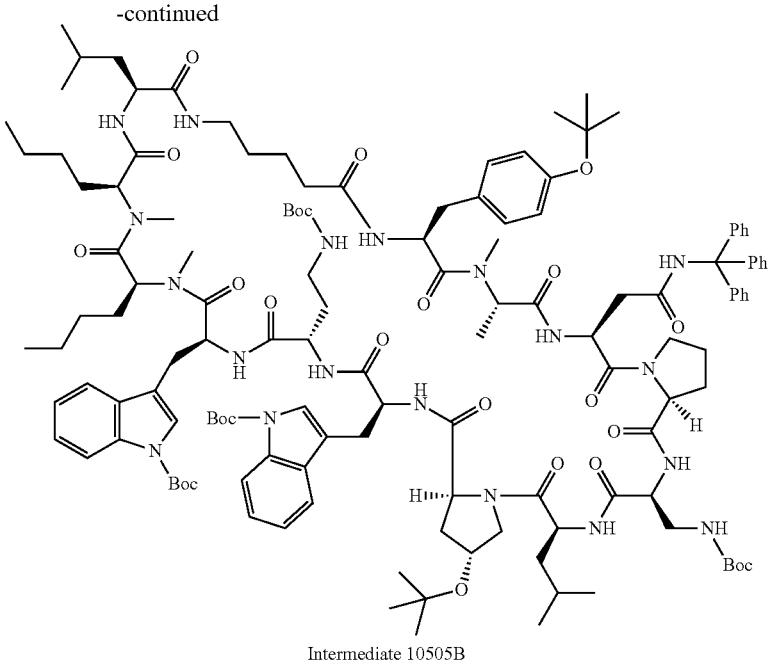

Intermediate 10505B

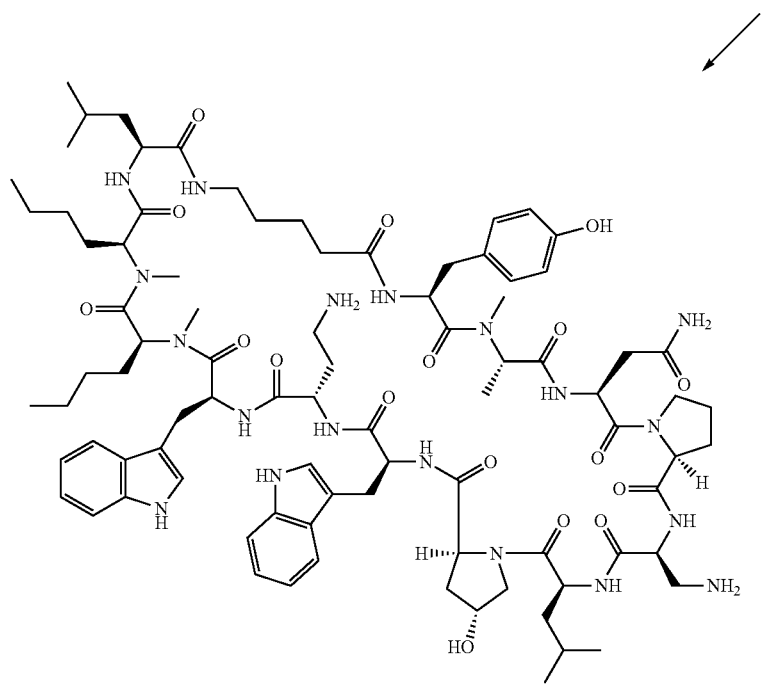

Example 10505

Preparation of Intermediate 10505A

"General Synthetic Sequence A" was followed with the exception that the loading step was not necessary since preloaded Fmoc-L-Pro-2-Chlorotrityl resin was used. 5-((((9H-fluoren-9-yl)methoxy)carbonyl)amino)pentanoic acid was used in the 4$^{th}$ amide bond forming step. To the reaction vessel containing resin from the automated sequence was added piperidine:DMF (20:80 v/v, 2.0 mL). The mixture was periodically agitated for 4 minutes and then the solution was drained through the frit. To the reaction vessel was added piperidine:DMF (20:80 v/v, 2.0 mL). The mixture was periodically agitated for 4 minutes and then the solution was drained through the frit. The resin was washed successively five times as follows: for each wash, DMF (2.0 mL) was added through the top of the vessel and the resulting mixture was periodically agitated for 90 seconds before the solution was drained through the frit. The resin was washed successively five times as follows: for each wash, DCM (2.0 mL) was added through the top of the vessel and the resulting mixture was periodically agitated for 90 seconds before the solution was drained through the frit.

The resin was then immediately transferred using DCM (8 mL) to a 15 mL vial. To the solution was added hexafluoroisopropanol (2 mL). The resin immediately turned deep red; the solution remained colorless. The mixture briefly manually agitated, then was allowed to stand at r.t. for 15 minutes, and then was filtered. The filtrate was transferred to a 15 mL vial and was concentrated under a N2 stream to afford a solid residue, Intermediate 10501A.

Preparation of Intermediate 10505B

To a 40 mL vial charged with the entirety of Intermediate 10504A prepared above was added DCM (20 mL), then HATU (76 mg, 0.20 mmol) then DIPEA (0.052 mL, 0.30 mmol). The solution was stirred for 2 h. The solution was dried under vacuum to afford Intermediate 10504B.

PREPARATION OF EXAMPLE 10505

A "deprotection solution" was prepared by combining in a 40 mL glass vial trifluoroacetic acid (23.75 mL), 1,4-Dithio-DL-threitol (625 mg), triisopropylsilane (0.625 mL). To a 5 dram vial charged with the entirety of Intermediate 10504A prepared above was added the "deprotection solution" (2.0 mL). The solution was mixed for 20 minutes in a shaker running at 500 rpm, then was poured into a 25 mL test tube charged with Et₂O (15 mL). A small amount of white solid precipitated. The mixture was centrifuged; the liquid was decanted. The solids were suspended in Et₂O (15 mL). The mixture was centrifuged, the liquid was decanted. The crude material was purified via preparative LC/MS with the following conditions: Column: XBridge C18, 19×200 mm, 5-μm particles; Mobile Phase A: 5:95 cetonitrile:water with 10-mM ammonium acetate; Mobile Phase B: 95:5 acetonitrile:water with 10-mM ammonium acetate; Gradient: 10-50% B over 30 minutes, then a 5-minute hold at 100% B; Flow: 20 mL/min. Fractions containing the desired product were combined and dried via centrifugal evaporation. The material was further purified via preparative LC/MS with the following conditions: Column: Waters CSH C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 0-40% B over 30 minutes, then a 5-minute hold at 100% B; Flow: 20 mL/min. Fractions containing the desired product were combined and dried via centrifugal evaporation. The yield of the product was 7.0 mg, and its estimated purity by LCMS analysis was 95%.

Analysis condition A: Retention time=1.56 min; ESI-MS (+) m/z 927.0 (M+2H). Analysis condition C: Retention time=1.49 min; ESI-MS(+) m/z 927.1 (M+2H). 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.52 minutes with corresponding ESI detection of 922.9 m/z. 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.52 minutes with corresponding ESI detection of 922.9 m/z.

PREPARATION OF EXAMPLE 10506

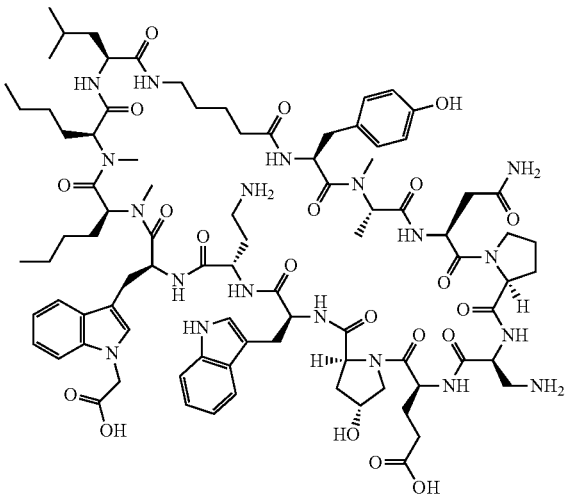

Example 10506

Example 10506 was prepared following the produre used for the preparation of Example 10505 to afford 9.3 mg of the product with 98.6% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.05% trifluoroacetic acid; Mobile Phase B: 95:5 acetonitrile:water with 0.05% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.43 minutes with corresponding ESI detection of 1785.1 m/z.

PREPARATION OF EXAMPLE 10507

Example 10507

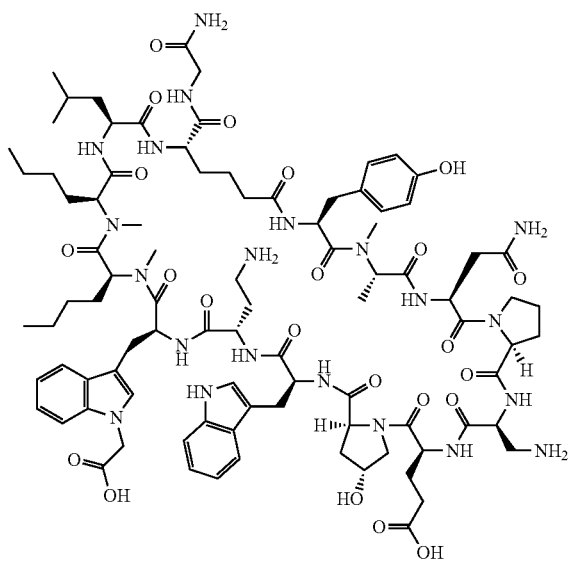

PREPARATION OF EXAMPLE 10508

Example 10508

Example 10507 was prepared following the produre used for the preparation of Example 10505 ((S)-5-((((9H-fluoren-9-yl)methoxy)carbonyl)amino)-6-((2-amino-2-oxoethyl)amino)-6-oxohexanoic acid used in 4th amide coupling step) to afford 2.3 mg of the product with 95.5% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.05% trifluoroacetic acid; Mobile Phase B: 95:5 acetonitrile:water with 0.05% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.36 minutes with corresponding ESI detection of 1885.9 m/z.

Example 10508 was prepared following the produre used for the preparation of Example 10505 ((S)-5-((((9H-fluoren-9-yl)methoxy)carbonyl)amino)-6-((2-amino-2-oxoethyl)amino)-6-oxohexanoic acid used in 4th amide coupling step) to afford 5.2 mg of the product with 97.5% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.05% trifluoroacetic acid; Mobile Phase B: 95:5 acetonitrile:water with 0.05% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.38 minutes with corresponding ESI detection of 956.2 m/z.

PREPARATION OF EXAMPLE 10509

Example 10509

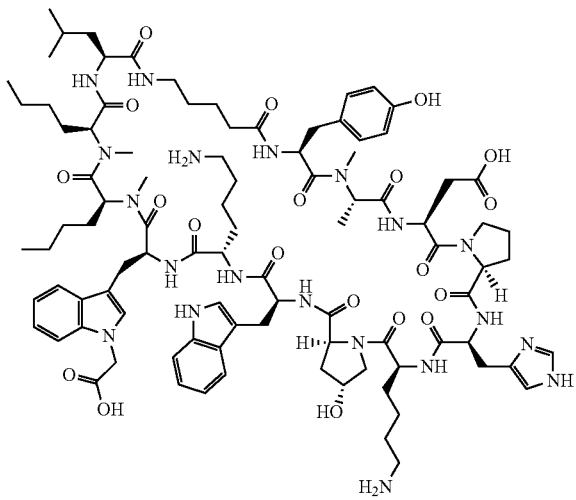

Example 10509 was prepared following the produre used for the preparation of Example 10505 to afford 5.3 mg of the product with 98.2% purity. Two analytical LC/MS injections were used to determine the final purity. Injection 1 conditions: Column: Waters BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-µm particles; Mobile Phase A: 5:95 acetonitrile:water with 0.05% trifluoroacetic acid; Mobile Phase B: 95:5 acetonitrile:water with 0.05% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.31 minutes with corresponding ESI detection of 622 m/z.

PREPARATION OF EXAMPLE 10510

Example 10510

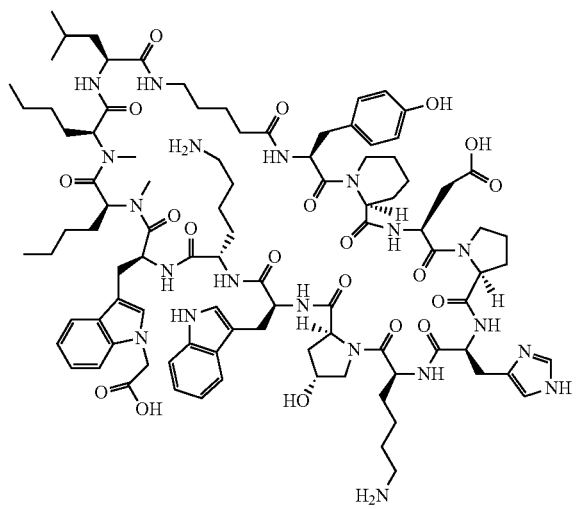

Example 10510 was prepared following the produre used for the preparation of Example 10505 ((S)-5-((((9H-fluoren-9-yl)methoxy)carbonyl)amino)-6-((2-amino-2-oxoethyl)amino)-6-oxohexanoic acid used in 4th amide coupling step) to afford 7 mg of the product with 100% purity. Two analytical LC/MS injections were used to determine the final purity. Injection 1 conditions: Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. Analysis results: Retention time=1.65 minutes with corresponding ESI detection of 946 m/z.

PREPARATION OF EXAMPLE 10511

Example 10511

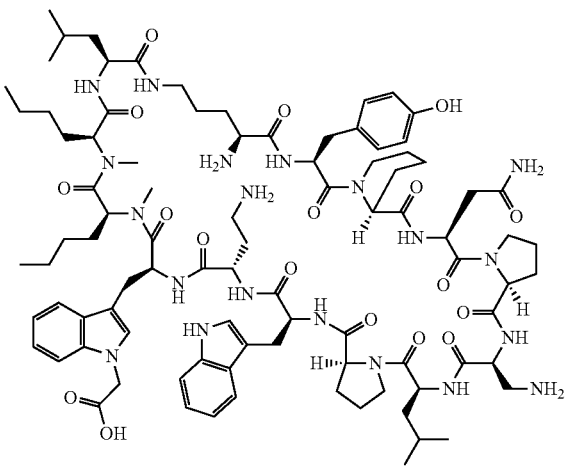

Example 10511 was prepared following the produre used for the preparation of Example 10505 ((S)-5-((((9H-fluoren-9-yl)methoxy)carbonyl)amino)-2-((tert-butoxycarbonyl)amino)pentanoic acid used in 4th amide coupling step) to afford 2.9 mg of the product with 95.1% purity. Two analytical LC/MS injections were used to determine the final purity. Injection 1 conditions: Column: Waters BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-µm particles; Mobile Phase A: 5:95 acetonitrile:water with 0.05% trifluoroacetic acid; Mobile Phase B: 95:5 acetonitrile:water with 0.05% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.73 minutes with corresponding ESI detection of 1795 m/z.

PREPARATION OF EXAMPLE 10512

Example 10512

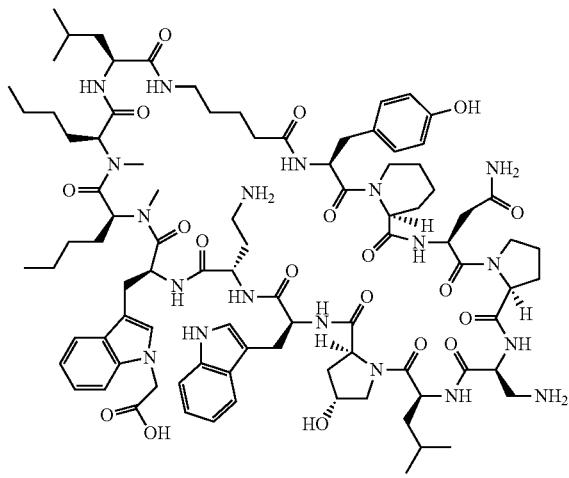

Example 10512 was prepared following the produre used for the preparation of Example 10505 to afford 8.6 mg of the product with 100% purity. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. Analysis results: Retention time=1.68 minutes with corresponding ESI detection of 898.2 m/z.

PREPARATION OF EXAMPLE 10513

Example 10513

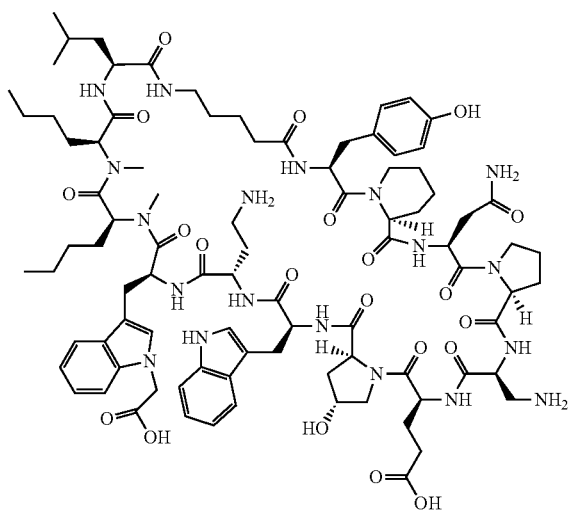

Example 10513 was prepared following the produre used for the preparation of Example 10505 to afford 7.4 mg of the product with 100% purity. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. Analysis results: Retention time=1.6 minutes with corresponding ESI detection of 906.2 m/z.

PREPARATION OF EXAMPLE 10514

Example 10514

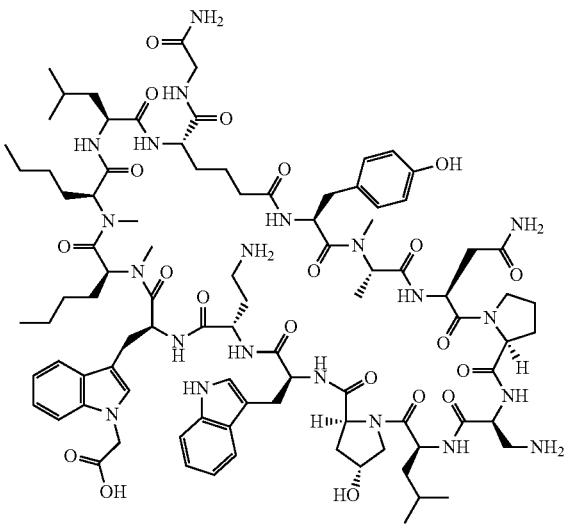

Example 10514 was prepared following the produre used for the preparation of Example 10505 ((S)-5-((((9H-fluoren-9-yl)methoxy)carbonyl)amino)-6-((2-amino-2-oxoethyl) amino)-6-oxohexanoic acid used in 4th amide coupling step) to afford 1.8 mg of the product with 100% purity. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. Analysis results: Retention time=1.61 minutes with corresponding ESI detection of 935.2 m/z.

PREPARATION OF EXAMPLE 10515

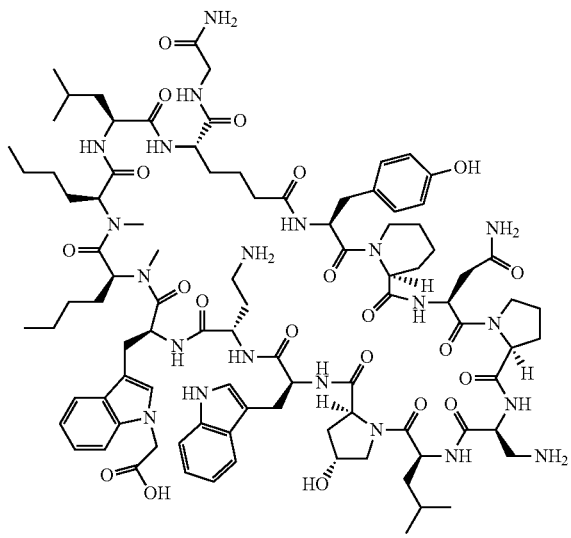

Example 10515

Example 10515 was prepared following the produre used for the preparation of Example 10505 ((S)-5-((((9H-fluoren-9-yl)methoxy)carbonyl)amino)-6-((2-amino-2-oxoethyl)amino)-6-oxohexanoic acid used in 4th amide coupling step) to afford 0.3 mg of the product with 96.7% purity. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. Analysis results: Retention time=1.65 minutes with corresponding ESI detection of 948.3 m/z.

PREPARATION OF EXAMPLE 10516

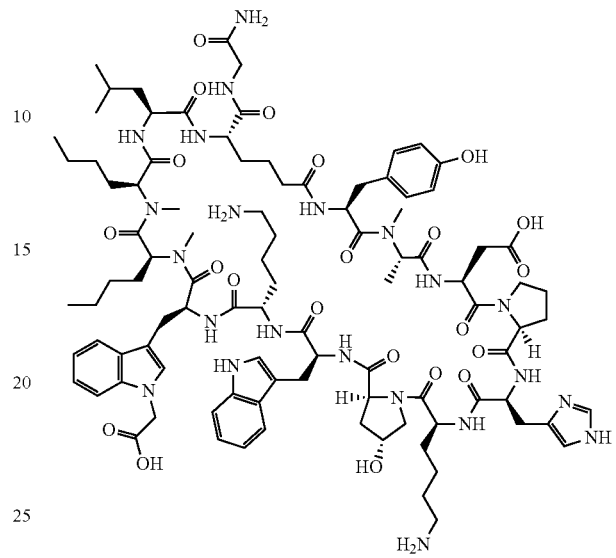

Example 10516

Example 10516 was prepared following the produre used for the preparation of Example 10505 ((S)-5-((((9H-fluoren-9-yl)methoxy)carbonyl)amino)-6-((2-amino-2-oxoethyl)amino)-6-oxohexanoic acid used in 4th amide coupling step) to afford 1.5 mg of the product with 100% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.05% trifluoroacetic acid; Mobile Phase B: 95:5 acetonitrile:water with 0.05% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.27 minutes with corresponding ESI detection of 983 m/z.

PREPARATION OF EXAMPLE 10517

Example 10517

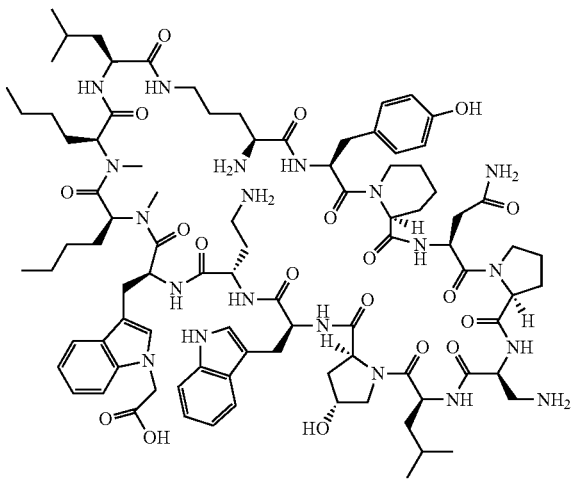

Example 10517 was prepared following the produre used for the preparation of Example 10505 ((S)-5-((((9H-fluoren-9-yl)methoxy)carbonyl)amino)-2-((tert-butoxycarbonyl)amino)pentanoic acid used in 4th amide coupling step) to afford 15.3 mg of the product with 97% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.39 minutes with corresponding ESI detection of 1809.7 m/z.

PREPARATION OF EXAMPLE 10518

Example 10518

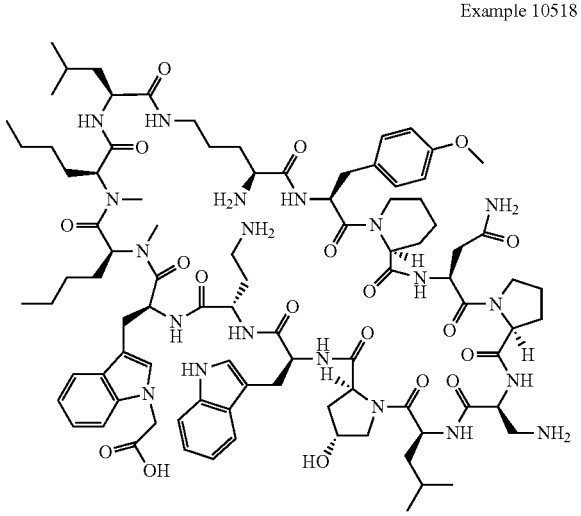 [SMILES: CCCC[C@H]1C(=O)N(C)[C@@H](CCCC)C(=O)N[C@@H](CC(C)C)C(=O)NCCC[C@H](N)C(=O)N[C@@H](Cc2ccc(C)cc2)C(=O)N2CCCC[C@H]2C(=O)N[C@@H](CC(N)=O)C(=O)N2CCC[C@H]2C(=O)N[C@@H](CN)C(=O)N[C@@H](CC(C)C)C(=O)N2C[C@H](O)C[C@H]2C(=O)N[C@@H](Cc2c[nH]c3ccccc23)C(=O)N[C@@H](CCN)C(=O)N[C@@H](Cc2cn(CC(=O)O)c3ccccc23)C(=O)N1C]

Example 10518 was prepared following the produre used for the preparation of Example 10505 ((S)-5-((((9H-fluoren-9-yl)methoxy)carbonyl)amino)-2-((tert-butoxycarbonyl)amino)pentanoic acid used in 4th amide coupling step) to afford 10.9 mg of the product with 97.5% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.79 minutes with corresponding ESI detection of 1822.1 m/z.

PREPARATION OF EXAMPLE 10519

Example 10519

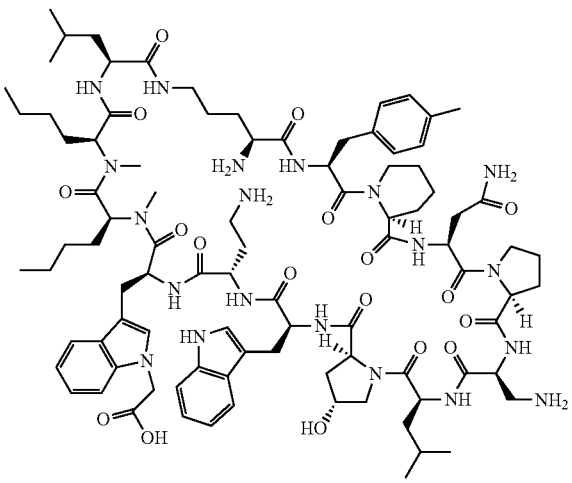

Example 10519 was prepared following the produre used for the preparation of Example 10505 ((S)-5-((((9H-fluoren-9-yl)methoxy)carbonyl)amino)-2-((tert-butoxycarbonyl)amino)pentanoic acid used in 4th amide coupling step) to afford 8.5 mg of the product with 94.5% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.89 minutes with corresponding ESI detection of 1807.1 m/z.

PREPARATION OF EXAMPLE 10520

Example 10520

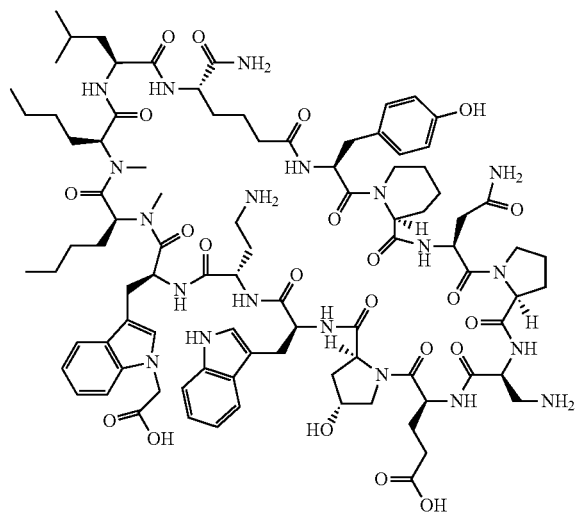

Example 10520 was prepared following the produre used for the preparation of Example 10505 ((S)-5-((((9H-fluoren-9-yl)methoxy)carbonyl)amino)-6-amino-6-oxohexanoic acid used in 4th amide coupling step) to afford 7 mg of the product with 95.4% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.55 minutes with corresponding ESI detection of 1853.1 m/z.

PREPARATION OF EXAMPLE 10521

Example 10521

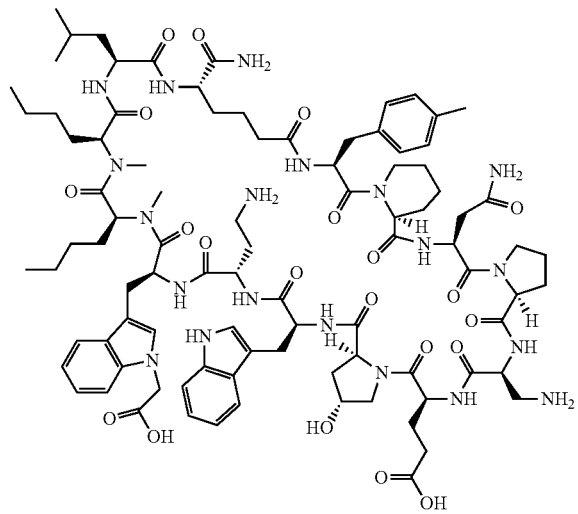

Example 10521 was prepared following the produre used for the preparation of Example 10505 ((S)-5-((((9H-fluoren-9-yl)methoxy)carbonyl)amino)-6-amino-6-oxohexanoic acid used in 4th amide coupling step) to afford 5.6 mg of the product with 100% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.85 minutes with corresponding ESI detection of 1853.3 m/z.

PREPARATION OF EXAMPLE 10522

Example 10522

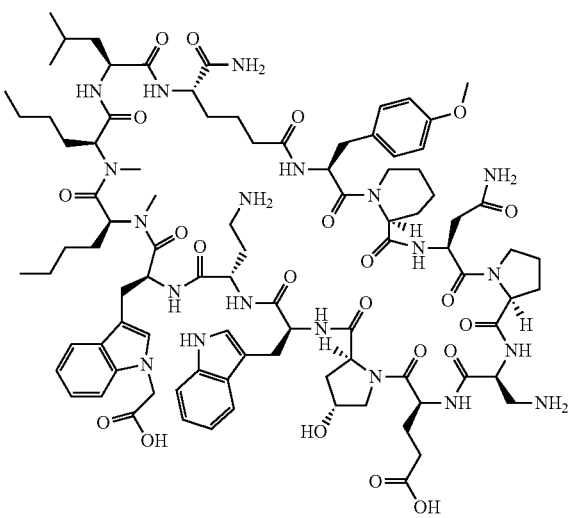

Example 10522 was prepared following the produre used for the preparation of Example 10505 ((S)-5-((((9H-fluoren-9-yl)methoxy)carbonyl)amino)-6-amino-6-oxohexanoic acid used in 4th amide coupling step) to afford 5.9 mg of the product with 94.1% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.74 minutes with corresponding ESI detection of 1867.1 m/z.

PREPARATION OF EXAMPLE 10525

Example 10525

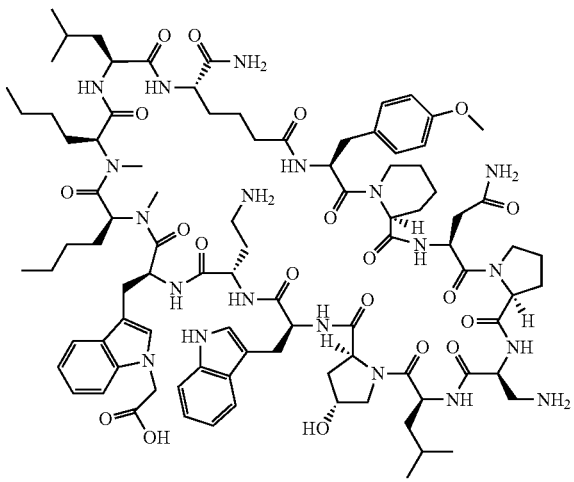

Example 10525 was prepared following the produre used for the preparation of Example 10505 ((S)-5-((((9H-fluoren-9-yl)methoxy)carbonyl)amino)-6-amino-6-oxohexanoic acid used in 4th amide coupling step) to afford 2.8 mg of the product with 99.1% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.72 minutes with corresponding ESI detection of 926.8 m/z.

PREPARATION OF EXAMPLE 10526

Example 10526

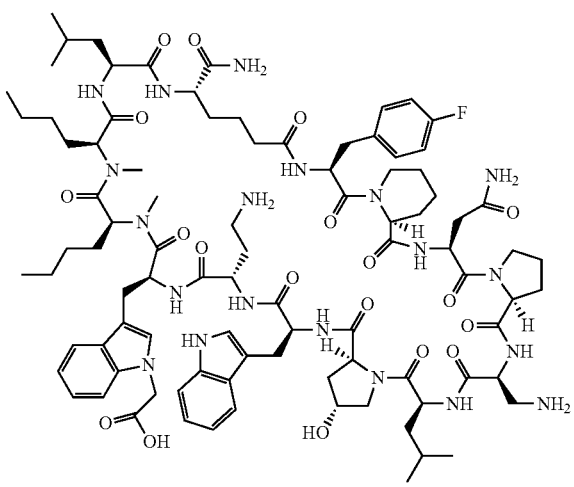

Example 10526 was prepared following the produre used for the preparation of Example 10505 ((S)-5-((((9H-fluoren-9-yl)methoxy)carbonyl)amino)-6-amino-6-oxohexanoic acid used in 4th amide coupling step) to afford 4.5 mg of the product with 99.2% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.72 minutes with corresponding ESI detection of 920.9 m/z.

PREPARATION OF EXAMPLE 10527

Example 10527

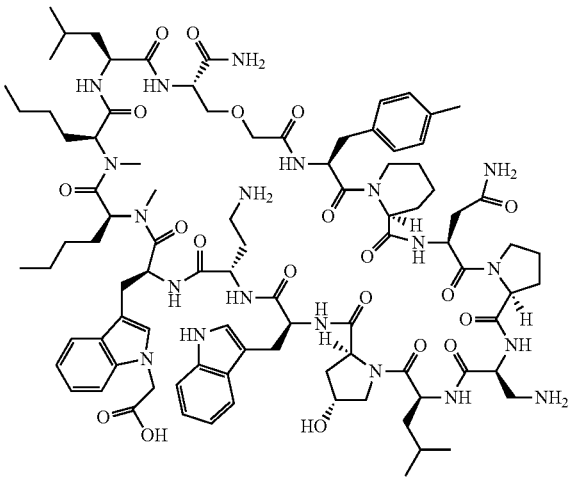

Example 10527 was prepared following the produre used for the preparation of Example 10505 ((S)-2-(2-((((9H-fluoren-9-yl)methoxy)carbonyl)amino)-3-amino-3-oxo-propoxy)acetic acid used in 4th amide coupling step) to afford 2.8 mg of the product with 97.4% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.97 minutes with corresponding ESI detection of 1835.8 m/z.

PREPARATION OF EXAMPLE 10528

Example 10528

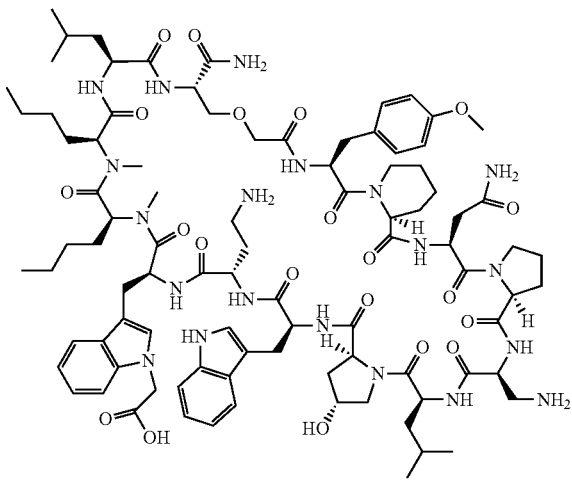

Example 10528 was prepared following the produre used for the preparation of Example 10505 ((S)-2-(2-((((9H-fluoren-9-yl)methoxy)carbonyl)amino)-3-amino-3-oxo-propoxy)acetic acid used in 4th amide coupling step) to afford 3.4 mg of the product with 99% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.74 minutes with corresponding ESI detection of 927.1 m/z.

PREPARATION OF EXAMPLE 10529

Example 10529

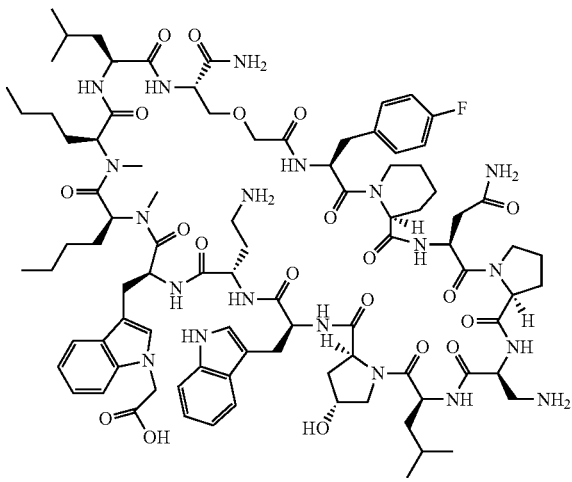

Example 10529 was prepared following the produre used for the preparation of Example 10505 ((S)-2-(2-((((9H-fluoren-9-yl)methoxy)carbonyl)amino)-3-amino-3-oxo-propoxy)acetic acid used in 4th amide coupling step) to afford 2.8 mg of the product with 98.9% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.89 minutes with corresponding ESI detection of 1841.2 m/z.

PREPARATION OF EXAMPLE 10530

Example 10530

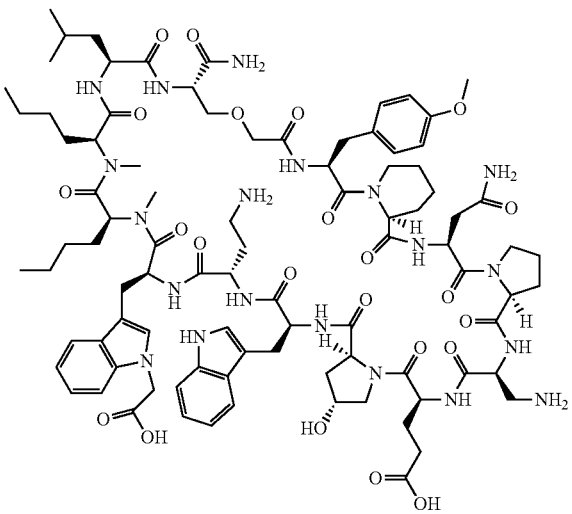

Example 10530 was prepared following the produre used for the preparation of Example 10505 ((S)-2-(2-((((9H-fluoren-9-yl)methoxy)carbonyl)amino)-3-amino-3-oxo-propoxy)acetic acid used in 4th amide coupling step) to afford 4.5 mg of the product with 97.3% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow:

0.75 mL/min; Detection: UV at 220 nm. Analysis results: Retention time=1.77 minutes with corresponding ESI detection of 935.4 m/z.

PREPARATION OF EXAMPLE 10531

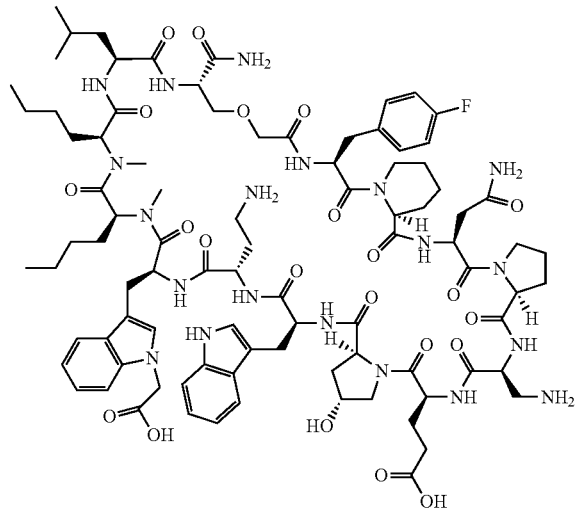

Example 10531

Example 10531 was prepared following the produre used for the preparation of Example 10505 ((S)-2-(2-((((9H-fluoren-9-yl)methoxy)carbonyl)amino)-3-amino-3-oxopropoxy)acetic acid used in 4th amide coupling step) to afford 5.8 mg of the product with 97.5% purity. Two analytical LC/MS injections were used to determine the final purity. Injection 1 conditions: Column: Waters BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-µm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.81 minutes with corresponding ESI detection of 1859 m/z.

PREPARATION OF EXAMPLE 10532

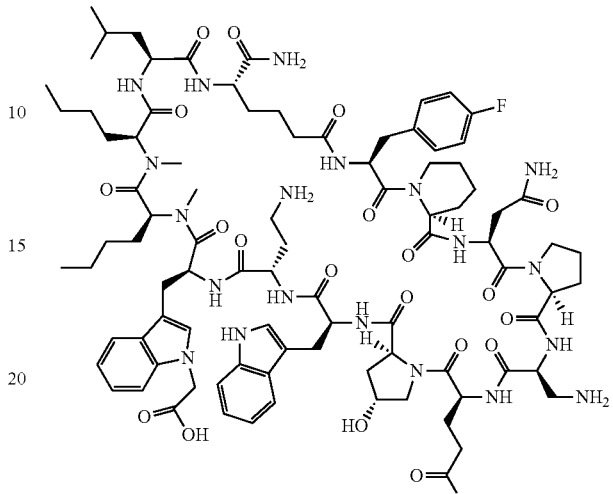

Example 10532

Example 10532 was prepared following the produre used for the preparation of Example 10505 ((S)-5-((((9H-fluoren-9-yl)methoxy)carbonyl)amino)-6-amino-6-oxohexanoic acid used in 4th amide coupling step) to afford 3.7 mg of the product with 95.4% purity. Two analytical LC/MS injections were used to determine the final purity. Injection 1 conditions: Column: Waters BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-µm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.67 minutes with corresponding ESI detection of 1854 m/z.

PREPARATION OF EXAMPLE 10533

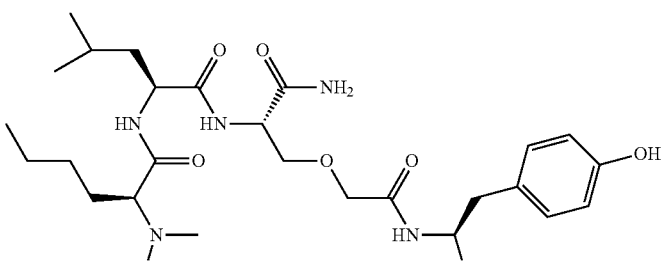

Example 10533

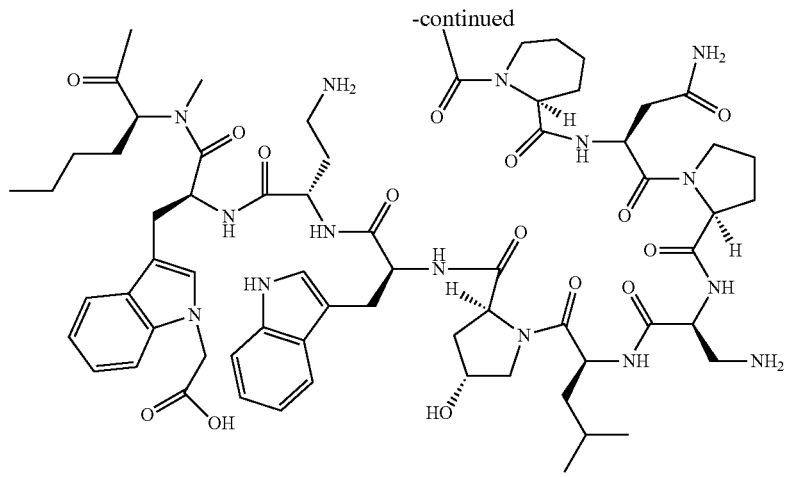

Example 10533 was prepared following the produre used for the preparation of Example 10505 ((S)-2-(2-((((9H-fluoren-9-yl)methoxy)carbonyl)amino)-3-amino-3-oxo-propoxy)acetic acid used in 4th amide coupling step) to afford 3.5 mg of the product with 92.7% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.62 minutes with corresponding ESI detection of 1839.9 m/z.

PREPARATION OF EXAMPLE 10534

Example 10534

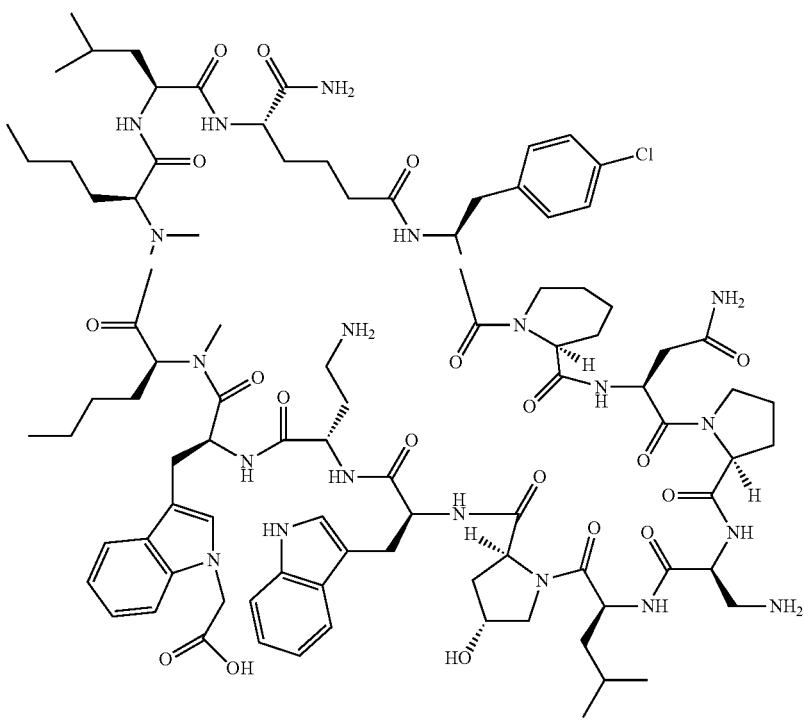

Example 10534 was prepared following the produre used for the preparation of Example 10505 ((S)-5-((((9H-fluoren-9-yl)methoxy)carbonyl)amino)-6-amino-6-oxohexanoic acid used in 4th amide coupling step) to afford 3.8 mg of the product with 100% purity. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. Analysis results: Retention time=2 minutes with corresponding ESI detection of 929.2 m/z.

PREPARATION OF EXAMPLE 10535

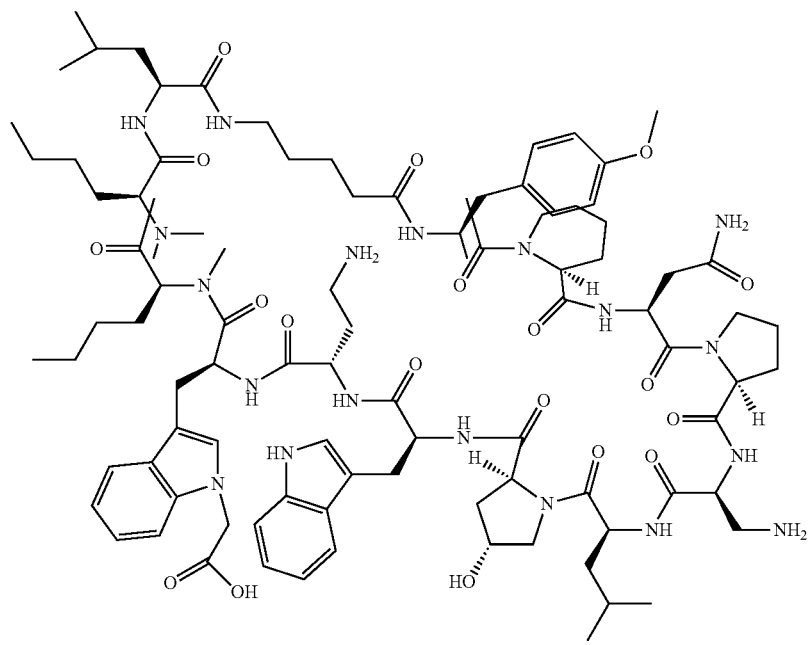

Example 10535

Example 10535 was prepared following the produre used for the preparation of Example 10505 to afford 9.3 mg of the product with 95.8% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.78 minutes with corresponding ESI detection of 904.7 m/z.

PREPARATION OF EXAMPLE 10536

Example 10536

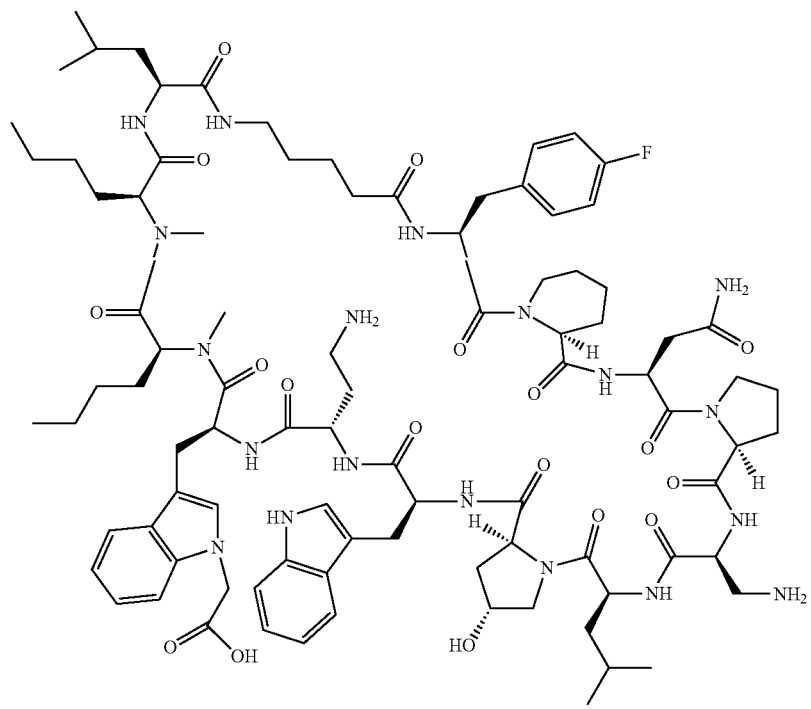

Example 10536 was prepared following the produre used for the preparation of Example 10505 to afford 11.6 mg of the product with 100% purity. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. Analysis results: Retention time=1.9 minutes with corresponding ESI detection of 899.1 m/z.

PREPARATION OF EXAMPLE 10537

Example 10537

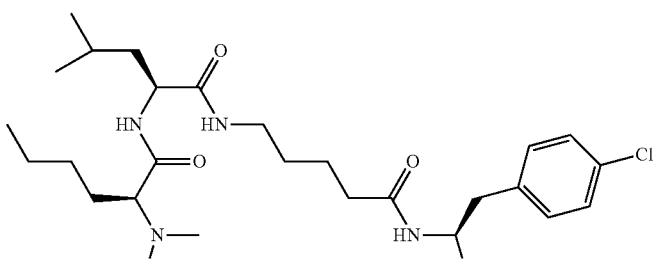

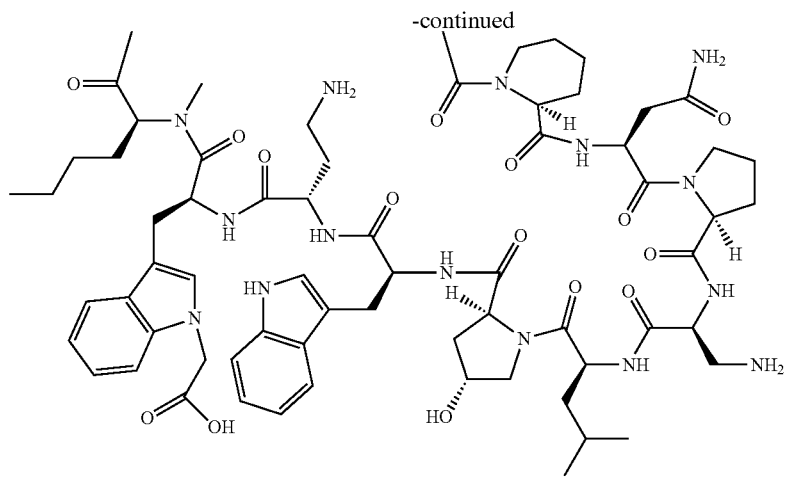

Example 10537 was prepared following the produre used for the preparation of Example 10505 to afford 5.9 mg of the product with 100% purity. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. Analysis results: Retention time=1.94 minutes with corresponding ESI detection of 605.1 m/z.

PREPARATION OF EXAMPLE 10538

Example 10538

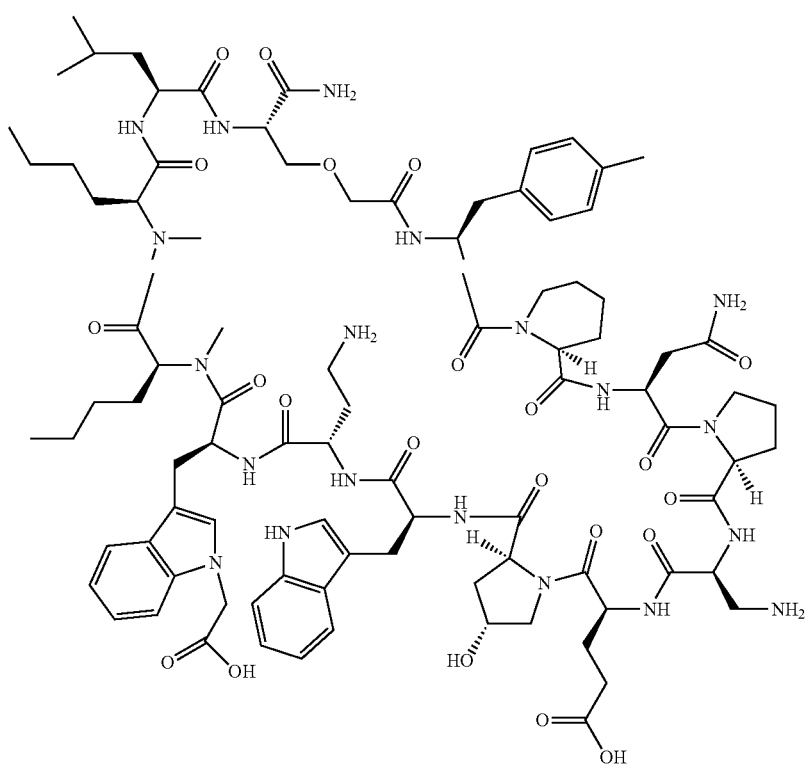

Example 10538 was prepared following the produre used for the preparation of Example 10505 ((S)-2-(2-((((9H-fluoren-9-yl)methoxy)carbonyl)amino)-3-amino-3-oxo-propoxy)acetic acid used in 4th amide coupling step) to afford 1.1 mg of the product with 99% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.78 minutes with corresponding ESI detection of 1852.7 m/z.

PREPARATION OF EXAMPLE 10539

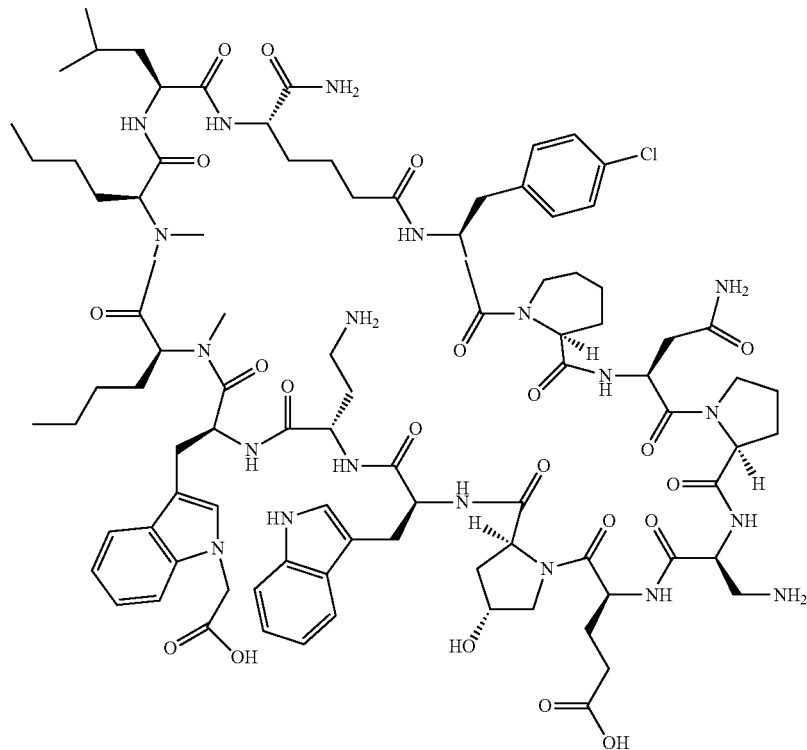

Example 10539

Example 10539 was prepared following the produre used for the preparation of Example 10505 ((S)-5-((((9H-fluoren-9-yl)methoxy)carbonyl)amino)-6-amino-6-oxohexanoic acid used in 4th amide coupling step) to afford 2.8 mg of the product with 97.8% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.64 minutes with corresponding ESI detection of 923.0 m/z.

PREPARATION OF EXAMPLE 10540

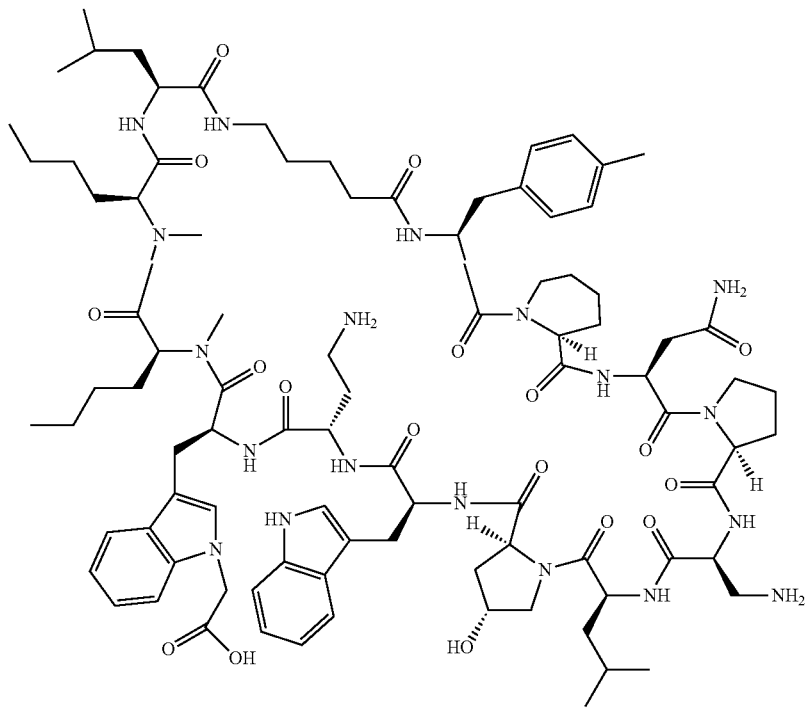

Example 10540

Example 10540 was prepared following the produre used for the preparation of Example 10505 to afford 5.5 mg of the product with 95.7% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.96 minutes with corresponding ESI detection of 1793.2 m/z.

PREPARATION OF EXAMPLE 10541

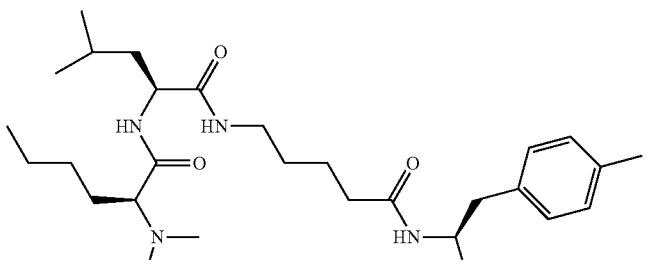

Example 10541

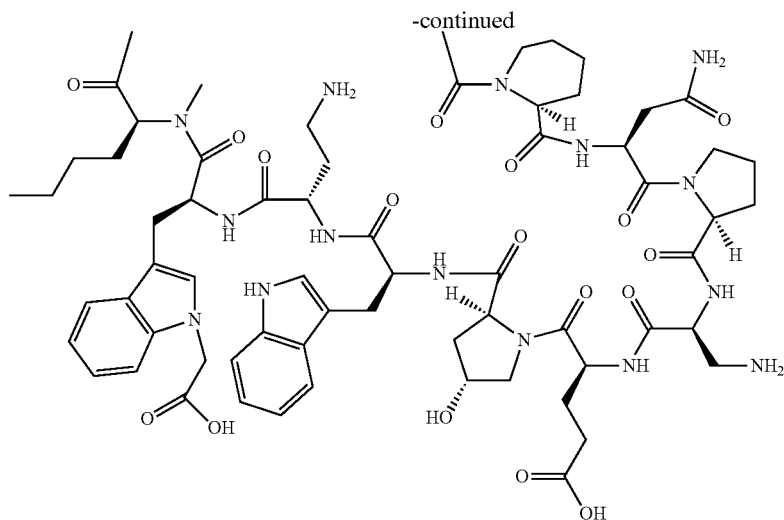

Example 10541 was prepared following the produre used for the preparation of Example 10505 to afford 9.2 mg of the product with 96.7% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.86 minutes with corresponding ESI detection of 1810 m/z.

PREPARATION OF EXAMPLE 10542

Example 10542

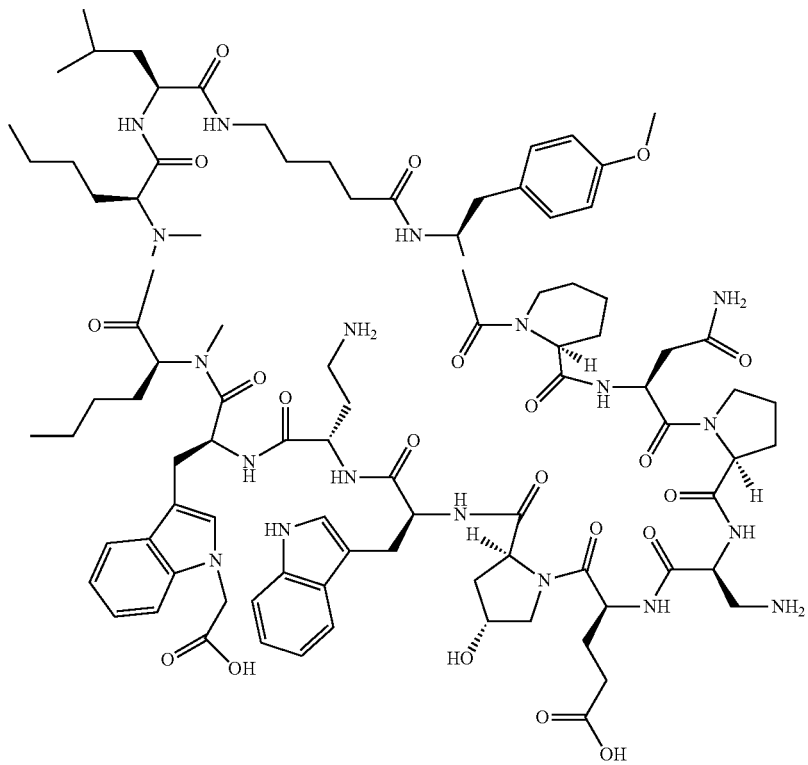

Example 10542 was prepared following the produre used for the preparation of Example 10505 to afford 10.6 mg of the product with 94.5% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.76 minutes with corresponding ESI detection of 1824.8 m/z.

PREPARATION OF EXAMPLE 10543

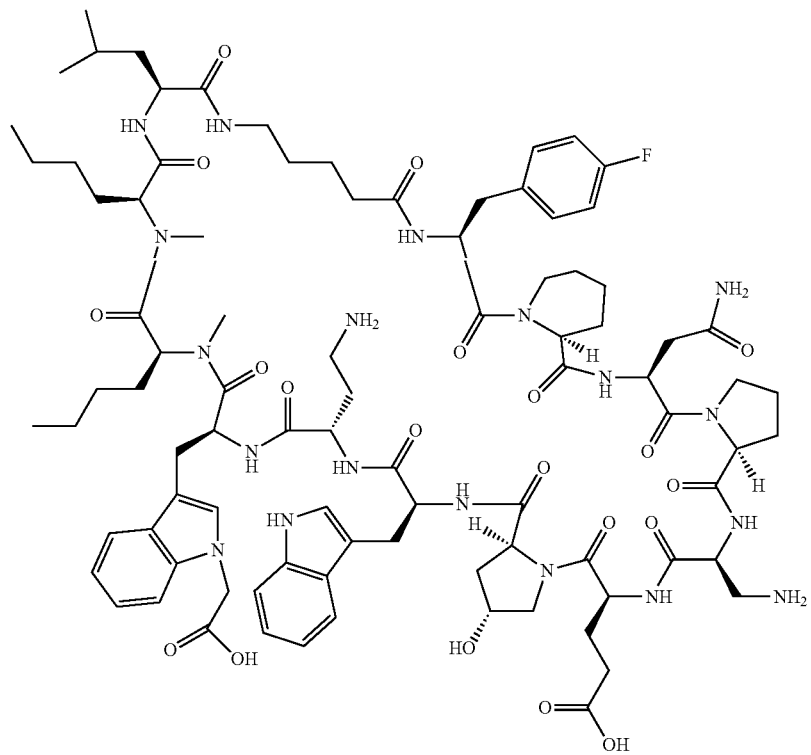

Example 10543

Example 10543 was prepared following the produre used for the preparation of Example 10505 to afford 6.4 mg of the product with 95.4% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.79 minutes with corresponding ESI detection of 1811.9 m/z.

PREPARATION OF EXAMPLE 10544

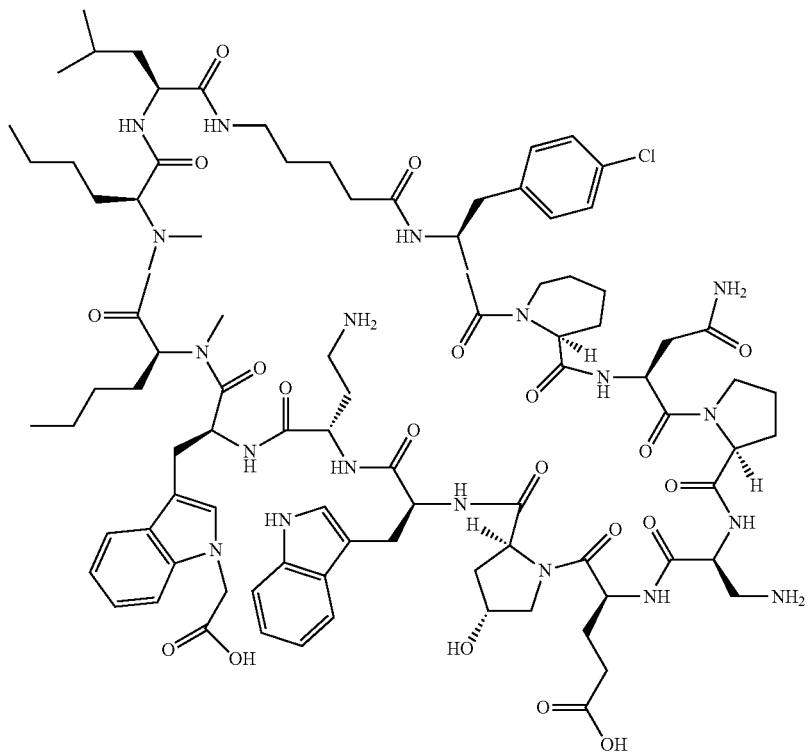

Example 10544

Example 10544 was prepared following the produre used for the preparation of Example 10505 to afford 6.6 mg of the product with 98.6% purity. Two analytical LC/MS injections were used to determine the final purity. Injection 1 conditions: Column: Waters BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-µm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.86 minutes with corresponding ESI detection of 1829.9 m/z.

PREPARATION OF EXAMPLE 10545

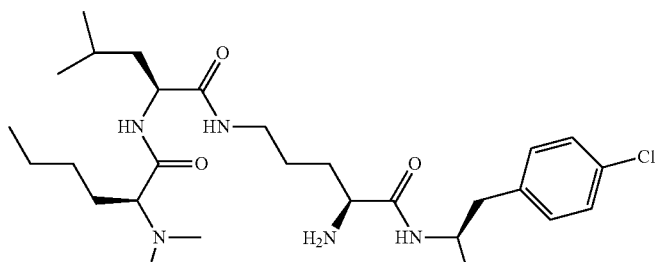

Example 10545

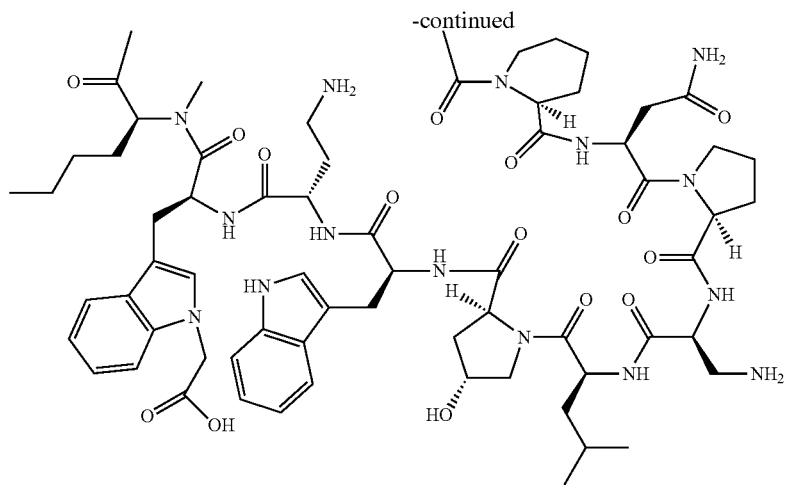

Example 10545 was prepared following the produre used for the preparation of Example 10505 ((S)-5-((((9H-fluoren-9-yl)methoxy)carbonyl)amino)-2-((tert-butoxycarbonyl)amino)pentanoic acid used in 4th amide coupling step) to afford 3 mg of the product with 94.6% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.91 minutes with corresponding ESI detection of 1826.2 m/z.

PREPARATION OF EXAMPLE 10546

Example 10546

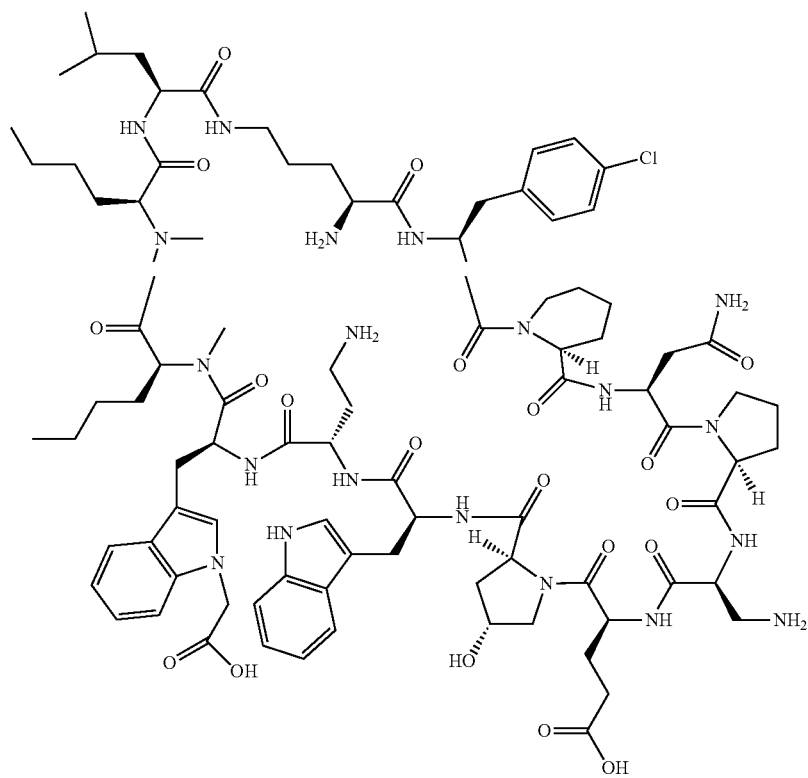

Example 10546 was prepared following the produre used for the preparation of Example 10505 ((S)-5-((((9H-fluoren-9-yl)methoxy)carbonyl)amino)-2-((tert-butoxycarbonyl)amino)pentanoic acid used in 4th amide coupling step) to afford 6.4 mg of the product with 100% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.64 minutes with corresponding ESI detection of [ERROR] m/z.

PREPARATION OF EXAMPLE 10547

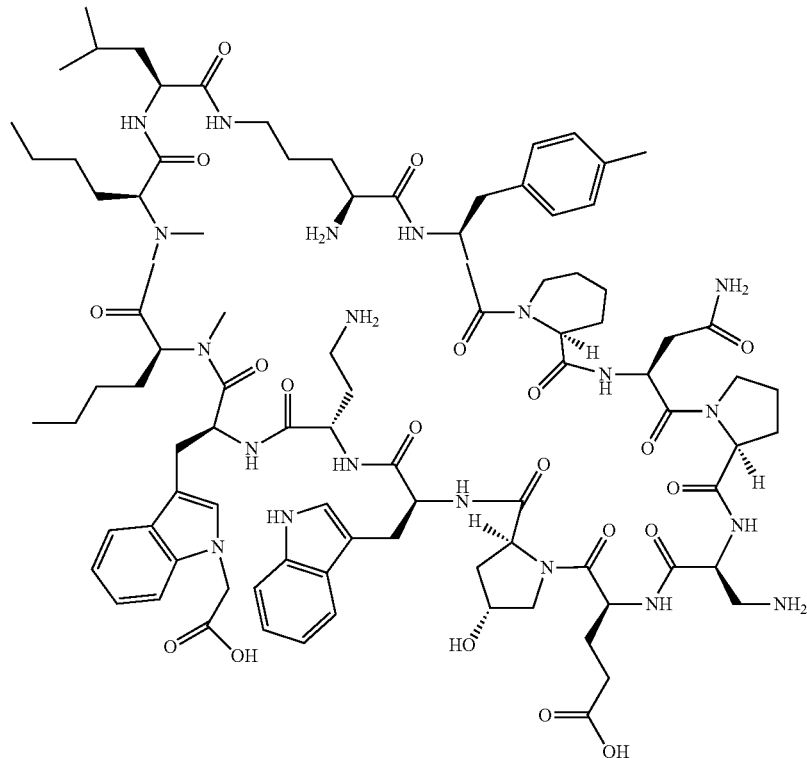

Example 10547

Example 10547 was prepared following the produre used for the preparation of Example 10505 ((S)-5-((((9H-fluoren-9-yl)methoxy)carbonyl)amino)-2-((tert-butoxycarbonyl)amino)pentanoic acid used in 4th amide coupling step) to afford 5.5 mg of the product with 97.6% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.89 minutes with corresponding ESI detection of 1822.1 m/z.

PREPARATION OF EXAMPLE 10548

Example 10548

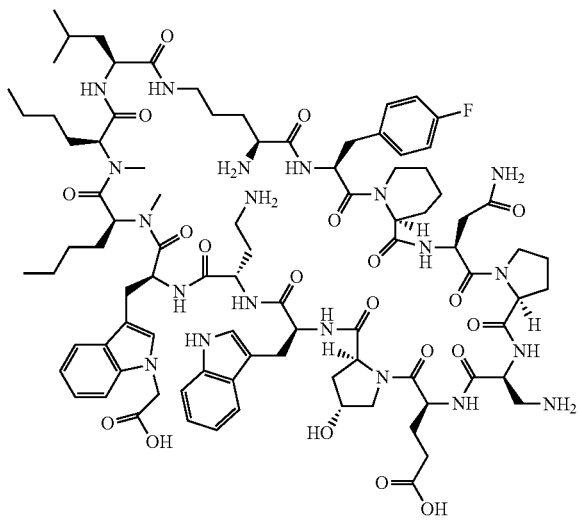

Example 10548 was prepared following the produre used for the preparation of Example 10505 ((S)-5-((((9H-fluoren-9-yl)methoxy)carbonyl)amino)-2-((tert-butoxycarbonyl)amino)pentanoic acid used in 4th amide coupling step) to afford 5.2 mg of the product with 97.7% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.8 minutes with corresponding ESI detection of 1828.7 m/z.

PREPARATION OF EXAMPLE 10549

Example 10549

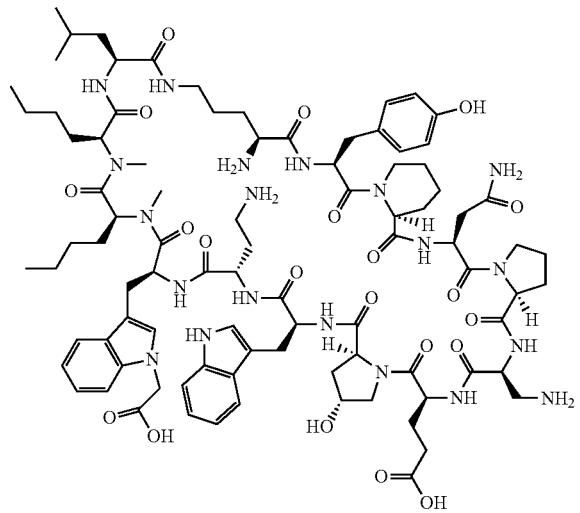

Example 10549 was prepared following the produre used for the preparation of Example 10505 ((S)-5-((((9H-fluoren-9-yl)methoxy)carbonyl)amino)-2-((tert-butoxycarbonyl)amino)pentanoic acid used in 4th amide coupling step) to afford 1.9 mg of the product with 98% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.39 minutes with corresponding ESI detection of 1824.8 m/z.

PREPARATION OF EXAMPLE 10550

Example 10550

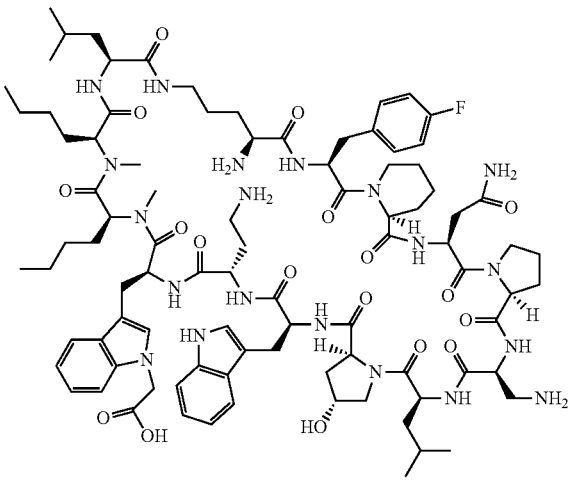

Example 10550 was prepared following the produre used for the preparation of Example 10505 ((S)-5-((((9H-fluoren-9-yl)methoxy)carbonyl)amino)-2-((tert-butoxycarbonyl)amino)pentanoic acid used in 4th amide coupling step) to afford 1.8 mg of the product with 98.3% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.83 minutes with corresponding ESI detection of 1810.6 m/z.

PREPARATION OF EXAMPLE 10551

Example 10551

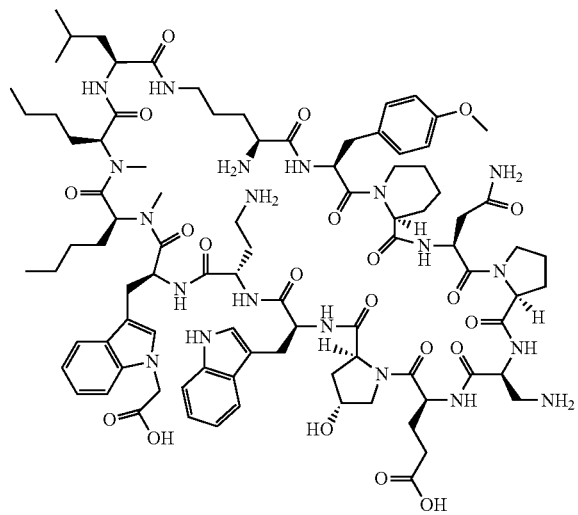

Example 10551 was prepared following the produre used for the preparation of Example 10505 ((S)-5-((((9H-fluoren-9-yl)methoxy)carbonyl)amino)-2-((tert-butoxycarbonyl)amino)pentanoic acid used in 4th amide coupling step) to afford 3.8 mg of the product with 95.5% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.79 minutes with corresponding ESI detection of 1840.9 m/z.

PREPARATION OF EXAMPLE 10552

Example 10552

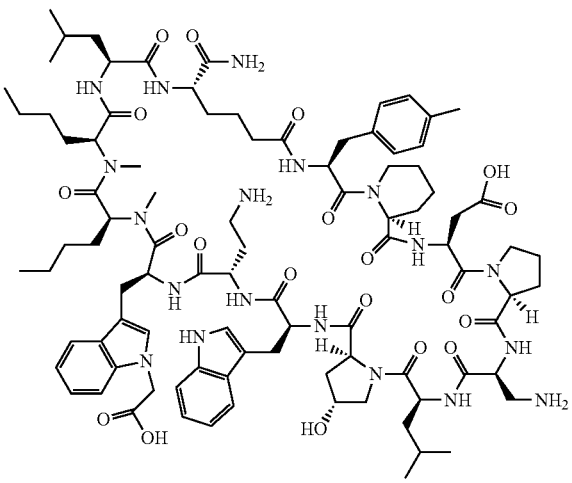

Example 10552 was prepared following the produre used for the preparation of Example 10505 ((S)-5-((((9H-fluoren-9-yl)methoxy)carbonyl)amino)-6-amino-6-oxohexanoic acid used in 4th amide coupling step) to afford 4.9 mg of the product with 100% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.5 minutes with corresponding ESI detection of 1837 m/z.

PREPARATION OF EXAMPLE 10553

Example 10553

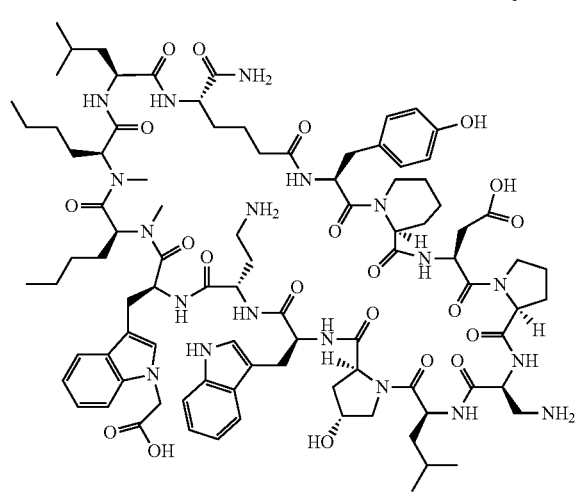

Example 10553 was prepared following the produre used for the preparation of Example 10505 ((S)-5-((((9H-fluoren-9-yl)methoxy)carbonyl)amino)-6-amino-6-oxohexanoic acid used in 4th amide coupling step) to afford 4.2 mg of the product with 94.3% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.74 minutes with corresponding ESI detection of 1834.9 m/z.

PREPARATION OF EXAMPLE 10554

Example 10554

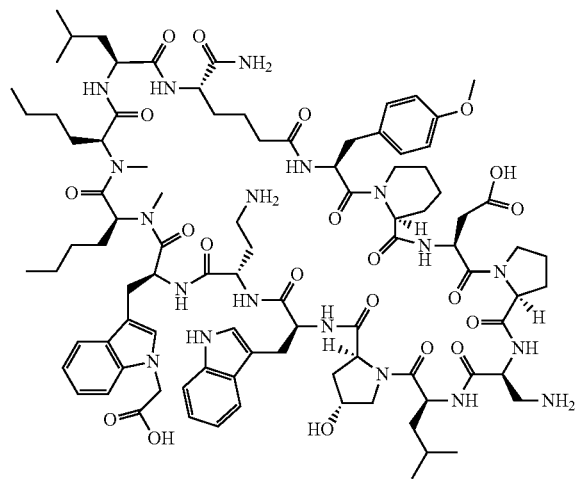

Example 10554 was prepared following the produre used for the preparation of Example 10505 ((S)-5-((((9H-fluoren-9-yl)methoxy)carbonyl)amino)-6-amino-6-oxohexanoic acid used in 4th amide coupling step) to afford 5.1 mg of the product with 100% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile: water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile: water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.79 minutes with corresponding ESI detection of 1851.7 m/z.

PREPARATION OF EXAMPLE 10555

Example 10555

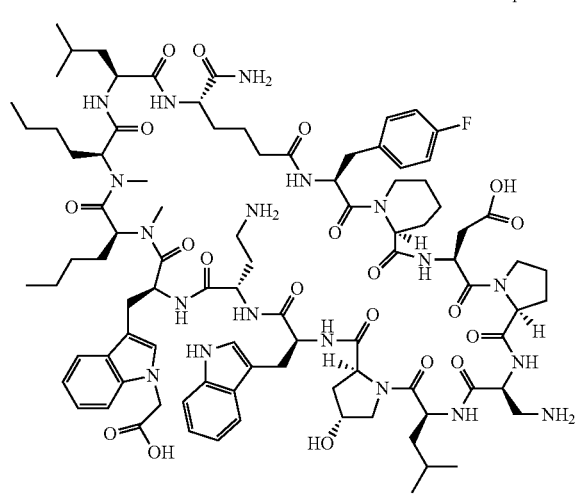

Example 10555 was prepared following the produre used for the preparation of Example 10505 ((S)-5-((((9H-fluoren-9-yl)methoxy)carbonyl)amino)-6-amino-6-oxohexanoic acid used in 4th amide coupling step) to afford 8.6 mg of the product with 98.8% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile: water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile: water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.82 minutes with corresponding ESI detection of 1841 m/z.

PREPARATION OF EXAMPLE 10556

Example 10556

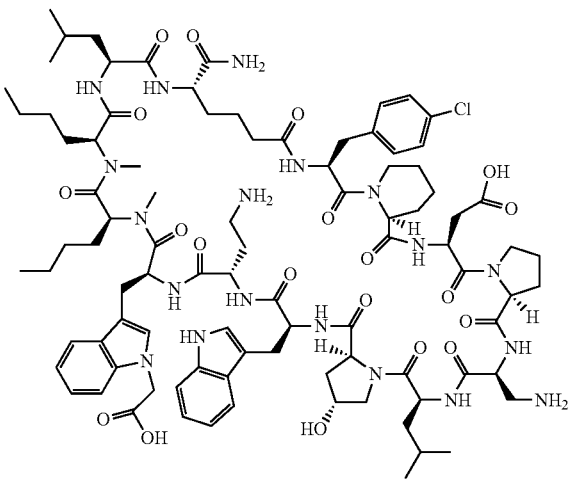

Example 10556 was prepared following the produre used for the preparation of Example 10505 ((S)-5-((((9H-fluoren-9-yl)methoxy)carbonyl)amino)-6-amino-6-oxohexanoic acid used in 4th amide coupling step) to afford 4.3 mg of the product with 98.5% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile: water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile: water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.9 minutes with corresponding ESI detection of 1855.6 m/z.

PREPARATION OF EXAMPLE 10557

Example 10557

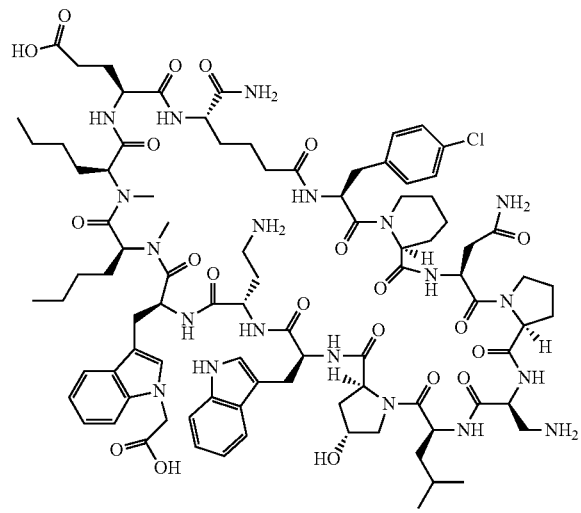

Example 10557 was prepared following the produre used for the preparation of Example 10505 ((S)-5-((((9H-fluoren-9-yl)methoxy)carbonyl)amino)-6-amino-6-oxohexanoic acid used in 4th amide coupling step) to afford 2.2 mg of the product with 100% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.69 minutes with corresponding ESI detection of 1870.1 m/z.

PREPARATION OF EXAMPLE 10558

Example 10558

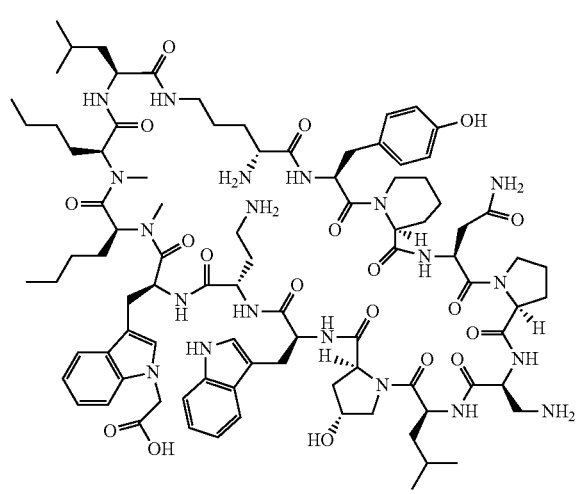

Example 10558 was prepared following the produre used for the preparation of Example 10505 ((R)-5-((((9H-fluoren-9-yl)methoxy)carbonyl)amino)-2-((tert-butoxycarbonyl)amino)pentanoic acid used in 4th amide coupling step) to afford 1.4 mg of the product with 100% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.37 minutes with corresponding ESI detection of 905.7 m/z.

PREPARATION OF EXAMPLE 10559

Example 10559

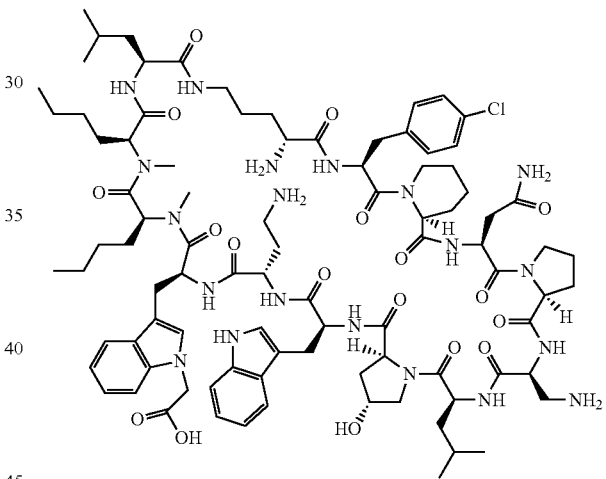

Example 10559 was prepared following the produre used for the preparation of Example 10505 ((R)-5-((((9H-fluoren-9-yl)methoxy)carbonyl)amino)-2-((tert-butoxycarbonyl)amino)pentanoic acid used in 4th amide coupling step) to afford 1.9 mg of the product with 100% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.91 minutes with corresponding ESI detection of 1826.8 m/z.

PREPARATION OF EXAMPLE 10560

Example 10560

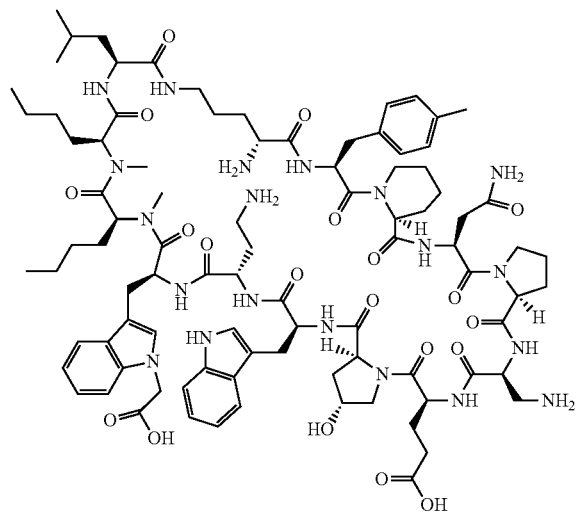

Example 10560 was prepared following the produre used for the preparation of Example 10505 ((R)-5-((((9H-fluoren-9-yl)methoxy)carbonyl)amino)-2-((tert-butoxycarbonyl)amino)pentanoic acid used in 4th amide coupling step) to afford 3.4 mg of the product with 95.9% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.47 minutes with corresponding ESI detection of 1823.1 m/z.

PREPARATION OF EXAMPLE 10561

Example 10561

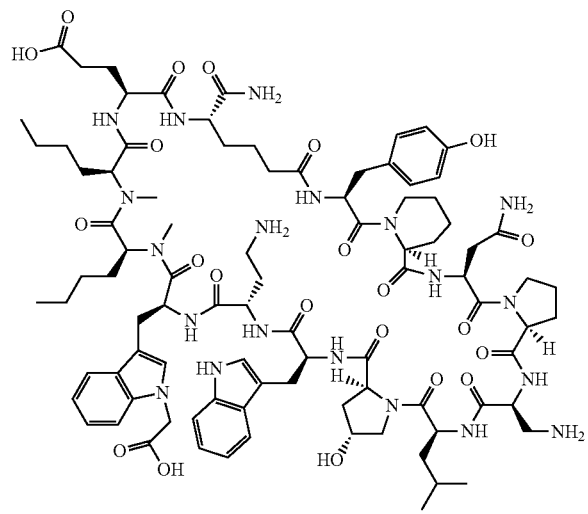

Example 10561 was prepared following the produre used for the preparation of Example 10505 ((S)-5-((((9H-fluoren-9-yl)methoxy)carbonyl)amino)-6-amino-6-oxohexanoic acid used in 4th amide coupling step) to afford 3.1 mg of the product with 96.6% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.37 minutes with corresponding ESI detection of 1852.8 m/z.

PREPARATION OF EXAMPLE 10562

Example 10562

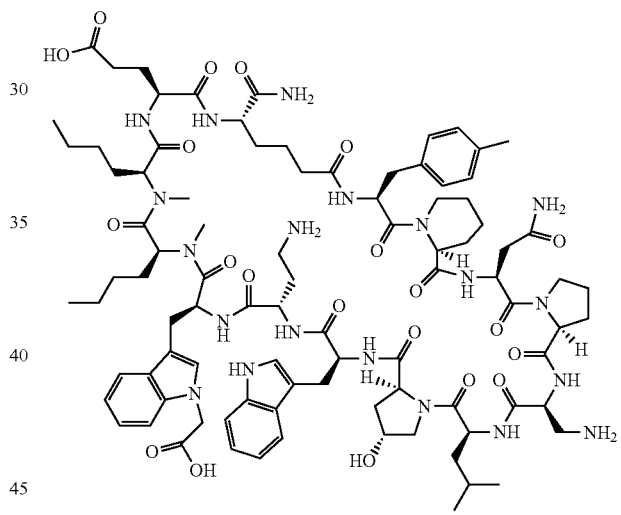

Example 10562 was prepared following the produre used for the preparation of Example 10505 ((S)-5-((((9H-fluoren-9-yl)methoxy)carbonyl)amino)-6-amino-6-oxohexanoic acid used in 4th amide coupling step) to afford 3.6 mg of the product with 96.9% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.69 minutes with corresponding ESI detection of 1851.3 m/z.

PREPARATION OF EXAMPLE 10563

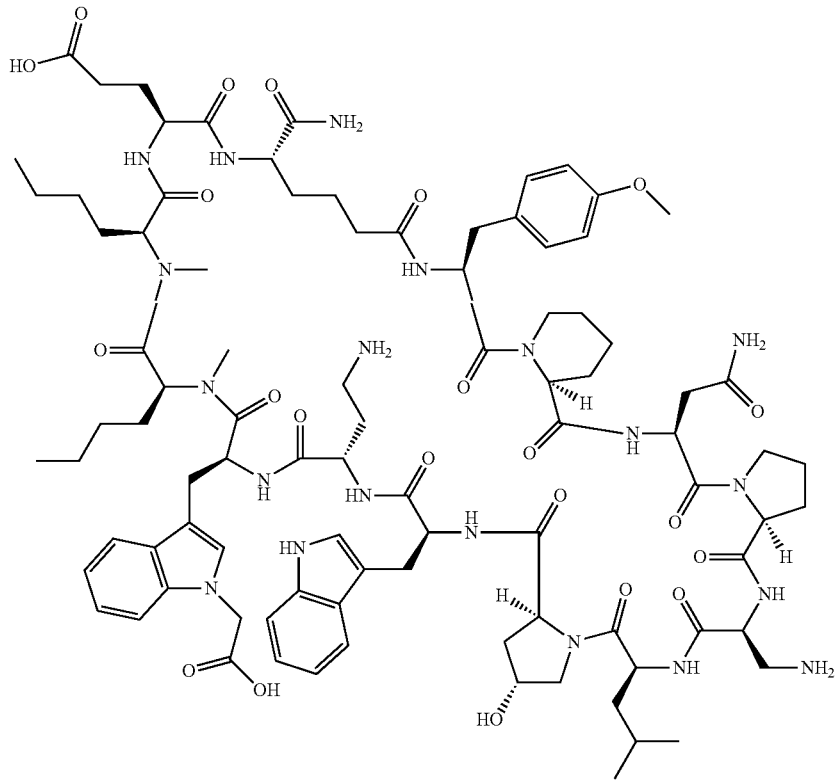

Example 10563

Example 10563 was prepared following the produre used for the preparation of Example 10505 ((S)-5-((((9H-fluoren-9-yl)methoxy)carbonyl)amino)-6-amino-6-oxohexanoic acid used in 4th amide coupling step) to afford 1.6 mg of the product with 97% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm.

Injection 2 conditions: Column: Waters CSH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.6 minutes with corresponding ESI detection of 1867.1 m/z.

PREPARATION OF EXAMPLE 10564

Example 10564

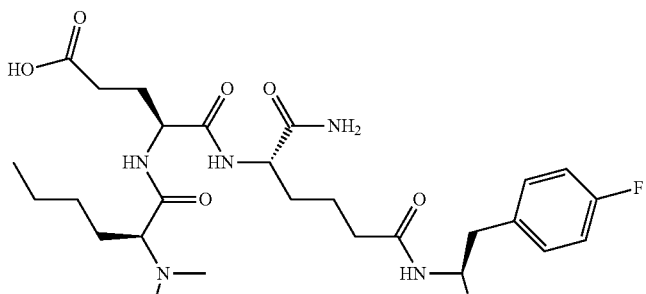

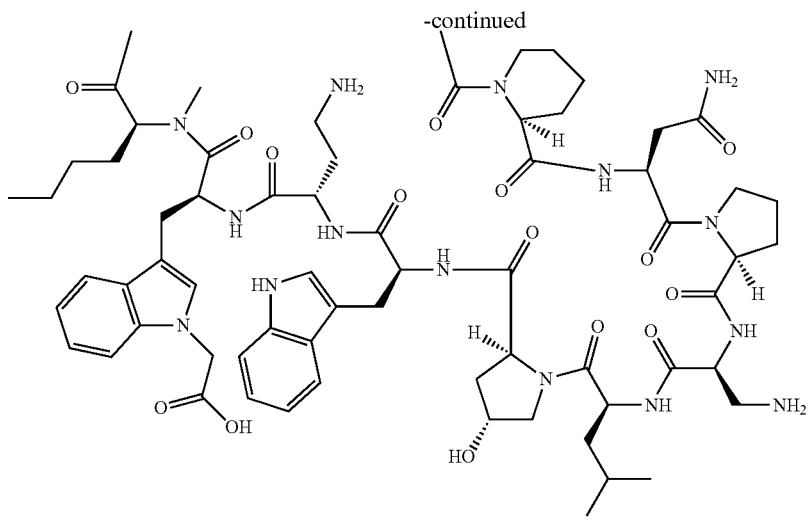

Example 10564 was prepared following the produre used for the preparation of Example 10505 ((S)-5-((((9H-fluoren-9-yl)methoxy)carbonyl)amino)-6-amino-6-oxohexanoic acid used in 4th amide coupling step) to afford 3.2 mg of the product with 97.1% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm.

Injection 2 conditions: Column: Waters CSH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.62 minutes with corresponding ESI detection of 1854 m/z.

PREPARATION OF EXAMPLE 10566

Example 10566

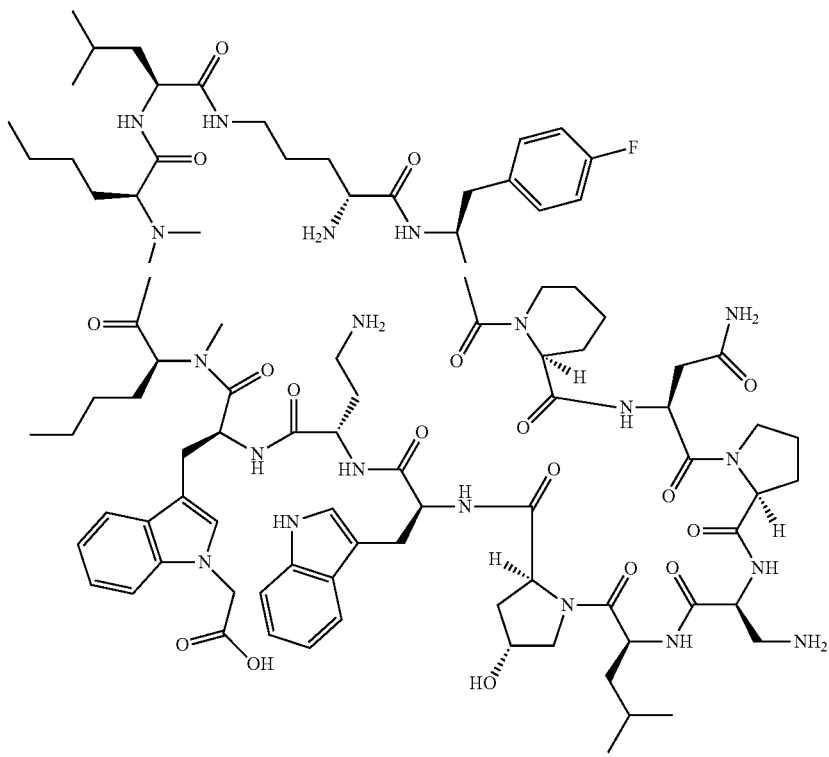

Example 10566 was prepared following the produre used for the preparation of Example 10505 ((R)-5-((((9H-fluoren-9-yl)methoxy)carbonyl)amino)-2-((tert-butoxycarbonyl)amino)pentanoic acid used in 4th amide coupling step) to afford 5.9 mg of the product with 96.6% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.47 minutes with corresponding ESI detection of 1811.2 m/z.

PREPARATION OF EXAMPLE 10567

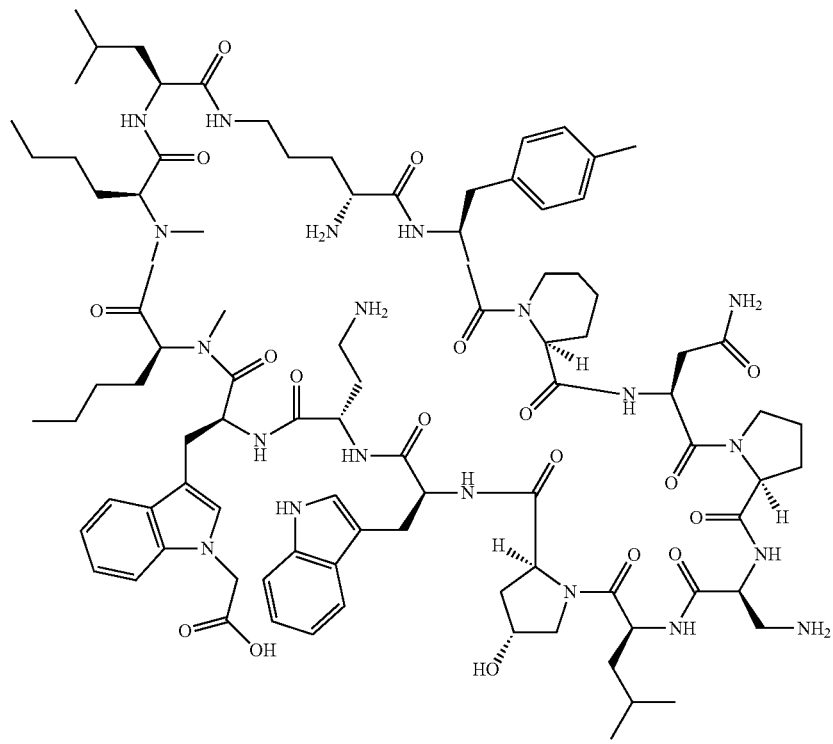

Example 10567

Example 10567 was prepared following the produre used for the preparation of Example 10505 ((R)-5-((((9H-fluoren-9-yl)methoxy)carbonyl)amino)-2-((tert-butoxycarbonyl)amino)pentanoic acid used in 4th amide coupling step) to afford 4.3 mg of the product with 93.9% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.52 minutes with corresponding ESI detection of 1807.4 m/z.

PREPARATION OF EXAMPLE 10568

Example 10568

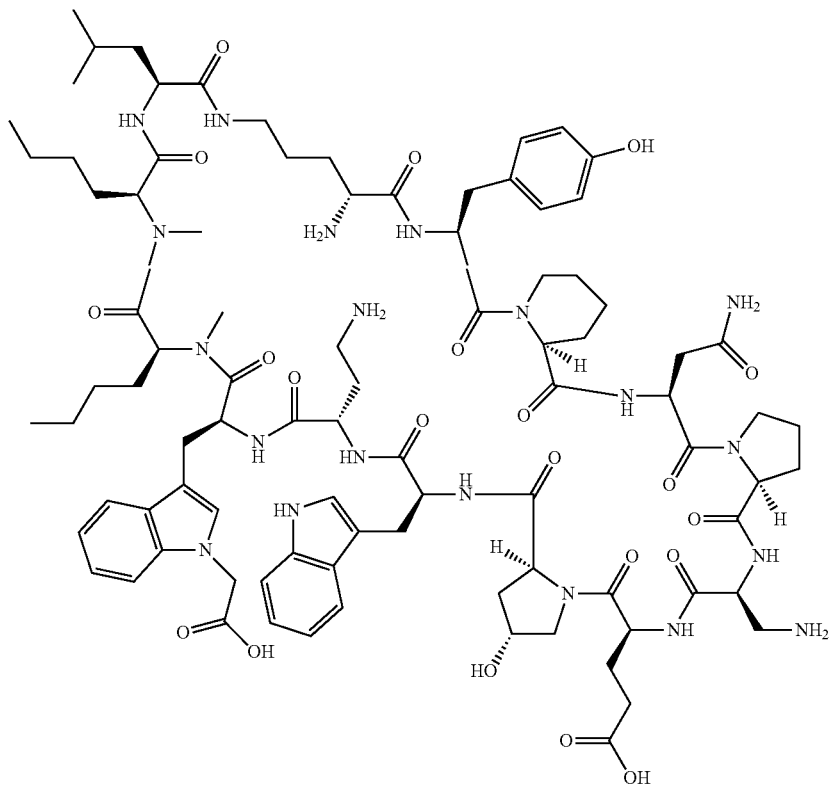

Example 10568 was prepared following the produre used for the preparation of Example 10505 ((R)-5-((((9H-fluoren-9-yl)methoxy)carbonyl)amino)-2-((tert-butoxycarbonyl)amino)pentanoic acid used in 4th amide coupling step) to afford 4.5 mg of the product with 97.6% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.6 minutes with corresponding ESI detection of 1826.1 m/z.

PREPARATION OF EXAMPLE 10569

Example 10569

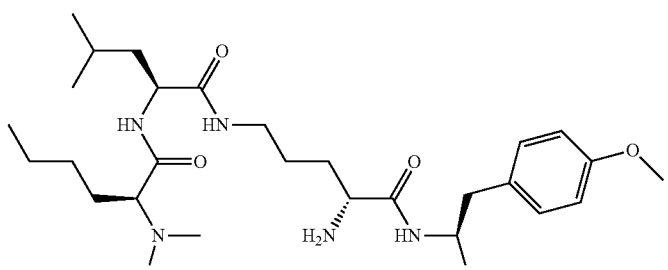

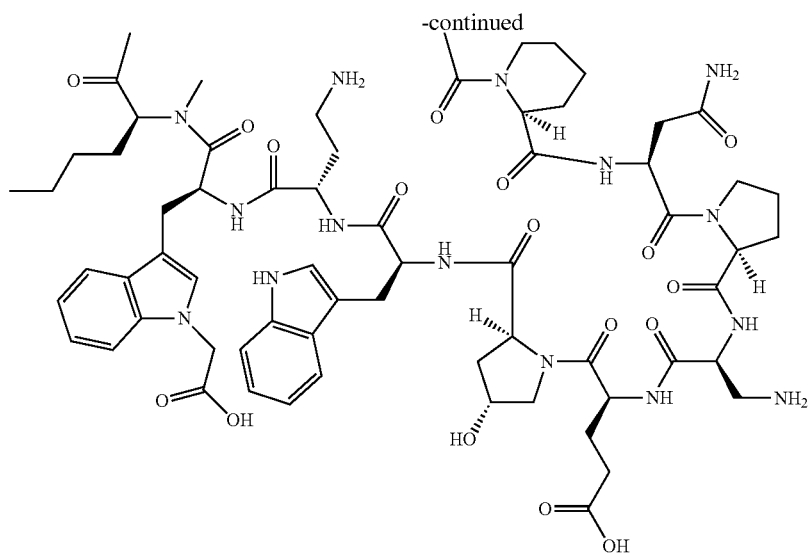

Example 10569 was prepared following the produre used for the preparation of Example 10505 ((R)-5-((((9H-fluoren-9-yl)methoxy)carbonyl)amino)-2-((tert-butoxycarbonyl) amino)pentanoic acid used in 4th amide coupling step) to afford 6.1 mg of the product with 100% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.78 minutes with corresponding ESI detection of 1838.1 m/z.

PREPARATION OF EXAMPLE 10570

Example 10570

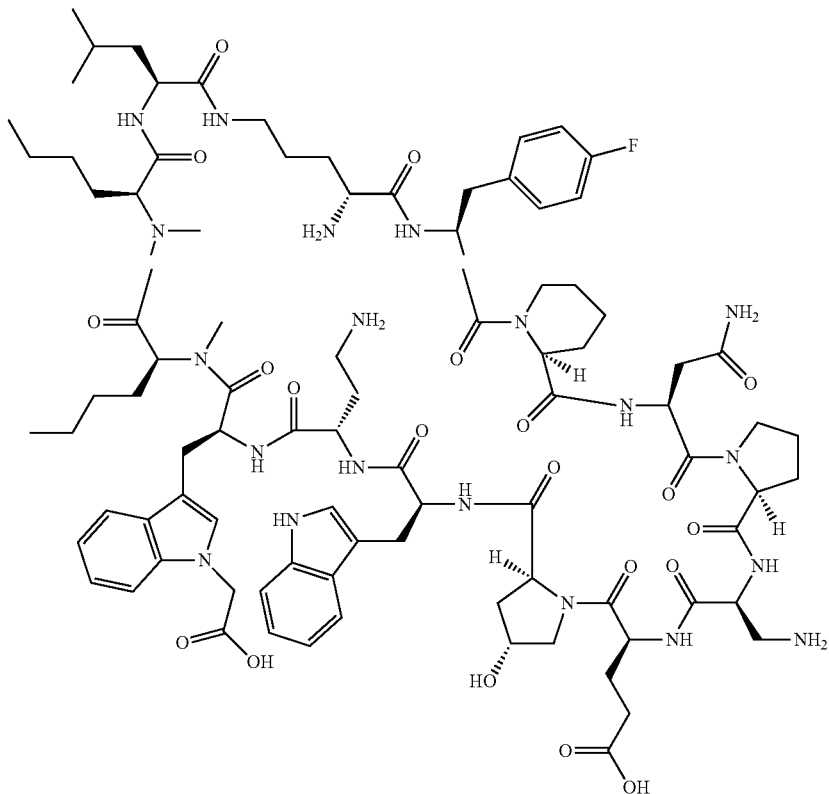

Example 10570 was prepared following the produre used for the preparation of Example 10505 ((R)-5-((((9H-fluoren-9-yl)methoxy)carbonyl)amino)-2-((tert-butoxycarbonyl)amino)pentanoic acid used in 4th amide coupling step) to afford 1.8 mg of the product with 97% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.47 minutes with corresponding ESI detection of 1827.2 m/z.

PREPARATION OF EXAMPLE 10571

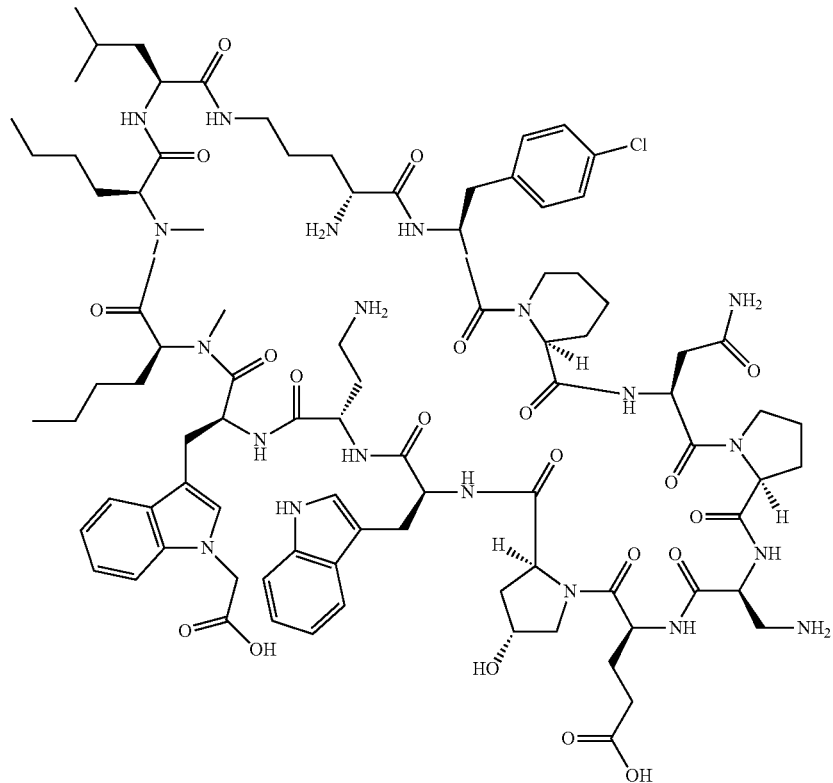

Example 10571

Example 10571 was prepared following the produre used for the preparation of Example 10505 ((R)-5-((((9H-fluoren-9-yl)methoxy)carbonyl)amino)-2-((tert-butoxycarbonyl)amino)pentanoic acid used in 4th amide coupling step) to afford 0.7 mg of the product with 91.3% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.52 minutes with corresponding ESI detection of 922.9 m/z.

PREPARATION OF EXAMPLE 10572

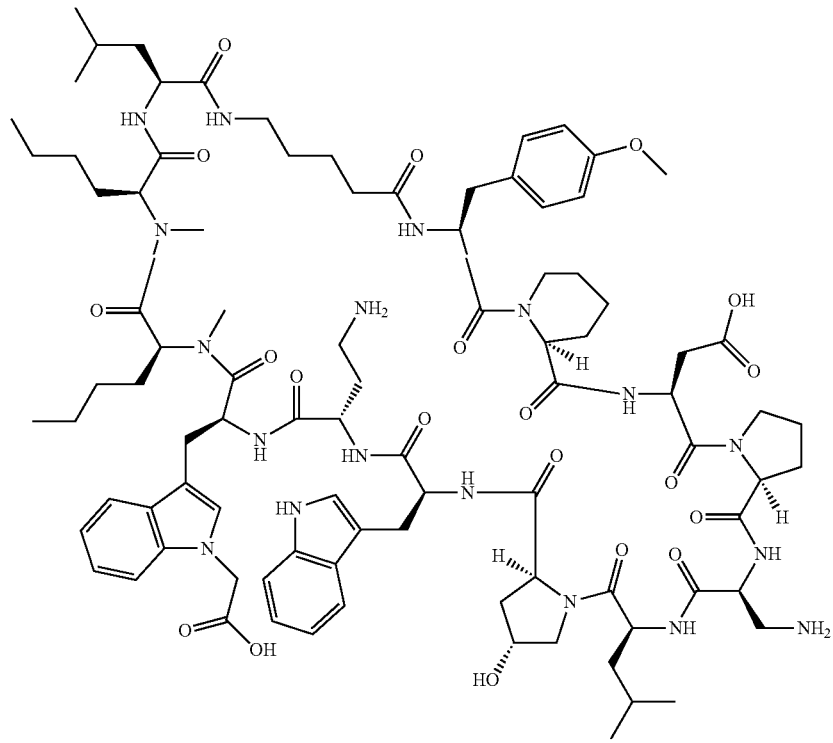

Example 10572

Example 10572 was prepared following the produre used for the preparation of Example 10505 to afford 21.7 mg of the product with 94.8% purity. Two analytical LC/MS injections were used to determine the final purity. Injection 1 conditions: Column: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 70° C.; Gradient: 0-100% B over 3 minutes, then a 2.0-minute hold at 100% B; Flow: 0.75 mL/min; Detection: UV at 220 nm. Injection 2 conditions: Column: Waters CSH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 70° C.; Gradient: 0-100% B over 3 minutes, then a 2.0-minute hold at 100% B; Flow: 0.75 mL/min; Detection: UV at 220 nm. Analysis results: Retention time=1.59 minutes with corresponding ESI detection of 1810.8 m/z.

Methods for Testing the Ability of Macrocyclic Peptides to Compete for the Binding of PD-1 to PD-L1 Using Homogenous Time-Resolved Fluorescence (HTRF) Binding Assays The ability of the macrocyclic peptides of the present disclosure to bind to PD-L1 was investigated using a PD-1/PD-L1 Homogenous Time-Resolved Fluorescence (HTRF) binding assay.
Methods
Homogenous Time-Resolved Fluorescence (HTRF) Assays of Binding of Soluble PD-1 to Soluble PD-L1. Soluble PD-1 and soluble PD-L1 refers to proteins with carboxyl-end truncations that remove the transmembrane-spanning regions and are fused to heterologous sequences, specifically the Fc portion of the human immunoglobuling G sequence (Ig) or the hexahistidine epitope tag (His). All binding studies were performed in an HTRF assay buffer consisting of dPBS supplemented with 0.1% (w/v) bovine serum albumin and 0.05% (v/v) Tween-20. For the PD-1-Ig/PD-L1-His binding assay, inhibitors were pre-incubated with PD-L1-His (10 nM final) for 15 m in 4 μl of assay buffer, followed by addition of PD-1-Ig (20 nM final) in 1 μl of assay buffer and further incubation for 15 m. PD-L1 fusion proteins from either human, cynomologous macaques, mouse, or other species were used. HTRF detection was achieved using europium crypate-labeled anti-Ig monoclonal antibody (1 nM final) and allophycocyanin (APC) labeled anti-His monoclonal antibody (20 nM final). Antibodies were diluted in HTRF detection buffer and 5 μl was dispensed on top of binding reaction. The reaction was allowed to equilibrate for 30 minutes and signal (665 nm/620 nm ratio) was obtained using an EnVision fluorometer. Additional binding assays were established between PD-1-Ig/PD-L2-His (20 and 5 nM, respectively), CD80-His/PD-L1-Ig (100 and 10 nM, respectively) and CD80-His/CTLA4-Ig (10 and 5 nM, respectively).

Binding/competition studies between biotinylated Compound No. 71 and human PD-L1-His were performed as follows. Macrocyclic peptide inhibitors were pre-incubated with PD-L1-His (10 nM final) for 60 minutes in 4 μl of assay buffer followed by addition of biotinylated Compound No. 71 (0.5 nM final) in 1 μl of assay buffer. Binding was allowed to equilibrate for 30 minutes followed by addition of europium crypated labeled Streptavidin (2.5 µM final) and APC-labeled anti-His (20 nM final) in 5 µl of HTRF buffer. The reaction was allowed to equilibrate for 30 m and signal (665 nm/620 nm ratio) was obtained using an EnVision fluorometer.

Recombinant Proteins. Carboxyl-truncated human PD-1 (amino acids 25-167) with a C-terminal human Ig epitope tag [hPD-1 (25-167)-3S-IG] and human PD-L1 (amino acids 18-239) with a C-terminal His epitope tag [hPD-L1(19-239)-tobacco vein mottling virus protease cleavage site (TVMV)-His] were expressed in HEK293T cells and purified sequentially by recombinant Protein A affinity chromatography and size exclusion chromatography. Human PD-L2-His (Sino Biologicals), CD80-His (Sino Biologicals), CTLA4-Ig (RnD Systems) were all obtained through commercial sources.

Sequence of Recombinant Human PD-1-Ig hPD1(25-167)-3S-IG
(SEQ ID NO: 1)
```
  1 LDSPDRPWNP PTFSPALLVV TEGDNATFTC SFSNTSESFV LNWYRMSPSN

51 QTDKLAAFPE DRSQPGQDCR FRVTQLPNGR DFHMSVVRAR RNDSGTYLCG

101 AISLAPKAQI KESLRAELRV TERRAEVPTA HPSPSPRPAG QFQGSPGGGG

151 GREPKSSDKT HTSPPSPAPE LLGGSSVFLF PPKPKDTLMI SRTPEVTCVV

201 VDVSHEDPEV KFNWYVDGVE VHNAKTKPRE EQYNSTYRVV SVLTVLHQDW

251 LNGKEYKCKV SNKALPAPIE KTISKAKGQP REPQVYTLPP SRDELTKNQV

301 SLTCLVKGFY PSDIAVEWES NGQPENNYKT TPPVLDSDGS FFLYSKLTVD

351 KSRWQQGNVF SCSVMHEALH NHYTQKSLSL SPGK
```

Sequence of Recombinant Human PD-L1-TVMV-His (PD-L1-His)

hPDL1(19-239)-TVMV-His
(SEQ ID NO: 2)
```
  1 FTVTVPKDLY VVEYGSNMTI ECKFPVEKQL DLAALIVYWE MEDKNIIQFV

51 HGEEDLKVQH SSYRQRARLL KDQLSLGNAA LQITDVKLQD AGVYRCMISY

101 GGADYKRITV KVNAPYNKIN QRILVVDPVT SEHELTCQAE GYPKAEVIWT

151 SSDHQVLSGK TTTTNSKREE KLFNVTSTLR INTTTNEIFY CTFRRLDPEE

201 NHTAELVIPE LPLAHPPNER TGSSETVRFQ GHHHHHH
```

The results are shown in Table 1. As shown, the macrocyclic peptides of the present disclosure demonstrated potent inhibition of PD-1-Ig binding activity to PD-L1-TVMV-His (PD-L1-His). Ranges are as follows: A=0.10-10 µM; B=0.01-0.099 µM; C=0.001-0.0099 µM.

TABLE 1

| Example Number | HTRF IC50 (µM) |
| --- | --- |
| Example 5001 | C |
| Example 5002 | C |
| Example 5003 | A |
| Example 5004 | A |
| Example 5005 | A |
| Example 5006 | B |
| Example 5007 | C |
| Example 5008 | C |
| Example 5009 | C |
| Example 10001 | C |
| Example 10002 | B |

TABLE 1-continued

| Example Number | HTRF IC50 (µM) |
| --- | --- |
| Example 10003 | C |
| Example 10004 | C |
| Example 10005 | 10.00 |
| Example 10006 | B |
| Example 10007 | C |
| Example 10008 | C |
| Example 10009 | A |
| Example 10010 | A |
| Example 10011 | C |
| Example 10012 | B |
| Example 10013 | 0.07 |
| Example 10014 | C |
| Example 10015 | C |
| Example 10016 | C |
| Example 10017 | C |

TABLE 1-continued

| Example Number | HTRF IC50 (µM) |
| --- | --- |
| Example 10018 | B |
| Example 10019 | A |
| Example 10020 | B |
| Example 10021 | B |
| Example 10022 | B |
| Example 10023 | A |
| Example 10024 | B |
| Example 10025 | A |
| Example 10026 | B |
| Example 10027 | 6.95E−03 |
| Example 10028 | A |
| Example 10500 | A |
| Example 10501 | C |
| Example 10502 | C |
| Example 10503 | B |
| Example 9005 | C |
| Example 9006 | C |
| Example 9007 | 0.005 |

TABLE 1-continued

| Example Number | HTRF IC50 (µM) |
| --- | --- |
| Example 9008 | C |
| Example 9009 | C |
| Example 9010 | B |
| Example 9011 | B |
| Example 9012 | B |
| Example 9013 | B |
| Example 9014 | C |
| Example 9015 | 0.015 |
| Example 9016 | C |
| Example 9017 | B |
| Example 9018 | C |
| Example 9019 | C |
| Example 9020 | B |
| Example 9021 | B |
| Example 9022 | B |
| Example 9023 | B |
| Example 9024 | B |
| Example 9025 | 0.016 |
| Example 9026 | C |
| Example 9027 | C |
| Example 9028 | C |
| Example 9029 | C |
| Example 9030 | B |
| Example 9031 | C |
| Example 9032 | C |
| Example 9033 | C |
| Example 9034 | C |
| Example 9035 | C |
| Example 9036 | C |
| Example 9037 | C |
| Example 9038 | C |
| Example 9039 | C |
| Example 9040 | C |
| Example 9041 | 0.005 |
| Example 9042 | C |
| Example 9043 | C |
| Example 9044 | C |
| Example 9045 | C |
| Example 9046 | C |
| Example 9047 | C |
| Example 9048 | C |
| Example 9049 | C |
| Example 9050 | C |
| Example 9051 | C |
| Example 9052 | 0.010 |
| Example 9053 | C |
| Example 9054 | C |
| Example 9055 | C |
| Example 9056 | C |
| Example 9057 | C |
| Example 9058 | C |
| Example 9059 | C |
| Example 1029 | B |
| Example 1030 | C |
| Example 1031 | C |
| Example 1032 | C |
| Example 1033 | B |
| Example 1034 | C |
| Example 1035 | C |
| Example 1036 | C |
| Example 1037 | C |
| Example 1038 | C |
| Example 1039 | C |
| Example 1040 | C |
| Example 1041 | C |
| Example 1042 | B |
| Example 10504 | B |
| Example 10505 | C |
| Example 10506 | C |
| Example 10507 | C |
| Example 10508 | B |
| Example 10509 | 0.765 |
| Example 10510 | A |
| Example 10511 | A |
| Example 10512 | A |
| Example 10513 | 0.354 |
| Example 10514 | B |
| Example 10515 | B |
| Example 10516 | B |
| Example 10517 | B |
| Example 10518 | B |
| Example 10519 | B |
| Example 10520 | B |
| Example 10521 | B |
| Example 10522 | B |
| Example 10525 | B |
| Example 10526 | B |
| Example 10527 | B |
| Example 10528 | B |
| Example 10529 | B |
| Example 10530 | C |
| Example 10531 | C |
| Example 10532 | C |
| Example 10533 | C |
| Example 10534 | C |
| Example 10535 | C |
| Example 10536 | C |
| Example 10537 | B |
| Example 10538 | C |
| Example 10539 | C |
| Example 10540 | C |
| Example 10541 | C |
| Example 10542 | C |
| Example 10543 | C |
| Example 10544 | C |
| Example 10545 | 0.008 |
| Example 10546 | B |
| Example 10547 | B |
| Example 10548 | B |
| Example 10549 | B |
| Example 10550 | B |
| Example 10551 | C |
| Example 10552 | C |
| Example 10553 | B |
| Example 10554 | C |
| Example 10555 | B |
| Example 10556 | C |
| Example 10557 | C |
| Example 10558 | B |
| Example 10559 | B |
| Example 10560 | B |
| Example 10561 | C |
| Example 10562 | B |
| Example 10563 | C |
| Example 10564 | B |
| Example 10566 | C |
| Example 10567 | B |
| Example 10568 | C |
| Example 10569 | C |
| Example 10570 | 0.012 |
| Example 10571 | C |
| Example 10572 | C |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:
1. A compound of formula (I)

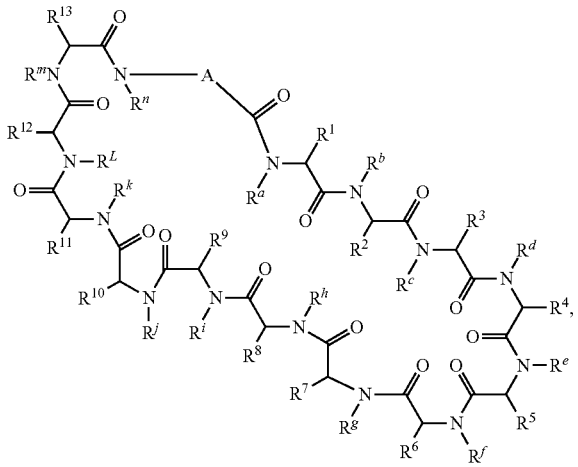

or a pharmaceutically acceptable salt thereof, wherein:
A is selected from —$CH_2CH_2$—;

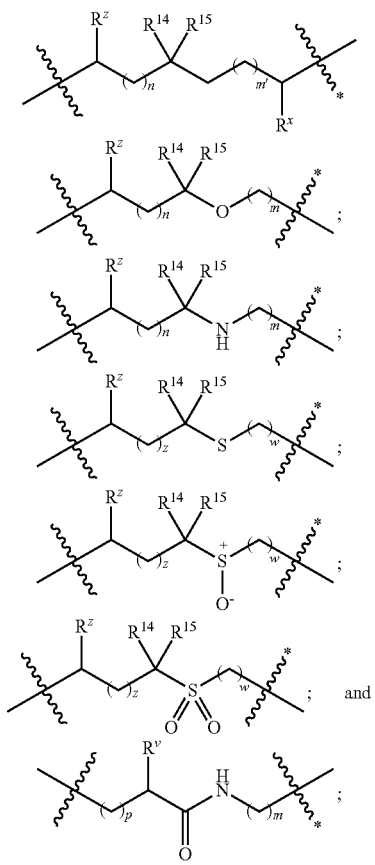

wherein:
$\overset{*}{\sim}$ denotes the point of attachment to the carbonyl group and $\sim$ denotes the point of attachment to the nitrogen atom;

n is 0, 1, or 2;
m is 1 or 2;
m' is 0 or 1;
z is 1 or 2;
when z is 1, w is 2;
when z is 2, w is 1 or 2;
p is 0, 1, or 2;
$R^{14}$ and $R^{15}$ are independently selected from hydrogen and methyl;
$R^x$ is selected from hydrogen, amino, hydroxy, and methyl; and
$R^z$ is selected from hydrogen and —C(O)NHR$^{16}$; wherein $R^{16}$ is selected from hydrogen, —CHR$^{17}$C(O)NH$_2$, —CHR$^{17}$C(O)NHCHR$^{18}$C(O)NH$_2$, and —CHR$^{17}$C(O)NHCHR$^{18}$C(O)NHCH$_2$C(O)NH$_2$;
wherein $R^{17}$ is selected from hydrogen and CH$_2$OH and wherein $R^{18}$ is selected from hydrogen and methyl;
$R^v$ is hydrogen, methyl, or a natural amino acid side chain;
$R^c$, $R^f$, $R^h$, $R^i$, and $R^m$ are hydrogen;
$R^n$ is hydrogen or methyl or $R^v$ and $R^n$ form a pyrrolidine ring;
$R^a$, $R^e$, $R^j$ and $R^k$, are each independently selected from hydrogen and methyl;
$R^1$, $R^2$, $R^3$, $R^4$, $R^5$, $R^6$, $R^7$, $R^8$, $R^9$, $R^{10}$, $R^{11}$, $R^{12}$, and $R^{13}$ are independently selected from a natural amino acid side chain and an unnatural amino acid side chain or form a ring with the corresponding vicinal R group as described below;
$R^e$ and $R^k$ can each form a ring with the corresponding vicinal R group and the atoms to which they are attached selected from azetidine, pyrollidine, morpholine, piperidine, piperazine, and tetrahydrothiazole; wherein each ring is optionally substituted with one to four groups independently selected from amino, cyano, methyl, halo, and hydroxy;
$R^b$ is methyl or, $R^b$ and $R^2$, together with the atoms to which they are attached, form a ring selected from azetidine, pyrollidine, morpholine, piperidine, piperazine, and tetrahydrothiazole; wherein each ring is optionally substituted with one to four groups independently selected from amino, cyano, methyl, halo, and hydroxy;
$R^d$ is hydrogen or methyl, or, $R^d$ and $R^4$, together with the atoms to which they are attached, can form a ring selected from azetidine, pyrollidine, morpholine, piperidine, piperazine, and tetrahydrothiazole; wherein each ring is optionally substituted with one to four groups independently selected from amino, cyano, methyl, halo, hydroxy, and phenyl;
$R^g$ is hydrogen or methyl or $R^g$ and $R^7$, together with the atoms to which they are attached, can form a ring selected from azetidine, pyrollidine, morpholine, piperidine, piperazine, and tetrahydrothiazole; wherein each ring is optionally substituted with one to four groups independently selected from amino, benzyl optionally substituted with a halo group, benzyloxy, cyano, cyclohexyl, methyl, halo, hydroxy, isoquinolinyloxy optionally substituted with a methoxy group, quinolinyloxy optionally substituted with a halo group, and tetrazolyl; and wherein the pyrrolidine and the piperidine ring are optionally fused to a cyclohexyl, phenyl, or indole group; and
$R^L$ is methyl or, $R^L$ and $R^{12}$, together with the atoms to which they are attached, form a ring selected from azetidine and pyrollidine, wherein each ring is optionally substituted with one to four groups independently selected from amino, cyano, methyl, halo, and hydroxy.

2. A compound of claim 1, or a pharmaceutically acceptable salt thereof, wherein
$R^d$ and $R^4$, together with the atoms to which they are attached, form a pyrollidine ring;
$R^g$ and $R^7$, together with the atoms to which they are attached, form a pyrollidine ring, wherein said ring is optionally substituted with one hydroxy group; and
$R^k$ is methyl.

3. A compound of claim 2, or a therapeutically acceptable salt thereof, wherein:
$R^a$, $R^e$, and $R^j$ hydrogen;
$R^b$ and $R^2$ are each methyl or, $R^b$ and $R^2$, together with the atoms to which they are attached, form a piperidine ring;
$R^L$ is methyl;
$R^n$ is hydrogen, methyl, or $R^n$ and $R^v$ form a pyrrolidine ring;
$R^1$ is phenylmethyl wherein the phenyl is substituted with one group selected from halo, hydroxy, methoxy, or methyl;
$R^3$ is selected from —CH$_2$C(O)NH$_2$ and —CH$_2$CO$_2$H;
$R^5$ is selected from hydrogen, —CH$_2$NH$_2$, —CH$_2$(imidazolyl), and —CH$_2$C(O)NH$_2$;
$R^6$ is selected from —CH$_2$CH(CH$_3$)$_2$, —(CH$_2$)$_4$NH$_2$, —(CH$_2$)$_2$CO$_2$H, and (CH$_2$)$_2$C(O)NH$_2$;
$R^8$ and $R^{10}$ are —CH$_2$(indolyl), wherein the indolyl is optionally substituted with —CH$_2$CO$_2$H;
$R^9$ is selected from hydrogen, —(CH$_2$)$_2$NH$_2$, —(CH$_2$)$_4$NH$_2$, —CH$_2$OH, and —CH$_2$C(O)NH$_2$;
$R^{11}$ and $R^{12}$ are —(CH$_2$)$_3$CH$_3$; and
$R^{13}$ is selected from methyl, —CH$_2$OH, —CH$_2$CH(CH$_3$)$_2$, and —(CH$_2$)$_2$CO$_2$H.

4. A compound of claim 3, or a therapeutically acceptable salt thereof, wherein
A is

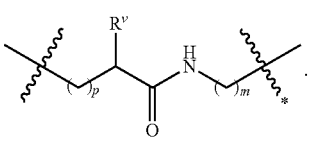

5. A compound of claim 3, or a therapeutically acceptable salt thereof, wherein A is

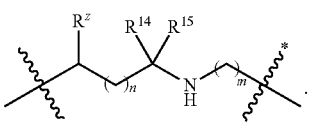

6. A compound of claim 3, or a therapeutically acceptable salt thereof, wherein A is

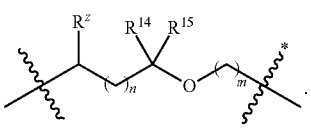

7. A compound of claim 3, or a therapeutically acceptable salt thereof, wherein A is

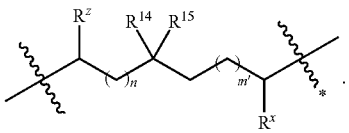

8. A compound selected from
Example 5001, Example 5002, Example 5003, Example 5004, Example 5005, Example 5006, Example 5007, Example 5008, Example 5009, Example 10001, Example 10002, Example 10003, Example 10004, Example 10005, Example 10006, Example 10007, Example 10008, Example 10009, Example 10010, Example 10011, Example 10012, Example 10013, Example 10014, Example 10015, Example 10016, Example 10017, Example 10018, Example 10019, Example 10020, Example 10021, Example 10022, Example 10023, Example 10024, Example 10025, Example 10026, Example 10027, Example 10028, Example 10500, Example 10501, Example 10502, Example 10503, Example 9005, Example 9006, Example 9007, Example 9008, Example 9009, Example 9010, Example 9011, Example 9012, Example 9013, Example 9014, Example 9015, Example 9016, Example 9017, Example 9018, Example 9019, Example 9020, Example 9021, Example 9022, Example 9023, Example 9024, Example 9025, Example 9026, Example 9027, Example 9028, Example 9029, Example 9030, Example 9031, Example 9032, Example 9033, Example 9034, Example 9035, Example 9036, Example 9037, Example 9038, Example 9039, Example 9040, Example 9041, Example 9042, Example 9043, Example 9044, Example 9045, Example 9046, Example 9047, Example 9048, Example 9049, Example 9050, Example 9051, Example 9052, Example 9053, Example 9054, Example 9055, Example 9056, Example 9057, Example 9058, Example 9059, Example 10029, Example 10030, Example 10031, Example 10032, Example 10033, Example 10034, Example 10035, Example 10036, Example 10037, Example 10038, Example 10039, Example 10040, Example 10041, Example 10042, Example 10504, Example 10505, Example 10506, Example 10507, Example 10508, Example 10509, Example 10510, Example 10511, Example 10512, Example 10513, Example 10514, Example 10515, Example 10516, Example 10517, Example 10518, Example 10519, Example 10520, Example 10521, Example 10522, Example 10525, Example 10526, Example 10527, Example 10528, Example 10529, 10530, Example 10531, Example 10532, Example 10533, Example 10534, Example 10535, Example 10536, Example 10537, Example 10538, Example 10539, Example 10540, Example 10541, Example 10542, Example 10543, Example 10544, Example 10545, Example 10546, Example 10547, Example 10548, Example 10549, Example 10550, Example 10551, Example 10552, Example 10553, Example 10554, Example 10555, Example 10556, Example 10557, Example 10558, Example 10559, Example 10560, Example 10561, Example 10562, Example 10563, Example 10564, Example 10566, Example 10567, Example 10568, Example 10569, Example 10570, Example 10571, and Example 10572, or a pharmaceutically acceptable salt thereof.

\* \* \* \* \*

UNITED STATES PATENT AND TRADEMARK OFFICE
CERTIFICATE OF CORRECTION

Page 1 of 2

PATENT NO. : 9,732,119 B2
APPLICATION NO. : 14/874886
DATED : August 15, 2017
INVENTOR(S) : Sun et al.

It is certified that error appears in the above-identified patent and that said Letters Patent is hereby corrected as shown below:

On the Title Page

Column 2, Lines 27-28, item (56) Other Publications:
Delete "Accesion," and insert -- Accession --.

In the Claims

Claim 1, Column 326, Line 16:
Delete "$CH_2OH$" and insert -- —$CH_2OH$ --.

Claim 1, Column 326, Line 24:
Delete "$R^j$" and insert -- $R^j$, --, therefor.

Claim 1, Column 326, Line 33:
Delete "pyrollidine," and insert -- pyrrolidine, --.

Claim 1, Column 326, Line 40:
Delete "pyrollidine," and insert -- pyrrolidine, --.

Claim 1, Column 326, Line 47:
Delete "pyrollidine," and insert -- pyrrolidine, --.

Claim 1, Column 326, Line 54:
Delete "pyrollidine," and insert -- pyrrolidine, --.

Claim 1, Column 327, Line 1:
Delete "pyrollidine," and insert -- pyrrolidine, --.

Claim 2, Column 327, Line 8:
Delete "pyrollidine" and insert -- pyrrolidine --.

Signed and Sealed this
Eleventh Day of December, 2018

Andrei Iancu
*Director of the United States Patent and Trademark Office*

Claim 2, Column 327, Line 10:
Delete "pyrollidine" and insert -- pyrrolidine --.

Claim 3, Column 327, Line 15:
After "$R^j$" insert -- are --.